United States Patent
Su et al.

(10) Patent No.: US 11,661,437 B2
(45) Date of Patent: May 30, 2023

(54) STEROID DERIVATIVE REGULATORS, METHOD FOR PREPARING THE SAME, AND USES THEREOF

(71) Applicants: Jiangsu Hansoh Pharmaceutical Group Co., Ltd., Jiangsu (CN); Shanghai Hansoh Biomedical Co., Ltd., Shanghai (CN)

(72) Inventors: Yidong Su, Jiangsu (CN); Xiaopo Chen, Jiangsu (CN); Jun Wang, Jiangsu (CN); Rudi Bao, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 6 days.

(21) Appl. No.: 16/969,137

(22) PCT Filed: Jan. 31, 2019

(86) PCT No.: PCT/CN2019/074108
§ 371 (c)(1),
(2) Date: Aug. 11, 2020

(87) PCT Pub. No.: WO2019/154247
PCT Pub. Date: Aug. 15, 2019

(65) Prior Publication Data
US 2022/0017565 A1 Jan. 20, 2022

(30) Foreign Application Priority Data

Feb. 11, 2018 (CN) .......................... 201810141153.6
Mar. 5, 2018 (CN) .......................... 201810180543.4
May 21, 2018 (CN) .......................... 201810491114.9
Nov. 23, 2018 (CN) .......................... 201811407557.1

(51) Int. Cl.
*C07J 43/00* (2006.01)
*A61P 25/24* (2006.01)
*A61P 25/08* (2006.01)
*C07J 7/00* (2006.01)
*C07J 41/00* (2006.01)
*C07J 53/00* (2006.01)

(52) U.S. Cl.
CPC ............. *C07J 43/003* (2013.01); *A61P 25/08* (2018.01); *A61P 25/24* (2018.01); *C07J 7/009* (2013.01); *C07J 41/005* (2013.01); *C07J 41/0094* (2013.01); *C07J 53/004* (2013.01)

(58) Field of Classification Search
CPC .. C07J 41/0038; C07J 41/005; C07J 41/0094; C07J 43/003; C07J 53/004; C07J 7/009
See application file for complete search history.

(56) References Cited

U.S. PATENT DOCUMENTS

2014/0148412 A1* 5/2014 Hogenkamp ........... A61P 25/18
548/193

FOREIGN PATENT DOCUMENTS

| CN | 104136452 | A | 11/2014 | |
| CN | 105339381 | A | 2/2016 | |
| TW | 201629015 | A | 8/2016 | |
| WO | WO-9805337 | A1 * | 2/1998 | ............. A61K 31/56 |
| WO | 2013019711 | A2 | 2/2013 | |
| WO | 2014169831 | A1 | 10/2014 | |
| WO | 2016061537 | A1 | 4/2016 | |
| WO | WO-2016061527 | A1 * | 4/2016 | ............. A61K 31/56 |

OTHER PUBLICATIONS

Covey, D.F. et al. "Neurosteroid Analogues & Structure Activity Studies of N-Acylated 17a-Azra-D-Homosteroid Analogues of the Anesthetic Steroids (3,5)- and (3,5-3-Hydroxypregnam-20-one" Journal of Medicinal Chemistry, vol. 43, No. (17), Aug. 5, 2000, pp. 3201-3202.
Veleiro, A.S. et al. "Synthesis and GABAA Receptor Activity of a 6, 19-Oxido Analogue of Pregnanolone" Bioorganic & Medicinal Chemistry Letters, vol. 13, Dec. 31, 2003 pp. 343-345.
Anderson, A. et al. "Conformationally Constrained Anesthetic Steroids that Modulate GABAA Receptors" Journal of Medicinal Chemistry, vol. 43, Oct. 19, 2000, pp. 4118-4121.
International Search Report dated May 5, 2019 in International Patent Application No. PCT/CN2019/074108.
Written Opinion dated May 5, 2019 in International Patent Application No. PCT/CN2019/074108.

* cited by examiner

*Primary Examiner* — Susanna Moore
(74) *Attorney, Agent, or Firm* — Ice Miller LLP

(57) ABSTRACT

Steroid derivative regulators, a method for preparing the same, and uses thereof are described. Specifically, a compound as shown in formula (I), a preparation method therefor, a pharmaceutical composition containing the compound, and uses thereof as a regulator of GABA$_A$ receptor for treating depression, convulsion, Parkinson's disease, and nervous system diseases are described, wherein the substituents of the formula (I) are as defined in the description.

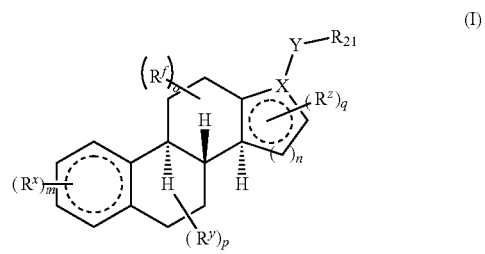

(I)

4 Claims, No Drawings

STEROID DERIVATIVE REGULATORS, METHOD FOR PREPARING THE SAME, AND USES THEREOF

CROSS-REFERENCE TO RELATED APPLICATION

This application is a Section 371 of International Application No. PCT/CN2019/074108, filed Jan. 31, 2019, which was published in the Chinese language Aug. 15, 2019, under International Publication No. WO 2019/154247 A1, which claims priority under 35 U.S.C. § 119(b) to Chinese Patent Application No. 201810141153.6, filed Feb. 11, 2018, Chinese Patent Application No. 201810180543.4 filed Mar. 5, 2018, Chinese Patent Application No. 201810491114.9 filed May 21, 2018, and Chinese Patent Application No. 201811407557.1 filed Nov. 23, 2018, the disclosures of which are incorporated herein by reference in their entireties.

FIELD OF THE INVENTION

The present invention belongs to the field of drug synthesis, and in particular relates to a steroid derivative regulator, a method for preparing the same, and a use thereof.

BACKGROUND OF THE INVENTION $GABA_A$ receptor is a chemically-gated channel on the cell membrane and belongs to ionic receptors. $GABA_A$ receptor is widely distributed in the nervous system, and can bind to inhibitory neurotransmitter GABA (gamma-aminobutyric acid), leading to the opening of chloride channels and inhibition of neurons. $GABA_A$ receptor regulator (tetrahydroprogesterone) is a positive regulator of $GABA_A$ receptor. The binding of tetrahydroprogesterone to intrasynaptic $GABA_A$ receptor regulator can increase the opening frequency of chloride channel on the receptor and the influx of chloride ion, thereby increasing the Phasic current, producing a rapid inhibitory effect, reducing nerve excitability, and providing an anti-anxiety and anti-depression effect. The binding of tetrahydroprogesterone to extrasynaptic $GABA_A$ receptor provides a continuous chloride ion current, and mediates a lasting and sustained inhibitory effect. Tetrahydroprogesterone can also increase the content of brain derived neurotrophic factor (BDNF), promote the regeneration of hippocampal neurons, and provide a neuroprotective effect, thereby improving anxiety and depression symptoms; but the specific mechanism of action is not clear yet.

Major depressive disorder (MDD) is a common, chronic and recurrent disease. The burden and adverse consequence caused by it are becoming more and more serious. In the past 40 years, the research and clinical application of antidepressants have greatly developed. However, most antidepressants (fluoxetine, paroxetine, sertraline, fluvoxamine, citalopram, etc.) take 2 to 4 weeks to have an effect. The clinical treatment of major depressive disorder patients, especially patients with suicidal tendency, often needs to be prompt and rapid, thus there is an urgent need to develop fast-acting antidepressants.

In the past two decades, there has been little innovation in the research and development of depression treatment. The development goal of $GABA_A$ receptor regulators is to change the expectation of patients by changing the treatment regimen of MDD. If successfully developed, the $GABA_A$ receptor regulator may become the first drug that provides a truly new mechanism of action for the treatment of depression in more than two decades. At present, foreign pharmaceutical companies, including Sage Therapeutics and Marinus etc., are doing their best to develop $GABA_A$ receptor regulators.

Published patent applications related to $GABA_A$ receptor regulators include: WO2003077919, WO2014169833, WO2016061537, WO2015180679, and WO2015027227.

$GABA_A$ receptor regulators, as a popular target in the pharmaceutical industry, currently have a good application prospect.

First, $GABA_A$ receptor regulators can be applied to major depressive disorder (MDD). The annual incidence of MDD in China is about 2%, thus there is a huge market potential.

Second, existing antidepressants take a long time, commonly 3 to 4 weeks, to have an effect, have a high failure rate up to 40%, and require long-term medication. $GABA_A$ receptor regulators can provide a significant antidepressant effect within 24 hours, and the effect can last for several days to two weeks.

Third, $GABA_A$ receptor regulators can meet the treatment need of MDD patients with oral administration once a day.

SUMMARY OF THE INVENTION

The objective of the present invention is to provide a compound of formula (I), a stereoisomer thereof, or a pharmaceutically acceptable salt thereof, wherein the structure of the compound of formula (I) is as follows:

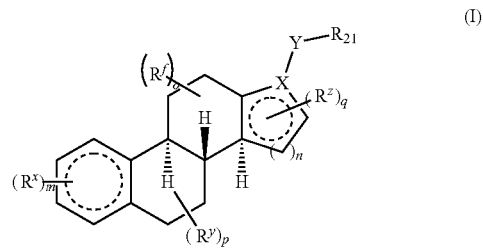

wherein:

X is selected from the group consisting of —$CR_{17}$— and —N—;

Y is selected from the group consisting of —$CR_{23}R_{24}$—, —$S(CH_2)_{n1}$—, —$P(CH_2)_{n1}$—, —$O(CH_2)_{n1}$—, —$(CH_2)_{n1}NR_{22}$—,

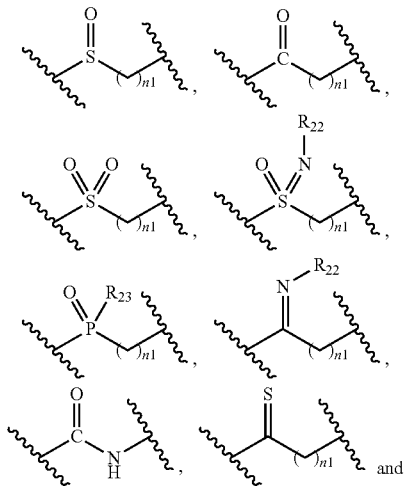

and

-continued

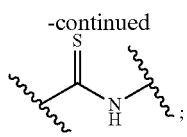

$R^x$, $R^y$, $R^z$ and $R^f$ are identical or different and are each independently selected from the group consisting of hydrogen atom, deuterium atom, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, thiol, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

or, any two adjacent or non-adjacent groups of $R^x$, $R^y$, $R^z$ and $R^f$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$;

or, any two adjacent groups of $R^x$, $R^y$, $R^z$ and $R^f$ are absent and can form a double bond;

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

when X is —$CR_{17}$—, $R_{17}$ is selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

or, $R_{17}$ and any group of $R^x$, $R^y$, $R^z$ and $R^f$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$;

$R_{22}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and $(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

$R_{23}$, $R_{24}$, $R_{25}$ and $R_{26}$ are identical or different and are each independently selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

m is an integer of 0, 1, 3, 4, 5, 6, 7, 8, 9 or 10;
n is an integer of 0, 1, 2 or 3;
o is an integer of 0, 1, 2, 3, 4 or 5;
p is an integer of 0, 1, 2, 3, 4, 5 or 6;
q is an integer of 0, 1, 2, 3, 4, 5 or 6;
$m_1$ is an integer of 0, 1 or 2; and
$n_1$ is an integer of 0, 1, 2, 3, 4 or 5.

In a preferred embodiment of the present invention, the compound of formula (I) is a compound of formula (II), a stereoisomer thereof, or a pharmaceutically acceptable salt thereof:

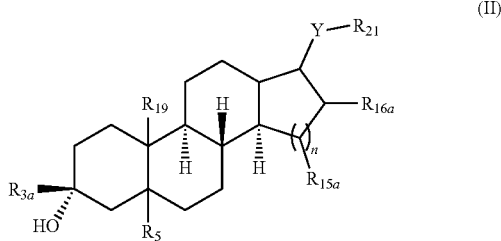
(II)

wherein:

Y is selected from the group consisting of

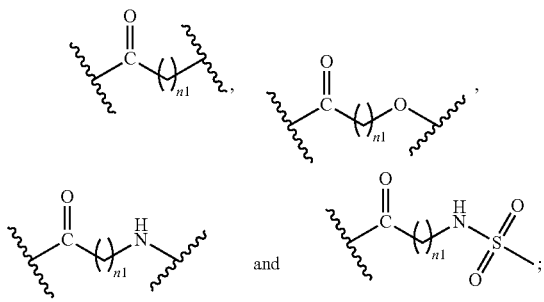
and $R_{3a}$ is selected from the group consisting of hydrogen atom, deuterium atom, alkyl, deuterated alkyl, haloalkyl, alkoxy, haloalkoxy, halogen, amino, thiol, nitro, hydroxy, cyano, alkenyl and alkynyl;

$R_5$ is selected from the group consisting of hydrogen atom, deuterium atom, alkyl, deuterated alkyl, haloalkyl, alkoxy, haloalkoxy, halogen, amino, nitro, hydroxy, cyano, alkenyl and alkynyl;

$R_{15a}$ is selected from the group consisting of hydrogen atom, deuterium atom, alkyl, deuterated alkyl, haloalkyl, alkoxy, haloalkoxy, halogen, amino, nitro, hydroxy, cyano, alkenyl and alkynyl;

$R_{16a}$ is selected from the group consisting of hydrogen atom, deuterium atom, alkyl, deuterated alkyl, haloalkyl, alkoxy, haloalkoxy, halogen, amino, nitro, hydroxy, cyano, alkenyl and alkynyl;

or, $R_{15a}$ and $R_{16a}$ are bonded to form a cycloalkyl or heterocyclyl, wherein the resulting cycloalkyl or heterocyclyl is optionally further substituted by one or more substituents selected from the group consisting of hydrogen atom, deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl;

$R_{19}$ is selected from the group consisting of hydrogen atom, deuterium atom, alkyl, deuterated alkyl, haloalkyl, alkoxy, haloalkoxy, halogen, amino, nitro, thiol, hydroxy, cyano, alkenyl, alkynyl, hydroxyalkyl, —$(CH_2)_{n1}OR_{23}$, —$(CH_2)_{n1}SR_{23}$, —$(CH_2)_{n1}C(O)OR_{23}$, —$(CH_2)_{n1}S(O)_{m1}R_{23}$, —$(CH_2)_{n1}S(O)(=NR_{23})R_{24}$ and —$(CH_2)_{n1}C(O)NR_{23}R_{24}$;

or, $R_5$ and $R_{19}$ are bonded to form a cycloalkyl or heterocyclyl, wherein the resulting cycloalkyl or heterocyclyl is optionally further substituted by one or more substituents selected from the group consisting of hydrogen atom, deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl;

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, hydroxyalkyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

$R_{23}$, $R_{24}$, $R_{25}$ and $R_{26}$ are identical or different and are each independently selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

n is an integer of 1 or 2;

$m_1$ is an integer of 0, 1 or 2; and $n_1$ is an integer of 0, 1, 2, 3, 4 or 5.

In a preferred embodiment of the present invention, the compound of formula (I) is a compound of formula (III-A), a stereoisomer thereof, or a pharmaceutically acceptable salt thereof:

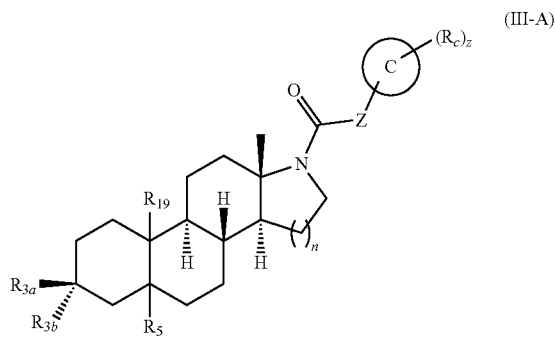
(III-A)

wherein:

Z is selected from the group consisting of —$CR_{23}R_{24}$—, —$NR_{23}$—, —$(CH_2)_{n1}O(CH_2)_{n2}$— and —O—, and preferably methylene;

ring C is selected from the group consisting of cycloalkyl, heterocyclyl, aryl and heteroaryl, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

each $R_c$ is identical or different and each is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)NR_{23}$, —$(CH_2)_{n1}NR_{23}R_{24}$, —$(CH_2)_{n1}C(O)NR_{23}R_{24}$, —$(CH_2)_{n1}NR_{23}C(O)R_{23}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

z is an integer of 0, 1, 3, 4 or 5; and $R_{3a}$, $R_{3b}$, $R_5$, $R_{19}$, $R_{23}$-$R_{26}$, n, $m_1$ and $n_1$ are as defined in the compound of formula (II).

In a preferred embodiment of the present invention, the compound of formula (II), a stereoisomer thereof, or a pharmaceutically acceptable salt thereof is a compound of formula (V-7) or (V-8), a stereoisomer thereof, or a pharmaceutically acceptable salt thereof:

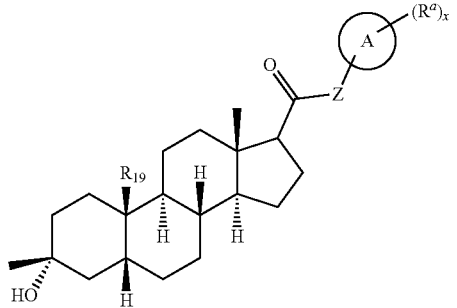

(V-7)

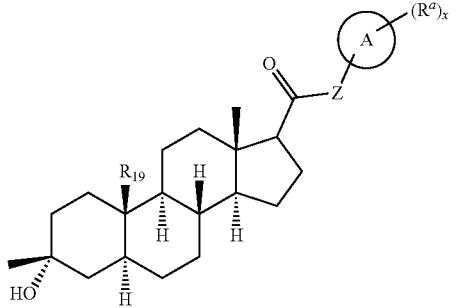

(V-8)

wherein:

ring A is selected from the group consisting of cycloalkyl, heterocyclyl, aryl and heteroaryl, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

each $R_a$ is identical or different and each is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)NR_{23}$, —$(CH_2)_{n1}NR_{23}R_{24}$, —$(CH_2)_{n1}C(O)NR_{23}R_{24}$, —$(CH_2)_{n1}NR_{23}C(O)R_{23}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

$R_{19}$ is selected from the group consisting of hydrogen atom, alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)NR_{23}$, —$(CH_2)_{n1}NR_{23}R_{24}$, —$(CH_2)_{n1}C(O)NR_{23}R_{24}$, —$(CH_2)_{n1}NR_{23}C(O)R_{23}$, —$(CH_2)_{n1}S(O)(=NR_{23})R_{24}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

x, m$_1$ and n$_1$ are as defined in formula (II).

In a preferred embodiment of the present invention, the compound of formula (I) is a compound of formula (III-B), a stereoisomer thereof, or a pharmaceutically acceptable salt thereof:

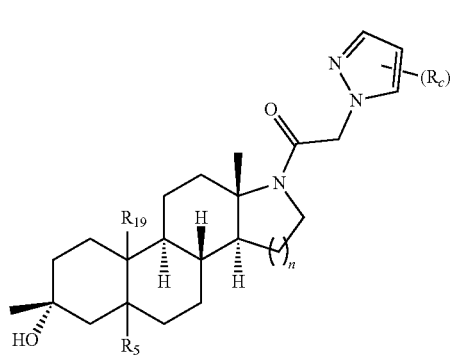

(III-B)

wherein:

R$_5$ is selected from the group consisting of hydrogen atom, C$_{1-6}$ alkyl, C$_{1-6}$ haloalkyl and C$_{1-6}$ alkoxy;

R$_{19}$ is selected from the group consisting of hydrogen atom, C$_{1-6}$ alkyl, C$_{1-6}$ haloalkyl, C$_{1-6}$ alkoxy, —(CH$_2$)$_{n1}$OR$_{23}$ and —(CH$_2$)$_{n1}$SR$_{23}$;

R$_c$ is selected from the group consisting of hydrogen atom, cyano and C$_{1-6}$ alkyl;

z is an integer of 0, 1 or 2; and n is 0, 1 or 2.

In a preferred embodiment of the present invention, the compound of formula (I), a stereoisomer thereof, or a pharmaceutically acceptable salt thereof is a compound of formula (IV-A) or (IV-B), a stereoisomer thereof, or a pharmaceutically acceptable salt thereof:

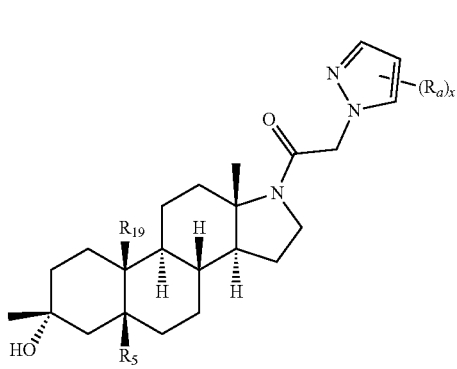

(IV-A)

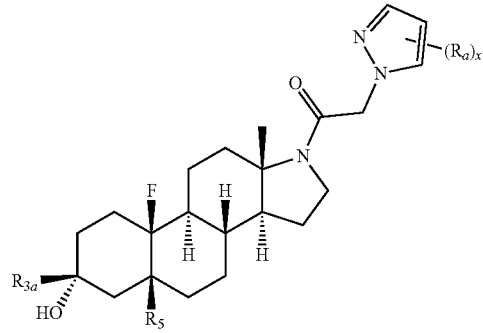

(IV-B)

wherein:

R$_{3a}$ is selected from the group consisting of C$_{1-6}$ alkyl, C$_{1-6}$ haloalkyl and C$_{1-6}$ alkoxy;

R$_{19}$ is selected from the group consisting of cyano, halogen, C$_{1-6}$ alkyl, C$_{1-6}$ haloalkyl, C$_{1-6}$ alkoxy, —(CH$_2$)$_{n1}$OR$_{23}$, —(CH$_2$)$_{n1}$S(O)$_{m1}$R$_{23}$, —(CH$_2$)$_{n1}$S(O)(=NR$_{23}$)R$_{24}$ and —(CH$_2$)$_{n1}$SR$_{23}$;

R$_a$ is selected from the group consisting of hydrogen atom, cyano, halogen, nitro, alkyl, alkoxy, haloalkyl, cycloalkyl, hydroxyalkyl, heterocyclyl, heteroaryl, —(CH$_2$)$_{n1}$CR$_{23}$R$_{24}$R$_{25}$, —(CH$_2$)$_{n1}$SR$_{23}$, —(CH$_2$)$_{n1}$C(O)OR$_{23}$, —(CH$_2$)$_{n1}$S(O)$_{m1}$R$_{23}$, —(CH$_2$)$_{n1}$S(O)(=NR$_{23}$)R$_{24}$ and —(CH$_2$)$_{n1}$C(O)NR$_{23}$R$_{24}$, wherein the alkyl, cycloalkyl, heterocyclyl and heteroaryl are each optionally further substituted by one or more substituents selected from the group consisting of hydrogen atom, alkyl, halogen, cyano, hydroxy, cycloalkyl, heterocyclyl and heteroaryl;

x is an integer of 0, 1 or 2; and

R$_5$, m$_1$ and n$_1$ are as defined in the compound of formula (II).

In a preferred embodiment of the present invention, the compound of formula (II), a stereoisomer thereof, or a pharmaceutically acceptable salt thereof is a compound of formula (VIII), a stereoisomer thereof, or a pharmaceutically acceptable salt thereof:

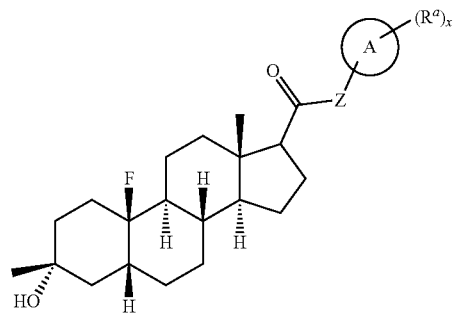

(VIII)

wherein:

ring A, Z, R$_a$ and x are as defined in formula (V-7) or formula (V-8).

In a preferred embodiment of the present invention, the compound of formula (I), the stereoisomer thereof, or the pharmaceutically acceptable salt thereof is a compound of formula (IX), a stereoisomer thereof, or a pharmaceutically

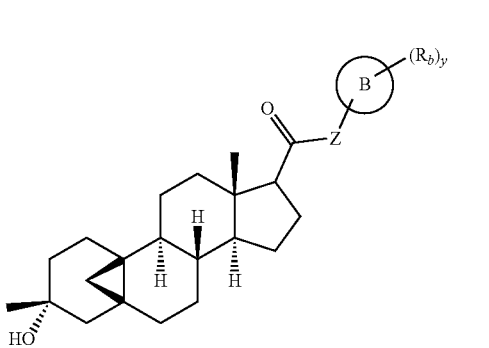

wherein:

Z is selected from the group consisting of —CR$_{23}$R$_{24}$—, —(CH$_2$)$_{n1}$NR$_{23}$—, —(CH$_2$)$_{n1}$O(CH$_2$)$_{n2}$— and —O—, and preferably methylene;

ring B is selected from the group consisting of cycloalkyl, heterocyclyl, aryl and heteroaryl, wherein the cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

each R$_b$ is identical or different and each is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, (CH$_2$)$_{n1}$C(O)OR$_{23}$, —(CH$_2$)$_{n1}$S(O)$_{m1}$R$_{23}$, —(CH$_2$)$_{n1}$S(O)NR$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{23}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$; and y is an integer of 0, 1, 2, 3 or 4.

In a preferred embodiment of the present invention, the compound of formula (I), the stereoisomer thereof, or the pharmaceutically acceptable salt thereof is a compound of formula (XI), a stereoisomer thereof, or a pharmaceutically acceptable salt thereof:

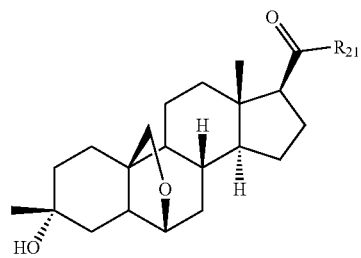

wherein:

R$_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

R$_{23}$-R$_{26}$, m$_1$ and n$_1$ are as defined in the compound of formula (I).

In a preferred embodiment of the present invention, the compound of formula (I), the stereoisomer thereof, or the pharmaceutically acceptable salt thereof is a compound of formula (X), a stereoisomer thereof, or a pharmaceutically acceptable salt thereof:

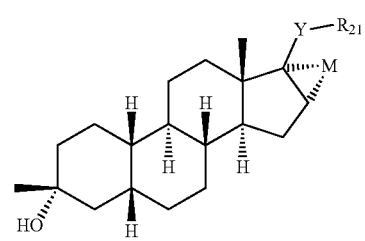

wherein:

M is selected from the group consisting of —CR$_{23}$— and oxygen atom;

Y is selected from the group consisting of —S(CH$_2$)$_{n1}$—,

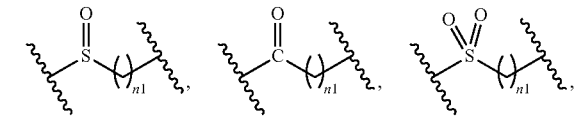

-continued

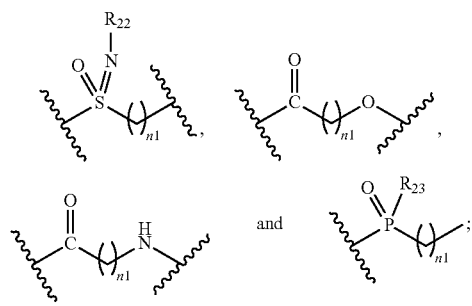

R$_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

R$_{22}$-R$_{26}$, m$_1$ and n$_1$ are as defined in the compound of formula (I).

In a preferred embodiment of the present invention, in the compound of formula (III-A), formula (V-7), formula (V-8), formula (VIII) or formula (IX), the stereoisomer thereof, or the pharmaceutically acceptable salt thereof, the ring A, B and C are each selected from the group consisting of:

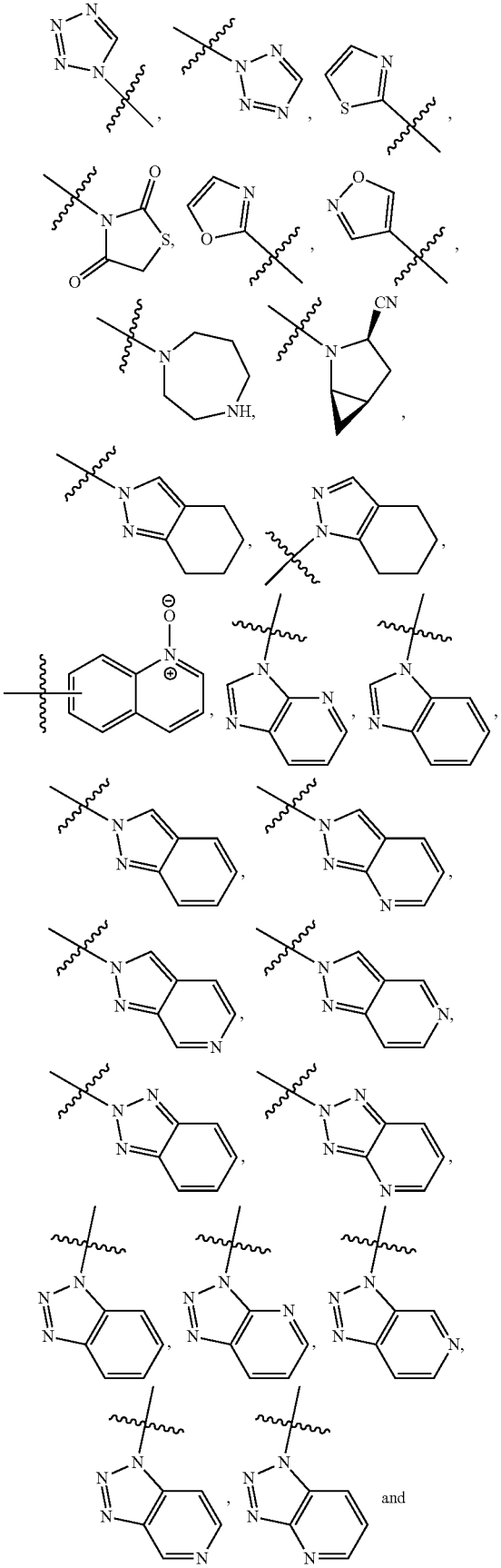

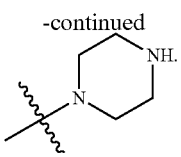

In a preferred embodiment of the present invention, the compound of (III-A), formula (V-7), formula (V-8), formula (III-B), formula (IV-A), formula (IV-B), formula (VIII) or formula (IX), the stereoisomer thereof, or the pharmaceutically acceptable salt thereof, wherein $R_a$, $R_b$ and $R_c$ are each selected from the group consisting of hydrogen atom, cyano, halogen, nitro, $C_{1-6}$ alkyl, $C_{2-6}$ alkynyl, $C_{1-6}$ alkoxy, $C_{1-6}$ haloalkyl, $C_{3-6}$ cycloalkyl, $C_{1-6}$ hydroxyalkyl, 5 to 10 membered heterocyclyl, 5 to 10 membered heteroaryl, —$(CH_2)_{n1}OR_{23}$, —$(CH_2)_{n1}SR_{23}$, —$(CH_2)_{n1}C(O)R_{23}$, —$(CH_2)_{n1}C(O)NR_{23}R_{24}$, —$(CH_2)_{n1}C(O)OR_{23}$ and —$(CH_2)_{n1}S(O)_{m1}R_{23}$, wherein the $C_{1-6}$ alkyl, $C_{1-6}$ alkoxy, $C_{1-6}$ haloalkyl, $C_{3-6}$ cycloalkyl, $C_{1-6}$ hydroxyalkyl, wherein the 5 to 10 membered heterocyclyl and 5 to 10 membered heteroaryl are each optionally further substituted by one or more substituents selected from the group consisting of hydrogen atom, $C_{1-6}$ alkyl, halogen, cyano, hydroxy, $C_{3-6}$ cycloalkyl, $C_{1-6}$ hydroxyalkyl, 5 to 10 membered heterocyclyl and 5 to 10 membered heteroaryl;

$R_{23}$ and $R_{24}$ are each independently selected from the group consisting of hydrogen atom, $C_{1-6}$ alkyl and 3 to 8 membered heterocyclyl.

In a preferred embodiment of the present invention, the compound of formula (II), formula (III-A), formula (V-7), formula (V-8), formula (III-B), formula (IV-A), formula (IV-B) or formula (VIII), the stereoisomer thereof, or the pharmaceutically acceptable salt thereof, wherein:

Z is selected from the group consisting of —$CH_2$—, —$CH_2NH$—, —$CH_2O$—, —$CH_2$—, —NH— and —$NHSO_2$—;

$R_{3a}$ is selected from the group consisting of $C_{1-6}$ alkyl, $C_{1-6}$ haloalkyl and $C_{1-6}$ alkoxy, preferably $C_{1-3}$ alkyl and $C_{1-3}$ alkoxy, and more preferably methyl and methoxymethyl;

$R_5$ is selected from the group consisting of hydrogen atom, halogen, cyano, $C_{1-6}$ alkyl, $C_{1-6}$ haloalkyl and $C_{1-6}$ alkoxy, and preferably hydrogen atom and $C_{1-3}$ alkyl;

$R_{19}$ is selected from the group consisting of cyano, halogen, $C_{1-6}$ alkyl, $C_{1-6}$ haloalkyl, $C_{1-6}$ alkoxy, —$(CH_2)_{n1}OR_{23}$, —$(CH_2)_{n1}S(O)_{m1}R_{23}$, —$(CH_2)_{n1}S(O)(=NR_{23})R_{24}$ and —$(CH_2)_{n1}SR_{23}$, preferably cyano, halogen, $C_{1-3}$ alkoxy, $C_{1-3}$ haloalkyl, —$(CH_2)_{n1}SR_{23}$, —$(CH_2)_{n1}S(O)_{m1}R_{23}$ and —$(CH_2)_{n1}S(O)(=NR_{23})R_{24}$, and more preferably halogen;

or, a $C_{3-6}$ cycloalkyl, and preferably cyclopropyl can be formed between any two adjacent groups of $R_5$ and $R_{19}$.

In a preferred embodiment of the present invention, the compound of formula (I), or the stereoisomer thereof, is selected from the group consisting of:

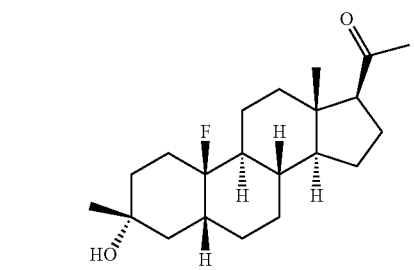

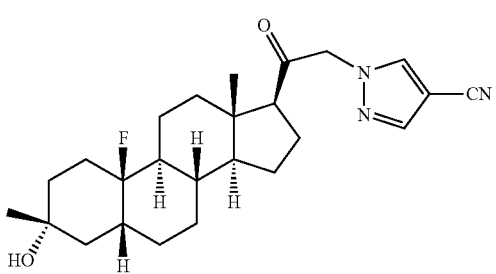

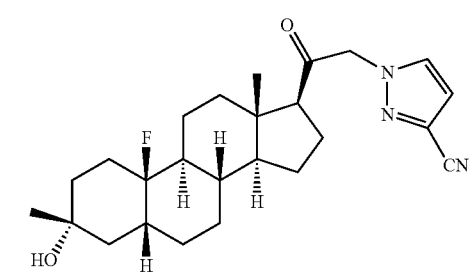

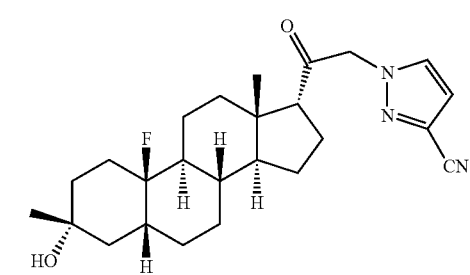

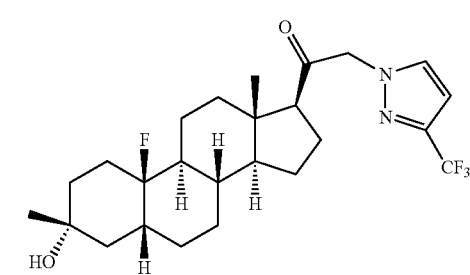

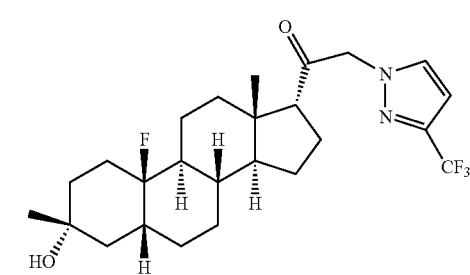

17
-continued
5
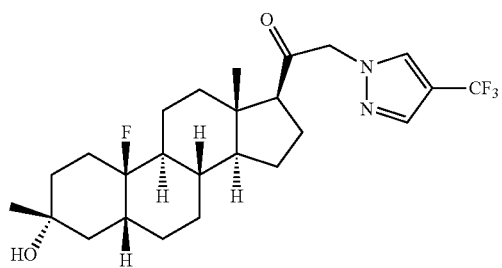
8
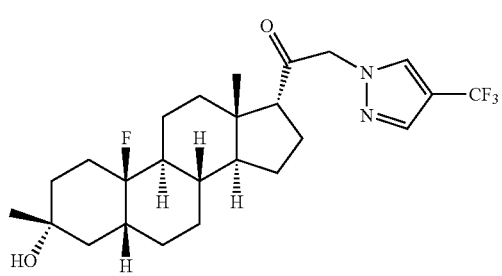
9
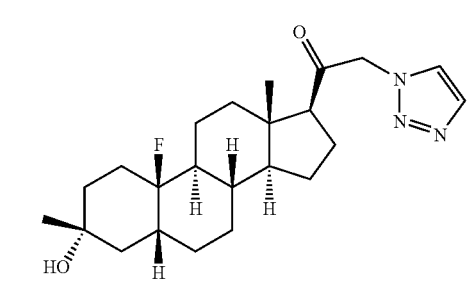
10
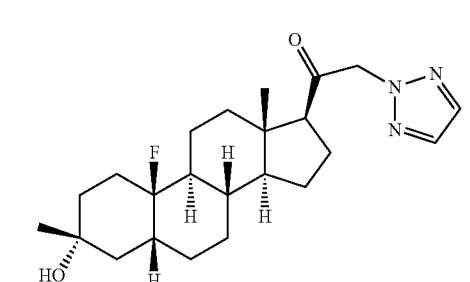
11
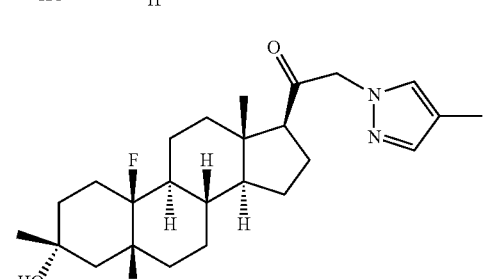
12
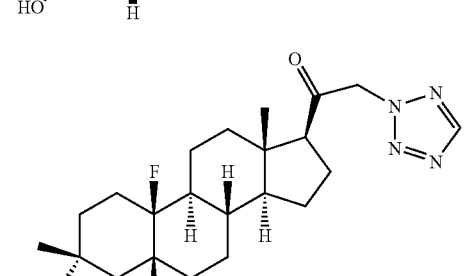
18
-continued
13
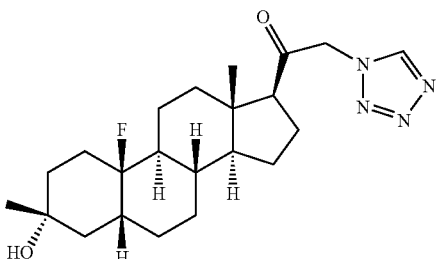
14
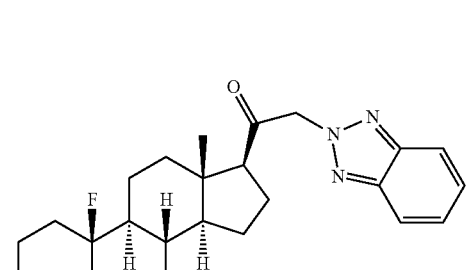
15
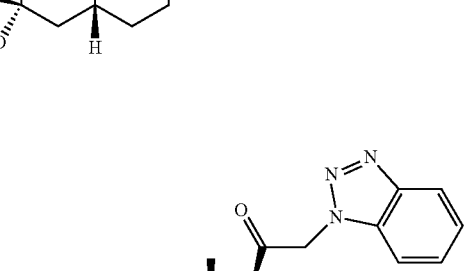
16
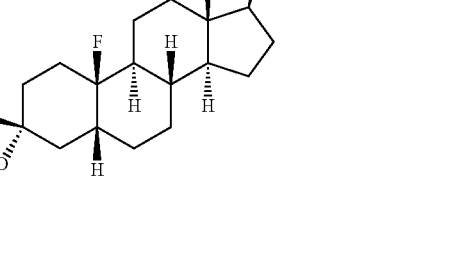
17
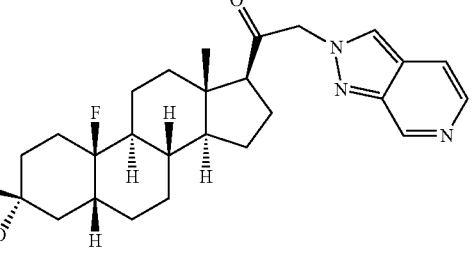
17
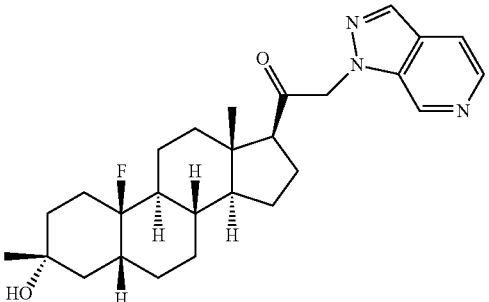

-continued
18
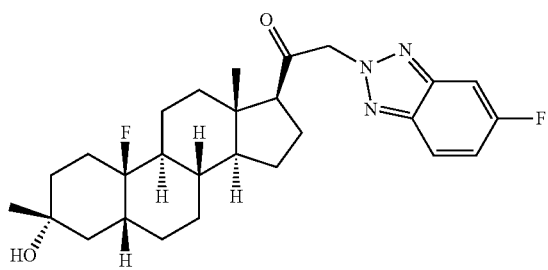
19
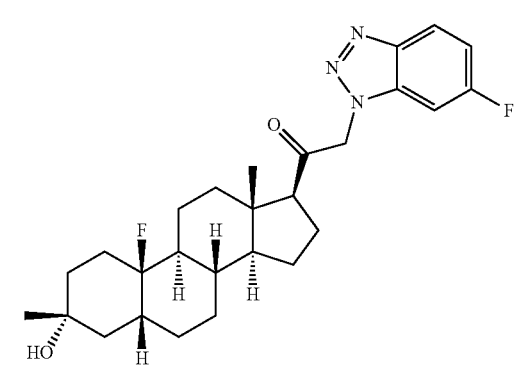
20
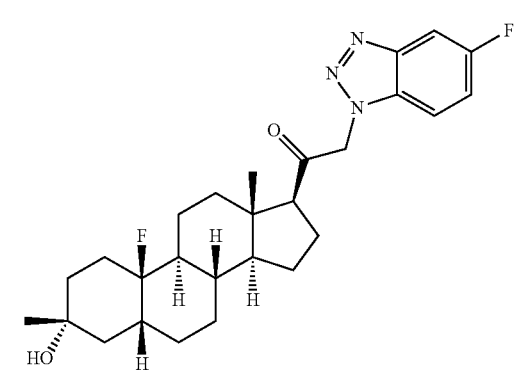
21
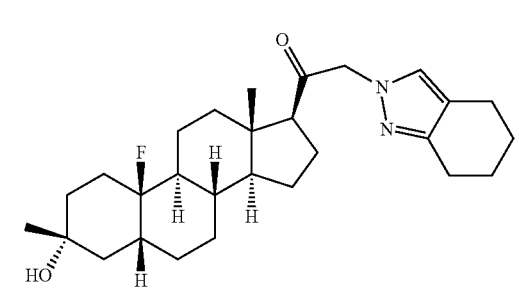
22
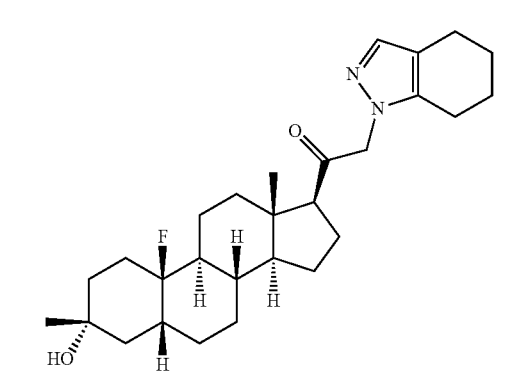
-continued
23
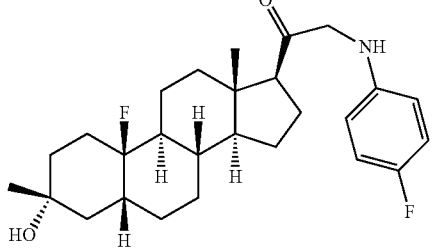
24
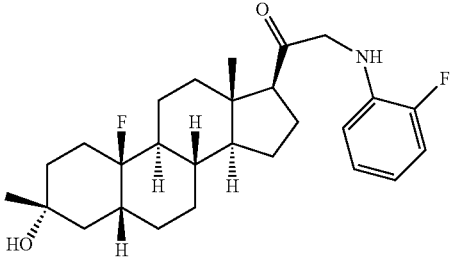
25
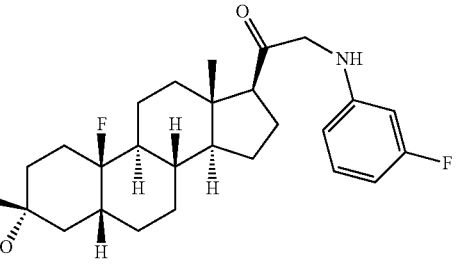
26
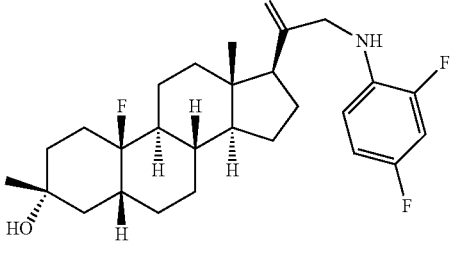
27
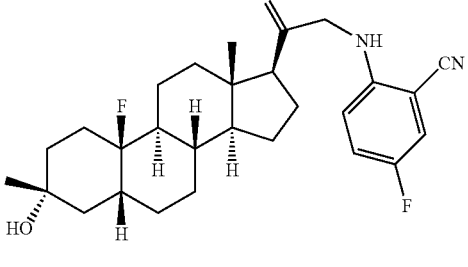
28
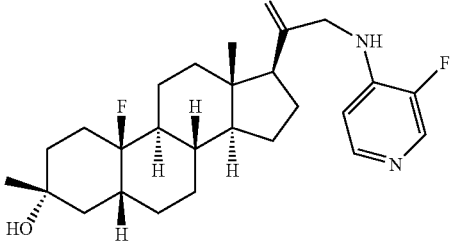

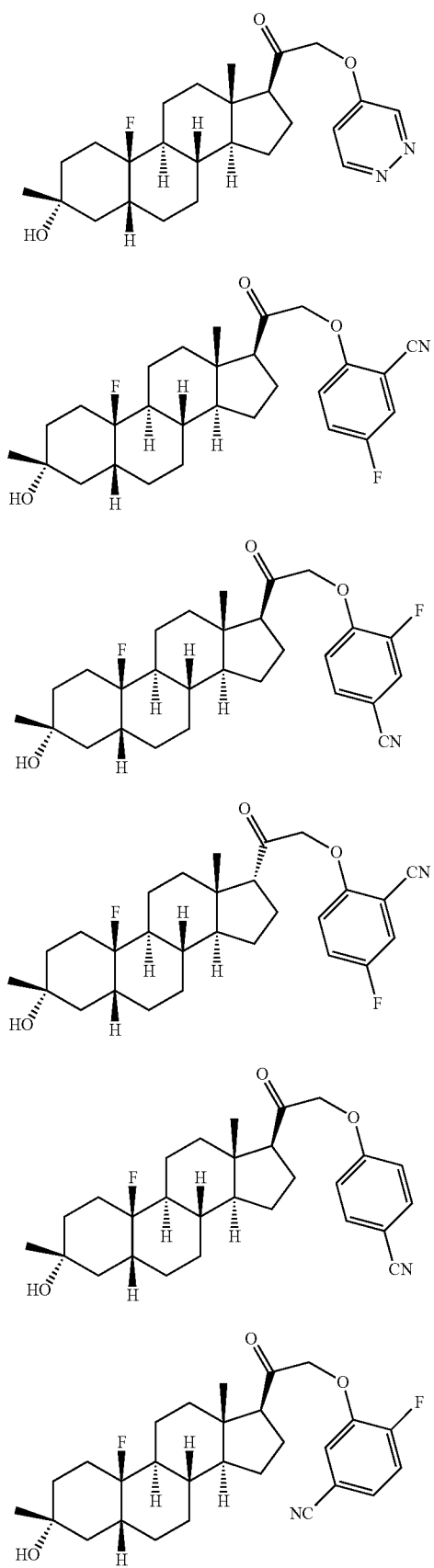
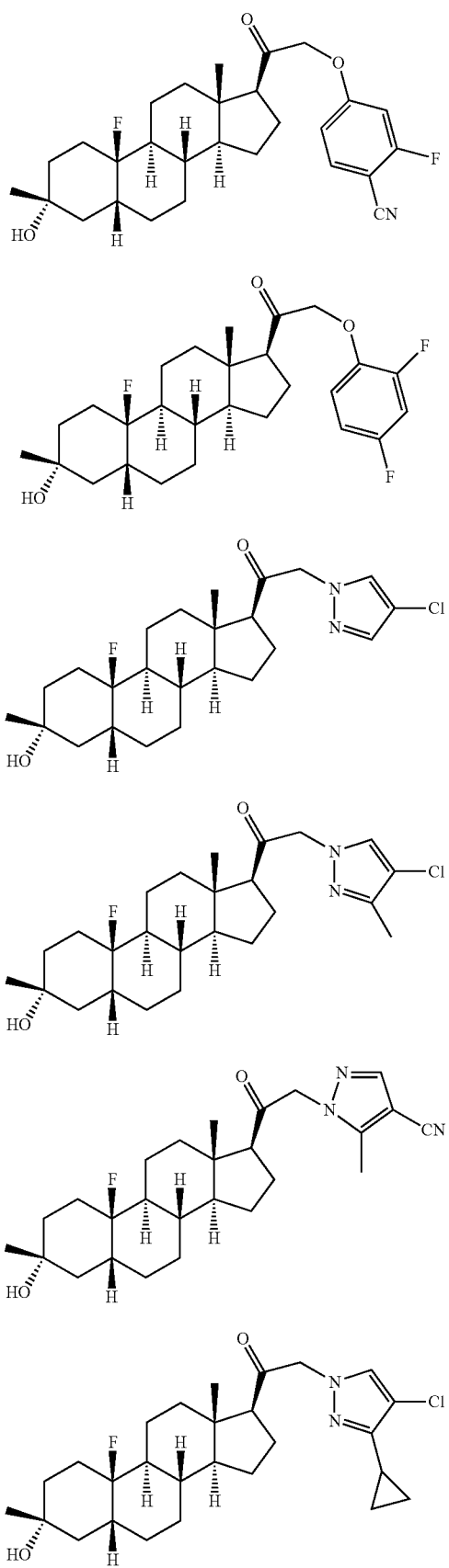

41
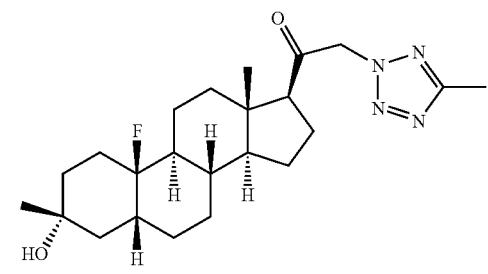
42
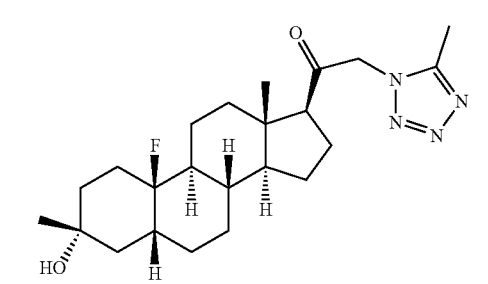
43
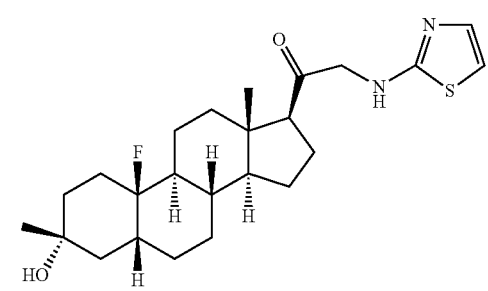
44
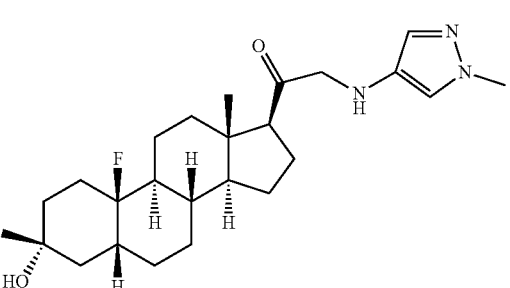
45
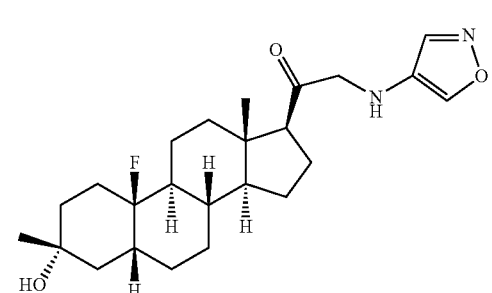
46
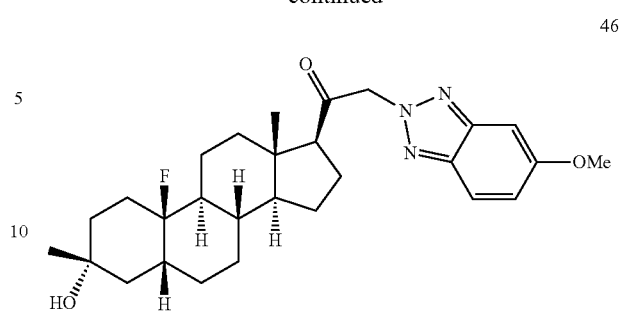
47
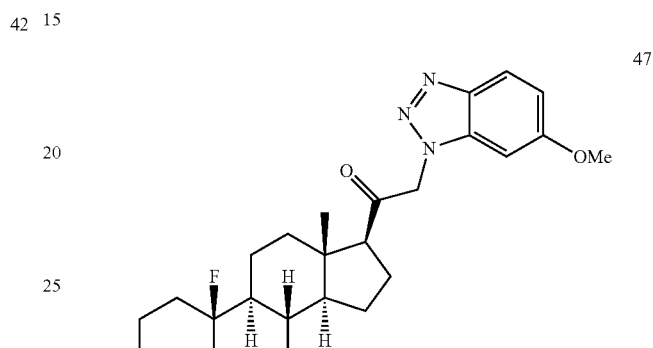
48
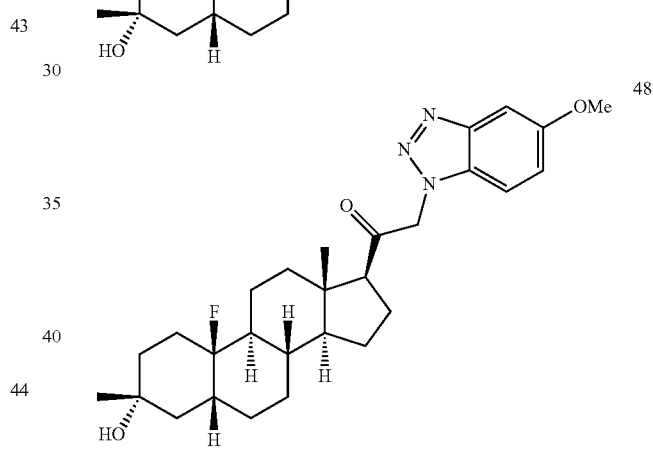
49
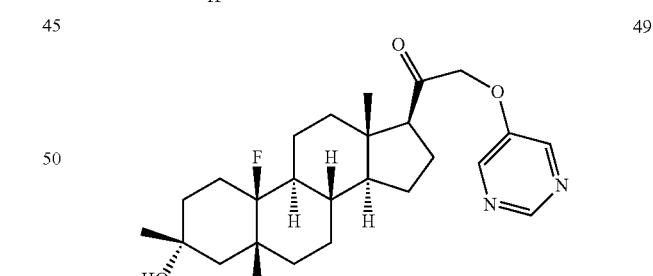
50
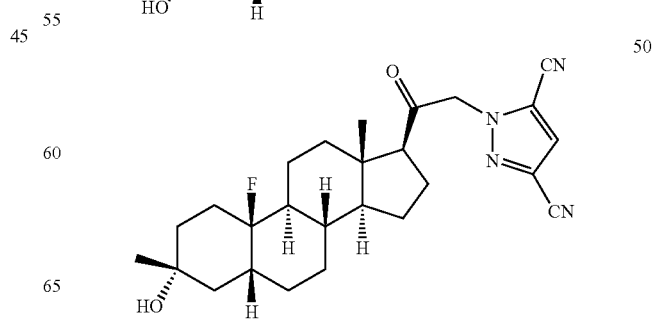

51
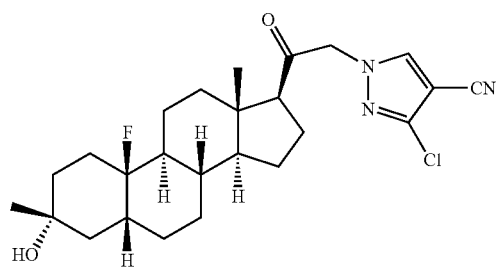
52
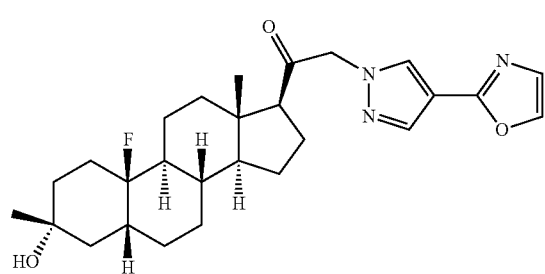
53
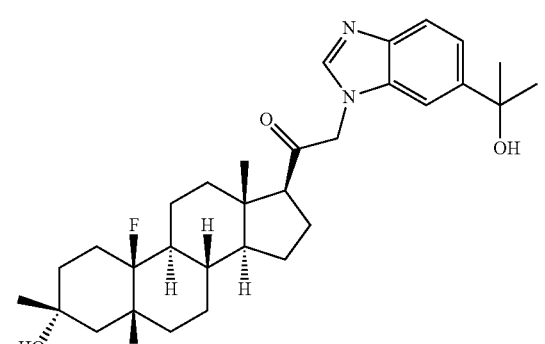
54
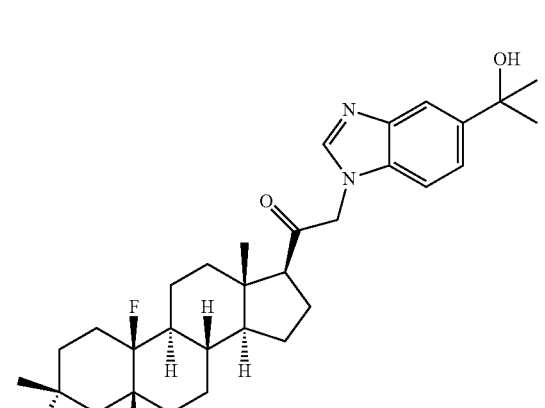
55
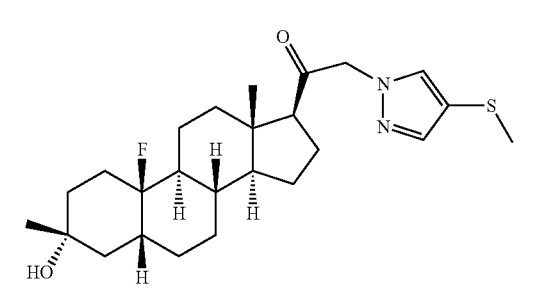
56
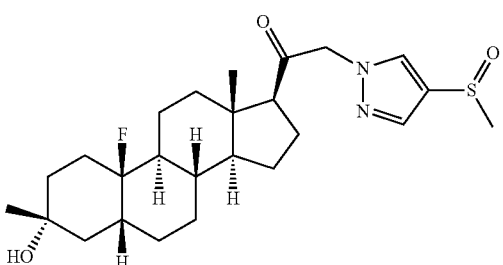
57
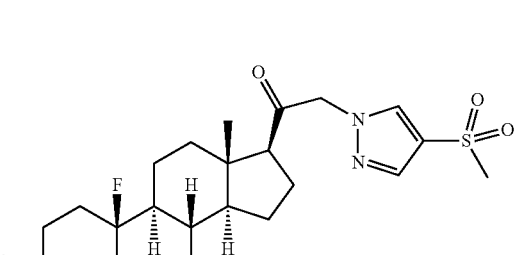
58
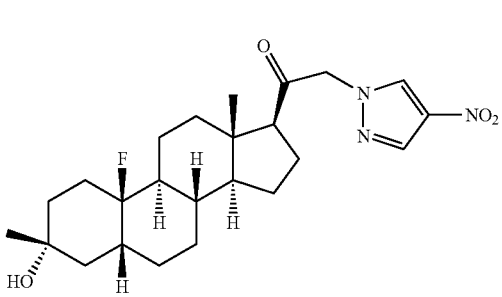
59
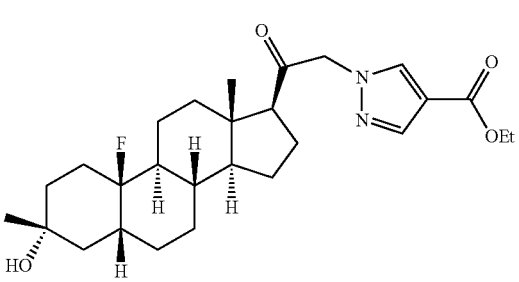
60
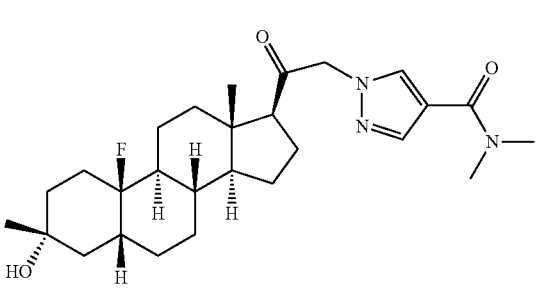

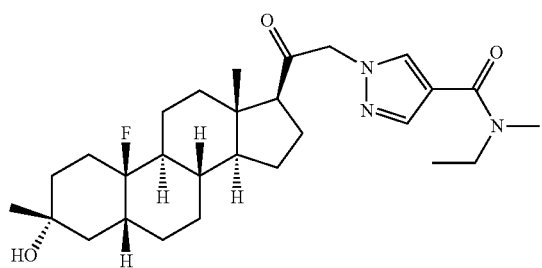
61
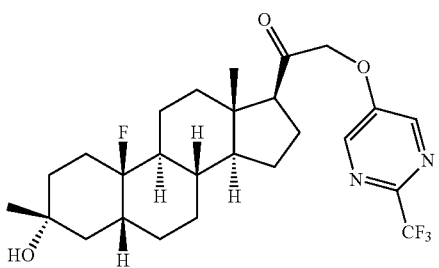
66
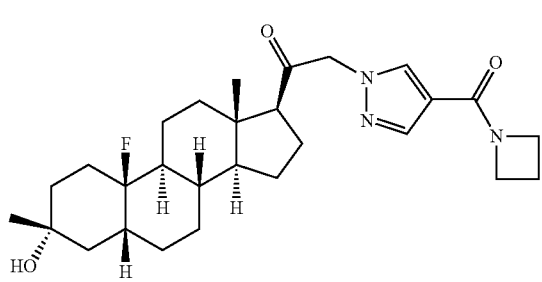
62
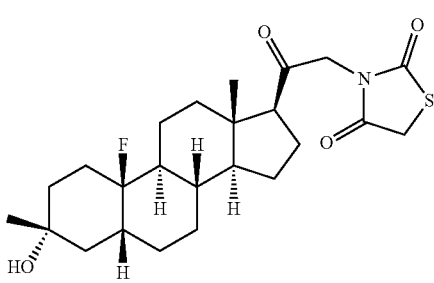
67
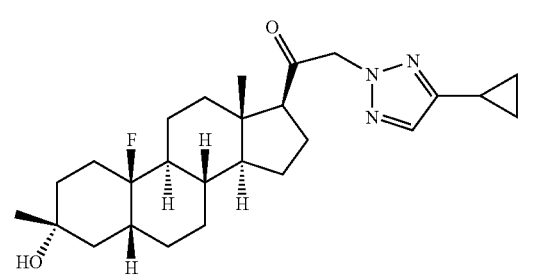
63
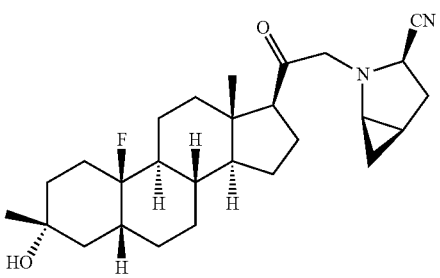
68
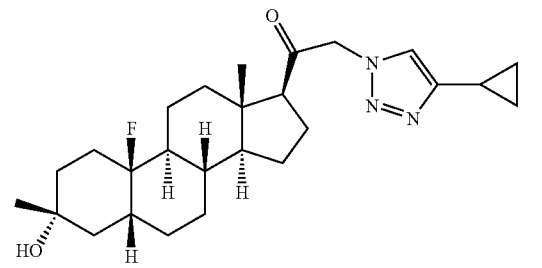
64
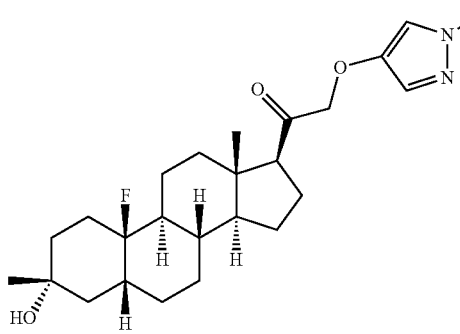
69
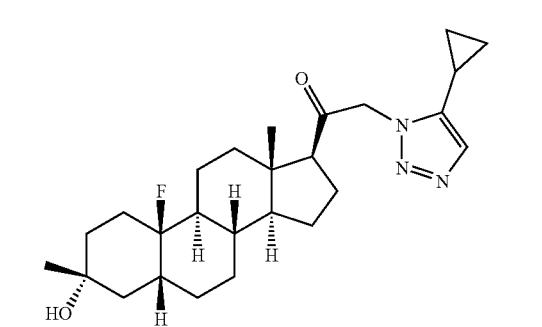
65
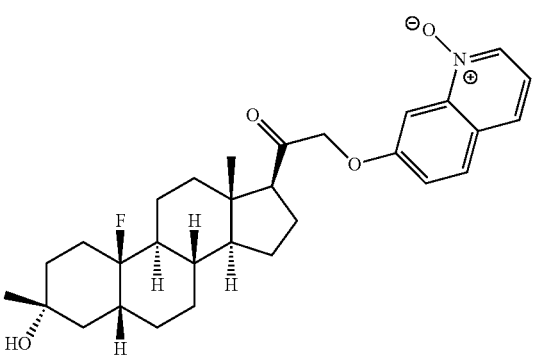
70

71
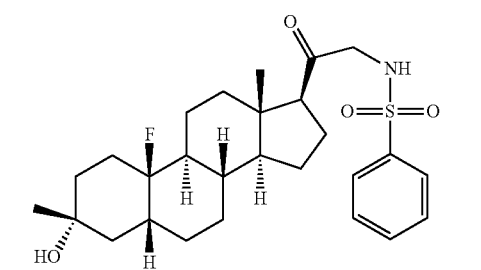
72
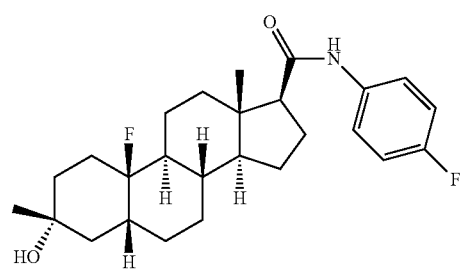
73
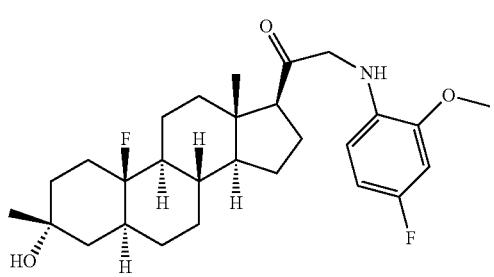
74
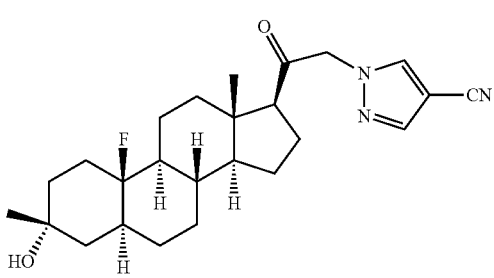
75
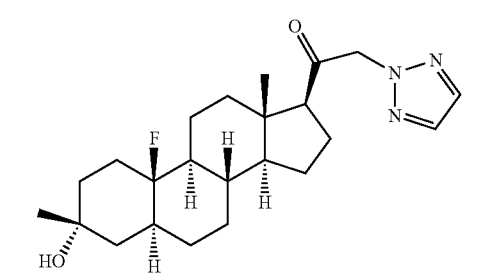
76
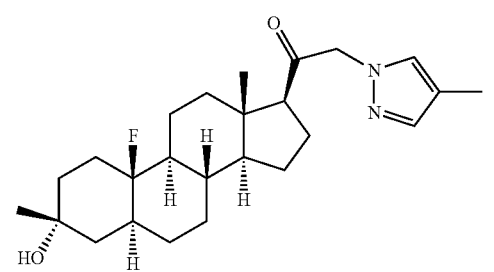
77
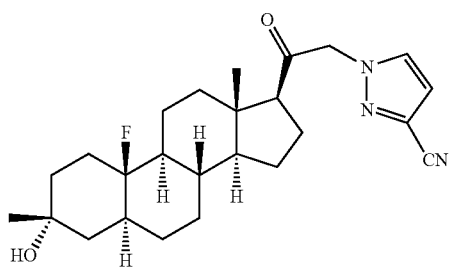
78
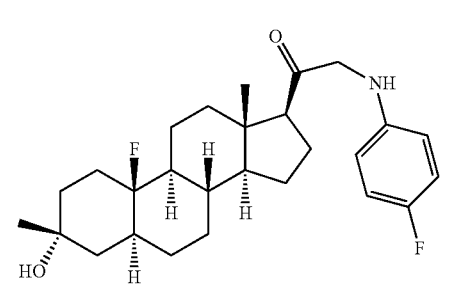
79A
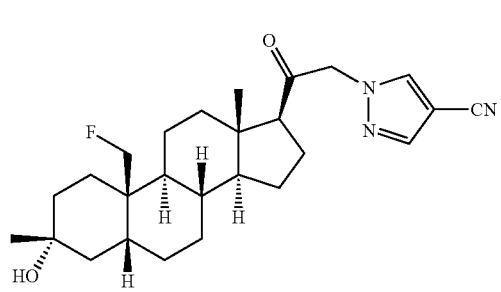
79B
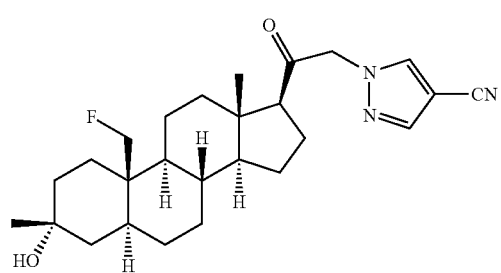
80A
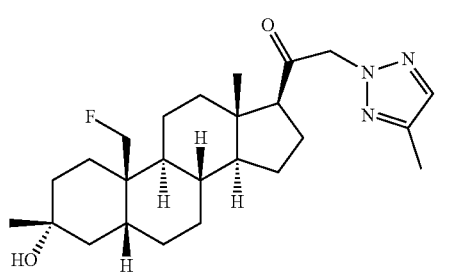
80B
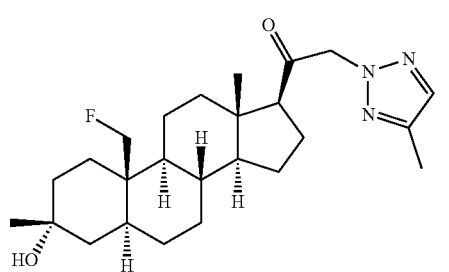

81A
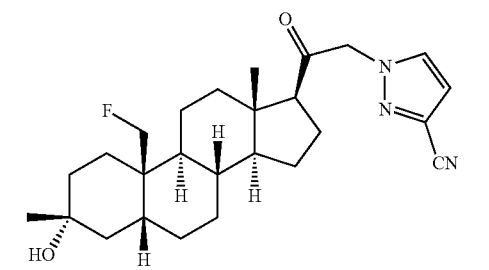
81B
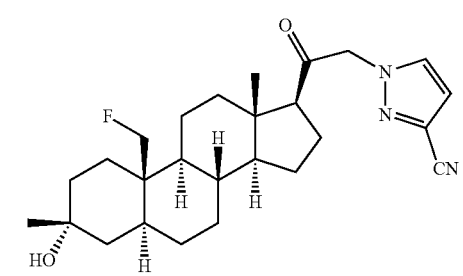
82A
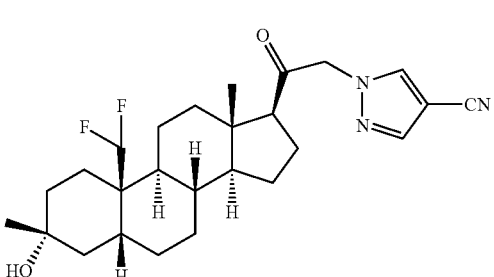
82B
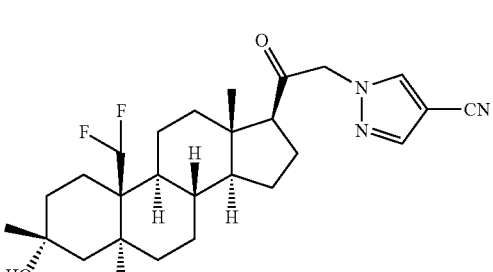
83A
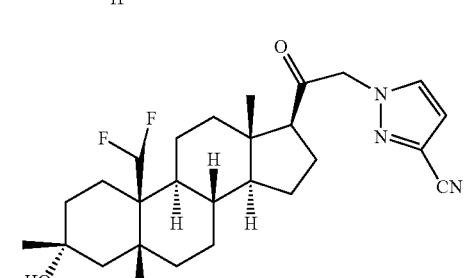
83B
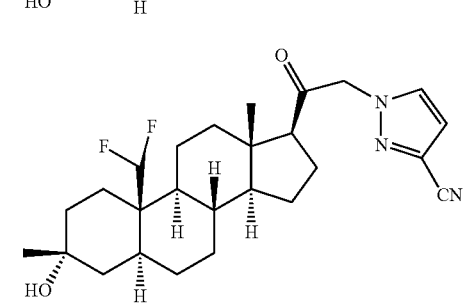
84A
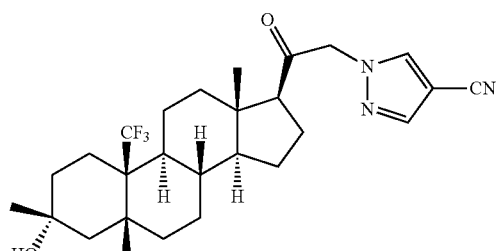
84B
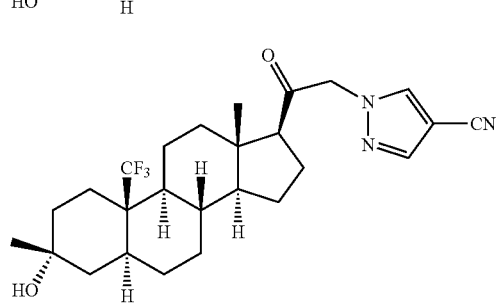
85A
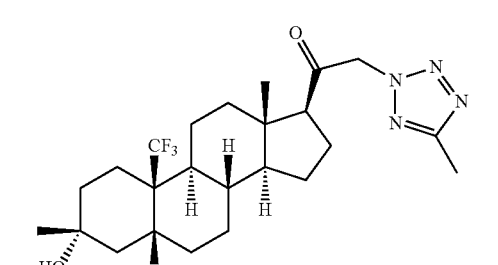
85B
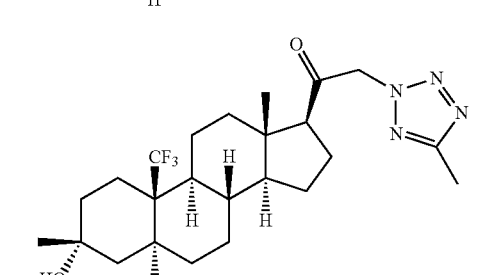
86A
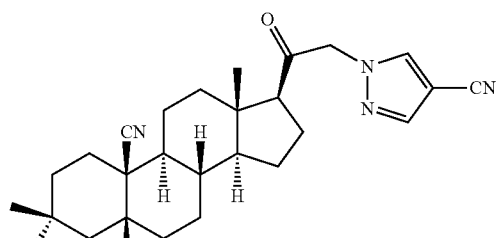
86B
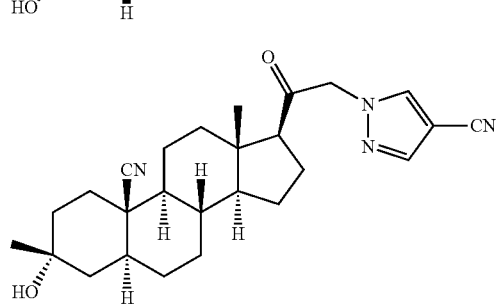

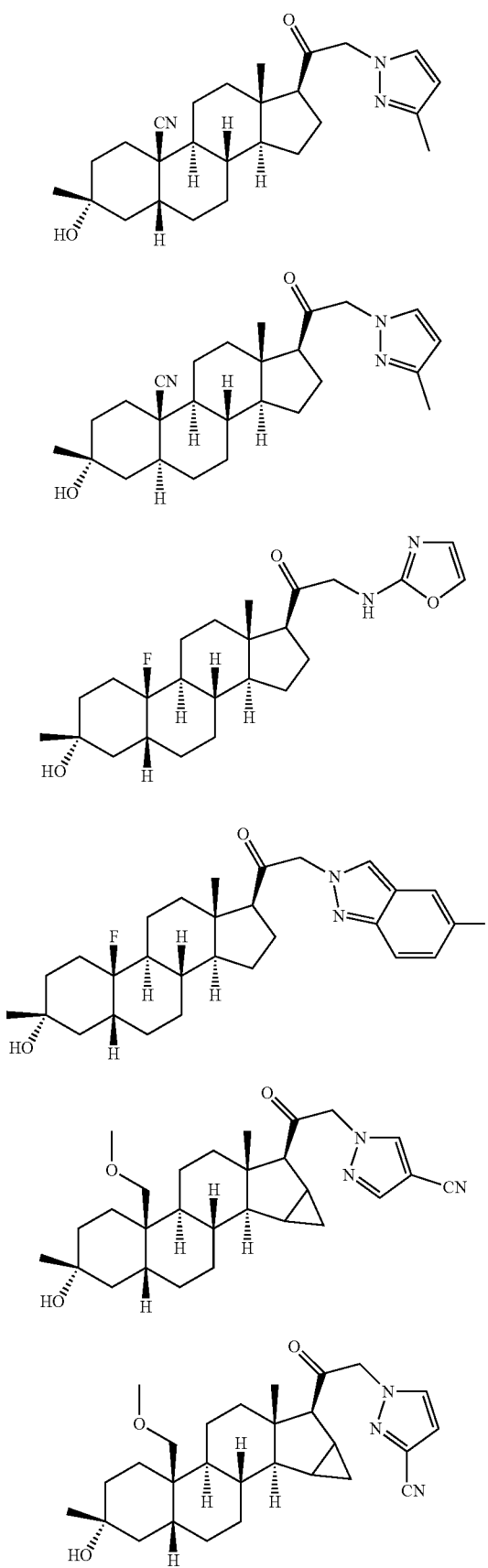
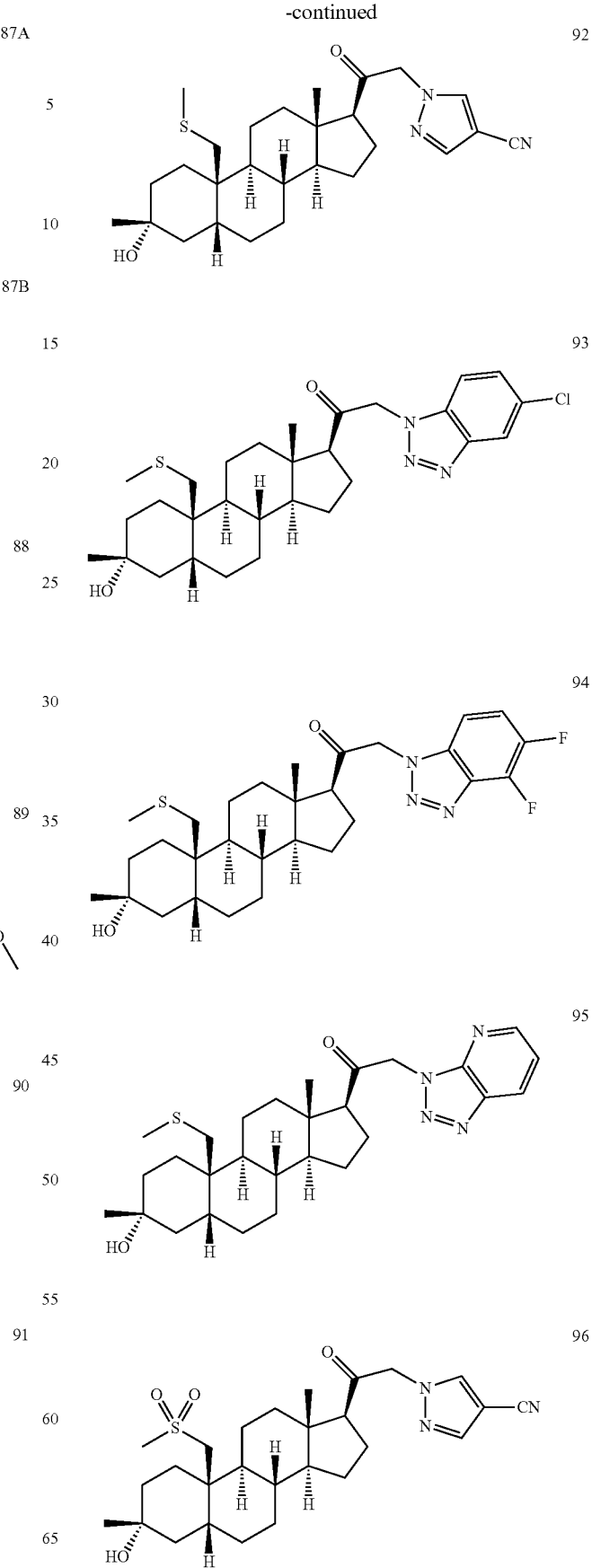

97
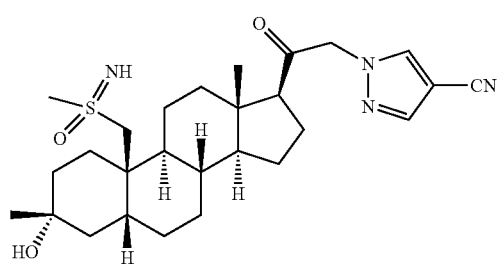
98
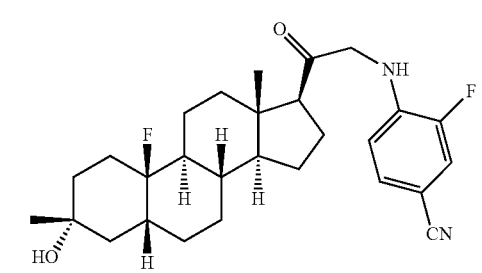
99
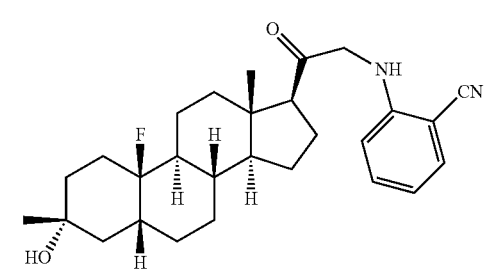
100
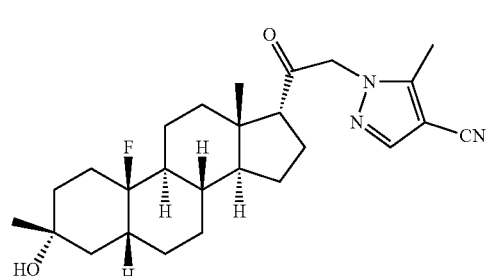
101
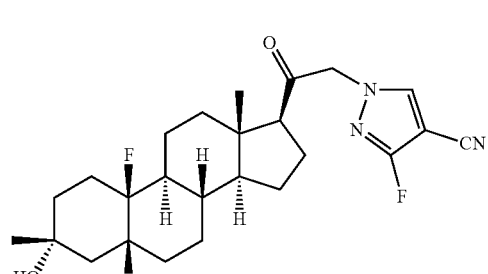
102
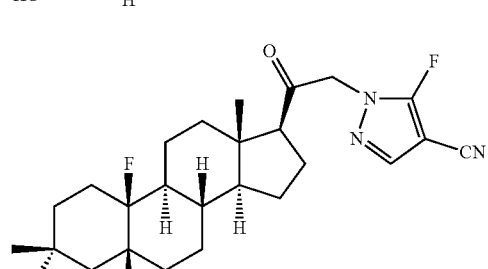
103
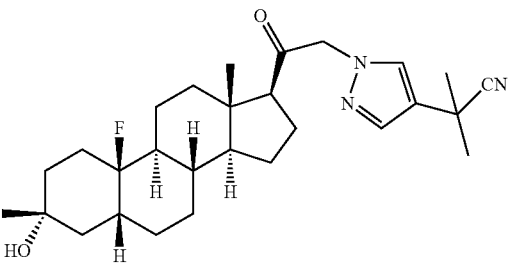
104
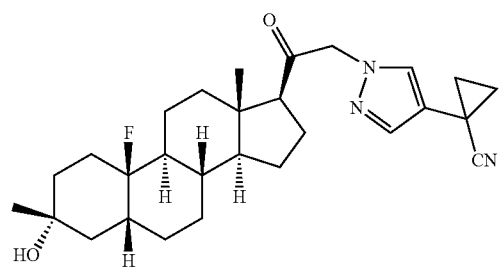
105
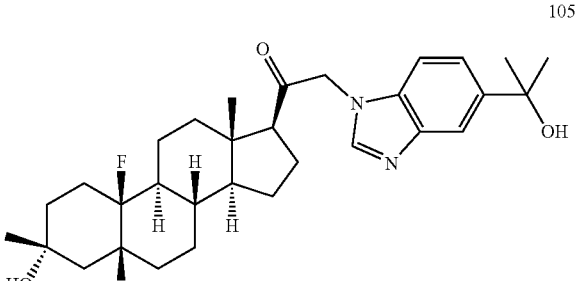
106
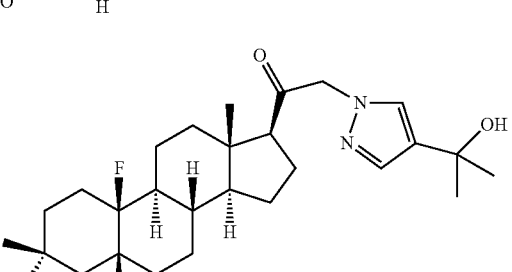
107
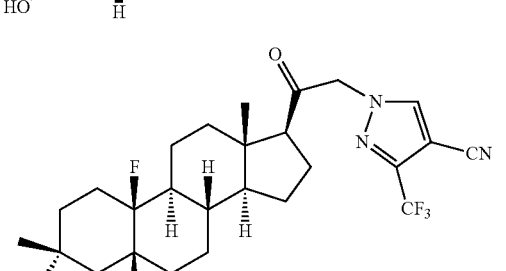
108
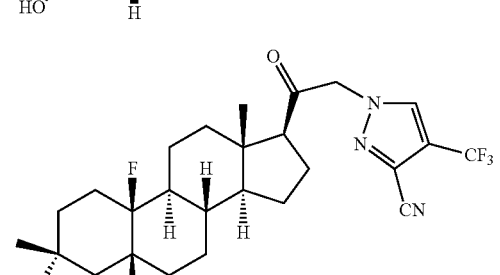

109 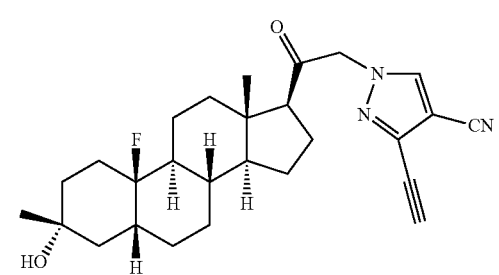
110 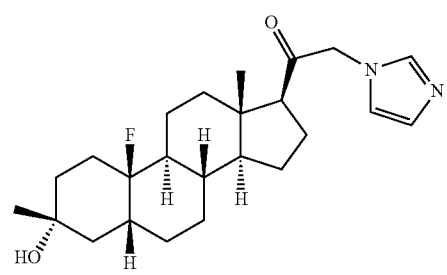
111 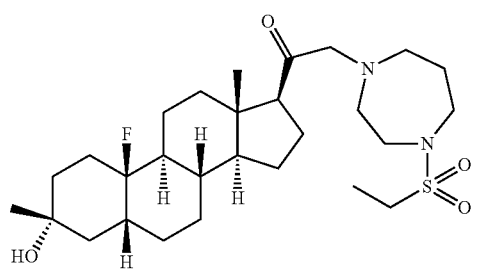
112 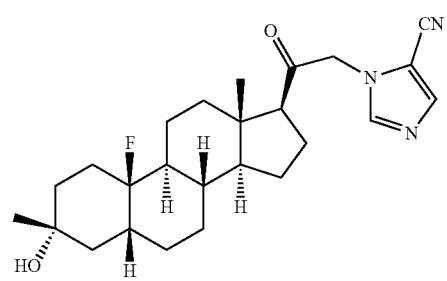
113 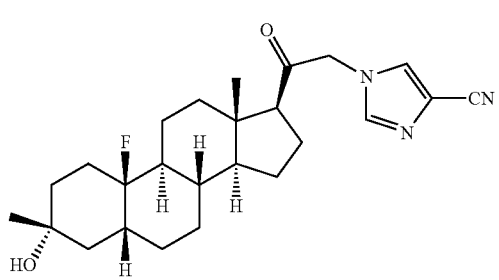
114 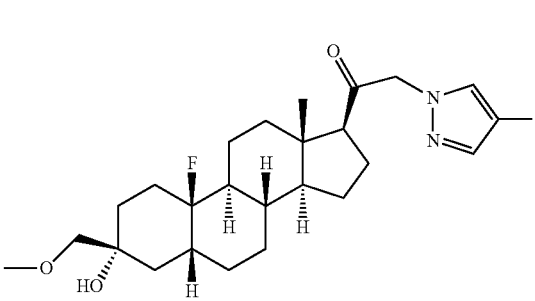
115 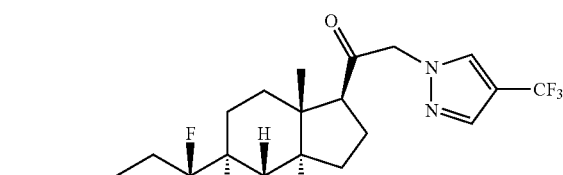
116 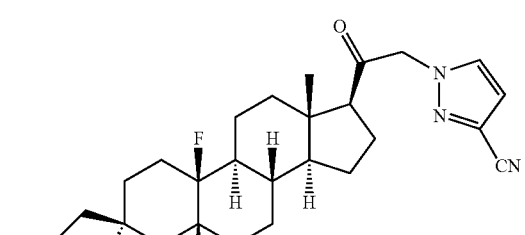
117 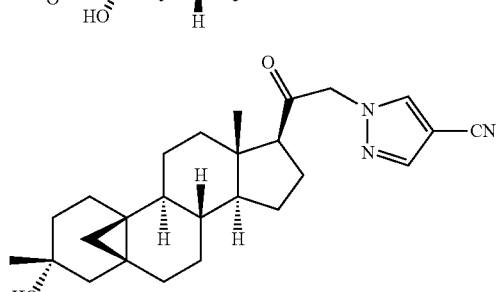
118 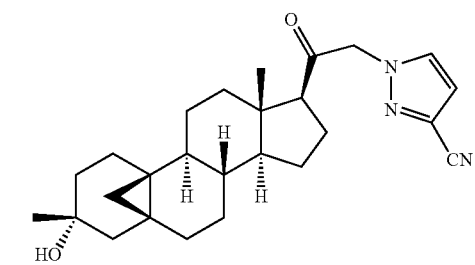
119 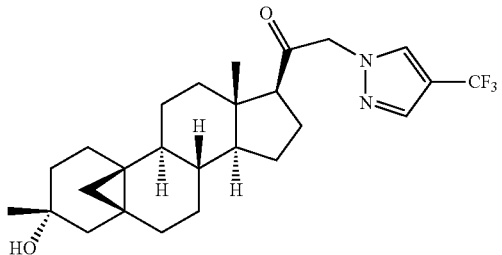
120 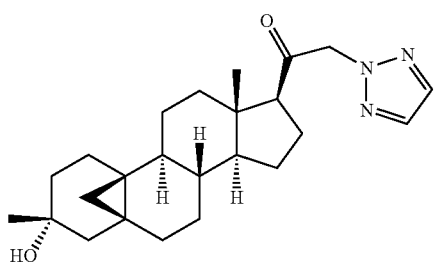

39
-continued
121
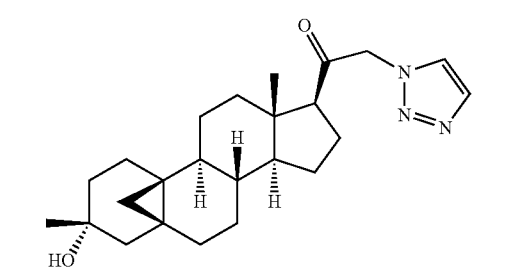
122
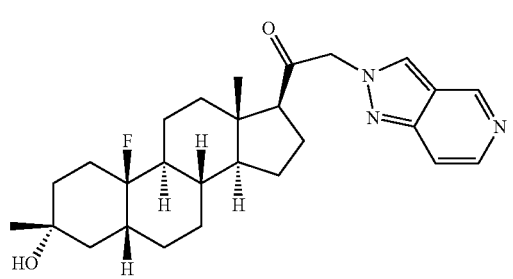
123
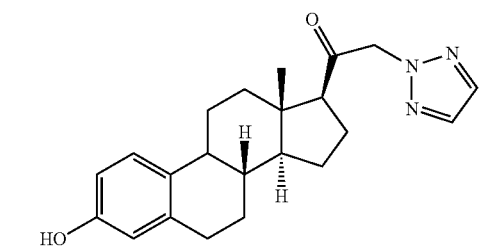
124
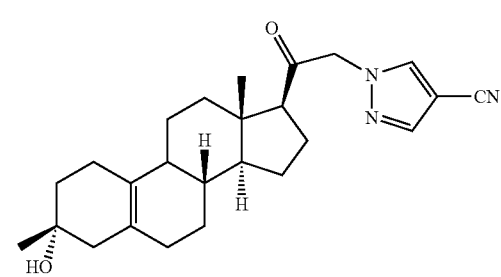
125
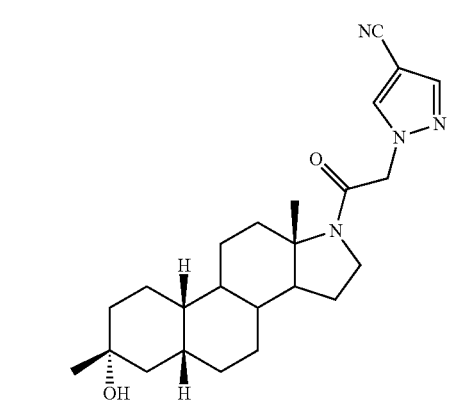
40
-continued
126
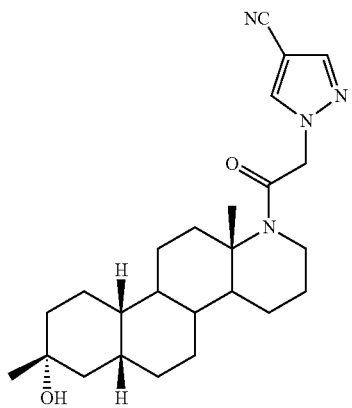
127
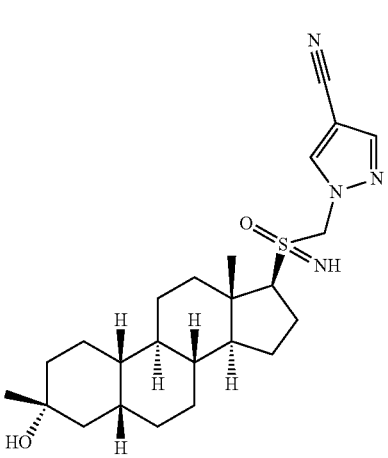
128
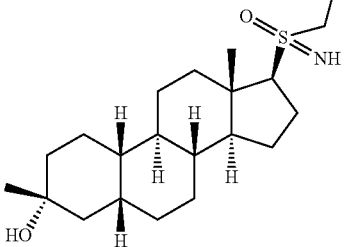
128
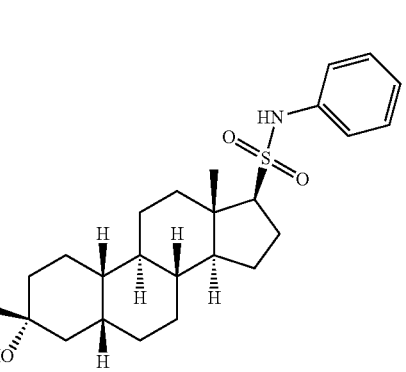

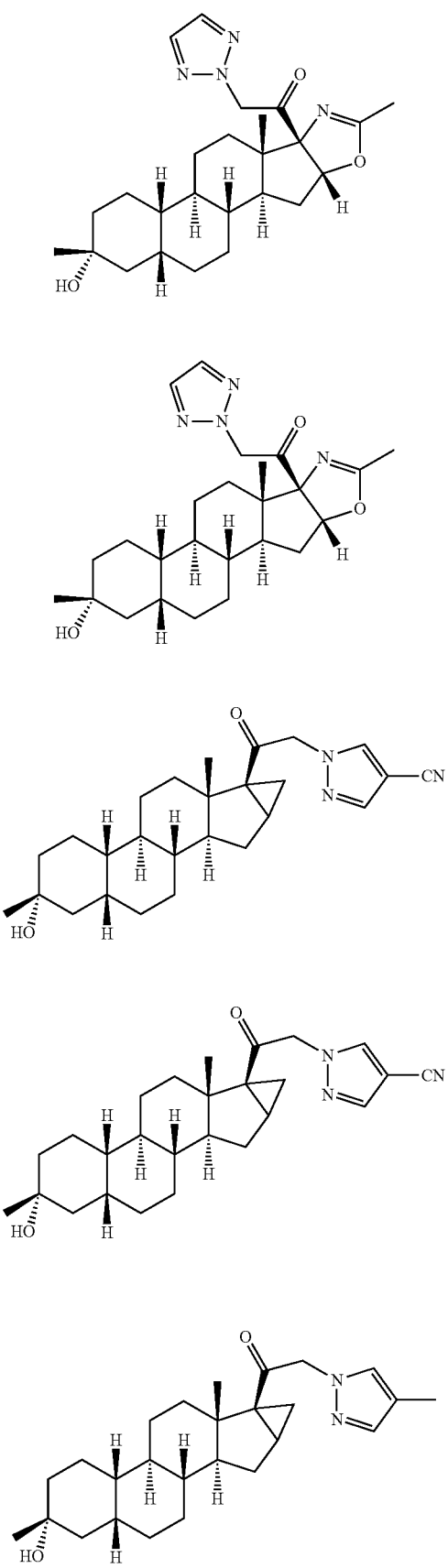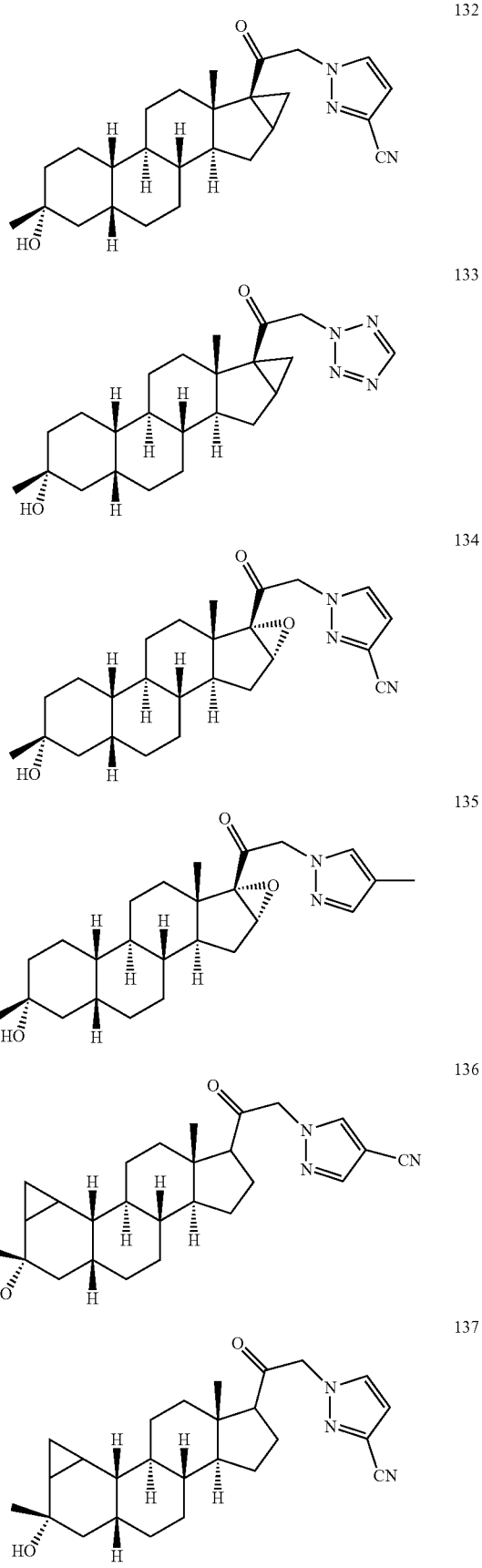

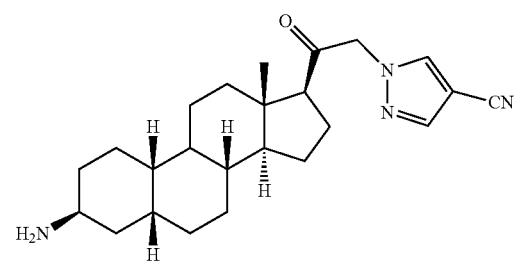
138
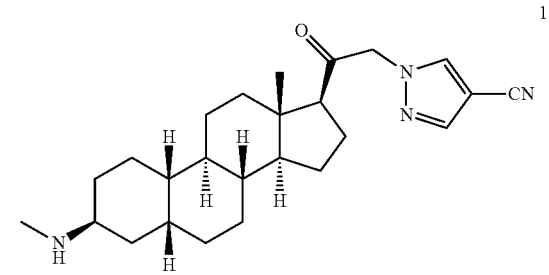
139
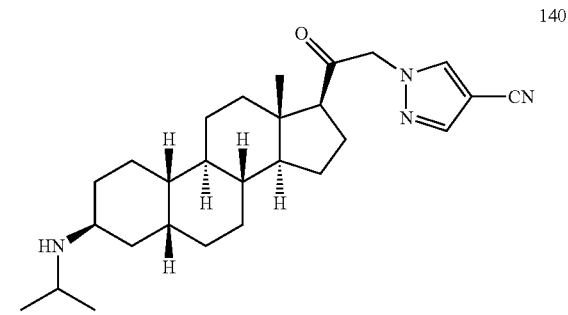
140
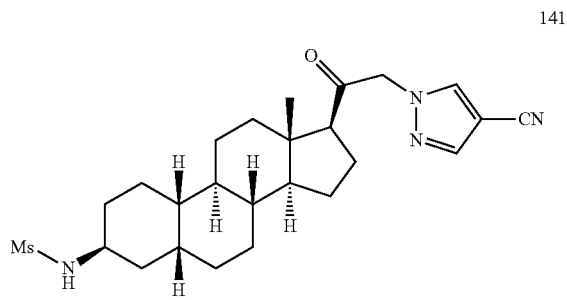
141
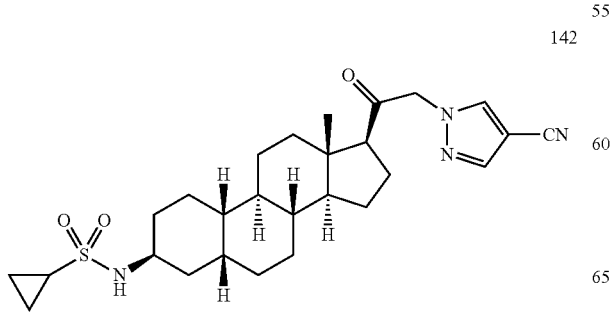
142
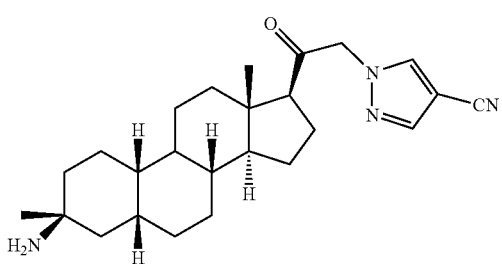
143
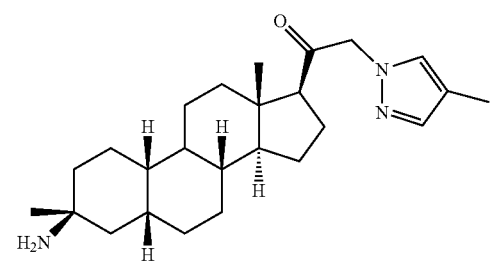
144
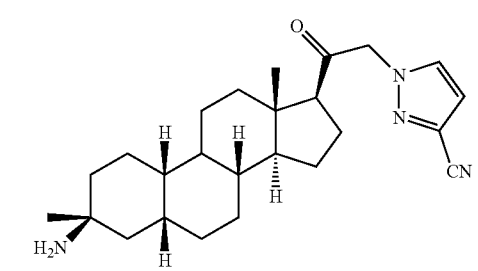
145
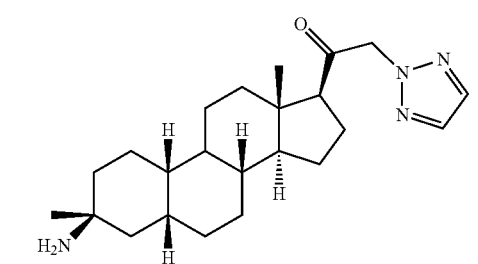
146
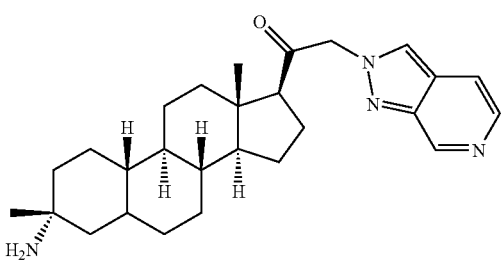
147
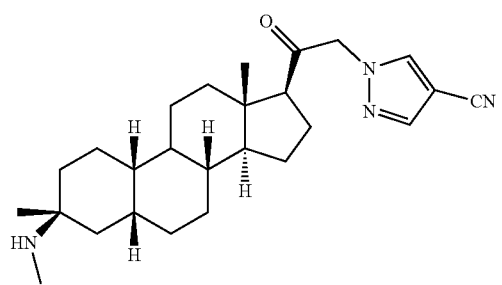
148

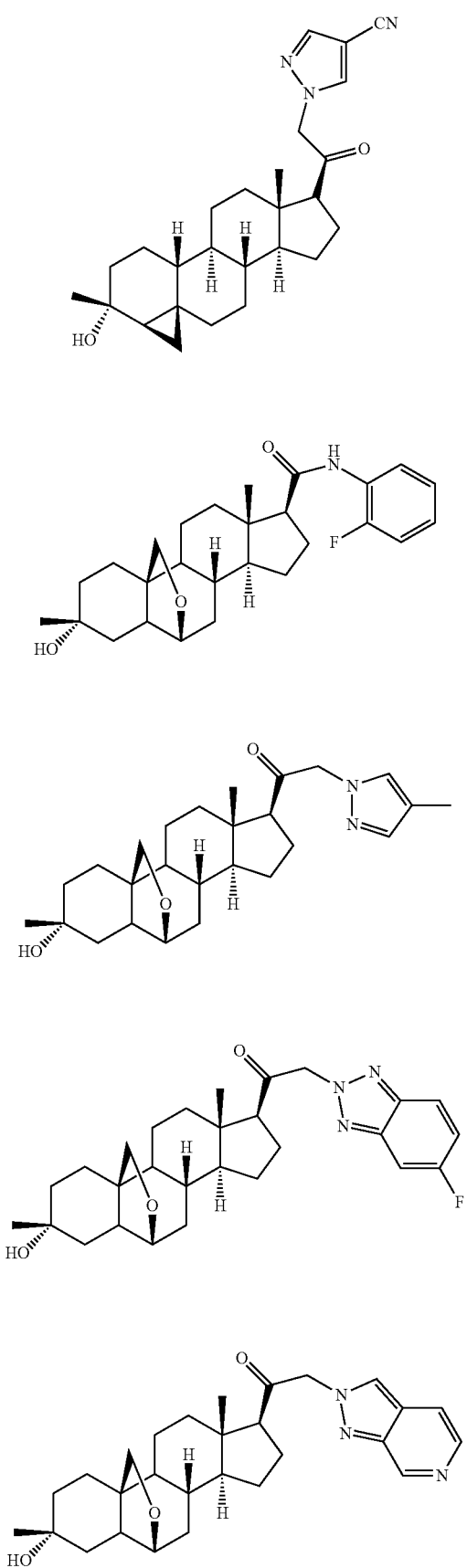
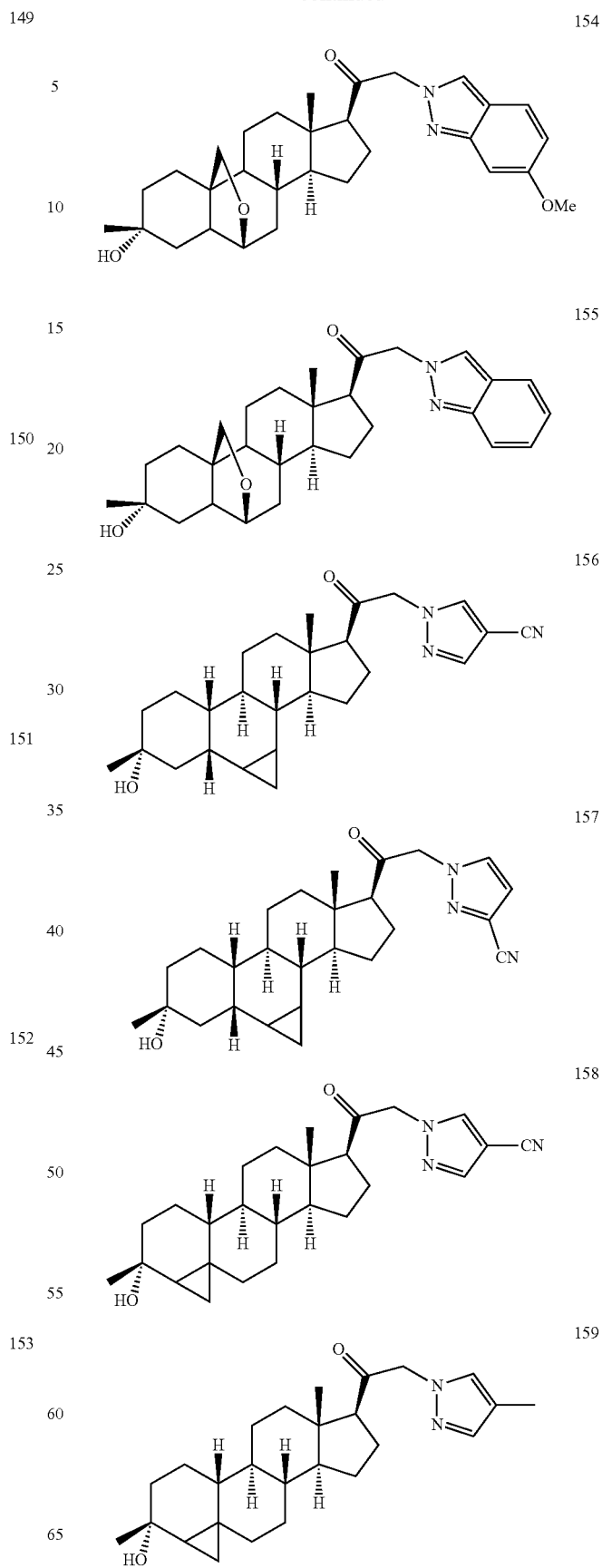

160
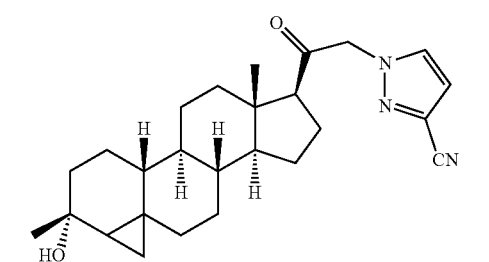
161
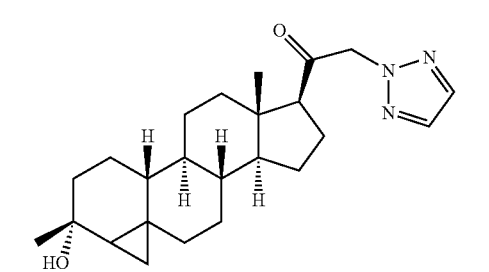
162
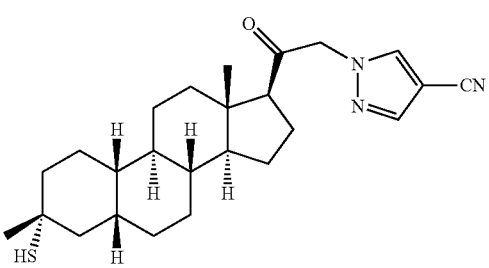
163
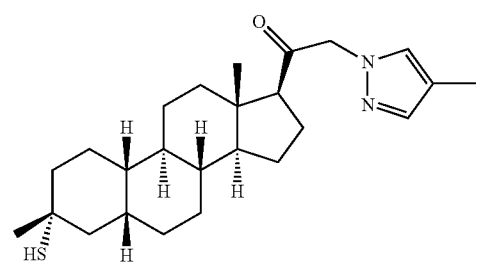
164
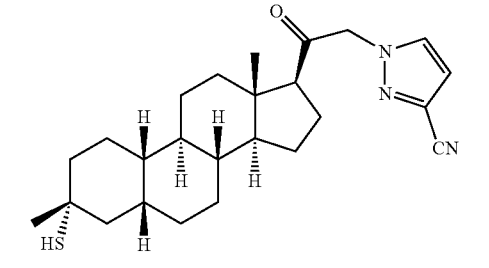
165
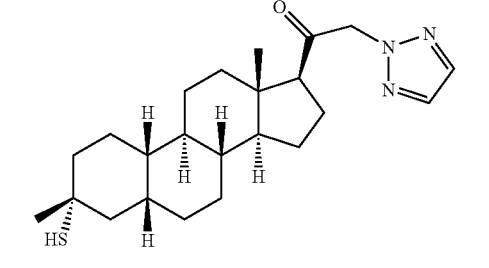
166
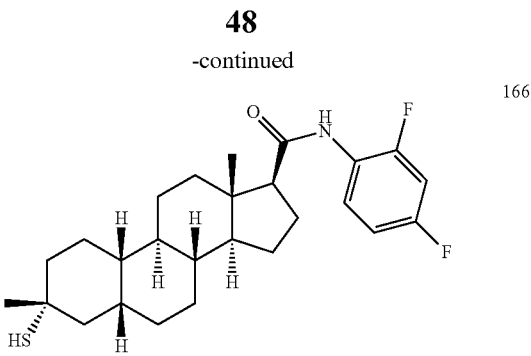
167
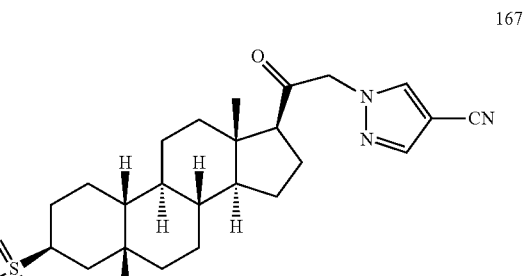
168
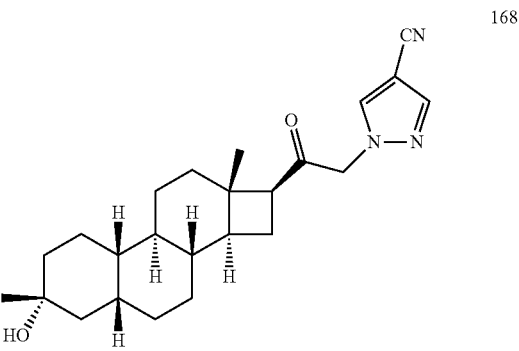
169
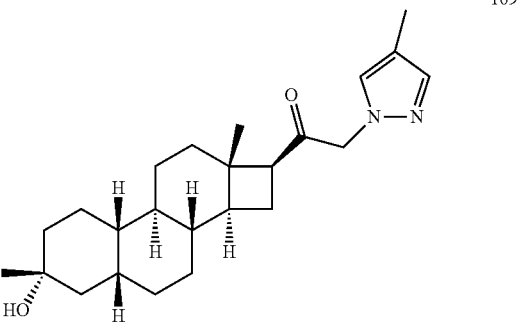
170
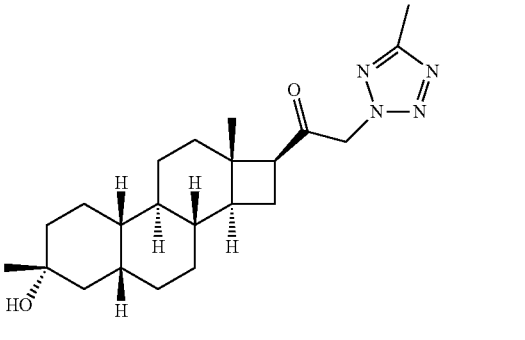

-continued
171
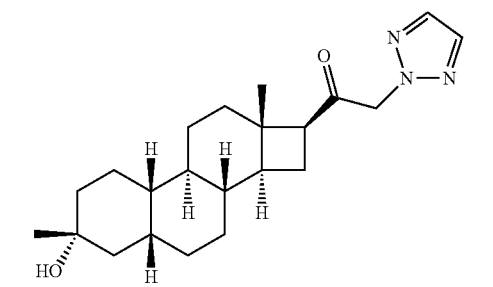
172
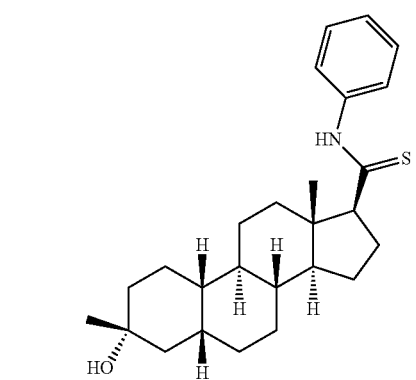
173
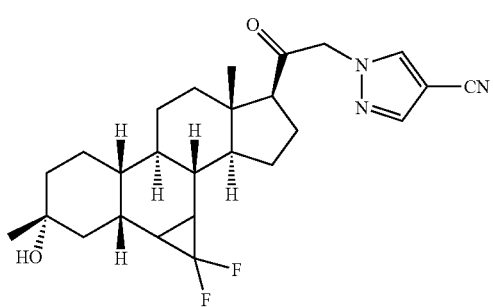
174
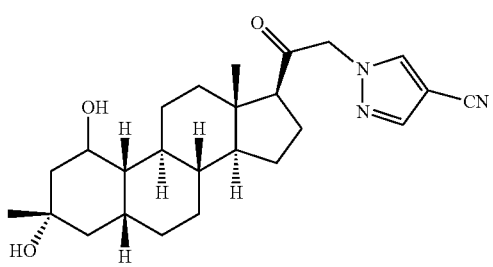
174
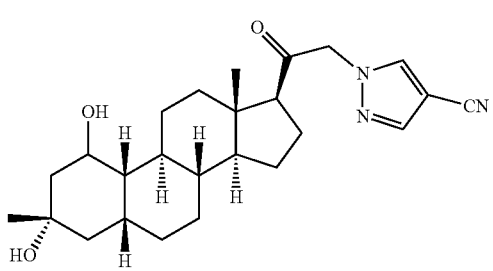
-continued
175
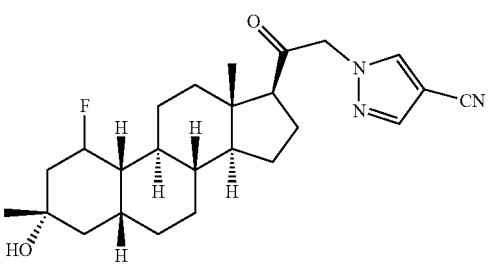
175
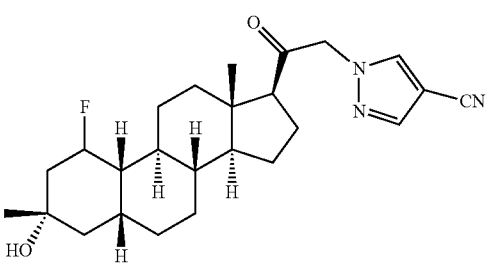
176
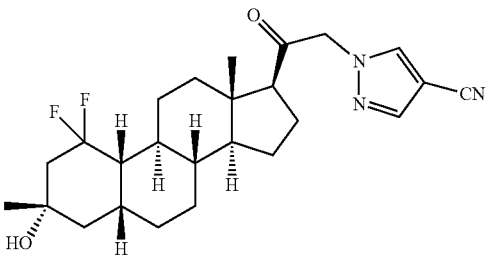
177
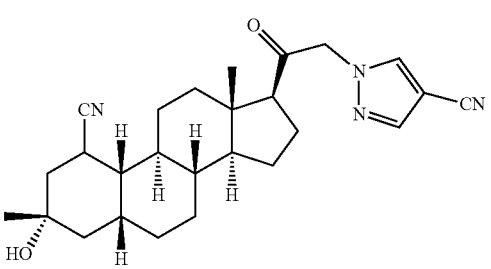
178
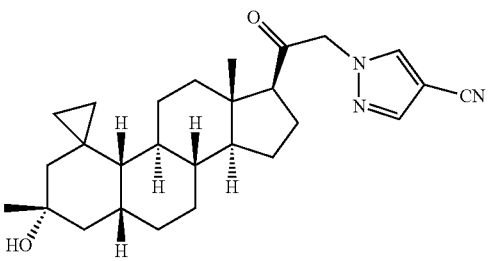
179
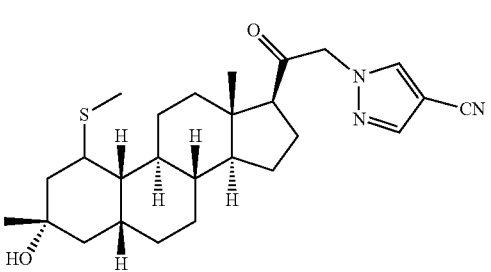

180 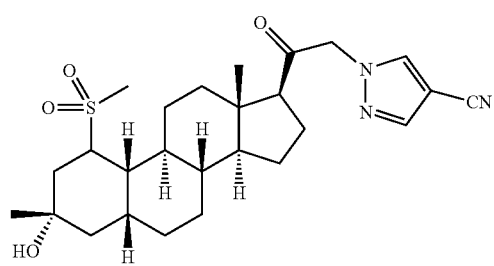
181 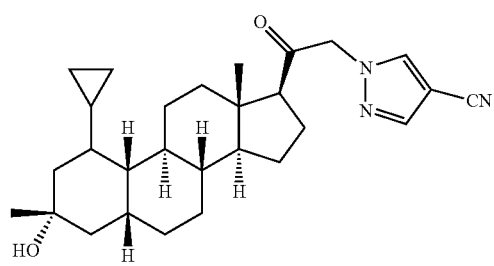
182 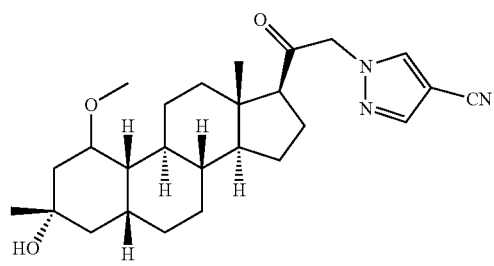
183 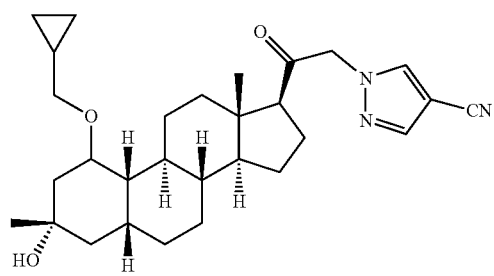
184 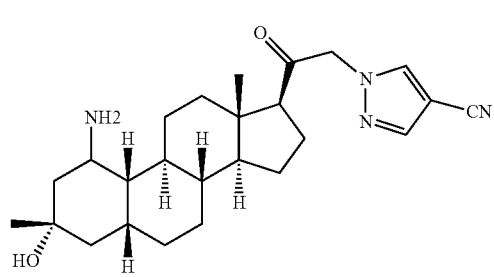
185 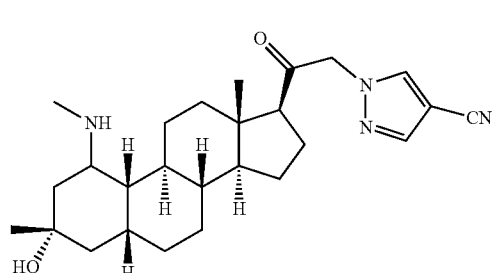
186 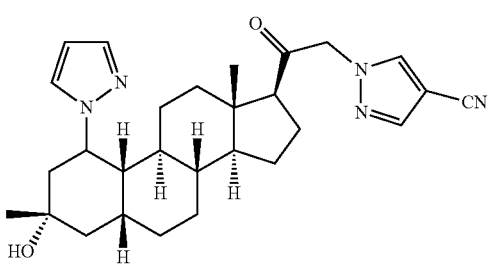
187 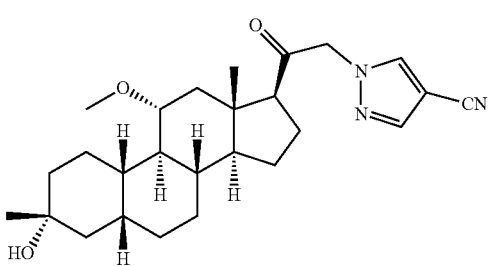
188 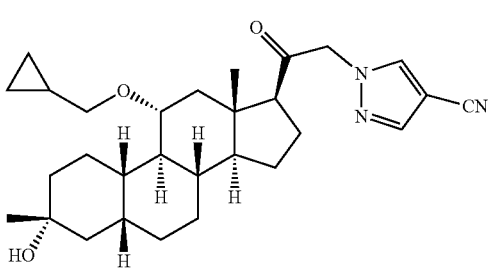
189 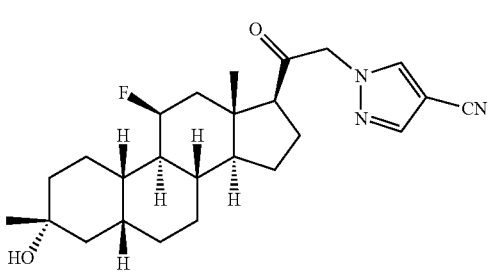
190 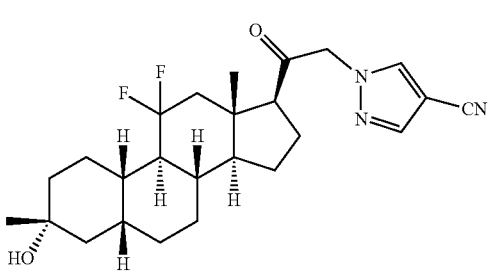
191 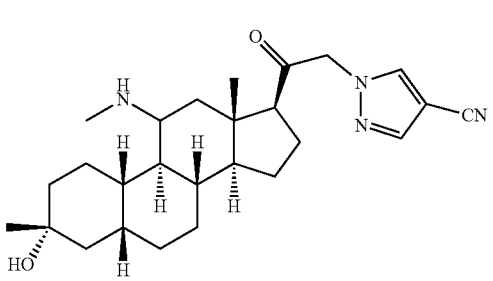

192

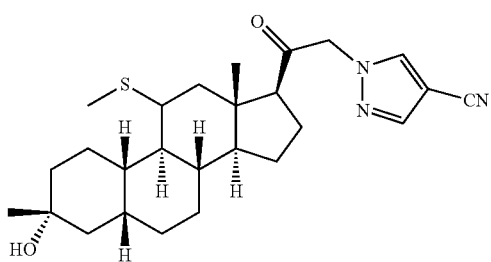

193

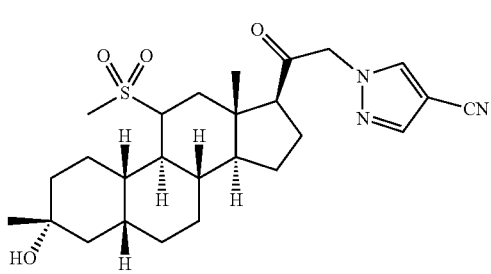

194

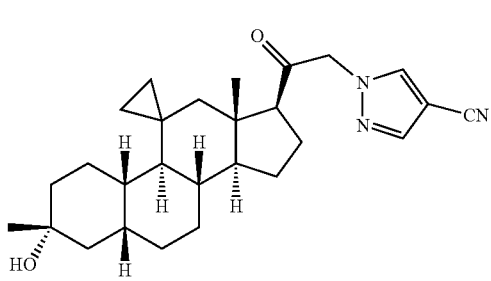

195

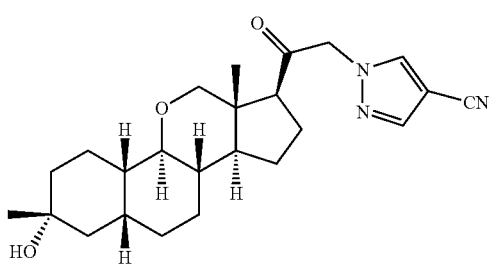

196

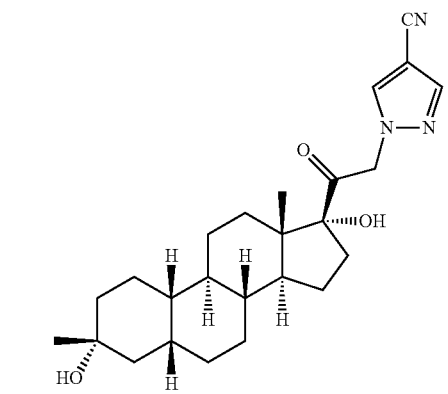

197

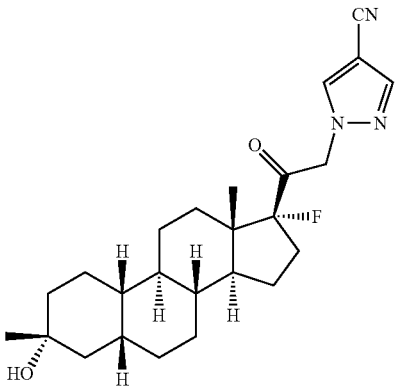

and

198

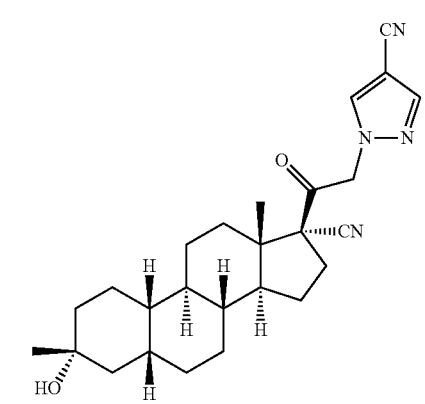

or a pharmaceutically acceptable salt thereof.

The present invention further relates to a pharmaceutical composition comprising a therapeutically effective amount of any compound of formula (I), the stereoisomer thereof, or the pharmaceutically acceptable salt thereof, and one or more pharmaceutically acceptable carriers, diluents or excipients.

The present invention further relates to a use of any compound of formula (I), the stereoisomer thereof, or the pharmaceutically acceptable salt thereof, or the pharmaceutical composition comprising the same in the preparation of a $GABA_A$ receptor regulator medicament.

The present invention further relates to a use of the compound of formula (I), the stereoisomer thereof, or the pharmaceutically acceptable salt thereof, or the pharmaceutical composition comprising the same in the preparation of a medicament for treating a Central Nervous System (CNS)-related disease, wherein the CNS-related disease is selected from the group consisting of sleep disorder, mood disorder, schizophrenia spectrum disorder, spasmodic disorder, memory disorder and/or cognitive disorder, dyskinesia, personality disorder, autism spectrum disorder, pain, traumatic brain injury, vascular disease, substance abuse disorder and/or withdrawal syndrome or tinnitus.

The present invention further relates to the compound of formula (I), the stereoisomer thereof, or the pharmaceutically acceptable salt thereof, or the pharmaceutical composition comprising the same for use in treating a CNS-related disease.

The present invention also relates to a method for treating and/or preventing a CNS-related disease, comprising administrating to a patient a therapeutically effective amount of the compound of formula (I), the stereoisomer thereof, or the pharmaceutically acceptable salt thereof, or the pharmaceutical composition comprising the same.

Definitions

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2 methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2 methyl-3-ethylhexyl, 2,2-diethylpentyl, n-decyl, 3,3-diethylhexyl, 2,2-diethylhexyl, and various branched isomers thereof. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, oxo, carboxy and alkoxycarbonyl, and preferably methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to —$CH_2$—, "ethylene" refers to —$(CH_2)_2$—, "propylene" refers to —$(CH_2)_3$—, "butylene" refers to —$(CH_2)_4$— and the like. The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated n-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and more preferably a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

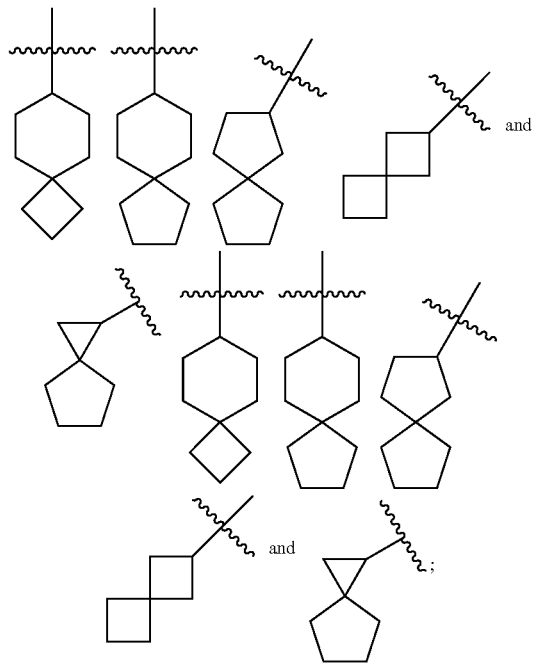

and also include spiro cycloalkyl in which a cycloalkyl and a heterocyclyl are connected through one spiro atom, non-limiting examples thereof include:

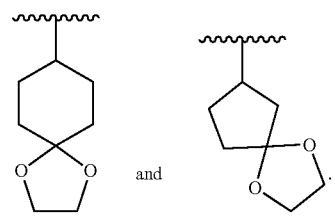 [SMILES: *C1CCC2(CC1)OCCO2 ; *C1CCC2(C1)OCCO2]

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated n-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered, or 5-membered/6-membered bicyclic fused cycloalkyl. Non-limiting examples of fused cycloalkyl include:

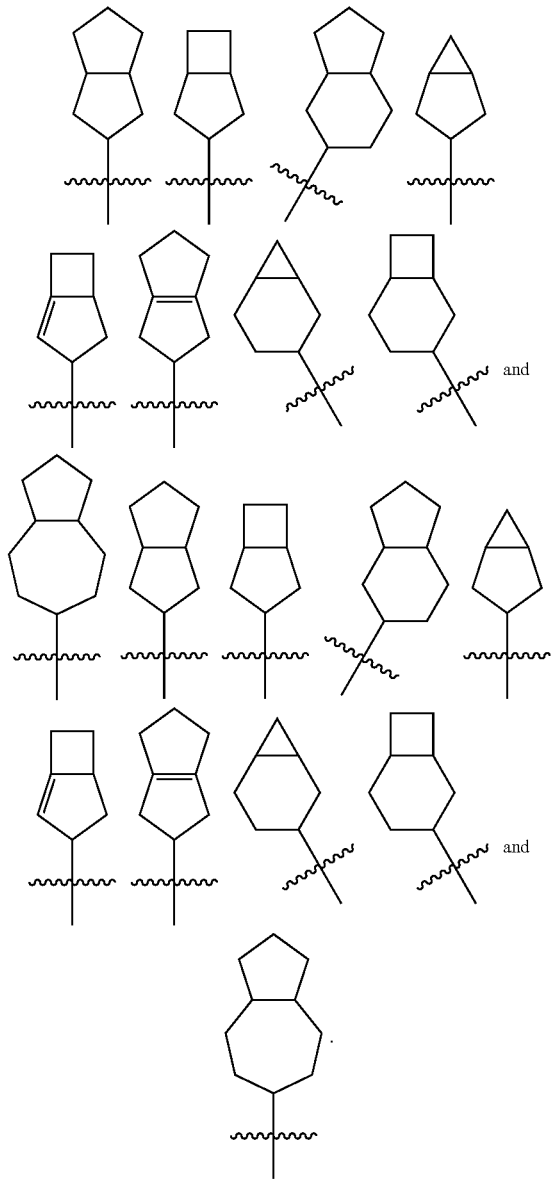

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

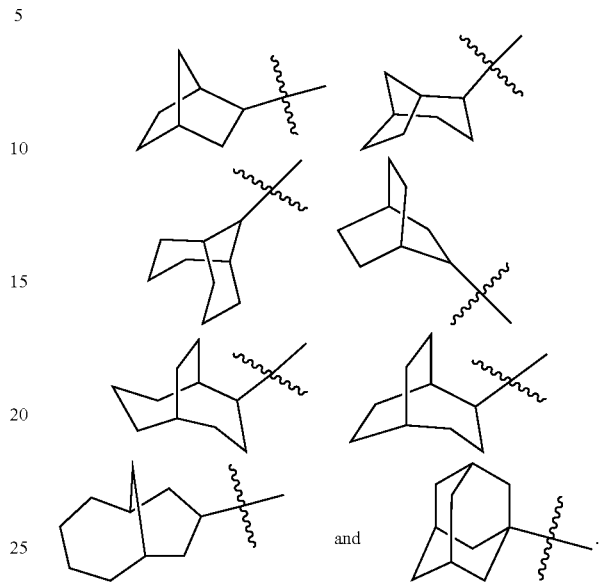

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon substituent group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, the heterocyclyl has 3 to 8 ring atoms; and most preferably 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, pyranyl, 1,4-diazacyclyl and the like, and preferably tetrahydrofuranyl, pyrazolidinyl, morpholinyl, 1,4-diazacyclyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and S(O)$_m$ (wherein m is an integer of 0 to 2), with the remaining ring atoms being carbon atoms, where the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

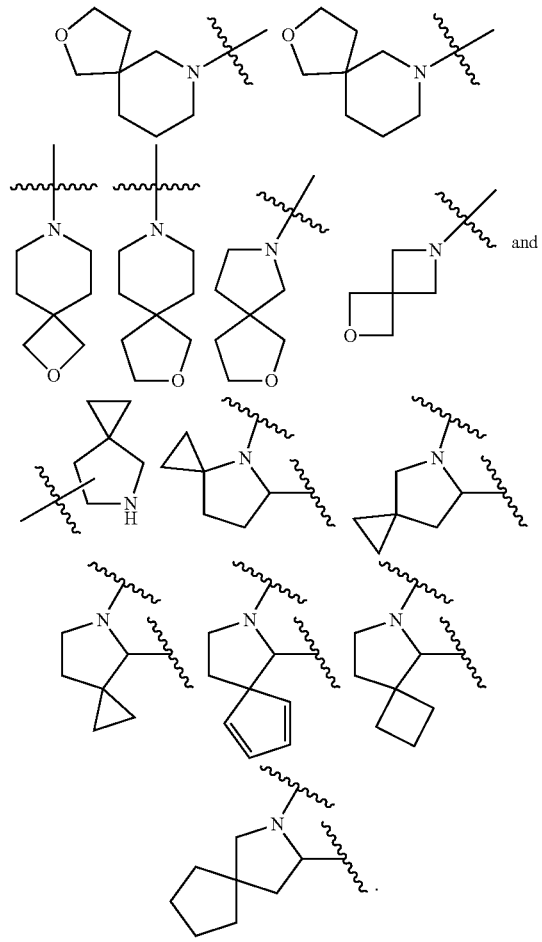

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and S(O)$_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and the fused heterocyclyl is preferably a bicyclic or tricyclic fused heterocyclyl, and more preferably a 5-membered/5-membered or 5-membered/6-membered bicyclic fused heterocyclyl. Non-limiting examples of fused heterocyclyl include:

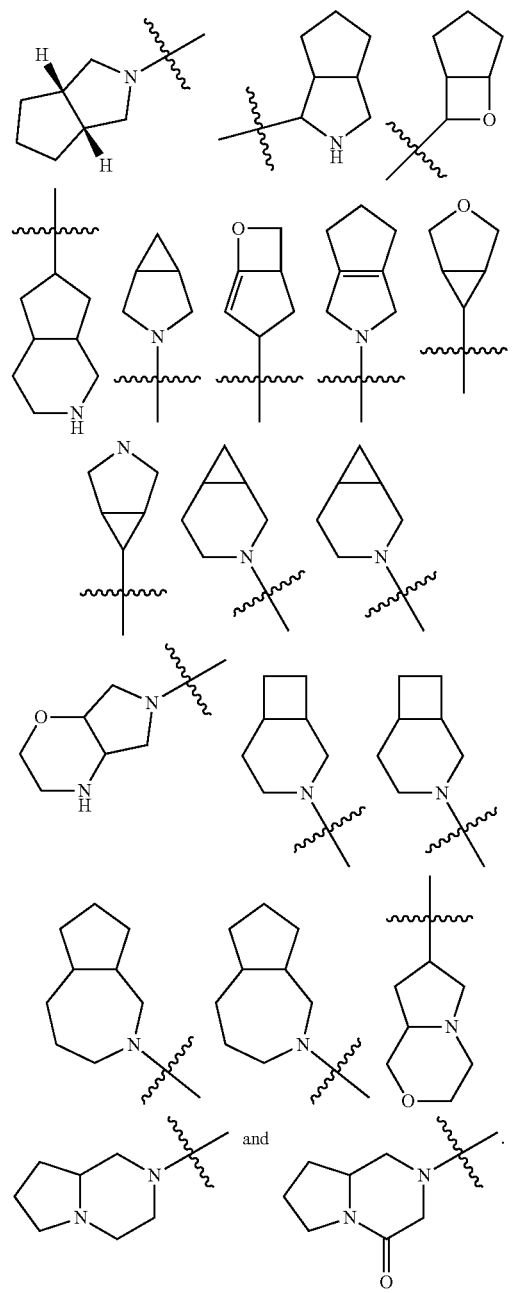

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and S(O)$_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

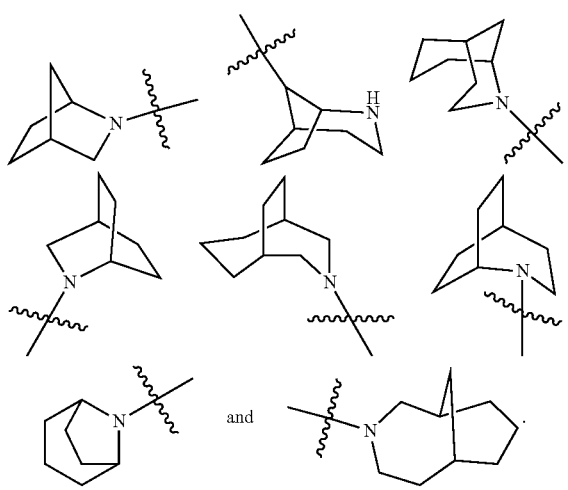

The heterocyclyl ring can be fused to the ring of aryl, heteroaryl or cycloalkyl, wherein the ring bound to the parent structure is heterocyclyl. Non-limiting examples thereof include:

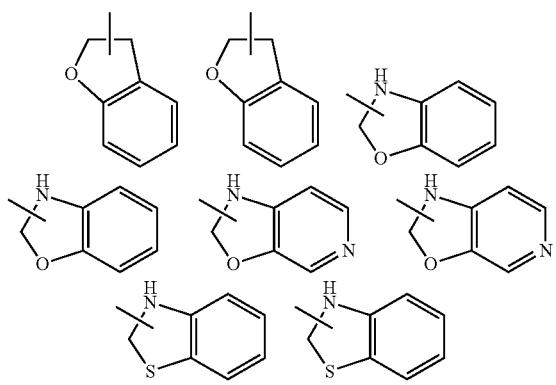

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl. The aryl is more preferably phenyl.

The aryl ring can be fused to the ring of heteroaryl, heterocyclyl or cycloalkyl, wherein the ring bound to the parent structure is aryl ring. Non-limiting examples thereof include:

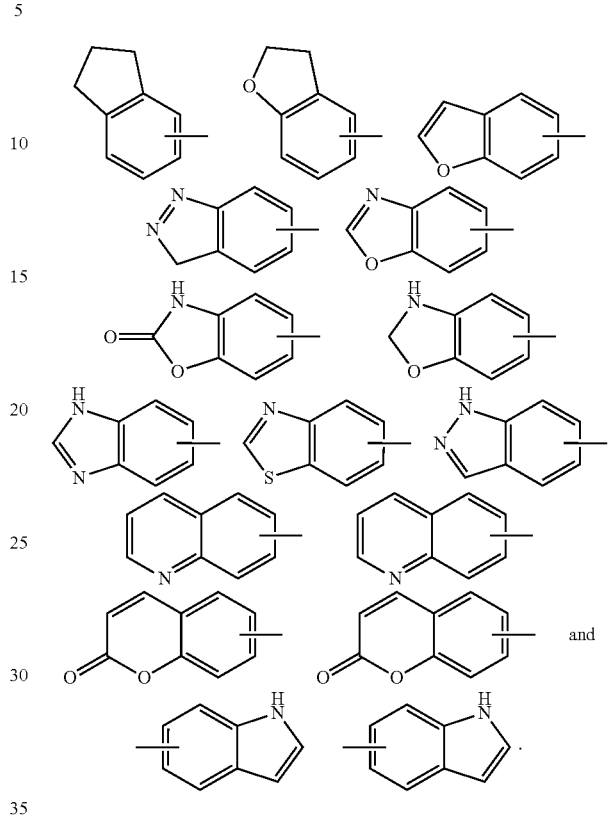

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of O, S and N. The heteroaryl is preferably a 5 to 10 membered heteroaryl, and more preferably a 5 or 6 membered heteroaryl, for example imidazolyl, furyl, thienyl, thiazolyl, pyrazolyl, oxazolyl, pyrrolyl, triazolyl, tetrazolyl, pyridyl, pyrimidinyl, thiadiazolyl, pyrazinyl and the like, preferably triazolyl, tetrazolyl, thienyl, imidazolyl, pyrazolyl, pyridazinyl, pyrimidinyl, thiazolyl, oxazolyl, isoxazolyl or pyrimidinyl, and more preferably triazolyl, tetrazolyl, pyrazolyl, pyridyl, pyridazinyl, pyrimidinyl, thiazolyl, oxazolyl, isoxazolyl or imidazolyl. The heteroaryl ring can be fused to the ring of aryl, heterocyclyl or cycloalkyl, wherein the ring bound to the parent structure is heteroaryl ring. Non-limiting examples thereof include:

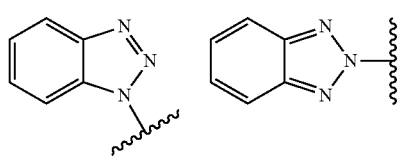

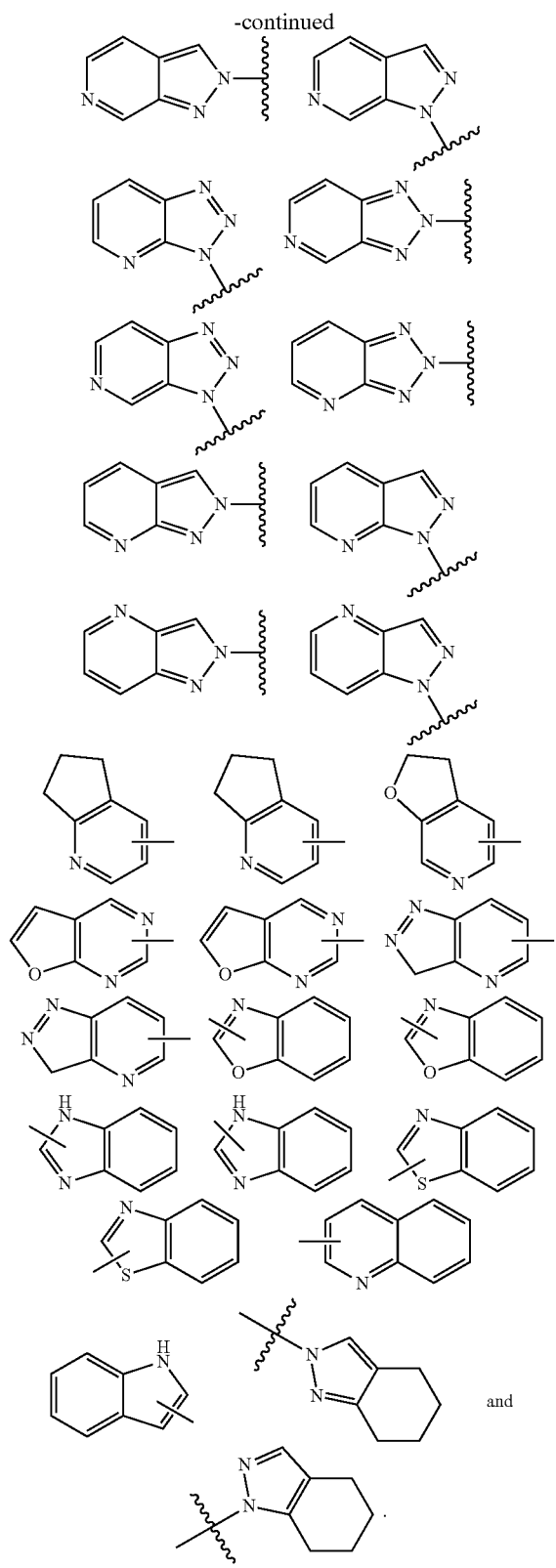

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O— (alkyl) or an —O— (unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy group can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy and alkoxycarbonyl.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl group substituted by hydroxy(s), wherein the alkyl is as defined above.

"Alkenyl" refers to chain alkenyl, also known as alkene group. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy or alkoxycarbonyl.

"Alkynyl" refers to (CH≡C—). The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocyclylthio, carboxy or alkoxycarbonyl.

"Hydroxy" refers to an —OH group.
"Halogen" refers to fluorine, chlorine, bromine or iodine.
"Amino" refers to a —NH$_2$ group.
"Cyano" refers to a —CN group.
"Nitro" refers to a —NO$_2$ group.
"Carboxy" refers to a —C(O)OH group.
"THF" refers to tetrahydrofuran.
"EtOAc" refers to ethyl acetate.
"MeOH" refers to methanol.
"DMF" refers to N,N-dimethylformamide.
"DIPEA" refers to diisopropylethylamine.
"TFA" refers to trifluoroacetic acid.
"MeCN" refers to acetonitrile.
"DMA" refers to N,N-dimethylacetamide.
"Et$_2$O" refers to diethyl ether.
"DCE" refers to 1,2-dichloroethane.
"DIPEA" refers to N,N-diisopropylethylamine.
"NBS" refers to N-bromosuccinimide.
"NIS" refers to N-iodosuccinimide.
"Cbz-Cl" refers to benzyl chloroformate.
"Pd$_2$(dba)$_3$" refers to tris(dibenzylideneacetone)dipalladium.
"Dppf" refers to 1,1'-bisdiphenylphosphinoferrocene.
"HATU" refers to 2-(7-azabenzotriazol-1-yl)-N,N,N',N'-tetramethyluronium hexafluorophosphate.
"KHMDS" refers to potassium hexamethyldisilazide.
"LiHMDS" refers to lithium bis(trimethylsilyl)amide.
"MeLi" refers to methyl lithium.
"n-BuLi" refers to n-butyl lithium.
"NaBH(OAc)$_3$" refers to sodium triacetoxyborohydride.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

The hydrogen atom of the present invention can be substituted by its isotope deuterium. Any of the hydrogen atoms in the compound of the examples of the present invention can also be substituted by deuterium atom.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive effort. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

DETAILED DESCRIPTION OF THE INVENTION

The present invention is further described in combination with the following examples, which are not intended to limit the scope of the present invention.

EXAMPLES

The structures of the compounds of the present invention were identified by nuclear magnetic resonance (NMR) and/or liquid chromatography-mass spectrometry (LC-MS). NMR chemical shifts (δ) are given in parts per million (ppm). NMR was determined by a Bruker AVANCE-400 machine. The solvents for determination were deuterated-dimethyl sulfoxide (DMSO-$d_6$), deuterated-methanol (CD$_3$OD) and deuterated-chloroform (CDCl$_3$), and the internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm. Yantai Huanghai 200 to 300 mesh silica gel was generally used as a carrier for column chromatography.

The starting materials used in the examples of the present invention are known and commercially available, or can be synthesized by adopting or according to known methods in the art.

Unless otherwise stated, all reactions of the present invention were carried out under continuous magnetic stirring in a dry nitrogen or argon atmosphere, the solvent was dry, and the reaction temperature was in degrees Celsius.

Example 1

1-((3R,5R,8S,10R,13S,14S,17S)-10-Fluoro-3-hydroxy-3,13-dimethylhexadecahydro-1H-cyclopenta[a]phenanthren-17-yl)ethan-1-one

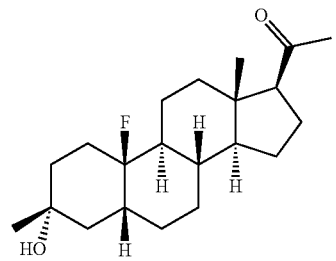

Step 1: (8S,9S,10S,13S,14S)-10-Fluoro-13-methyl-7,8,9,10,11,12,13,14,15,16-decahydro-3H-cyclopenta[a]phenanthrene-3,17(6H)-dione

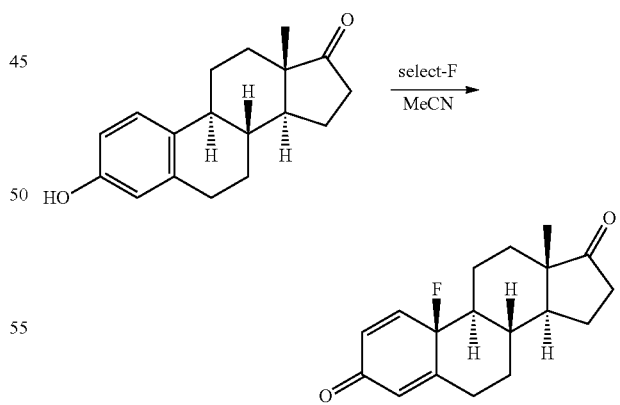

(8R,9S,13S,14S)-3-Hydroxy-13-methyl-6,7,8,9,11,12,13,14,15,16-decahydro-17H-cyclopenta[a]phenanthren-17-one (2.7 g, 10 mmol) and acetonitrile (100 mL) were added successively to a 100 mL three-necked flask, followed by the addition of 1 chloromethyl-4-fluoro-1,4-diazoniabicyclo[2.2.2]octane bis(tetrafluoroborate) (3.6 g, 10 mmol) under stirring. The reaction solution was heated to 45° C. in an oil bath, and reacted for 5 hours. The reaction solution was cooled to room temperature and concentrated. The resulting residue was dissolved in dichloromethane (100 mL), and washed with saturated saline (30 mL×3). The organic phase was dried over anhydrous sodium sulfate, filtrated and concentrated by rotary evaporation to dryness. The crude product was purified by column chromatography (petroleum ether/ethyl acetate: 3/1) to obtain (8S,9S,10S,13S,14S)-10-fluoro-13-methyl-7,8,9,10,11,12,13,14,15,16-decahydro-3H-cyclopenta[a]phenanthrene-3,17(6H)-dione (1.8 g, light yellow solid, yield: 62.5%).

MS m/z (ESI): 289.1[M+H]⁺.

¹H NMR (400 MHz, CDCl₃) δ 7.12-7.05 (m, 1H), 6.30-6.19 (m, 1H), 6.04 (s, 1H), 2.70-2.60 (m, 1H), 2.52-2.45 (m, 2H), 2.16-1.86 (m, 7H), 1.65-1.18 (m, 5H), 0.98 (s, 3H).

¹⁹F NMR (376 MHz, CDCl₃) δ−165.20.

Step 2: (5R,8S,9S,10R,13S,14S)-10-Fluoro-13-methyltetradecahydro-3H-cyclopenta[a]phenanthrene-3,17(2H)-dione

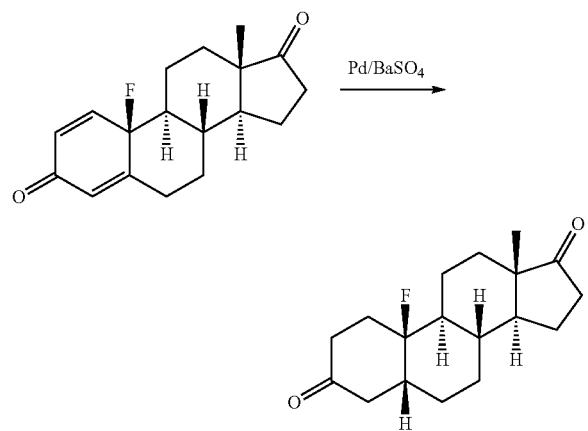

(8S,9S,10S,13S,14S)-10-Fluoro-13-methyl-7,8,9,10,11,12,13,14,15,16-decahydro-3H-cyclopenta[a]phenanthrene-3,17(6H)-dione (1.8 g, 6.25 mmol) was dissolved in ethanol (50 mL) in a 100 mL single-necked flask. After stirring at room temperature for 2-3 minutes, to the solution was added the catalyst Pd/barium sulfate (300 mg). After completion of the addition, the reaction solution was stirred at room temperature under a hydrogen atmosphere for 5 hours. The reaction solution was filtrated, and dissolved in 20 mL of dichloromethane to precipitate a white solid. The mixture was filtrated, and the filtrate was concentrated by rotary evaporation to dryness. The crude product was purified by column chromatography (petroleum ether/ethyl acetate: 3/1) to obtain (5R,8S,9S,10R,13S,14S)-10-fluoro-13-methyltetradecahydro-3H-cyclopenta[a]phenanthrene-3,17(2H)-dione (600 mg, white solid, yield: 32.9%).

¹H NMR (400 MHz, CDCl₃) δ 2.63-2.45 (m, 2H), 2.43-2.33 (m, 3H), 2.30-1.80 (m, 8H), 1.75-1.55 (m, 5H), 1.45-1.35 (m, 3H), 1.25-1.18 (m, 1H), 0.94 (s, 3H).

¹⁹F NMR (376 MHz, CDCl₃) δ−159.89.

Step 3: (3R,5R,8S,10R,13S,14S)-10-Fluoro-3-hydroxy-3,13-dimethylhexadecahydro-17H-cyclopenta[a]phenanthren-17-one

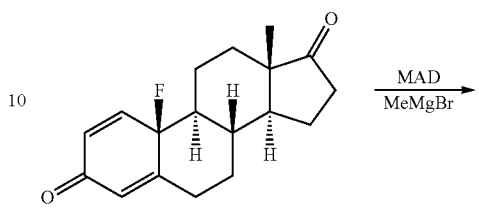

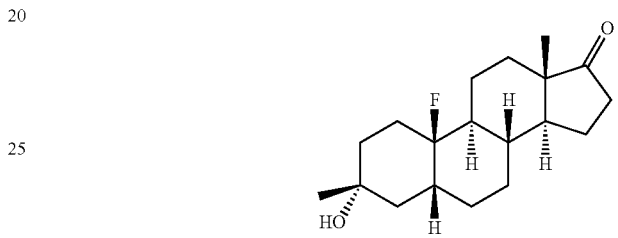

2,6-Di-tert-butyl-4-methylphenol (1.45 g, 6.6 mmol) was dissolved in anhydrous toluene (15 mL) in a 100 mL three-necked flask. The solution was cooled to 0-5° C. in an ice bath, and trimethylaluminum (1.7 mL, 2 M, 3.3 mmol) was added dropwise under a nitrogen atmosphere. After completion of the addition, the reaction solution was naturally warmed to room temperature, and stirred for 1 hour. The reaction solution was cooled to −78° C., and then a solution of (5R,8S,9S,10R,13S,14S)-10-fluoro-13-methyltetradecahydro-3H-cyclopenta[a]phenanthrene-3,17(2H)-dione (320 mg, 1.1 mmol) in toluene (5 mL) was added dropwise to the above reaction solution. The reaction solution was reacted at −78° C. for 1 hour. After methylmagnesium bromide (1.0 mL, 3 M, 3 mmol) was added dropwise, the reaction solution was reacted at −78° C. for 1 hour. The reaction was quenched with saturated aqueous ammonium chloride solution, and the reaction solution was extracted with ethyl acetate (20 mL) to precipitate a large amount of white solid. The mixture was filtrated, and the filtrate was separated into two phases. The organic phase was dried over anhydrous sodium sulfate, and concentrated by rotary evaporation to dryness. The resulting residue was purified by column chromatography (petroleum ether/ethyl acetate: 2/1) to obtain (3R,5R,8S,10R,13S,14S)-10-fluoro-3-hydroxy-3,13-dimethylhexadecahydro-17H-cyclopenta[a]phenanthren-17-one (250 mg, white solid, yield: 74.0%).

¹H NMR (400 MHz, CDCl₃) δ 2.46 (dd, J=19.3, 8.7 Hz, 1H), 2.17-1.72 (m, 8H), 1.71-1.44 (m, 10H), 1.38 (s, 3H), 1.34-1.11 (m, 3H), 0.90 (s, 3H).

¹⁹F NMR (376 MHz, CDCl₃) δ−158.16.

Step 4: (3R,5R,8S,10R,13S,14S)-17-Ethylidene-10-fluoro-3,13-dimethylhexadecahydro-1H-cyclopenta[a]phenanthren-3-ol

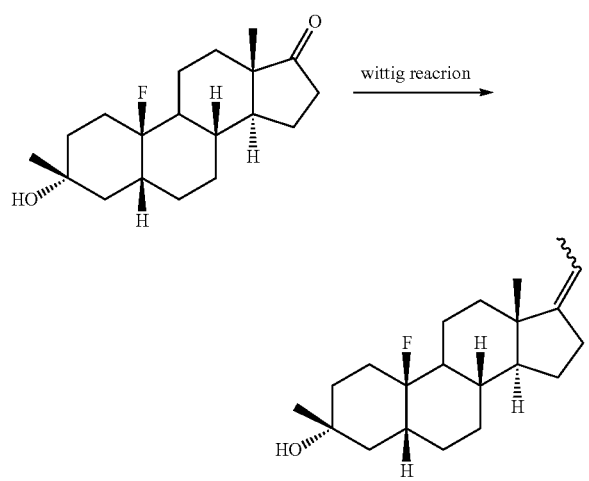

Potassium tert-butoxide (500 mg, 4.5 mmol) and tetrahydrofuran (15 mL) were added successively to a 100 mL three-necked flask. The reaction solution was cooled to 0° C., and ethyltriphenylphosphine bromide (1.82 g, 4.8 mmol) was added in batches. The reaction solution was stirred at 60° C. for 2 hours, and then (3R,5R,8S,10R,13S,14S)-10-fluoro-3-hydroxy-3,13-dimethylhexadecahydro-17H-cyclopenta[a]phenanthren-17-one (250 mg, 0.75 mmol) was added to the above reaction solution. The reaction solution was reacted at 60° C. for 8 hours. The reaction was quenched with saturated ammonium chloride solution, and then the reaction solution was extracted with ethyl acetate (20 mL) and washed with saturated saline (10 mL×2). The organic phase was dried over anhydrous sodium sulfate, filtrated and concentrated by rotary evaporation to dryness. The resulting residue was purified by column chromatography (petroleum ether/ethyl acetate: 5/1) to obtain (3R,5R,8S,10R,13S,14S)-17-ethylidene-10-fluoro-3,13-dimethylhexadecahydro-1H-cyclopenta[a]phenanthren-3-ol (110 mg, white solid, yield: 42%).

$^1$H NMR (400 MHz, CDCl$_3$) δ 5.15-5.08 (m, 1H), 2.40-1.80 (m, 8H), 1.65-1.45 (m, 13H), 1.36 (s, 3H), 1.31-1.05 (m, 4H), 0.89 (s, 3H).
$^{19}$F NMR (376 MHz, CDCl$_3$) δ−157.91.

Step 5: (3R,5R,8S,10R,13S,14S)-10-Fluoro-17-(1-hydroxyethyl)-3,13-dimethylhexadecahydro-1H-cyclopenta[a]phenanthren-3-ol

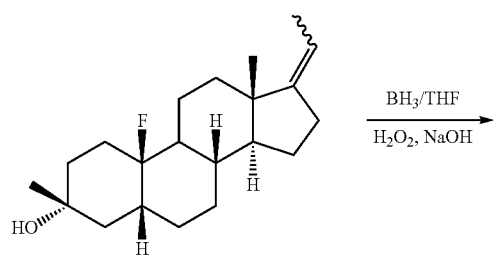

(3R,5R,8S,10R,13S,14S)-17-Ethylidene-10-fluoro-3,13-dimethylhexadecahydro-1H-cyclopenta[a]phenanthren-3-ol (110 mg, 0.35 mmol) was dissolved in dry tetrahydrofuran (5 mL). A complex of borane and tetrahydrofuran (1.1 mL, 1 M, 1.05 mmol) was added at room temperature. After completion of the addition, the reaction solution was stirred for 1 hour. The reaction solution was cooled in an ice-water bath, and NaOH (10%, 1.5 mL) was slowly added dropwise to produce a lot of gas. Hydrogen peroxide (30%, 2 mL) was slowly added dropwise, and the reaction solution was stirred at room temperature for 1 hour. The reaction solution was extracted with ethyl acetate (10 mL×2), and washed with 10% sodium thiosulfate solution. The organic phase was dried over anhydrous sodium sulfate, and concentrated under reduced pressure to obtain (3R,5R,8S,10R,13S,14S)-10-fluoro-17-(1-hydroxyethyl)-3,13-dimethylhexadecahydro-1H-cyclopenta[a]phenanthren-3-ol (100 mg, white solid).

Step 6: 1-((3R,5R,8S,10R,13S,14S,17S)-10-Fluoro-3-hydroxy-3,13-dimethylhexadecahydro-1H-cyclopenta[a]phenanthren-17-yl)ethan-1-one

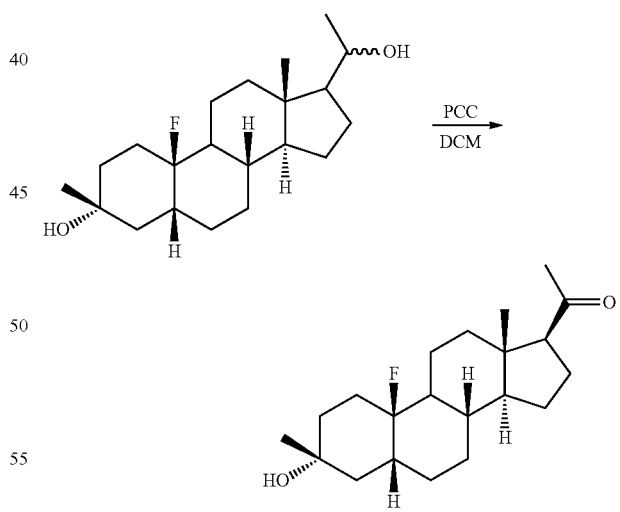

(3R,5R,8S,10R,13S,14S)-10-Fluoro-17-(1-hydroxyethyl)-3,13-dimethylhexadecahydro-1H-cyclopenta[a]phenanthren-3-ol (100 mg, 0.3 mmol) was dissolved in dichloromethane (5 mL). Pyridinium chlorochromate (130 mg, 0.6 mmol) was added, and the reaction solution was stirred at room temperature for 12 hours. The reaction solution was filtrated and concentrated under reduced pressure. The resulting residue was purified by column chromatography (petroleum ether/ethyl acetate: 5/1) to obtain 1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, white solid, yield: 81%).

$^1$H NMR (400 MHz, CDCl$_3$) δ 2.53 (t, J=9.0 Hz, 1H), 2.23-2.16 (m, 1H), 2.12 (s, 3H), 2.10-1.83 (m, 5H), 1.73-1.42 (m, 12H), 1.38 (s, 3H), 1.35-1.02 (m, 4H), 0.64 (s, 3H).

Example 2

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-1H-pyrazole-4-carbonitrile

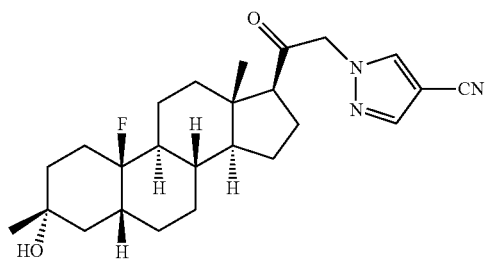

Step 1: 2-Bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one

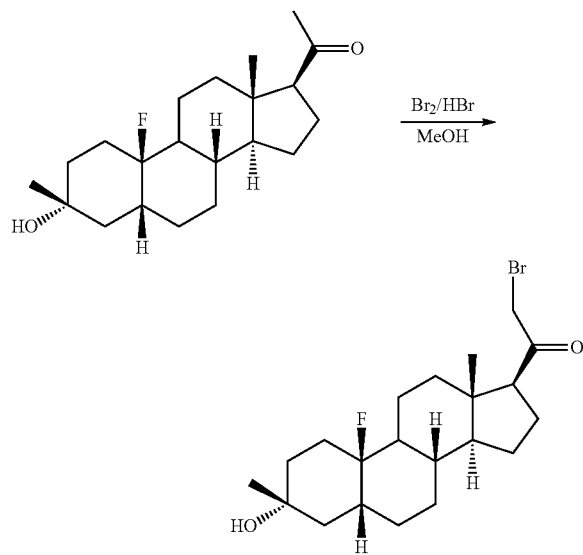

1-((3R,5R,8S,10R,13S,14S,17S)-10-Fluoro-3-hydroxy-3,13-dimethylhexadecahydro-1H-cyclopenta[a]phenanthren-17-yl)ethan-1-one (80 mg, 0.25 mmol) was dissolved in methanol (5 mL). 3 Drops of hydrogen bromide and 3 drops of liquid bromine were added. After stirring at room temperature for 12 hours, the reaction solution was added to ice-water, and extracted with ethyl acetate (10 mL×2). The organic phase was dried over anhydrous sodium sulfate, and concentrated under reduced pressure to obtain 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 81%), which was used directly in the next step.

Step 2: 1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-1H-pyrazole-4-carbonitrile

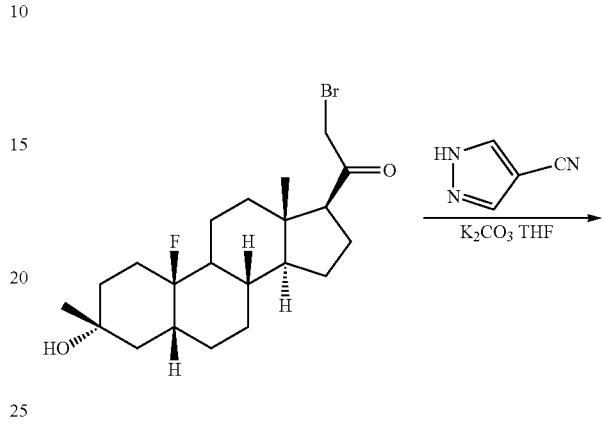

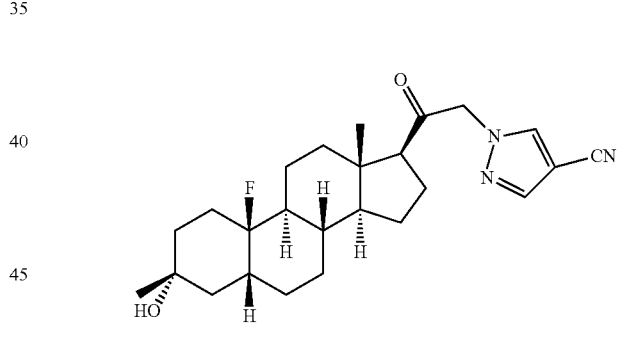

2-Bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 0.2 mmol) was dissolved in tetrahydrofuran (5 mL). 4-Cyanopyrazole (46 mg, 0.5 mmol) and potassium carbonate (84 mg, 0.6 mmol) were added, and the reaction solution was stirred at room temperature for 5 hours. The reaction solution was filtrated and concentrated, and the resulting residue was purified by prep-HPLC to obtain the product (25 mg, white solid, yield: 30.3%).

MS m/z (ESI): 428.3[M+H]$^+$.

$^1$H NMR (400 MHz, CDCl$_3$) δ 7.87 (s, 1H), 7.81 (s, 1H), 5.10-4.83 (m, 2H), 2.60 (t, J=8.8 Hz, 1H), 2.28-2.18 (m, 1H), 2.15-2.07 (m, 2H), 2.05-1.75 (m, 5H), 1.69-1.45 (m, 10H), 1.38 (s, 3H), 1.35-1.23 (m, 3H), 1.19-1.07 (m, 1H), 0.70 (s, 3H).

$^{19}$F NMR (376 MHz, CDCl$_3$) δ−158.28.

Example 3 and Example 4

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-1H-pyrazole-3-carbonitrile (3)

1-(2-((3R,5R,8S,9S,10R,13S,14S,17R)-10-Fluoro-3-hydroxy-3,13-dimethylhexadecahydro-1H-cyclopenta[a]phenanthren-17-yl)-2-oxoethyl)-1H-pyrazole-3-carbonitrile (4)

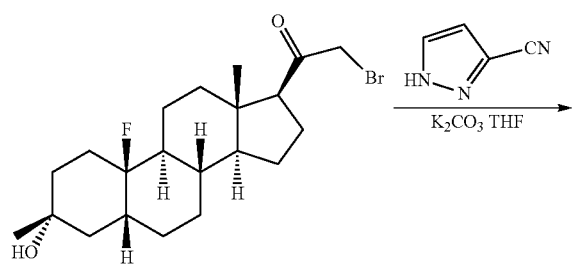

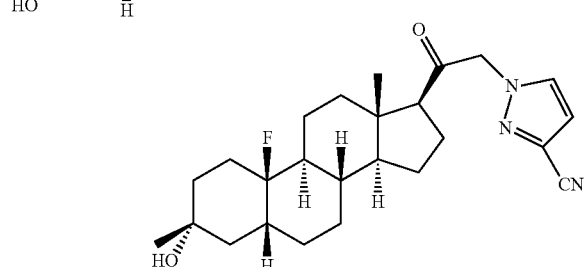

3

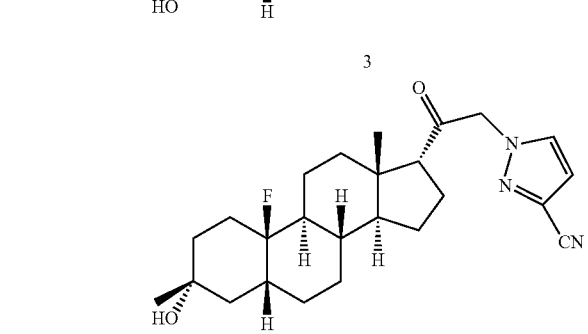

4

2-Bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 0.2 mmol) was dissolved in tetrahydrofuran (5 mL). 3-Cyanopyrazole (46 mg, 0.5 mmol) and potassium carbonate (84 mg, 0.6 mmol) were added, and the reaction solution was stirred at room temperature for 5 hours. The reaction solution was filtrated and concentrated, and the resulting residue was purified by prep-HPLC to obtain the product 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-3-carbonitrile (3) (18 mg, white solid, yield: 21.9%) and the product 1-(2-((3R,5R,8S,9S,10R,13S,14S,17R)-10-fluoro-3-hydroxy-3,13-dimethylhexadecahydro-1H-cyclopenta[a]phenanthren-17-yl)-2-oxoethyl)-1H-pyrazole-3-carbonitrile (4) (5 mg, white solid, yield: 6.0%).

Example 3

MS m/z (ESI): 428.1[M+H]$^+$.

$^1$H NMR (400 MHz, CDCl$_3$) δ 7.50 (d, J=2.4 Hz, 1H), 6.74 (d, J=2.4 Hz, 1H), 5.15-4.85 (m, 2H), 2.60 (t, J=8.9 Hz, 1H), 2.26-2.16 (m, 1H), 2.05-1.90 (m, 2H), 1.85-1.73 (m, 3H), 1.67-1.43 (m, 12H), 1.38 (s, 3H), 1.38-1.25 (m, 3H), 1.18-1.06 (m, 1H), 0.71 (s, 3H).

$^{19}$F NMR (376 MHz, CDCl$_3$) δ −158.21.

Example 4

MS m/z (ESI): 428.1 [M+H]$^+$.

$^1$H NMR (400 MHz, CDCl$_3$) δ 7.50 (d, J=2.4 Hz, 1H), 6.76 (d, J=2.4 Hz, 1H), 5.15-4.85 (m, 2H), 2.78 (dd, J=8.0, 2.8 Hz, 1H), 2.10-1.73 (m, 7H), 1.70-1.36 (m, 11H), 1.35 (s, 3H), 1.32-1.10 (m, 4H), 0.98 (s, 3H).

$^{19}$F NMR (376 MHz, CDCl$_3$) δ −158.42.

Example 5 and Example 6

1-((3R,5R,8S,9S,10R,13S,14S,17S)-10-Fluoro-3-hydroxy-3,13-dimethylhexadecahydro-1H-cyclopenta[a]phenanthren-17-yl)-2-(3-(trifluoromethyl)-1H-pyrazol-1-yl)ethan-1-one (5)

1-((3R,5R,8S,9S,10R,13S,14S,17R)-10-Fluoro-3-hydroxy-3,13-dimethylhexadecahydro-1H-cyclopenta[a]phenanthren-17-yl)-2-(3-(trifluoromethyl)-1H-pyrazol-1-yl)ethan-1-one (6)

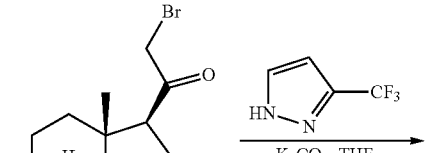

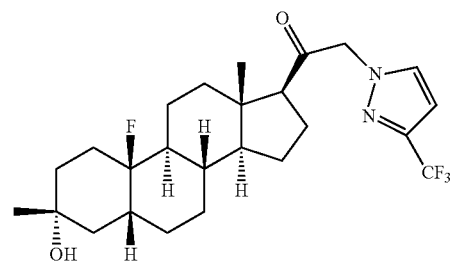

5

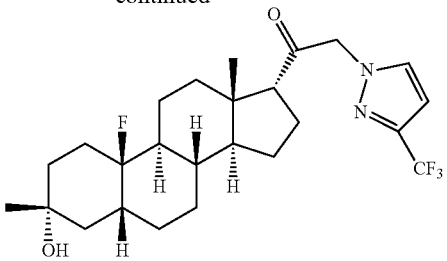

6

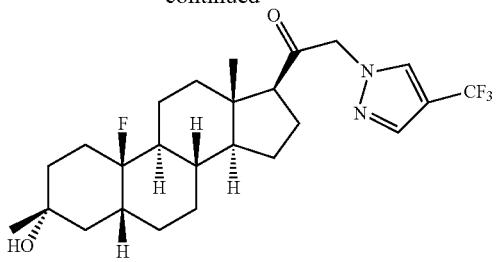

7

In accordance with Step 2 of Example 2, 2-bromo-1-((3R, 5R,8S,9S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-((3R,5R,8S,9S,10R,13S,14S,17S)-10-fluoro-3-hydroxy-3,13-dimethylhexadecahydro-1H-cyclopenta[a]phenanthren-17-yl)-2-(1H-tetrazol-1-yl)ethan-1-one (5) (35.5 mg, white solid, yield: 43%) and 1-((3R,5R,8S,9S,10R,13S,14S,17R)-10-fluoro-3-hydroxy-3,13-dimethylhexadecahydro-1H-cyclopenta[a]phenanthren-17-yl)-2-(3-(trifluoromethyl)-1H-pyrazol-1-yl)ethan-1-one (6) (12.3 mg, white solid, yield: 14.9%) were obtained.

Example 5

MS m/z (ESI): 471.3[M+H]$^+$.

$^1$H NMR (400 MHz, CDCl$_3$) δ 7.48 (s, 1H), 6.59 (d, J=2.1 Hz, 1H), 5.05-4.92 (m, 2H), 2.59 (t, J=8.8 Hz, 1H), 2.25-2.15 (m, 1H), 2.15-2.05 (m, 2H), 2.03-1.69 (m, 5H), 1.70-1.41 (m, 12H), 1.38 (s, 3H), 1.06 (m, 4H), 0.71 (s, 3H).

Example 6

MS m/z (ESI): 471.3[M+H]$^+$.

$^1$H NMR (400 MHz, CDCl$_3$) δ 7.48 (d, J=1.3 Hz, 1H), 6.61 (d, J=2.3 Hz, 1H), 5.07-4.90 (m, 2H), 2.77 (dd, J=7.9, 3.0 Hz, 1H), 2.12-1.72 (m, 9H), 1.72-1.38 (m, 11H), 1.34 (s, 3H), 1.33-1.04 (m, 4H), 0.96 (s, 3H).

Example 7 and Example 8

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(trifluoromethyl)-1H-pyrazol-1-yl)ethan-1-one (7)

1-((3R,5R,8S,9S,10R,13S,14S,17R)-10-Fluoro-3-hydroxy-3,13-dimethylhexadecahydro-1H-cyclopenta[a]phenanthren-17-yl)-2-(4-(trifluoromethyl)-1H-pyrazol-1-yl)ethan-1-one (8)

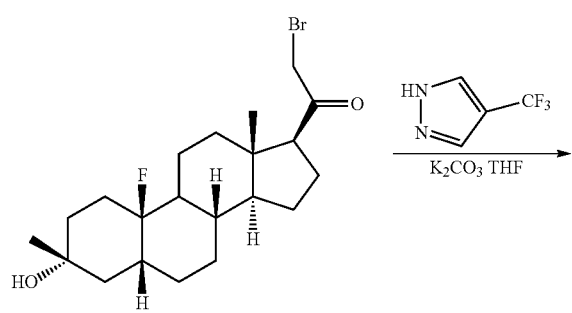

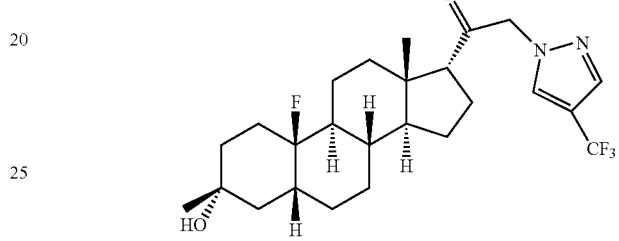

8

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(4-(trifluoromethyl)-1H-pyrazol-1-yl)ethan-1-one (7) (22 mg, white solid, yield: 32.9%) and the product 1 ((3R,5R,8S,9S,10R,13S,14S,17R)-10-fluoro-3-hydroxy-3,13-dimethylhexadecahydro-1H-cyclopenta[a]phenanthren-17-yl)-2-(4-(trifluoromethyl)-1H-pyrazol-1-yl)ethan-1-one (8) (8 mg, white solid, yield: 11.5%) were obtained.

Example 7

MS m/z (ESI): 471.2[M+H]$^+$.

$^1$H NMR (400 MHz, CDCl$_3$) δ 7.72 (s, 2H), 5.05-4.85 (m, 2H), 2.60 (t, J=8.0 Hz, 1H), 2.30-2.15 (m, 1H), 2.15-2.05 (m, 2H), 2.01-1.93 (m, 2H), 1.92-1.83 (m, 1H), 1.81-1.71 (m, 2H), 1.71-1.43 (m, 10H), 1.38 (s, 3H), 1.35-1.25 (m, 3H), 1.19-1.10 (m, 1H), 0.71 (s, 3H).

$^{19}$F NMR (376 MHz, CDCl$_3$) δ−56.44, −158.26.

Example 8

MS m/z (ESI): 471.3[M+H]$^+$.

$^1$H NMR (400 MHz, CDCl$_3$) δ 7.74 (s, 1H), 7.73 (s, 1H), 5.29-5.19 (m, 2H), 2.79 (dd, J=7.9, 2.7 Hz, 1H), 2.10-2.03 (m, 1H), 1.95-1.75 (m, 6H), 1.65-1.25 (m, 17H), 1.19-1.10 (m, 1H), 0.98 (s, 3H).

$^{19}$F NMR (376 MHz, CDCl$_3$) δ−56.42, −158.43.

Example 9 and Example 10

1-((3R,5R,8S,9S,10R,13S,14S,17S)-10-Fluoro-3-hydroxy-3,13-dimethylhexadecahydro-1H-cyclopenta[a]phenanthren-17-yl)-2-(1H-1,2,3-triazol-1-yl)ethan-1-one (9)

1-((3R,5R,8S,9S,10R,13S,14S,17S)-10-Fluoro-3-hydroxy-3,13-dimethylhexadecahydro-1H-cyclopenta[a]phenanthren-17-yl)-2-(2H-1,2,3-triazol-2-yl)ethan-1-one (10)

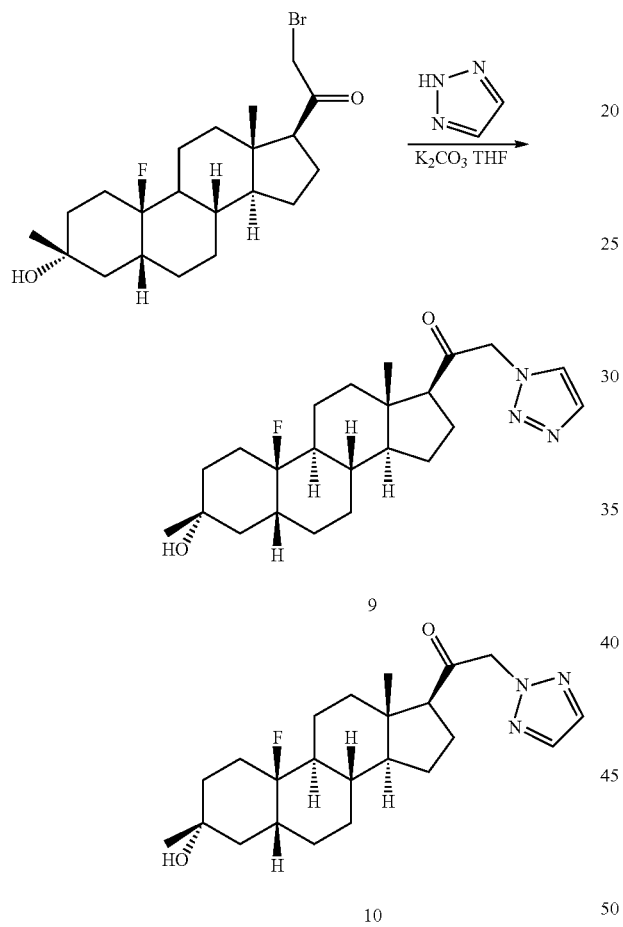

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(1H-1,2,3-triazol-1-yl)ethan-1-one (9) (32 mg, white solid, yield: 32.9%) and the product 1-((3R,5R,8S,9S,10R,13S,14S,17S)-10-fluoro-3-hydroxy-3,13-dimethylhexadecahydro-1H-cyclopenta[a]phenanthren-17-yl)-2-(2H-1,2,3-triazol-2-yl)ethan-1-one (10) (20 mg, white solid, yield: 20.5%) were obtained.

Example 9

MS m/z (ESI): 404.2[M+H]$^+$.

$^1$H NMR (400 MHz, CDCl$_3$) δ 7.76 (s, 1H), 7.65 (s, 1H), 5.30-5.13 (m, 2H), 2.65 (t, J=8.0 Hz, 1H), 2.25-2.15 (m, 1H), 2.13-2.03 (m, 2H), 2.05-1.75 (m, 5H), 1.68-1.43 (m, 10H), 1.38 (s, 3H), 1.35-1.25 (m, 3H), 1.19-1.10 (m, 1H), 0.71 (s, 3H).

$^{19}$F NMR (376 MHz, CDCl$_3$) δ−158.26.

Example 10

MS m/z (ESI): 404.2[M+H]$^+$.

$^1$H NMR (400 MHz, CDCl$_3$) δ 7.69 (s, 2H), 5.24 (s, 2H), 2.57 (t, J=8.0 Hz, 1H), 2.27-2.16 (m, 1H), 2.15-2.07 (m, 2H), 2.05-1.75 (m, 5H), 1.68-1.43 (m, 10H), 1.38 (s, 3H), 1.35-1.25 (m, 3H), 1.19-1.05 (m, 1H), 0.74 (s, 3H).

$^{19}$F NMR (376 MHz, CDCl$_3$) δ−158.24.

Example 11

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-methyl-1H-pyrazol-1-yl)ethan-1-one

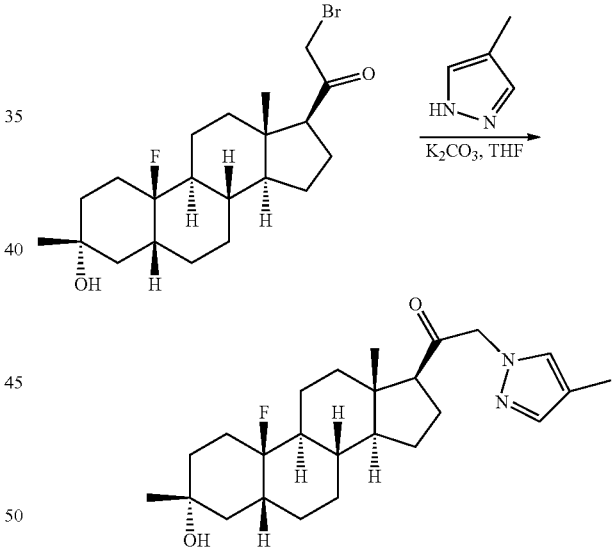

In accordance with Step 2 of Example 2, 2-bromo-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(4-methyl-1H-pyrazol-1-yl)ethan-1-one (11) (24 mg, white solid, yield: 29%) was obtained.

MS m/z (ESI): 417.3[M+H]$^+$.

$^1$H NMR (400 MHz, CDCl$_3$) δ 7.35 (s, 1H), 7.18 (s, 1H), 4.90-4.79 (m, 2H), 2.56 (t, J=8.9 Hz, 1H), 2.27-2.13 (m, 1H), 2.11 (s, 3H), 2.06-1.80 (m, 4H), 1.80-1.40 (m, 11H), 1.38 (s, 3H), 1.35-1.19 (m, 5H), 1.18-1.03 (m, 1H), 0.71 (s, 3H).

Example 12 and Example 13

1-((3R,5R,8S,9S,10R,13S,14S,17S)-10-Fluoro-3-hydroxy-3,13-dimethylhexadecahydro-1H-cyclopenta[a]phenanthren-17-yl)-2-(2H-tetrazol-2-yl)ethan-1-one (12)

1-((3R,5R,8S,9S,10R,13S,14S,17S)-10-Fluoro-3-hydroxy-3,13-dimethylhexadecahydro-1H-cyclopenta[a]phenanthren-17-yl)-2-(1H-tetrazol-1-yl)ethan-1-one (13)

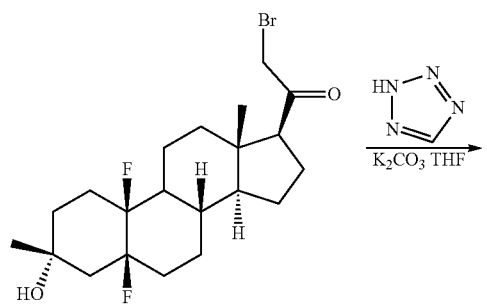

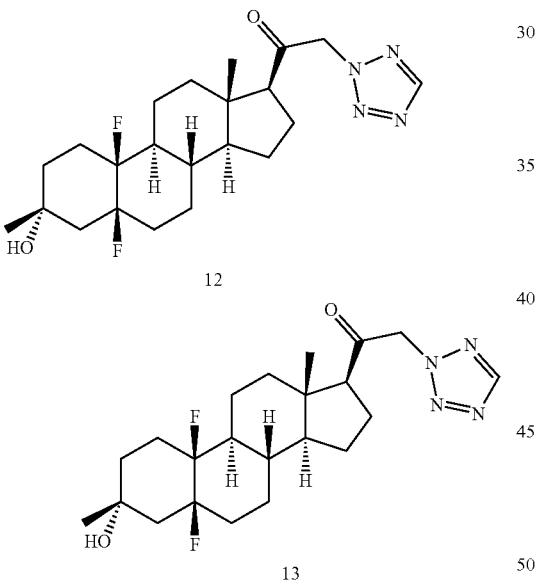

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-((3R,5R,8S,9S,10R,13S,14S,17S)-10-fluoro-3-hydroxy-3,13-dimethylhexadecahydro-1H-cyclopenta[a]phenanthren-17-yl)-2-(2H-tetrazol-2-yl)ethan-1-one (12) (12 mg, white solid, yield: 16%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(1H-tetrazol-1-yl)ethan-1-one (13) (9 mg, white solid, yield: 12%) were obtained.

Example 12

MS m/z (ESI): 405.2[M+H]$^+$.
$^1$H NMR (400 MHz, CDCl$_3$) δ 8.57 (s, 1H), 5.46 (s, 2H), 2.64 (t, J=8.0 Hz, 1H), 2.28-2.19 (m, 1H), 2.18-2.07 (m, 2H), 2.05-1.75 (m, 4H), 1.71-1.43 (m, 11H), 1.38 (s, 3H), 1.34-1.26 (m, 3H), 1.21-1.11 (m, 1H), 0.75 (s, 3H).

Example 13

MS m/z (ESI): 405.2[M+H]$^+$.
$^1$H NMR (400 MHz, CDCl$_3$) δ 8.75 (s, 1H), 5.35-5.15 (m, 2H), 2.67 (t, J=8.0 Hz, 1H), 2.30-2.19 (m, 1H), 2.15-2.07 (m, 1H), 2.05-1.75 (m, 4H), 1.68-1.45 (m, 11H), 1.39 (s, 3H), 1.35-1.25 (m, 4H), 1.20-1.10 (m, 1H), 0.71 (s, 3H).

Example 14 and Example 15

2-(2H-Benzo[d][1,2,3]triazol-2-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (15)

2-(1H-Benzo[d][1,2,3]triazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one

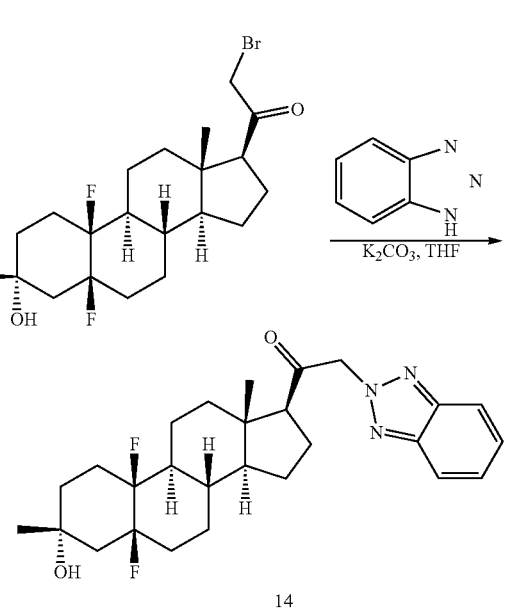

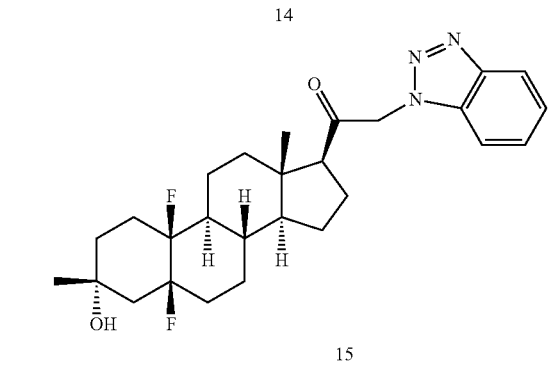

In accordance with Step 2 of Example 2, 2-bromo-1-((3R, 5R,8S,9S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 2-(2H-benzo[d][1,2,3]triazol-2-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (14) (11 mg, yield: 14%) and 2-(1H-benzo[d][1,2,3]triazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (15) (31 mg, yield: 41%) were obtained.

Example 14

MS m/z (ESI): 453.3[M+H]⁺.

¹H NMR (400 MHz, CDCl₃) δ 7.88 (dd, J=6.6, 3.0 Hz, 2H), 7.40 (dd, J=6.6, 3.0 Hz, 2H), 5.53 (t, J=4.7 Hz, 2H), 2.64 (t, J=8.9 Hz, 1H), 2.34-1.41 (m, 16H), 1.38 (s, 3H), 1.35-0.97 (m, 6H), 0.78 (s, 3H).

Example 15

MS m/z (ESI): 453.3[M+H]⁺.

¹H NMR (400 MHz, CDCl₃) δ 8.11 (d, J=7.5 Hz, 1H), 7.50 (t, J=7.5 Hz, 1H), 7.46-7.30 (m, 2H), 5.42 (s, 2H), 2.70 (t, J=8.5 Hz, 1H), 2.35-1.42 (m, 16H), 1.38 (s, 3H), 1.35-1.01 (m, 6H), 0.77 (s, 3H).

Example 16 and Example 17

1-((3R,5R,8S,9S,10R,13S,14S,17S)-10-Fluoro-3-hydroxy-3,13-dimethylhexadecahydro-1H-cyclopenta[a]phenanthren-17-yl)-2-(2H-pyrazolo[3,4-c]pyridin-2-yl)ethan-1-one (16)

1-((3R,5R,8S,9S,10R,13S,14S,17S)-10-Fluoro-3-hydroxy-3,13-dimethylhexadecahydro-1H-cyclopenta[a]phenanthren-17-yl)-2-(1H-pyrazolo[3,4-c]pyridin-1-yl)ethan-1-one (17)

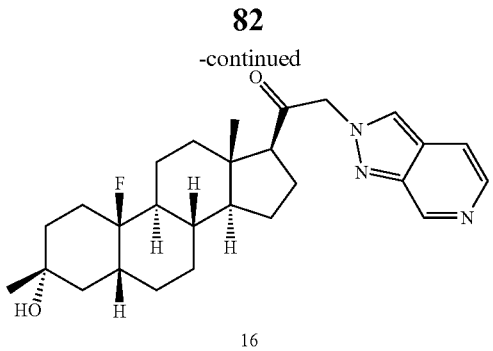

16

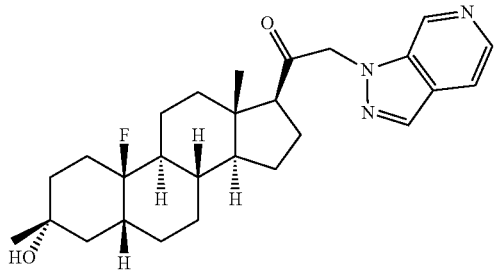

17

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-((3R,5R,8S,9S,10R,13S,14S,17S)-10-fluoro-3-hydroxy-3,13-dimethylhexadecahydro-1H-cyclopenta[a]phenanthren-17-yl)-2-(1H-tetrazol-1-yl)ethan-1-one (16) (9.2 mg, white solid, yield: 10.5%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(2H-tetrazol-2-yl)ethan-1-one (17) (16 mg, white solid, yield: 18.3%) were obtained.

Example 16

MS m/z (ESI): 454.2[M+H]⁺.

¹H NMR (400 MHz, CDCl₃) δ 9.33 (s, 1H), 8.19 (s, 1H), 8.13 (s, 1H), 7.72 (s, 1H), 5.42-5.25 (m, 2H), 2.70 (t, J=8.0 Hz, 1H), 2.30-2.10 (m, 3H), 2.05-1.85 (m, 8H), 1.70-1.45 (m, 7H), 1.39 (s, 3H), 1.32-1.25 (m, 3H), 0.90-0.85 (m, 1H), 0.75 (s, 3H).

Example 17

MS m/z (ESI): 454.2[M+H]⁺.

¹H NMR (400 MHz, CDCl₃) δ 8.88 (s, 1H), 8.36 (s, 1H), 8.13 (s, 1H), 7.71 (s, 1H), 5.32-5.25 (m, 2H), 2.69 (t, J=8.0 Hz, 1H), 2.25-2.10 (m, 3H), 2.05-1.75 (m, 5H), 1.70-1.45 (m, 10H), 1.39 (s, 3H), 1.35-1.25 (m, 3H), 1.20-1.10 (m, 1H), 0.76 (s, 3H).

Example 18, Example 19 and Example 20

2-(5-Fluoro-2H-benzo[d][1,2,3]triazol-2-yl)-1-((3R, 5R,8S,9S,10R,13S,14S,17S)-10-fluoro-3-hydroxy-3, 13-dimethylhexadecahydro-1H-cyclopenta[a] phenanthren-17-yl)ethan-1-one (18)

2-(6-Fluoro-1H-benzo[d][1,2,3]triazol-1-yl)-1-((3R, 5R,8S,9S,10R,13S,14S,17S)-10-fluoro-3-hydroxy-3, 13-dimethylhexadecahydro-1H-cyclopenta[a] phenanthren-17-yl)ethan-1-one (19)

2-(5-Fluoro-1H-benzo[d][1,2,3]triazol-1-yl)-1-((3R, 5R,8S,9S,10R,13S,14S,17S)-10-fluoro-3-hydroxy-3, 13-dimethylhexadecahydro-1H-cyclopenta[a] phenanthren-17-yl)ethan-1-one (20)

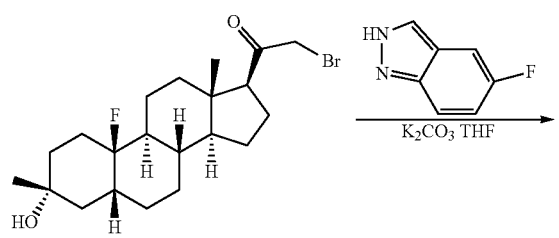

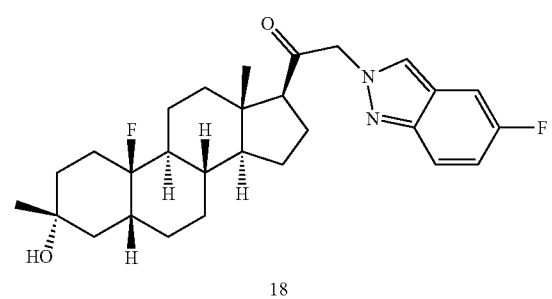

18

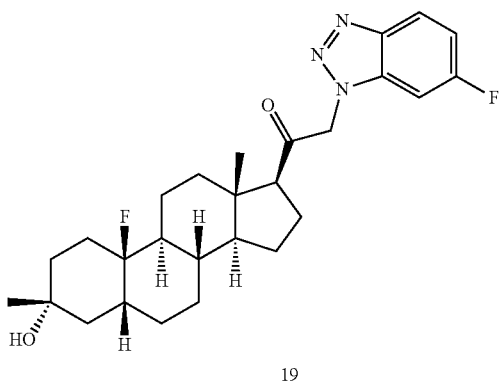

19

+

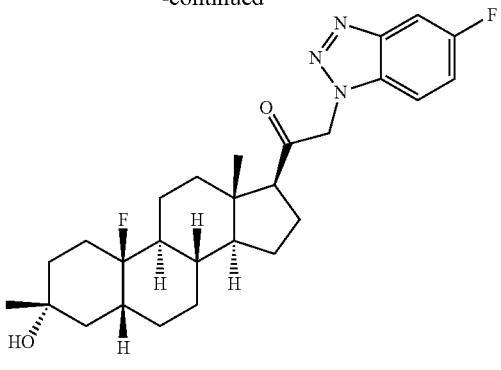

20

In accordance with Step 2 of Example 2, 2-bromo-1-((3R, 5R,8S,10R,13S,14S,17S)-10-fluoro-3-hydroxy-3,13-dimethylhexadecahydro-1H-cyclopenta[a]phenanthren-17-yl) ethan-1-one was used as the starting material, accordingly, 2-(5-fluoro-2H-benzo[d][1,2,3]triazol-2-yl)-1-((3R,5R,8S, 9S,10R,13S,14S,17S)-10-fluoro-3-hydroxy-3,13-dimethylhexadecahydro-1H-cyclopenta[a]phenanthren-17-yl)ethan-1-one (18) (20 mg, white solid, yield: 14.9%), 2-(6-fluoro-1H-benzo[d][1,2,3]triazol-1-yl)-1-((3R,5R,8S,9S,10R,13S, 14S,17S)-10-fluoro-3-hydroxy-3,13-dimethylhexadecahydro-1H-cyclopenta[a]phenanthren-17-yl)ethan-1-one (19) (18 mg, white solid, yield: 13.1%) and 2-(5-fluoro-1H-benzo[d][1,2,3]triazol-1-yl)-1-((3R,5R,8S, 9S,10R,13S,14S,17S)-10-fluoro-3-hydroxy-3,13-dimethylhexadecahydro-1H-cyclopenta[a]phenanthren-17-yl)ethan-1-one (20) (19 mg, white solid, yield: 13.9%) were obtained.

Example 18

MS m/z (ESI): 472.3[M+H]$^+$.

$^1$H NMR (400 MHz, CDCl$_3$) δ 7.86 (dd, J=9.3, 4.7 Hz, 1H), 7.47 (dd, J=8.7, 1.9 Hz, 1H), 7.21 (m, 1H), 5.55-5.45 (m, 2H), 2.65 (t, J=8.8 Hz, 1H), 2.32-2.08 (m, 3H), 2.04-1.45 (m, 15H), 1.38 (s, 3H), 1.35-1.23 (m, 3H), 1.20-1.10 (m, 1H), 0.78 (s, 3H).

Example 19

MS m/z (ESI): 472.3[M+H]$^+$.

$^1$H NMR (400 MHz, CDCl$_3$) δ 8.04 (dd, J=8.9, 4.4 Hz, 1H), 7.20-7.10 (m, 1H), 6.99 (d, J=7.6 Hz, 1H), 5.45-5.35 (m, 2H), 2.69 (d, J=8.7 Hz, 1H), 2.31-2.08 (m, 3H), 2.04-1.45 (m, 15H), 1.39 (s, 3H), 1.35-1.25 (m, 3H), 1.20-1.10 (m, 1H), 0.76 (s, 3H).

Example 20

MS m/z (ESI): 472.3[M+H]$^+$.

$^1$H NMR (400 MHz, CDCl$_3$) δ 7.71 (d, J=7.9 Hz, 1H), 7.35-7.28 (m, 2H), 5.45-5.35 (m, 2H), 2.69 (d, J=8.7 Hz, 1H), 2.31-2.08 (m, 3H), 2.04-1.45 (m, 15H), 1.39 (s, 3H), 1.35-1.25 (m, 3H), 1.20-1.10 (m, 1H), 0.76 (s, 3H).

Example 21 and Example 22

1-((3R,5R,8S,9S,10R,13S,14S,17S)-10-Fluoro-3-hydroxy-3,13-dimethylhexadecahydro-1H-cyclopenta[a]phenanthren-17-yl)-2-(4,5,6,7-tetrahydro-2H-indazol-2-yl)ethan-1-one (21)

1-((3R,5R,8S,9S,10R,13S,14S,17S)-10-Fluoro-3-hydroxy-3,13-dimethylhexadecahydro-1H-cyclopenta[a]phenanthren-17-yl)-2-(4,5,6,7-tetrahydro-1H-indazol-1-yl)ethan-1-one (22)

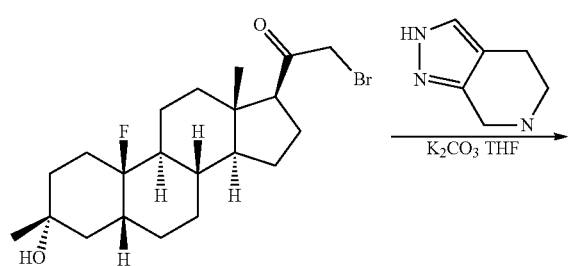

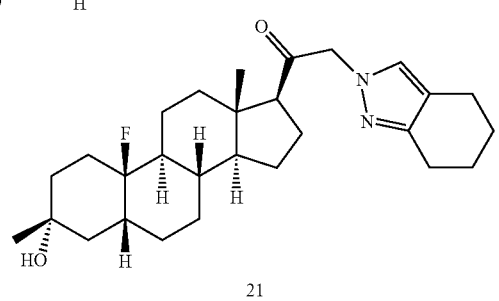

21

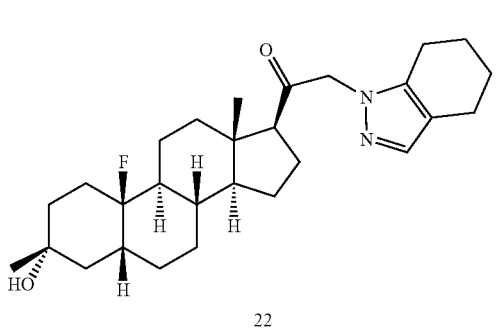

22

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, 1-((3R,5R,8S,9S,10R,13S,14S,17S)-10-fluoro-3-hydroxy-3,13-dimethylhexadecahydro-1H-cyclopenta[a]phenanthren-17-yl)-2-(4,5,6,7-tetrahydro-2H-indazol-2-yl)ethan-1-one (21) (15.0 mg, white solid, yield: 27.2%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(4,5,6,7-tetrahydro-1H-indazol-1-yl)ethan-1-one (22) (8.0 mg, white solid, yield: 12.1%) were obtained.

Example 21

MS m/z (ESI): 457.2[M+H]$^+$.

$^1$H NMR (400 MHz, CDCl$_3$) δ 7.10 (s, 1H), 4.90-4.85 (m, 2H), 2.72-2.66 (m, 2H), 2.62-2.52 (m, 3H), 2.25-1.40 (m, 22H), 1.37 (s, 3H), 1.33-1.23 (m, 3H), 1.17-1.07 (m, 1H), 0.71 (s, 3H).

Example 22

MS m/z (ESI): 457.2[M+H]$^+$.

$^1$H NMR (400 MHz, CDCl$_3$) δ 7.31 (s, 1H), 4.85-4.75 (m, 2H), 2.60-2.50 (m, 3H), 2.45-2.39 (m, 2H), 2.25-1.40 (m, 22H), 1.37 (s, 3H), 1.33-1.23 (m, 3H), 1.15-1.05 (m, 1H), 0.71 (s, 3H).

Example 23

1-((3R,5R,8S,9S,10R,13S,14S,17S)-10-Fluoro-3-hydroxy-3,13-dimethylhexadecahydro-1H-cyclopenta[a]phenanthren-17-yl)-2-((4-fluorophenyl)amino)ethan-1-one

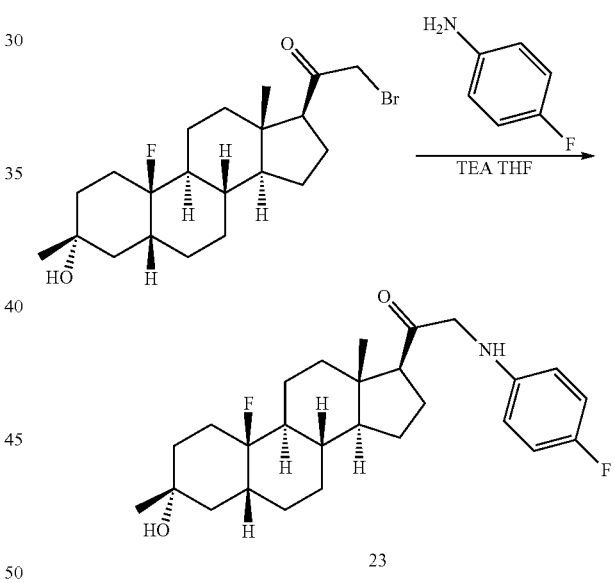

23

2-Bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 0.2 mmol) was dissolved in tetrahydrofuran (5 mL). 4-Fluoroaniline (42 mg, 0.4 mmol) and triethylamine (60 mg, 0.6 mmol) were added, and the reaction solution was stirred at room temperature for 5 hours. The reaction solution was concentrated, and the resulting residue was purified by prep-HPLC to obtain the product (18 mg, white solid, yield: 21%).

MS m/z (ESI): 446.3[M+H]$^+$.

$^1$H NMR (400 MHz, CDCl$_3$) δ 6.94-6.88 (m, 2H), 6.58-6.53 (m, 2H), 3.96-3.85 (m, 2H), 2.57 (t, J=8.0 Hz, 1H), 2.30-2.20 (m, 1H), 2.15-2.06 (m, 1H), 2.05-1.71 (m, 6H), 1.68-1.43 (m, 10H), 1.38 (s, 3H), 1.34-1.20 (m, 3H), 1.18-1.07 (m, 1H), 0.68 (s, 3H).

Example 24

1-((3R,5R,8S,9S,10R,13S,14S,17S)-10-Fluoro-3-hydroxy-3,13-dimethylhexadecahydro-1H-cyclopenta[a]phenanthren-17-yl)-2-((2-fluorophenyl)amino)ethan-1-one

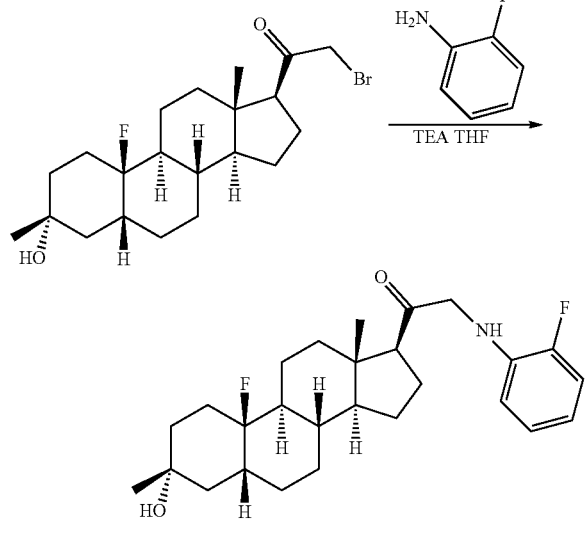

24

In accordance with Example 23, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-((2-fluorophenyl)amino)ethan-1-one (11 mg, white solid, yield: 20.5%) was obtained.

MS m/z (ESI): 446.2[M+H]+.

$^1$H NMR (400 MHz, CDCl$_3$) δ 7.04-6.92 (m, 2H), 6.71-6.61 (m, 1H), 6.60-6.52 (m, 1H), 4.03-3.86 (m, 2H), 2.58 (t, J=8.8 Hz, 1H), 2.33-1.44 (m, 18H), 1.38 (s, 3H), 1.33-1.05 (m, 4H), 0.69 (s, 3H).

Example 25

1-((3R,5R,8S,9S,10R,13S,14S,17S)-10-Fluoro-3-hydroxy-3,13-dimethylhexadecahydro-1H-cyclopenta[a]phenanthren-17-yl)-2-((3-fluorophenyl)amino)ethan-1-one

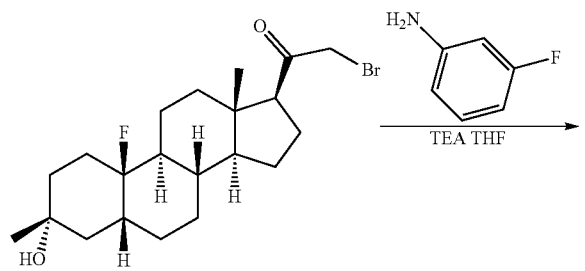

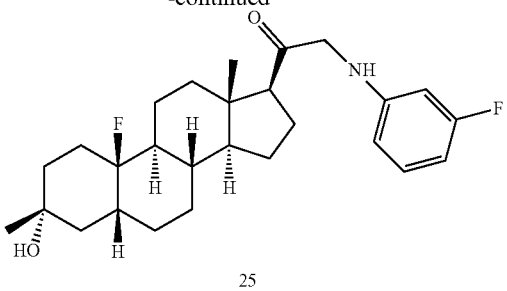

25

In accordance with Example 23, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-((3-fluorophenyl)amino)ethan-1-one (4.5 mg, white solid, yield: 7.0%) was obtained.

MS m/z (ESI): 446.2[M+H]+.

$^1$H NMR (400 MHz, CDCl$_3$) δ 7.15-7.07 (m, 1H), 6.51-6.38 (m, 2H), 6.30 (d, J=11.4 Hz, 1H), 3.98-3.85 (m, 2H), 2.57 (t, J=8.8 Hz, 1H), 2.12-1.64 (m, 18H), 1.38 (s, 3H), 1.30-1.26 (m, 3H), 1.18-1.11 (m, 1H), 0.68 (s, 3H).

Example 26

2-((2,4-Difluorophenyl)amino)-1-((3R,5R,8S,10R,13S,14S,17S)-10-fluoro-3-hydroxy-3,13-dimethylhexadecahydro-1H-cyclopenta[a]phenanthren-17-yl)ethan-1-one

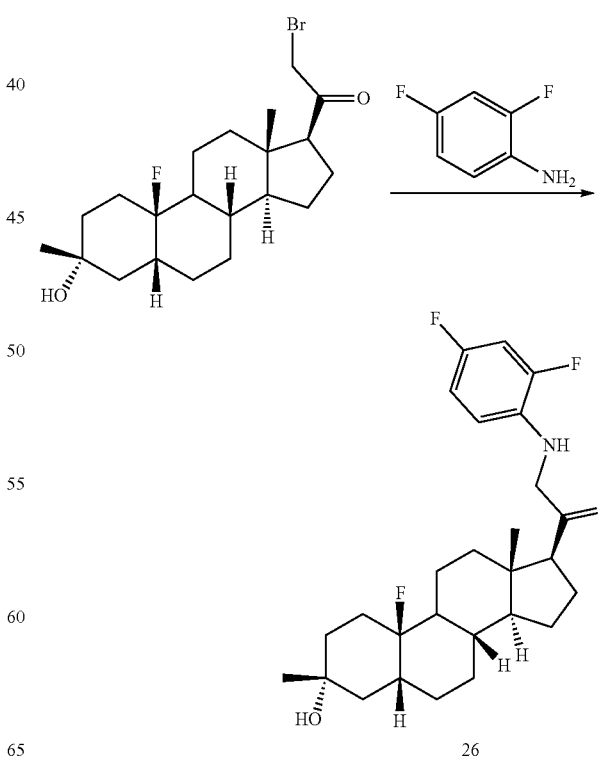

26

2-Bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 0.193 mmol) was dissolved in tetrahydrofuran (3 mL). 2,4-Difluoroaniline (37 mg, 0.289 mmol) and potassium carbonate (53 mg, 0.438 mmol) were added, and the reaction solution was stirred at room temperature for 16 hours. Water (15 mL) was added, and the reaction solution was extracted with ethyl acetate (20 mL×3). The organic phases were combined, washed with saturated saline (15 mL), dried over anhydrous sodium sulfate and filtrated. The filtrate was concentrated under reduced pressure, and the resulting residue was purified by preparative chromatography to obtain a white solid, 2-((2,4-difluorophenyl)amino)-1-((3R,5R,8S,10R,13S,14S,17S)-10-fluoro-3-hydroxy-3,13-dimethylhexadecahydro-1H-cyclopenta[a]phenanthren-17-yl)ethan-1-one (7 mg, yield: 7.8%).

MS m/z (ESI): 464.2[M+H]$^+$.

$^1$H NMR (400 MHz, CDCl$_3$) δ 6.84-6.70 (m, 2H), 6.50-6.45 (m, 1H), 3.98-3.88 (m, 2H), 2.57 (t, J=8.9 Hz, 1H), 2.31-2.19 (m, 1H), 2.10 (m, 1H), 2.04-1.74 (m, 7H), 1.51-1.44 (m, 5H), 1.38 (s, 3H), 1.37-1.20 (m, 8H), 1.13 (m, 2H), 0.69 (s, 3H).

Example 27

5-Fluoro-2-((2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)amino)benzonitrile

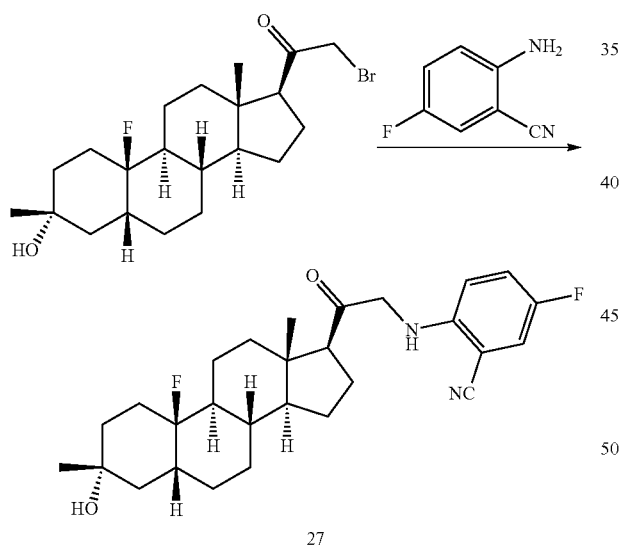

2-Amino-5-fluorobenzonitrile (147 mg, 1.08 mmol) was dissolved in tetrahydrofuran (5 mL) at 0° C. Sodium hydride (29 mg, 0.72 mmol) was added, and the reaction solution was stirred at 0° C. for 40 minutes. A mixed solution of 2-bromo-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (150 mg, 0.36 mmol) and tetrahydrofuran (2 mL) was added, and the reaction solution was stirred at 0° C. for 30 minutes. Water (20 mL) was added, and the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting residue was purified by preparative chromatography to obtain 5-fluoro-2-((2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)amino)benzonitrile (10 mg, white solid, yield: 6%).

MS m/z (ESI): 471.2 [M+H]$^+$.

$^1$H NMR (400 MHz, CDCl$_3$) δ 7.62 (dd, J=9.6, 3.0 Hz, 1H), 7.10-7.01 (m, 1H), 6.62 (dd, J=9.1, 4.5 Hz, 1H), 4.90-4.73 (m, 2H), 2.58 (t, J=8.8 Hz, 1H), 2.28-1.78 (m, 9H), 1.65-1.58 (m, 3H), 1.61-1.44 (m, 4H), 1.38 (s, 3H), 1.31-1.26 (m, 4H), 1.15-1.09 (m, 2H), 0.90-0.86 (m, 2H), 0.73 (s, 3H).

Example 28

1-((3S,5R,8S,9S,10R,13S,14S,17S)-10-Fluoro-3-hydroxy-3,13-dimethylhexadecahydro-1H-cyclopenta[a]phenanthren-17-yl)-2-((3-fluoropyridin-4-yl)amino)ethan-1-one

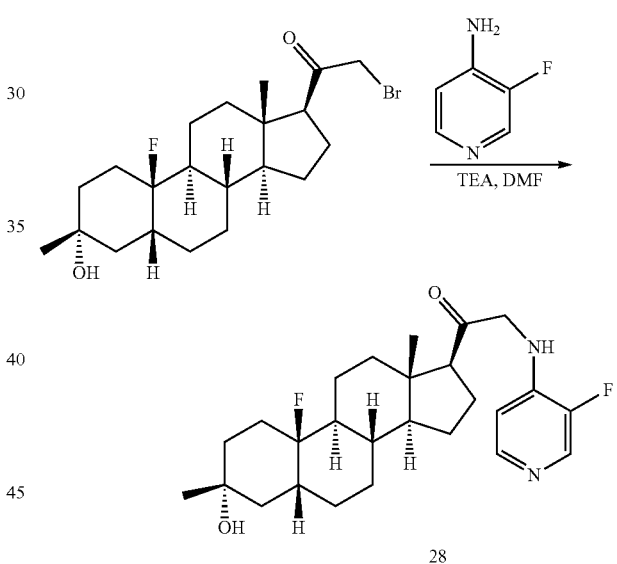

4-Amino-3-fluoropyridine (32.4 mg, 0.28 mmol) and 2-bromo-1-((3S,5R,8S,9S,10R,13S,14S,17S)-10-fluoro-3-hydroxy-3,13-dimethylhexadecahydro-1H-cyclopenta[a]phenanthren-17-yl)ethan-1-one (60 mg, 0.14 mmol) were dissolved in N,N-dimethylformamide (5 mL). Triethylamine (42.5 mg, 0.42 mmol) was added, and the reaction solution was stirred at room temperature overnight. 5 mL of water was added, and the reaction solution was extracted with ethyl acetate (30 mL×3). The organic phase was washed with saturated saline (20 mL) once, dried over anhydrous sodium sulfate and concentrated by rotary evaporation to dryness. The resulting residue was purified by prep-HPLC to obtain the product 1-((3S,5R,8S,9S,10R,13S,14S,17S)-10-fluoro-3-hydroxy-3,13-dimethylhexadecahydro-1H-cyclopenta[a]phenanthren-17-yl)-2-((3-fluoropyridin-4-yl)amino)ethan-1-one (6.1 mg, white solid, yield: 9.7%). MS m/z (ESI): 447.2[M+H]$^+$.

Example 29

1-((3R,5R,8S,9S,10R,13S,14S,17S)-10-Fluoro-3-hydroxy-3,13-dimethylhexadecahydro-1H-cyclopenta[a]phenanthren-17-yl)-2-(pyridazin-4-yloxy)ethan-1-one

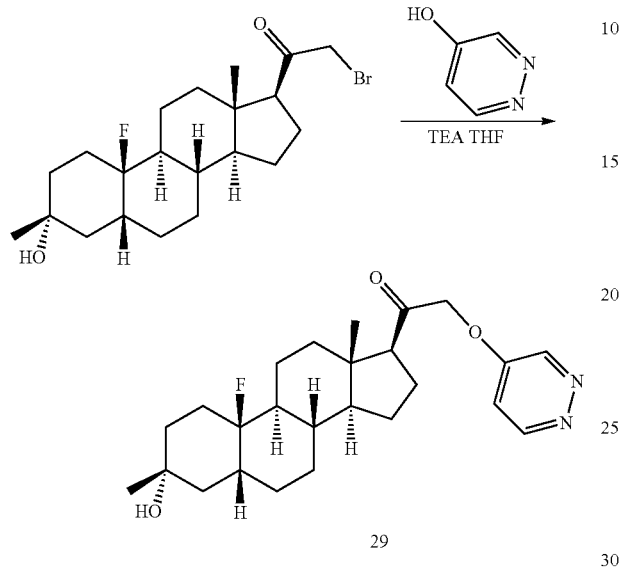

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(pyridazin-4-yloxy)ethan-1-one (19 mg, white solid, yield 30.5%) was obtained.

MS m/z (ESI): 431.2[M+H]$^+$.

$^1$H NMR (400 MHz, CDCl$_3$) δ 7.92 (s, 1H), 7.72 (s, 1H), 6.60 (s, 1H), 4.99-4.73 (m, 2H), 2.67-2.54 (m, 1H), 2.32-1.49 (m, 18H), 1.38 (s, 3H), 1.31-1.01 (m, 4H), 0.71 (s, 3H).

Example 30 and Example 32

5-Fluoro-2-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (30)

5-Fluoro-2-(2-((3R,5R,8S,9S,10R,13S,14S,17R)-10-fluoro-3-hydroxy-3,13-dimethylhexadecahydro-1H-cyclopenta[a]phenanthren-17-yl)-2-oxoethoxy)benzonitrile (32)

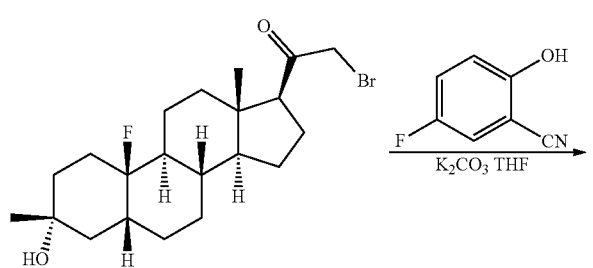

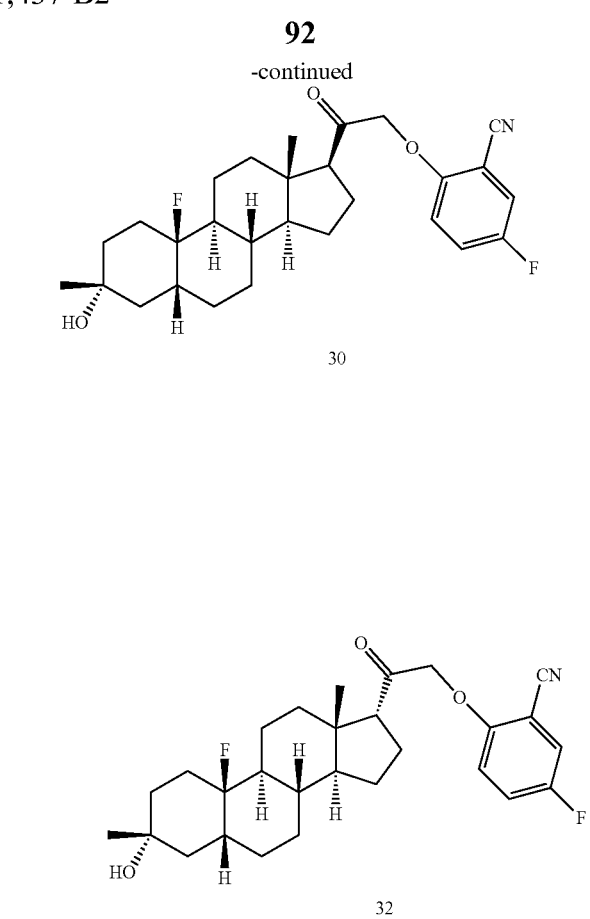

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 5-fluoro-2-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (30) (14.5 mg, white solid, yield: 21.2%) and 5-fluoro-2-(2-((3R,5R,8S,9S,10R,13S,14S,17R)-10-fluoro-3-hydroxy-3,13-dimethylhexadecahydro-1H-cyclopenta[a]phenanthren-17-yl)-2-oxoethoxy)benzonitrile (32) (13.5 mg, white solid, yield: 19.8%) were obtained.

Example 30

$^1$H NMR (400 MHz, CDCl$_3$) δ 7.31 (dd, J=7.4, 3.1 Hz, 1H), 7.25-7.18 (m, 1H), 6.74 (dd, J=9.3, 4.0 Hz, 1H), 4.69-4.53 (m, 2H), 2.90 (t, J=8.7 Hz, 1H), 2.32-1.43 (m, 18H), 1.37 (s, 3H), 1.31-1.03 (m, 4H), 0.70 (s, 3H).

Example 32

$^1$H NMR (400 MHz, CDCl$_3$) δ 7.37-7.32 (m, 1H), 7.25-7.17 (m, 2H), 5.67-5.40 (m, 2H), 3.40 (t, J=8.9 Hz, 1H), 2.44-1.08 (m, 25H), 0.73 (s, 3H).

Example 31

3-Fluoro-4-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile

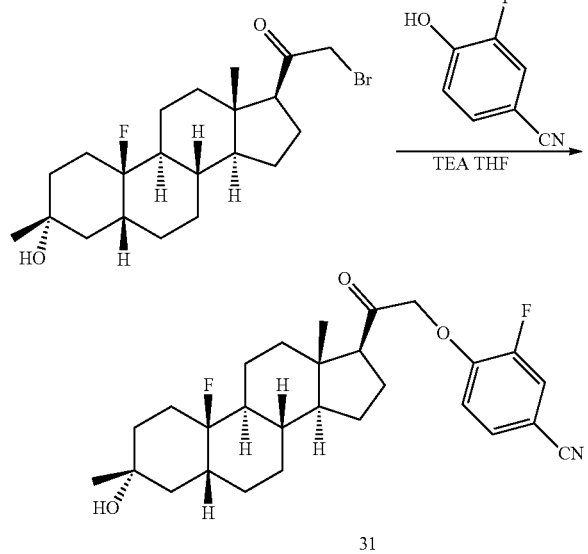

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 3-fluoro-4-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (13 mg, white solid, yield 19.0%) was obtained.

$^1$H NMR (400 MHz, CDCl$_3$) δ 7.50-7.34 (m, 2H), 6.86 (t, J=8.4 Hz, 1H), 4.76-4.59 (m, 2H), 2.79 (t, J=8.9 Hz, 1H), 2.29-1.42 (m, 17H), 1.38 (s, 3H), 1.34-1.07 (m, 5H), 0.70 (s, 3H).

Example 33

4-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethoxy)benzonitrile

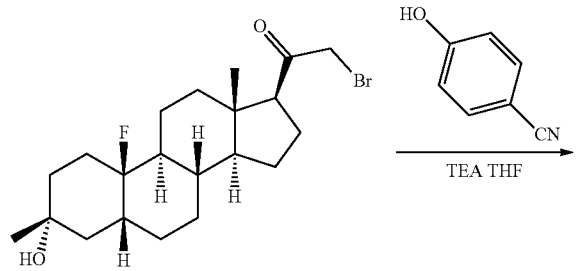

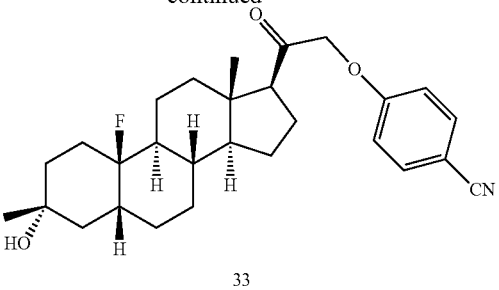

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 4-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (27.5 mg, white solid, yield: 41.9%) was obtained.

$^1$H NMR (400 MHz, CDCl$_3$) δ 7.60 (d, J=8.8 Hz, 2H), 6.92 (d, J=8.8 Hz, 2H), 4.65-4.52 (m, 2H), 2.77 (t, J=8.7 Hz, 1H), 2.24-1.49 (m, 18H), 1.38 (s, 3H), 1.32-1.25 (m, 3H), 1.18-1.06 (m, 1H), 0.71 (s, 3H).

Example 34

4-Fluoro-3-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile

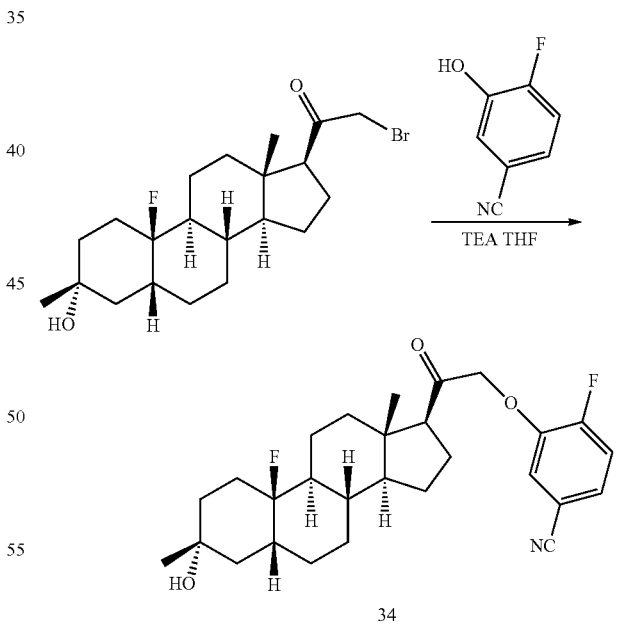

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 4-fluoro-3-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (32 mg, white solid, yield: 46.9%) was obtained.

$^1$H NMR (400 MHz, CDCl$_3$) δ 7.36-7.27 (m, 1H), 7.20 (dd, J=10.6, 8.4 Hz, 1H), 7.11 (dd, J=7.6, 1.9 Hz, 1H), 4.76-4.51 (m, 2H), 2.77 (t, J=8.9 Hz, 1H), 2.24-1.51 (m, 18H), 1.38 (s, 3H), 1.32-1.23 (m, 3H), 1.19-1.06 (m, 1H), 0.71 (s, 3H).

Example 35

2-Fluoro-4-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile

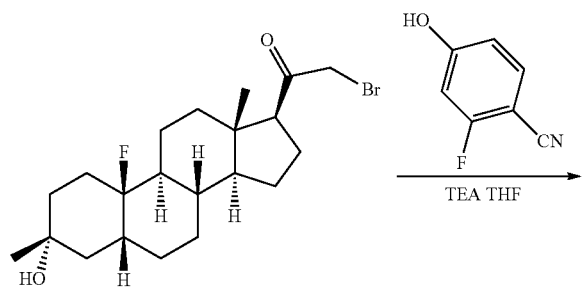

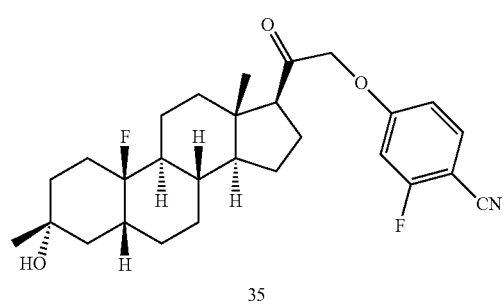

35

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 2-fluoro-4-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)benzonitrile (23 mg, white solid, yield: 33.7%) was obtained.

$^1$H NMR (400 MHz, CDCl$_3$) δ 7.36-7.27 (m, 1H), 7.20 (dd, J=10.6, 8.4 Hz, 1H), 7.11 (dd, J=7.6, 1.9 Hz, 1H), 4.76-4.51 (m, 2H), 2.77 (t, J=8.9 Hz, 1H), 2.24-1.51 (m, 18H), 1.38 (s, 3H), 1.32-1.23 (m, 3H), 1.19-1.06 (m, 1H), 0.71 (s, 3H).

Example 36

2-(2,4-Difluorophenoxy)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one

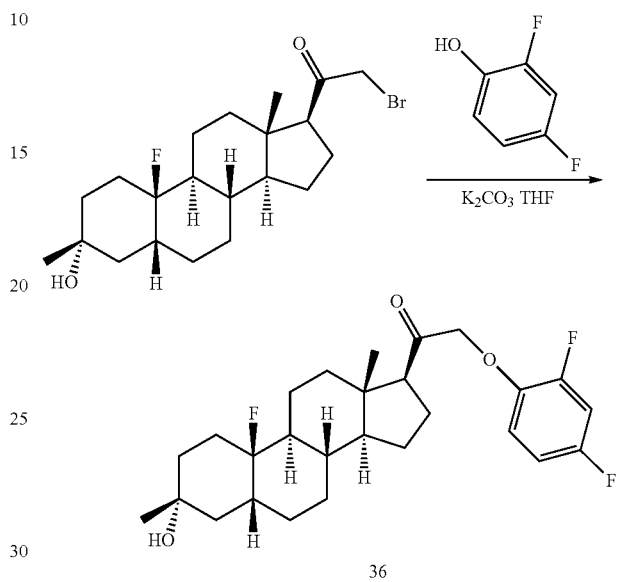

36

In accordance with Step 2 of Example 2, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, the product 2-(2,4-difluorophenoxy)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (16.4 mg, white solid, yield: 24.4%) was obtained.

$^1$H NMR (400 MHz, Chloroform-d) δ 6.95-6.83 (m, 2H), 6.82-6.69 (m, 1H), 4.67-4.45 (m, 2H), 2.81 (t, J=8.8 Hz, 1H), 2.36-2.16 (m, 1H), 2.14-2.04 (m, 1H), 2.03-1.78 (m, 4H), 1.76-1.69 (m, 1H), 1.65-1.44 (m, 11H), 1.37 (s, 3H), 1.32-1.21 (m, 3H), 1.19-0.99 (m, 1H), 0.69 (s, 3H).

Example 37

2-(4-Chloro-1H-pyrazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one

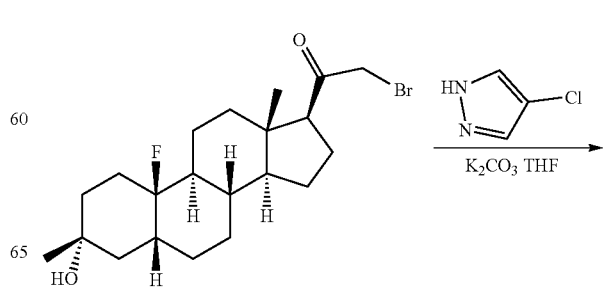

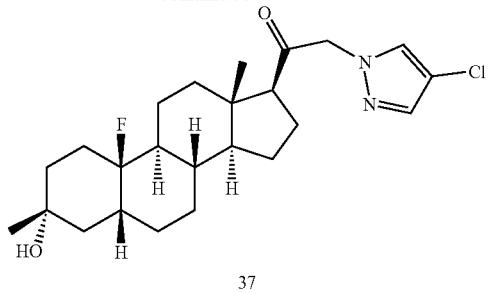

37

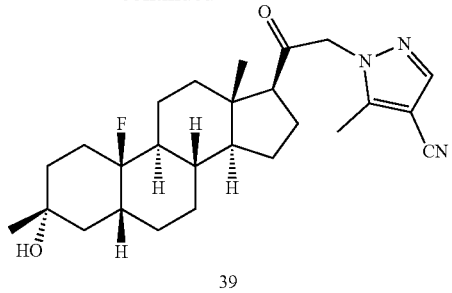

39

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 2-(4-chloro-1H-pyrazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (22 mg, white solid, yield: 34.9%) was obtained.

MS m/z (ESI): 437.2[M+H]$^+$.

$^1$H NMR (400 MHz, CDCl$_3$) δ 7.46 (s, 1H), 7.42 (s, 1H), 5.04-4.62 (m, 2H), 2.57 (t, J=8.8 Hz, 1H), 2.31-1.45 (m, 18H), 1.38 (s, 3H), 1.33-1.23 (m, 3H), 1.18-1.05 (m, 1H), 0.70 (s, 3H).

Example 38 and Example 39

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-3-methyl-1H-pyrazole-4-carbonitrile (38)

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-5-methyl-1H-pyrazole-4-carbonitrile (39)

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-3-methyl-1H-pyrazole-4-carbonitrile (38) (16.5 mg, white solid, yield: 19.5%) and 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-5-methyl-1H-pyrazole-4-carbonitrile (39) (9.5 mg, white solid, yield: 11%) were obtained.

Example 38

MS m/z (ESI): 442.2[M+H]$^+$.

$^1$H NMR (400 MHz, CDCl$_3$) δ 7.75 (s, 1H), 4.96-4.79 (m, 2H), 2.65-2.54 (m, 1H), 2.38 (s, 3H), 2.17-1.58 (m, 18H), 1.38 (s, 3H), 1.33-1.24 (m, 3H), 1.18-1.06 (m, 1H), 0.70 (s, 3H).

Example 39

MS m/z (ESI): 442.2[M+H]$^+$.

$^1$H NMR (400 MHz, CDCl$_3$) δ 7.71 (s, 1H), 4.86-4.80 (m, 2H), 2.61-2.54 (m, 1H), 2.33 (s, 3H), 2.23-1.55 (m, 18H), 1.38 (s, 3H), 1.30-1.27 (m, 3H), 1.15-1.11 (m, 1H), 0.71 (s, 3H).

Example 40

3-Cyclopropyl-1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carbonitrile

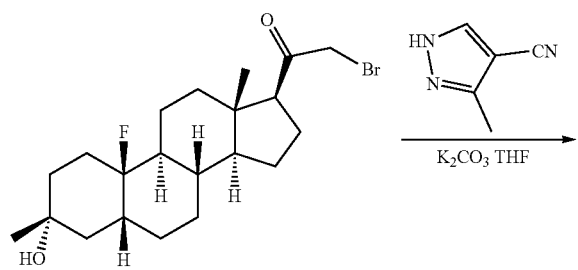

38

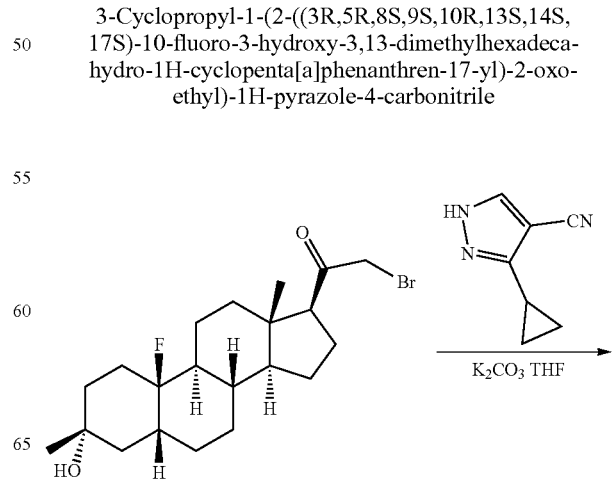

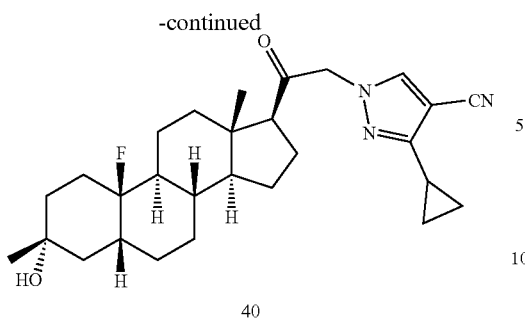

40

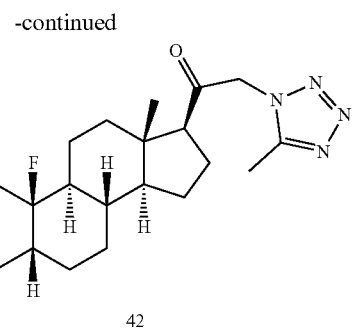

42

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 3-cyclopropyl-1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carbonitrile (15 mg, white solid, yield: 22.2%) was obtained.

MS m/z (ESI): 468.2[M+H]$^+$.

$^1$H NMR (400 MHz, CDCl$_3$) δ 7.72 (s, 1H), 4.92-4.72 (m, 2H), 2.57 (t, J=8.8 Hz, 1H), 2.26-1.40 (m, 19H), 1.38 (s, 3H), 1.37-1.05 (m, 4H), 1.05-0.91 (m, 4H), 0.69 (s, 3H).

Example 41 and Example 42

1-((3R,5R,8S,9S,10R,13S,14S,17S)-10-Fluoro-3-hydroxy-3,13-dimethylhexadecahydro-1H-cyclopenta[a]phenanthren-17-yl)-2-(5-methyl-2H-tetrazol-2-yl)ethan-1-one (41)

1-((3R,5R,8S,9S,10R,13S,14S,17S)-10-Fluoro-3-hydroxy-3,13-dimethylhexadecahydro-1H-cyclopenta[a]phenanthren-17-yl)-2-(5-methyl-1H-tetrazol-1-yl)ethan-1-one (42)

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-((3R,5R,8S,9S,10R,13S,14S,17S)-10-fluoro-3-hydroxy-3,13-dimethylhexadecahydro-1H-cyclopenta[a]phenanthren-17-yl)-2-(5-methyl-2H-tetrazol-2-yl)ethan-1-one (41) (23 mg, white solid, yield: 22.8%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(5-methyl-1H-tetrazol-1-yl)ethan-1-one (42) (6.5 mg, white solid, yield: 6.5%) were obtained.

Example 41

MS m/z (ESI): 419.2[M+H]$^+$.

$^1$H NMR (400 MHz, CDCl$_3$) δ 5.46-5.27 (m, 2H), 2.63 (d, J=8.5 Hz, 1H), 2.57 (s, 3H), 2.31-1.46 (m, 18H), 1.38 (s, 3H), 1.35-1.03 (m, 4H), 0.75 (s, 3H).

Example 42

MS m/z (ESI): 419.2[M+H]$^+$.

$^1$H NMR (400 MHz, CDCl$_3$) δ 5.19-5.02 (m, 2H), 2.66 (t, J=8.5 Hz, 1H), 2.48 (s, 3H), 2.30-1.48 (m, 18H), 1.39 (s, 3H), 1.33-1.07 (m, 4H), 0.72 (s, 3H).

Example 43

1-((3R,5R,8S,9S,10R,13S,14S,17S)-10-Fluoro-3-hydroxy-3,13-dimethylhexadecahydro-1H-cyclopenta[a]phenanthren-17-yl)-2-(thiazol-2-ylamino)ethan-1-one

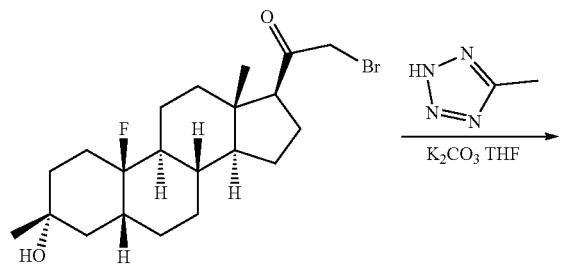

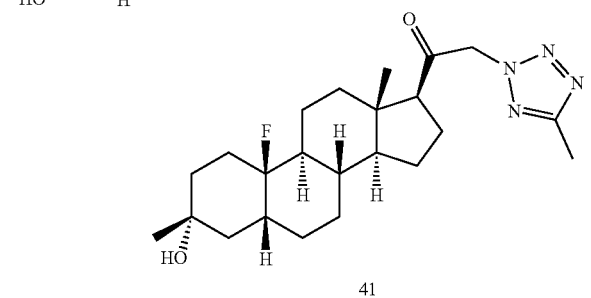

41

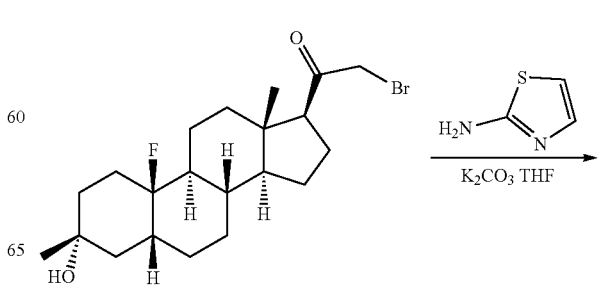

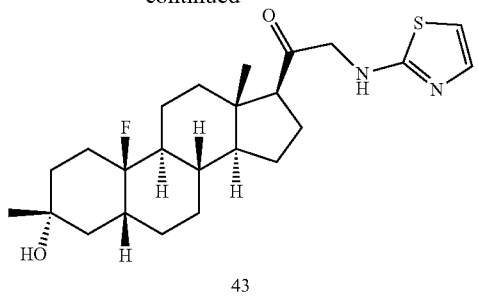

43

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(thiazol-2-ylamino)ethan-1-one (13 mg, white solid, yield: 20.7%) was obtained.

MS m/z (ESI): 435.2[M+H]+.

$^1$H NMR (400 MHz, CDCl$_3$) δ 6.37 (d, J=4.9 Hz, 1H), 5.92 (d, J=4.9 Hz, 1H), 4.70-4.46 (m, 2H), 2.68 (t, J=8.9 Hz, 1H), 2.32-1.46 (m, 17H), 1.37 (s, 3H), 1.35-1.20 (m, 4H), 1.16-1.06 (m, 1H), 0.70 (s, 3H).

Example 44

1-((3R,5R,8S,9S,10R,13S,14S,17S)-10-Fluoro-3-hydroxy-3,13-dimethylhexadecahydro-1H-cyclopenta[a]phenanthren-17-yl)-2-((1-methyl-1H-pyrazol-4-yl)amino)ethan-1-one

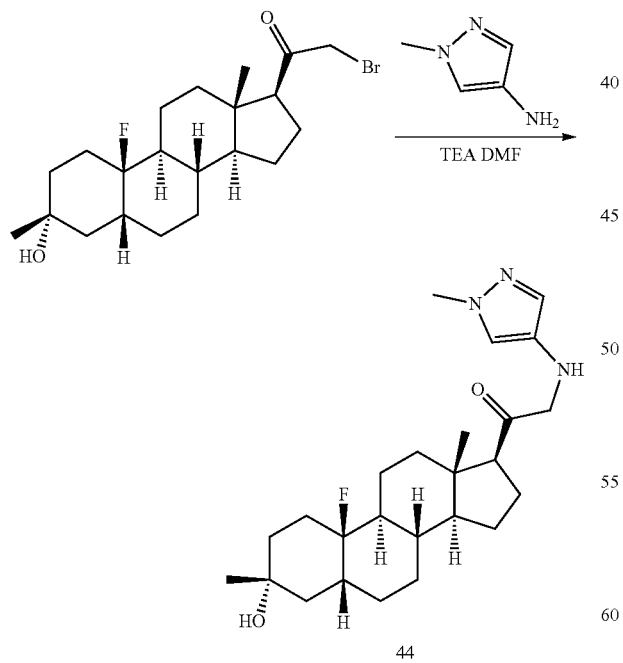

44

In accordance with Example 23, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-((1-methyl-1H-pyrazol-4-yl)amino)ethan-1-one (8.2 mg, white solid, yield: 13.2%) was obtained.

MS m/z (ESI): 432.3[M+H]+.

$^1$H NMR (400 MHz, CDCl$_3$) δ 7.30 (s, 1H), 7.26 (s, 1H), 3.94-3.88 (m, 2H), 3.83 (s, 3H), 2.52 (t, J=8.7 Hz, 1H), 2.27-1.46 (m, 16H), 1.37 (s, 3H), 1.33-1.05 (m, 6H), 0.65 (s, 3H).

Example 45

1-((3R,5R,8S,9S,10R,13S,14S,17S)-10-Fluoro-3-hydroxy-3,13-dimethylhexadecahydro-1H-cyclopenta[a]phenanthren-17-yl)-2-(isoxazol-4-ylamino)ethan-1-one

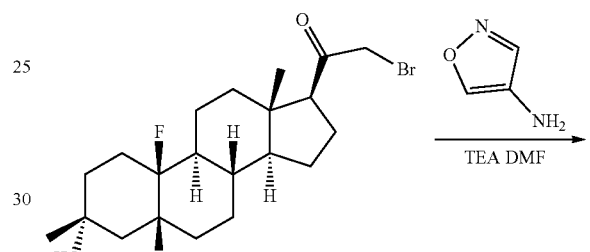

45

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(isoxazol-4-ylamino)ethan-1-one (8.5 mg, white solid, yield 14.0%) was obtained.

MS m/z (ESI): 419.2[M+H]+.

$^1$H NMR (400 MHz, CDCl$_3$) δ 8.08 (s, 1H), 7.91 (s, 1H), 3.85-3.65 (m, 2H), 2.53 (t, J=8.7 Hz, 1H), 2.23-1.72 (m, 8H), 1.51-1.13 (m, 17H), 0.67 (s, 3H).

Example 46, Example 47 and Example 48

1-((3R,5R,8S,9S,10R,13S,14S,17S)-10-Fluoro-3-hydroxy-3,13-dimethylhexadecahydro-1H-cyclopenta[a]phenanthren-17-yl)-2-(5-methoxy-2H-benzo[d][1,2,3]triazol-2-yl)ethan-1-one (46)

1-((3R,5R,8S,9S,10R,13S,14S,17S)-10-Fluoro-3-hydroxy-3,13-dimethylhexadecahydro-1H-cyclopenta[a]phenanthren-17-yl)-2-(6-methoxy-1H-benzo[d][1,2,3]triazol-1-yl)ethan-1-one (47)

1-((3R,5R,8S,9S,10R,13S,14S,17S)-10-Fluoro-3-hydroxy-3,13-dimethylhexadecahydro-1H-cyclopenta[a]phenanthren-17-yl)-2-(5-methoxy-1H-benzo[d][1,2,3]triazol-1-yl)ethan-1-one (48)

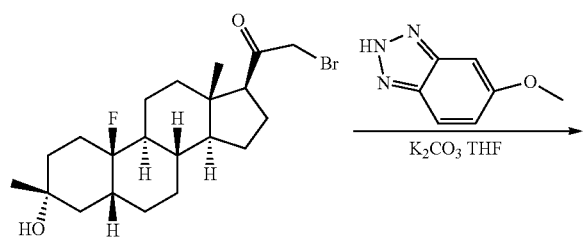

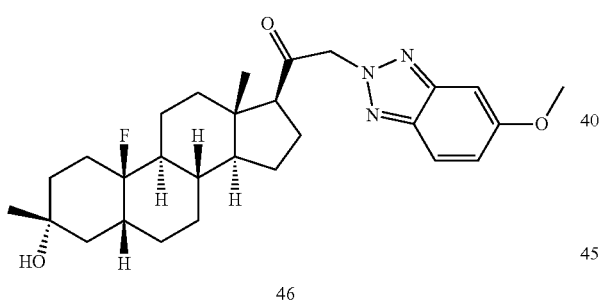

46

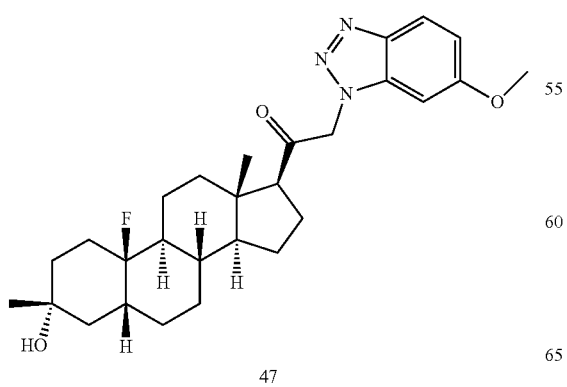

47

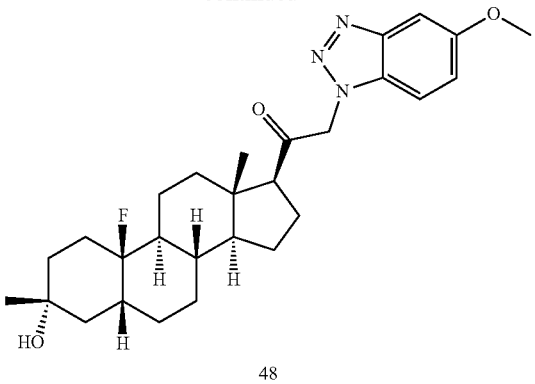

48

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the products 1-((3R,5R,8S,9S,10R,13S,14S,17S)-10-fluoro-3-hydroxy-3,13-dimethylhexadecahydro-1H-cyclopenta[a]phenanthren-17-yl)-2-(5-methoxy-2H-benzo[d][1,2,3]triazol-2-yl)ethan-1-one (46) (13.5 mg, white solid, yield: 11.6%), 1-((3R,5R,8S,9S,10R,13S,14S,17S)-10-fluoro-3-hydroxy-3,13-dimethylhexadecahydro-1H-cyclopenta[a]phenanthren-17-yl)-2-(6-methoxy-1H-benzo[d][1,2,3]triazol-1-yl)ethan-1-one (47) (14 mg, white solid, yield: 12.0%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(5-methoxy-1H-benzo[d][1,2,3]triazol-1-yl)ethan-1-one (48) (14 mg, white solid, yield: 12.0%) were obtained.

Example 46

MS m/z (ESI): 484.2[M+H]$^+$.

$^1$H NMR (400 MHz, CDCl$_3$) δ 7.75-7.70 (m, 1H), 7.11-7.04 (m, 2H), 5.49-5.40 (m, 2H), 3.88 (s, 3H), 2.62 (t, J=8.8 Hz, 1H), 2.30-1.46 (m, 18H), 1.38 (s, 3H), 1.34-1.10 (m, 4H), 0.78 (s, 3H).

Example 47

MS m/z (ESI): 484.2[M+H]$^+$.

$^1$H NMR (400 MHz, CDCl$_3$) δ 7.39 (d, J=2.2 Hz, 1H), 7.22 (d, J=9.0 Hz, 1H), 7.15 (dd, J=9.0, 2.2 Hz, 1H), 5.39-5.35 (m, 2H), 3.90 (s, 3H), 2.70-2.64 (m, 1H), 2.26-1.45 (m, 18H), 1.38 (s, 3H), 1.32-1.12 (m, 4H), 0.76 (s, 3H).

Example 48

MS m/z (ESI): 484.2[M+H]$^+$.

$^1$H NMR (400 MHz, CDCl$_3$) δ 7.92 (d, J=9.1 Hz, 1H), 7.01 (dd, J=9.1, 2.2 Hz, 1H), 6.60 (d, J=2.2 Hz, 1H), 5.35-5.31 (m, 2H), 3.87 (s, 3H), 2.73-2.65 (m, 1H), 2.26-1.46 (m, 18H), 1.38 (s, 3H), 1.34-1.10 (m, 4H), 0.77 (s, 3H).

Example 49

1-((3R,5R,8S,9S,10R,13S,14S,17S)-10-Fluoro-3-hydroxy-3,13-dimethylhexadecahydro-1H-cyclopenta[a]phenanthren-17-yl)-2-(pyrimidin-5-yloxy)ethan-1-one

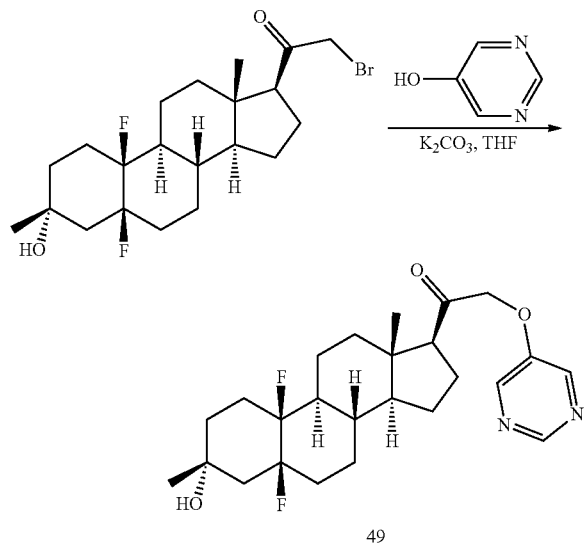

49

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(pyrimidin-5-yloxy)ethan-1-one (10.3 mg, white solid, yield: 20.0%) was obtained.

MS m/z (ESI): 431.2[M+H]$^+$.

$^1$H NMR (400 MHz, CDCl$_3$) δ 8.92 (s, 1H), 8.44 (s, 2H), 4.78-4.63 (m, 2H), 2.75-2.70 (m, 1H), 2.29-2.20 (m, 1H), 2.15-2.05 (m, 3H), 2.02-1.93 (m, 3H), 1.92-1.82 (m, 1H), 1.81-1.73 (m, 2H), 1.62-1.60 (m, 2H), 1.59-1.43 (m, 6H), 1.38 (s, 3H), 1.35-1.25 (m, 3H), 1.20-1.07 (m, 1H), 0.72 (s, 3H).

Example 50

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-1H-pyrazole-3,5-dicarbonitrile

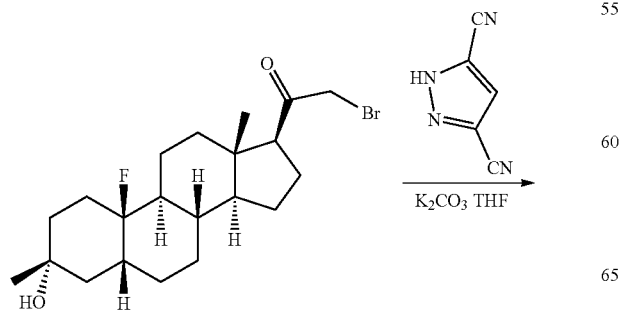

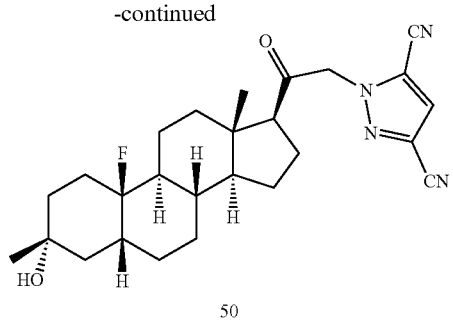

50

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-3,5-dicarbonitrile (26 mg, white solid, yield: 39.7%) was obtained.

MS m/z (ESI): 451.2[M−H]$^-$.

$^1$H NMR (400 MHz, CDCl$_3$) δ 7.21 (s, 1H), 5.19-5.14 (m, 2H), 2.63 (t, J=8.9 Hz, 1H), 2.29-1.49 (m, 18H), 1.38 (s, 3H), 1.32-1.30 (m, 3H), 1.20-1.10 (m, 1H), 0.75 (s, 3H).

Example 51

3-Chloro-1-(2-((3R,5R,8S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carbonitrile

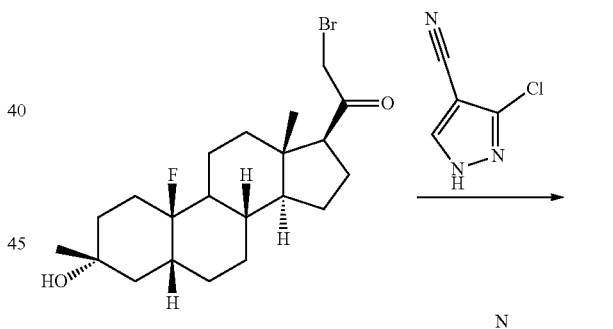

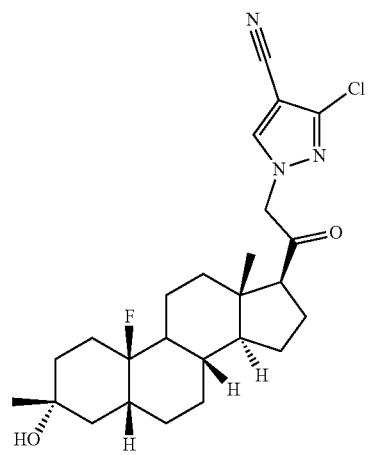

51

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 3-chloro-1-(2-((3R,5R,8S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carbonitrile (12 mg, white solid, yield: 22%) was obtained.

MS m/z (ESI): 462.2 [M+H]⁺.

¹H NMR (400 MHz, CDCl₃) δ 7.82 (s, 1H), 4.98-4.85 (m, 2H), 2.58 (t, J=8.5 Hz, 1H), 2.26-2.18 (m, 1H), 2.15-1.75 (m, 7H), 1.66-1.45 (m, 10H), 1.40-1.25 (m, 7H), 1.15-1.09 (m, 1H), 0.70 (s, 3H).

Example 52

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(oxazol-2-yl)-1H-pyrazol-1-yl)ethan-1-one

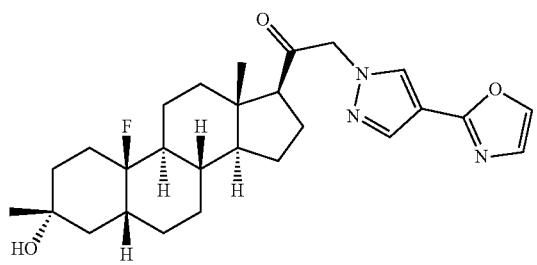

Step 1: Preparation of 2-(1H-pyrazol-4-yl)oxazole

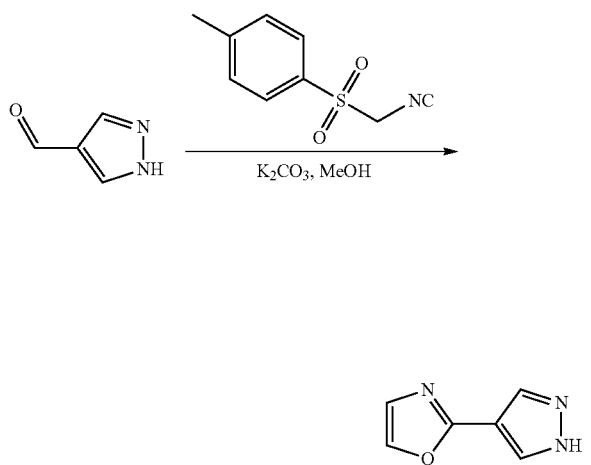

A mixture of 1H-pyrazole-4-carbaldehyde (0.8 g, 8.33 mmol), 1-((isocyanomethyl)sulfonyl)-4-methylbenzene (1.79 g, 9.16 mmol), potassium carbonate (2.53 g, 18.33 mmol) and methanol (20 mL) were stirred at 70° C. for 16 hours. The reaction solution was concentrated under reduced pressure to dryness, and the resulting residue was purified by column chromatography (dichloromethane/methanol=10:1) to obtain a white solid, 2-(1H-pyrazol-4-yl)oxazole (160 mg, yield: 14%).

MS m/z (ESI): 136.2 [M+H]⁺.

¹H NMR (400 MHz, DMSO) δ 13.19 (s, 1H), 8.30 (s, 1H), 8.15 (s, 1H), 7.83 (s, 1H), 7.26 (s, 1H).

Step 2: 1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(oxazol-2-yl)-1H-pyrazol-1-yl)ethan-1-one

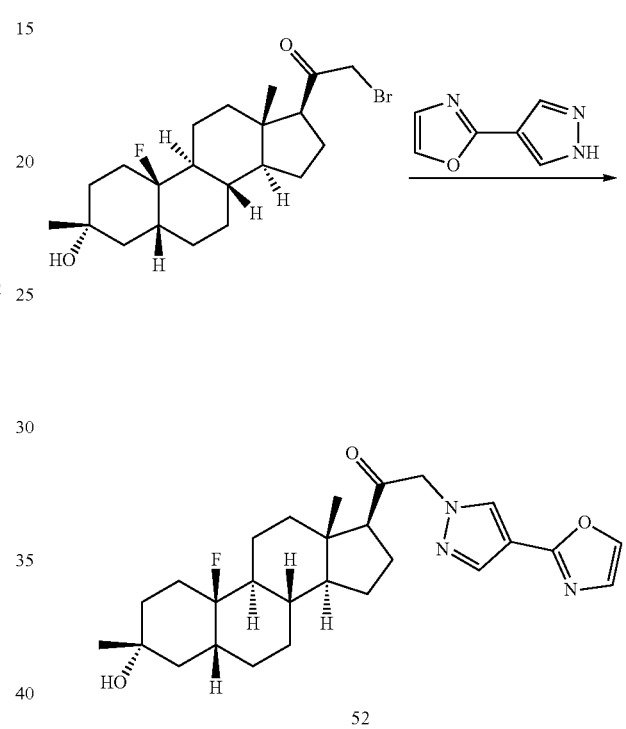

A mixture of 2-bromo-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (60 mg, 0.14 mmol), 2-(1H-pyrazol-4-yl)oxazole (28 mg, 0.21 mmol), potassium carbonate (39 mg, 0.28 mmol) and tetrahydrofuran (3 mL) were stirred at room temperature for 16 hours. The reaction solution was concentrated under reduced pressure to dryness, and the resulting residue was purified by preparative chromatography to obtain 1-((3R,5R,8S,9S,10R,13S,14S,17S)-10-fluoro-3-hydroxy-3,13-dimethylhexadecahydro-1H-cyclopenta[a]phenanthren-17-yl)-2-(4-(oxazol-2-yl)-1H-pyrazol-1-yl)ethan-1-one (13 mg, white solid, yield: 20%).

MS m/z (ESI): 470.2 [M+H]⁺.

¹H NMR (400 MHz, CDCl₃) δ 7.85 (s, 1H), 7.76 (s, 1H), 7.69 (s, 1H), 7.13 (s, 1H), 4.99-4.89 (m, 2H), 2.61 (t, J=8.8 Hz, 1H), 2.28-2.18 (m, 1H), 2.15-2.08 (m, 2H), 2.03-1.82 (m, 4H), 1.78-1.76 (m, 2H), 1.64-1.62 (m, 3H), 1.52-1.43 (m, 5H), 1.38 (s, 3H), 1.31-1.26 (m, 4H), 1.16-1.11 (m, 2H), 0.73 (s, 3H).

Example 53 and Example 54

1-((3R,5R,8S,9S,10R,13S,14S,17S)-10-Fluoro-3-hydroxy-3,13-dimethylhexadecahydro-1H-cyclopenta[a]phenanthren-17-yl)-2-(6-(2-hydroxypropan-2-yl)-1H-benzo[d]imidazol-1-yl)ethan-1-one (53)

1-((3R,5R,8S,9S,10R,13S,14S,17S)-10-Fluoro-3-hydroxy-3,13-dimethylhexadecahydro-1H-cyclopenta[a]phenanthren-17-yl)-2-(5-(2-hydroxypropan-2-yl)-1H-benzo[d]imidazol-1-yl)ethan-1-one (54)

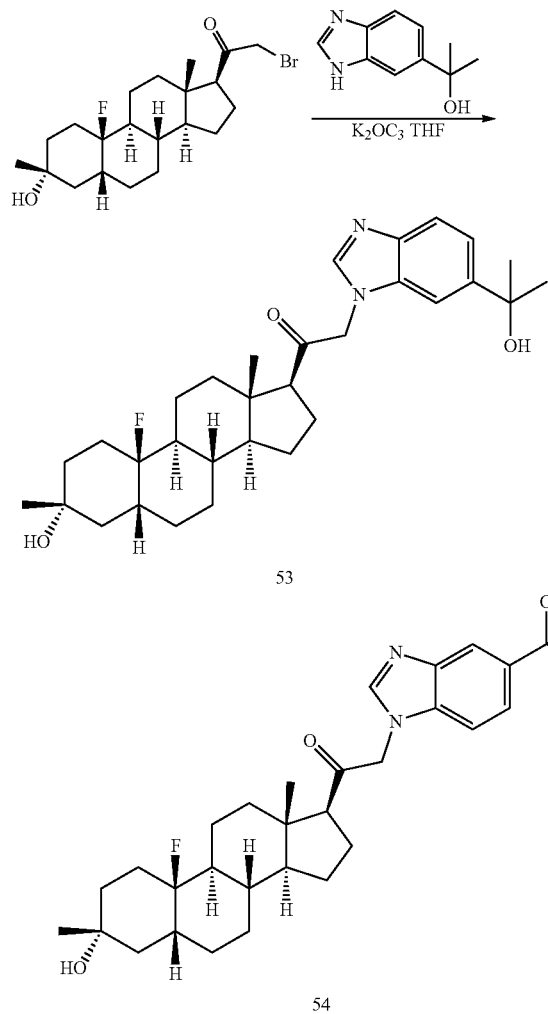

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, 1-((3R,5R,8S,9S,10R,13S,14S,17S)-10-fluoro-3-hydroxy-3,13-dimethylhexadecahydro-1H-cyclopenta[a]phenanthren-17-yl)-2-(6-(2-hydroxypropan-2-yl)-1H-benzo[d]imidazol-1-yl)ethan-1-one (53) (20 mg, white solid, yield: 27.1%) and 1-((3R,5R,8S,9S,10R,13S,14S,17S)-10-fluoro-3-hydroxy-3,13-dimethylhexadecahydro-1H-cyclopenta[a]phenanthren-17-yl)-2-(5-(2-hydroxypropan-2-yl)-1H-benzo[d]imidazol-1-yl)ethan-1-one (54) (15 mg, white solid, yield: 20.3%) were obtained.

Example 53

MS m/z (ESI): 511.3 [M+H]$^+$.

$^1$H NMR (400 MHz, Chloroform-d) δ 7.93 (s, 1H), 7.87 (s, 1H), 7.51 (d, J=8.5 Hz, 1H), 7.14 (d, J=8.5 Hz, 1H), 4.96-4.84 (m, 2H), 2.64 (t, J=8.7 Hz, 1H), 2.31-2.17 (m, 1H), 2.16-2.06 (m, 2H), 2.04-1.93 (m, 2H), 1.92-1.75 (m, 2H), 1.71-1.43 (m, 15H), 1.39 (s, 3H), 1.35-1.20 (m, 5H), 1.18-1.05 (m, 1H), 0.75 (s, 3H).

Example 54

MS m/z (ESI): 511.3 [M+H]$^+$.

$^1$H NMR (400 MHz, Chloroform-d) δ 8.19 (s, 1H), 7.77 (d, J=8.5 Hz, 1H), 7.46 (s, 1H), 7.39 (d, J=8.1 Hz, 1H), 5.12-4.89 (m, 2H), 2.68 (t, J=8.2 Hz, 1H), 2.31-2.06 (m, 7H), 2.04-1.47 (m, 15H), 1.38 (s, 3H), 1.35-1.21 (m, 5H), 1.20-1.02 (m, 1H), 0.75 (s, 3H).

Example 55

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(methylthio)-1H-pyrazol-1-yl)ethan-1-one

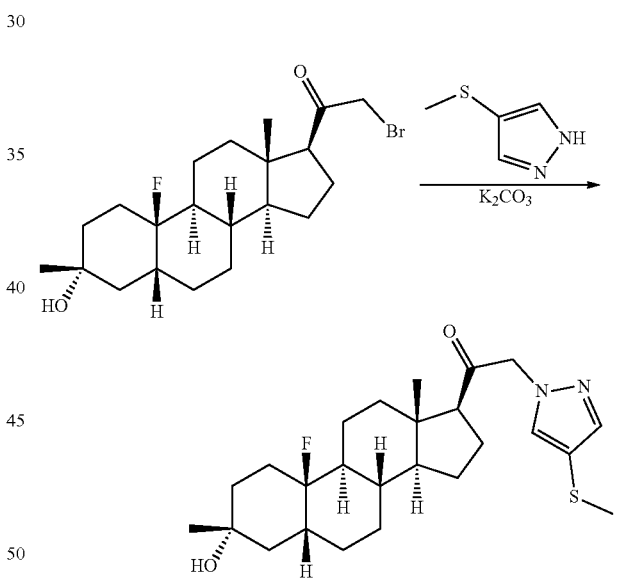

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(4-(methylthio)-1H-pyrazol-1-yl)ethan-1-one (25 mg, white solid, yield: 38%) was obtained.

MS m/z (ESI): 449.2 [M+H]$^+$.

$^1$H NMR (400 MHz, CDCl$_3$) δ 7.53 (s, 1H), 7.43 (s, 1H), 4.95-4.85 (m, 2H), 2.58 (t, J=8.9 Hz, 1H), 2.35 (s, 3H), 2.25-2.17 (m, 1H), 2.10 (d, J=11.4 Hz, 2H), 2.02-1.82 (m, 4H), 1.77-1.74 (m, 2H), 1.68-1.42 (m, 9H), 1.38 (s, 3H), 1.35-1.21 (m, 4H), 1.17-1.04 (m, 1H), 0.71 (s, 3H).

Example 56

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(methylsulfinyl)-1H-pyrazol-1-yl)ethan-1-one

Example 57

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(methylsulfonyl)-1H-pyrazol-1-yl) ethan-1-one

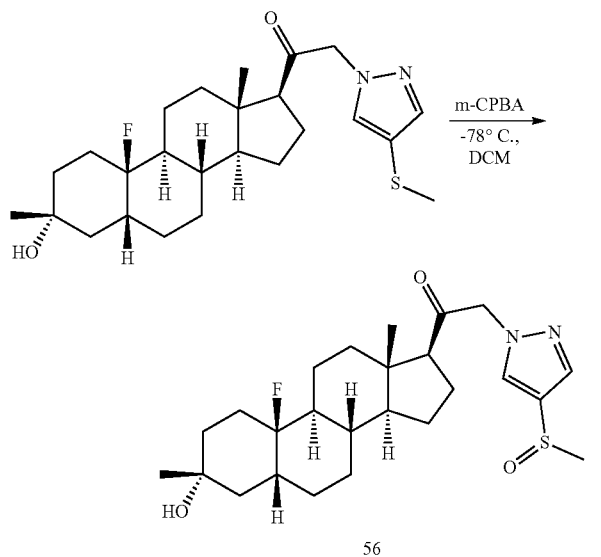

56

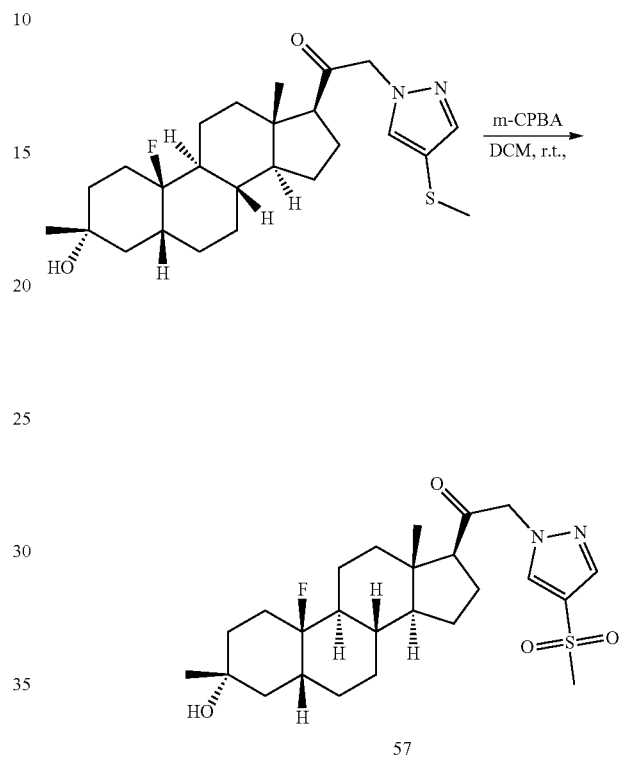

57

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(methylthio)-1H-pyrazol-1-yl)ethan-1-one (35 mg, 0.078 mmol) was dissolved in dichloromethane (3 mL). m-Chloroperoxybenzoic acid (17 mg, 0.0858 mmol) was added, and the reaction solution was stirred at −78° C. for 2 hours. The reaction was quenched with saturated sodium sulfite solution, and the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting residue was purified by preparative chromatography to obtain a white solid, 1-((3R,5R,8S,9S,10R,13S,14S,17S)-10-fluoro-3-hydroxy-3,13-dimethylhexadecahydro-1H-cyclopenta[a]phenanthren-17-yl)-2-(4-(methylsulfinyl)-1H-pyrazol-1-yl)ethan-1-one (25 mg, white solid, yield: 69%).

MS m/z (ESI): 465.2 [M+H]$^+$.

$^1$H NMR (400 MHz, CDCl$_3$) δ 7.81 (d, J=4.6 Hz, 2H), 4.96-4.85 (m, 2H), 2.90 (s, 3H), 2.61 (t, J=8.7 Hz, 1H), 2.27-2.17 (m, 1H), 2.13-2.07 (m, 2H), 2.04-1.73 (m, 4H), 1.66-1.62 (m, 4H), 1.50-1.48 (m, 5H), 1.38 (s, 3H), 1.33-1.22 (m, 5H), 1.14-1.11 (m, 2H), 0.71 (s, 3H).

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-(methylthio)-1H-pyrazol-1-yl)ethan-1-one (15 mg, 0.033 mmol) was dissolved in dichloromethane (3 mL). T m-Chloroperoxybenzoic acid (17 mg, 0.1 mmol) was added, and the reaction solution was stirred at room temperature for 6 hours. The reaction solution was concentrated under reduced pressure to dryness, and the resulting residue was purified by preparative chromatography to obtain 1-((3R,5R,8S,9S,10R,13S,14S,17S)-10-fluoro-3-hydroxy-3,13-dimethylhexadecahydro-1H-cyclopenta[a]phenanthren-17-yl)-2-(4-(methylsulfonyl)-1H-pyrazol-1-yl)ethan-1-one (10 mg, white solid, yield: 63%).

MS m/z (ESI): 481.2 [M+H]$^+$.

$^1$H NMR (400 MHz, CDCl$_3$) δ 7.93 (s, 1H), 7.87 (s, 1H), 4.99-4.90 (m, 2H), 3.13 (s, 3H), 2.62 (t, J=8.7 Hz, 1H), 2.24-2.20 (m, 1H), 2.12-2.09 (m, 2H), 2.03-1.74 (m, 5H), 1.66-1.63 (m, 4H), 1.53-1.42 (m, 6H), 1.38 (s, 3H), 1.28-1.26 (m, 3H), 1.15 (m, 1H), 0.89-0.86 (m, 1H), 0.71 (s, 3H).

Example 58

1-((3R,5R,8S,9S,10R,13S,14S,17S)-10-Fluoro-3-hydroxy-3,13-dimethylhexadecahydro-1H-cyclopenta[a]phenanthren-17-yl)-2-(4-nitro-1H-pyrazol-1-yl)ethan-1-one

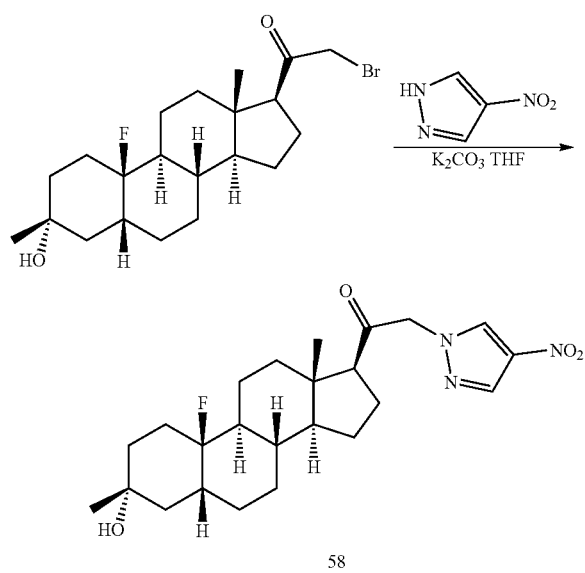

58

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(4-nitro-1H-pyrazol-1-yl)ethan-1-one (39 mg, white solid, yield: 60.3%) was obtained.

MS m/z (ESI): 448.2[M+H]$^+$.

$^1$H NMR (400 MHz, CDCl$_3$) δ 8.18 (s, 1H), 8.08 (s, 1H), 5.08-4.81 (m, 2H), 2.62 (t, J=8.7 Hz, 1H), 2.30-1.46 (m, 16H), 1.38 (s, 3H), 1.34-1.04 (m, 6H), 0.71 (s, 3H).

Example 59

Ethyl 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carboxylate

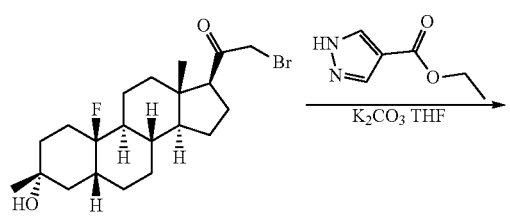

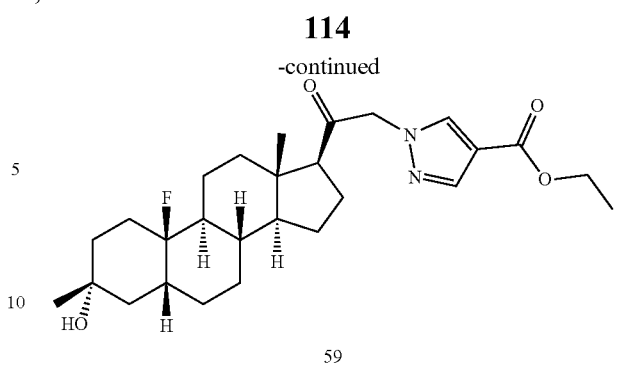

59

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product ethyl 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-1H-pyrazole-4-carboxylate (32 mg, white solid, yield: 46.6%) was obtained.

MS m/z (ESI): 475.3[M+H]$^+$.

$^1$H NMR (400 MHz, CDCl$_3$) δ 7.94 (s, 1H), 7.92 (s, 1H), 5.04-4.80 (m, 2H), 4.38-4.19 (m, 2H), 2.60 (t, J=8.7 Hz, 1H), 2.27-1.45 (m, 21H), 1.38 (s, 3H), 1.37-1.25 (m, 3H), 1.20-1.07 (m, 1H), 0.71 (s, 3H).

Example 60

1-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)-N,N-dimethyl-1H-pyrazole-4-carboxamide

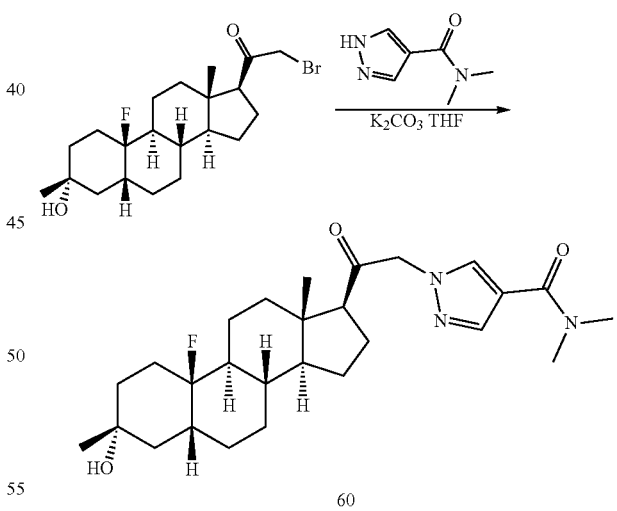

60

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-N,N-dimethyl-1H-pyrazole-4-carboxamide (10 mg, white solid, yield: 14.6%) was obtained.

MS m/z (ESI): 474.3[M+H]$^+$.

¹H NMR (400 MHz, CDCl₃) δ 7.75 (s, 2H), 5.09-4.82 (m, 2H), 3.16 (s, 6H), 2.69-2.53 (m, 1H), 2.30-1.45 (m, 18H), 1.38 (s, 3H), 1.32-1.05 (m, 4H), 0.72 (s, 3H).

Example 61

N-Ethyl-1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-N-methyl-1H-pyrazole-4-carboxamide

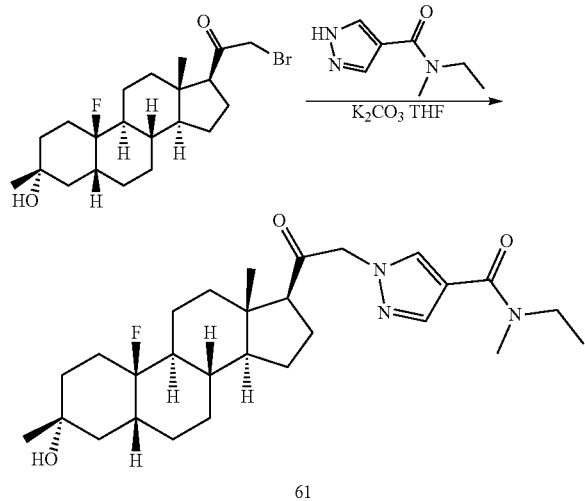

61

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product N-ethyl-1-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)-N-methyl-1H-pyrazole-4-carboxamide (14 mg, white solid, yield: 19.8%) was obtained.

MS m/z (ESI): 488.3[M+H]⁺.

¹H NMR (400 MHz, CDCl₃) δ 7.76 (s, 1H), 7.73 (s, 1H), 5.02-4.80 (m, 2H), 3.66-3.44 (m, 2H), 3.28-2.93 (m, 3H), 2.60 (t, J=8.6 Hz, 1H), 2.30-1.45 (m, 18H), 1.38 (s, 3H), 1.34-1.06 (m, 7H), 0.71 (s, 3H).

Example 62

2-(4-(Azetidine-1-carbonyl)-1H-pyrazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one

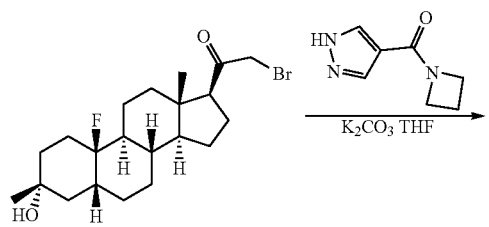

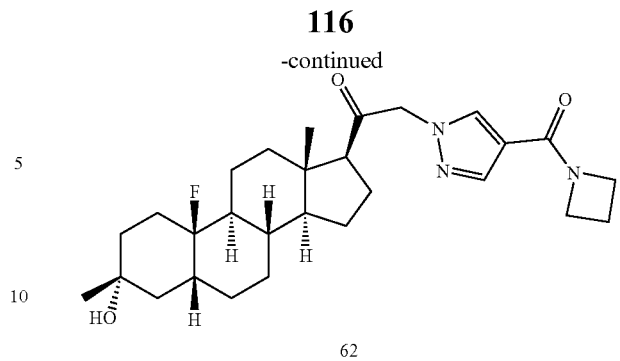

62

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 2-(4-(azetidine-1-carbonyl)-1H-pyrazol-1-yl)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (12 mg, white solid, yield: 17.1%) was obtained.

MS m/z (ESI): 486.2[M+H]⁺.

¹H NMR (400 MHz, CDCl₃) δ 7.87 (s, 1H), 7.76 (s, 1H), 5.02-4.82 (m, 2H), 4.39-4.21 (m, 4H), 2.59 (t, J=8.5 Hz, 1H), 2.46-1.59 (m, 20H), 1.38 (s, 3H), 1.34-1.19 (m, 3H), 1.17-1.05 (m, 1H), 0.71 (s, 3H).

Example 63 and Example 64

2-(4-Cyclopropyl-2H-1,2,3-triazol-2-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (63)

2-(4-Cyclopropyl-1H-1,2,3-triazol-1-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (64)

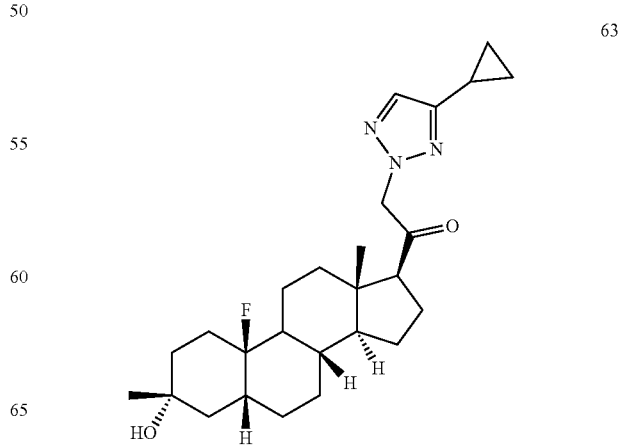

63

-continued

64

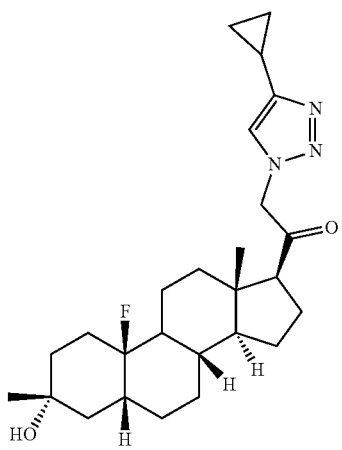

Step 1: Preparation of 4,5-dibromo-2H-1,2,3-triazole

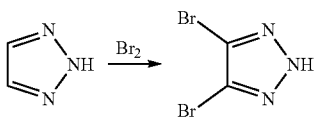

Liquid bromine (3 mL) was slowly added to a solution of 2H-1,2,3-triazole (3 g, 43.43 mmol) in water (30 mL) at 0° C. to precipitate a light yellow solid. The reaction solution was stirred at room temperature for 16 hours and then filtrated. The filter cake was washed with water (20 mL), and dried to obtain 4,5-dibromo-2H-1,2,3-triazole (5.7 g, white solid, yield: 58%), which was used directly in the next step without purification.

MS m/z (ESI): 227.2 [M+H]$^+$.

Step 2: Preparation of 4-bromo-2H-1,2,3-triazole

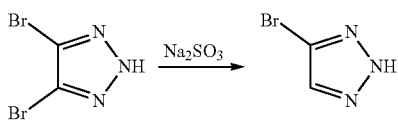

4,5-Dibromo-2H-1,2,3-triazole (5.7 g, 25.13 mmol) was suspended in water (50 mL). Sodium sulfite (9.5 g, 75.38 mmol) was added, and the reaction solution was stirred at 100° C. for 3 days. The reaction solution was cooled to room temperature, and extracted with ethyl acetate (30 mL×6). The organic phases were combined, washed with saturated saline (100 mL), dried over anhydrous sodium sulfate and filtrated. The filtrate was concentrated under reduced pressure to dryness to obtain 4-bromo-2H-1,2,3-triazole (3 g, white solid, yield: 81%).

MS m/z (ESI): 148.2 [M+H]$^+$, 150.2 [M+2+H]$^+$.

Step 3: Preparation of 4-bromo-2-((2-(trimethylsilyl)ethoxy)methyl)-2H-1,2,3-triazole

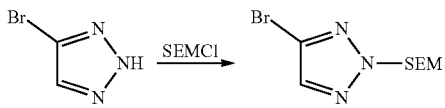 [SMILES: Brc1cn[nH]n1 ; "SEMCl" ; C[Si](C)(C)CCOCn1ncc(Br)n1]

Sodium hydride (760 mg, 18.9 mmol) was slowly added to a solution of 4-bromo-2H-1,2,3-triazole (2 g, 13.51 mmol) in tetrahydrofuran (20 mL) at 0° C., and the reaction solution was stirred at 0° C. for 0.5 hour. 2-(Trimethylsilyl)ethoxymethyl chloride (2.48 g, 14.86 mmol) was added dropwise. After completion of the addition, the reaction solution was stirred at room temperature for 2 hours. The reaction was quenched with water (50 mL), and the reaction solution was extracted with ethyl acetate (30 mL×3). The organic phases were combined, washed with saturated saline (50 mL), dried over anhydrous sodium sulfate and filtrated. The filtrate was concentrated under reduced pressure to dryness, and the resulting residue was purified by column chromatography to obtain 4-bromo-2-((2-(trimethylsilyl)ethoxy)methyl)-2H-1,2,3-triazole (1.4 g, white solid, yield: 38%).

MS m/z (ESI): 278.2 [M+H]$^+$, 280.2 [M+2+H]$^+$.

Step 4: Preparation of 4-cyclopropyl-2-((2-(trimethylsilyl)ethoxy)methyl)-2H-1,2,3-triazole

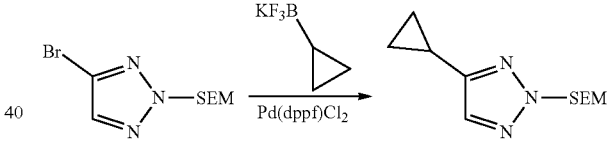

4-Bromo-2-((2-(trimethylsilyl)ethoxy)methyl)-2H-1,2,3-triazole (0.5 g, 1.79 mmol) and potassium cyclopropyltrifluoroborate (530 mg, 3.58 mmol) were dissolved in 1,4-dioxane (10 mL). [1,1'-Bis(diphenylphosphino)ferrocene]dichloropalladium(II) (0.5 g, 1.79 mmol) and sodium carbonate (0.5 g, 1.79 mmol) were added. After purging with nitrogen three times, the reaction solution was stirred under a nitrogen atmosphere at 100° C. for 16 hours. The reaction solution was filtrated through celite, and the filtrate was concentrated under reduced pressure to obtain a residue. To the residue was added water (30 mL), and the mixture was extracted with ethyl acetate (30 mL×3). The organic phases were combined, washed with saturated saline (50 mL), dried over anhydrous sodium sulfate and filtrated. The filtrate was concentrated under reduced pressure to dryness, and the resulting residue was purified by column chromatography (petroleum ether/ethyl acetate=4:1) to obtain 4-cyclopropyl-2-((2-(trimethylsilyl)ethoxy)methyl)-2H-1,2,3-triazole (70 mg, light yellow oil, yield: 16%).

MS m/z (ESI): 240.2 [M+H]$^+$.

Step 5: Preparation of 4-cyclopropyl-2H-1,2,3-triazole

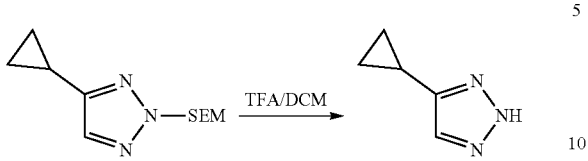

4-Cyclopropyl-2-((2-(trimethylsilyl)ethoxy)methyl)-2H-1,2,3-triazole (50 mg, 0.208 mmol) was dissolved in dichloromethane (1 mL). Trifluoroacetic acid (1 mL) was added, and the reaction solution was stirred at room temperature for 3 hours. Water (10 mL) was added, and then saturated sodium carbonate solution was added to the reaction solution to adjust pH=8, and the reaction solution was extracted with ethyl acetate (20 mL×3). The organic phases were combined, washed with saturated saline (50 mL), dried over anhydrous sodium sulfate and filtrated. The filtrate was concentrated under reduced pressure to dryness to obtain 4-cyclopropyl-2H-1,2,3-triazole (35 mg, white solid, crude product).

MS m/z (ESI): 110.2 [M+H]$^+$.

Step 6: Preparation of 2-(4-cyclopropyl-2H-1,2,3-triazol-2-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (63) and 2-(4-cyclopropyl-1H-1,2,3-triazol-1-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (64)

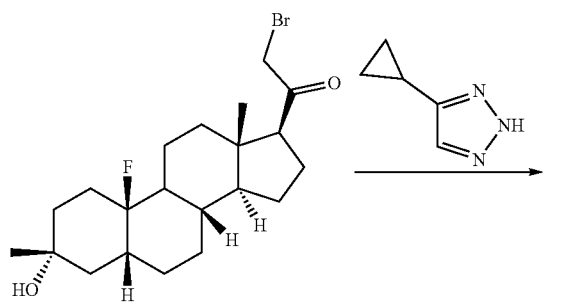

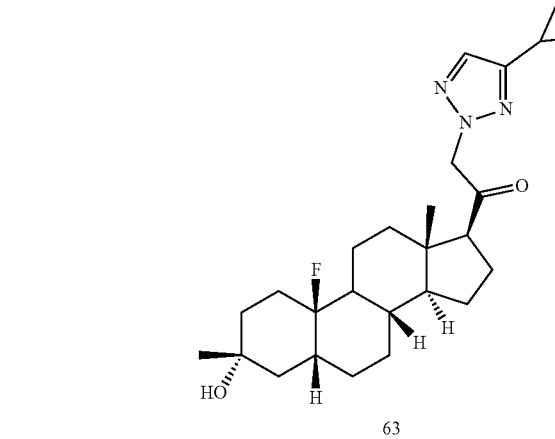

63

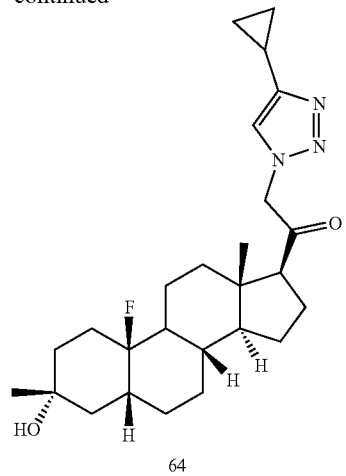

64

Potassium carbonate (80 mg, 0.579 mmol) was added to a mixed solution of 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one (80 mg, 0.193 mmol) and tetrahydrofuran (3 mL), and the reaction solution was stirred at room temperature for 16 hours. Water (20 mL) was added, and the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting residue was purified by preparative chromatography to obtain a white solid, 2-(4-cyclopropyl-2H-1,2,3-triazol-2-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (63) (34 mg, white solid, yield: 39.8%) and a white solid, 2-(4-cyclopropyl-1H-1,2,3-triazol-1-yl)-1-((3R,5R,8S,10R,13S,14S,17S)-10-fluoro-3-hydroxy-3,13-dimethylhexadecahydro-1H-cyclopenta[a]phenanthren-17-yl)ethan-1-one (64) (14 mg, white solid, yield: 16.4%).

Example 63

MS m/z (ESI): 444.2 [M+H]$^+$.

$^1$H NMR (400 MHz, CDCl$_3$) δ 7.35 (s, 1H), 5.15-5.05 (m, 2H), 3.91 (d, J=3.0 Hz, 1H), 2.61-2.47 (m, 1H), 2.25-2.08 (m, 4H), 2.04-1.81 (m, 5H), 1.78-1.71 (m, 2H), 1.54-1.42 (m, 6H), 1.37 (s, 3H), 1.33-1.20 (m, 4H), 1.18-1.04 (m, 2H), 0.99-0.96 (m, 2H), 0.80-0.75 (m, 2H), 0.73 (s, 3H).

Example 64

MS m/z (ESI): 444.2 [M+H]$^+$.

$^1$H NMR (400 MHz, CDCl$_3$) δ 7.35 (s, 1H), 5.16-5.06 (m, 2H), 3.91 (d, J=3.0 Hz, 1H), 2.54 (t, J=8.8 Hz, 1H), 2.24-2.09 (m, 4H), 2.04-1.81 (m, 5H), 1.78-1.70 (m, 2H), 1.54-1.42 (m, 6H), 1.37 (s, 3H), 1.31-1.22 (m, 4H), 1.18-1.04 (m, 2H), 0.99-0.96 (m, 2H), 0.80-0.76 (m, 2H), 0.73 (s, 3H).

Example 66

1-((3R,5R,8S,9S,10R,13S,14S,17S)-10-Fluoro-3-hydroxy-3,13-dimethylhexadecahydro-1H-cyclopenta[a]phenanthren-17-yl)-2-((2-(trifluoromethyl)pyrimidin-5-yl)oxy)ethan-1-one

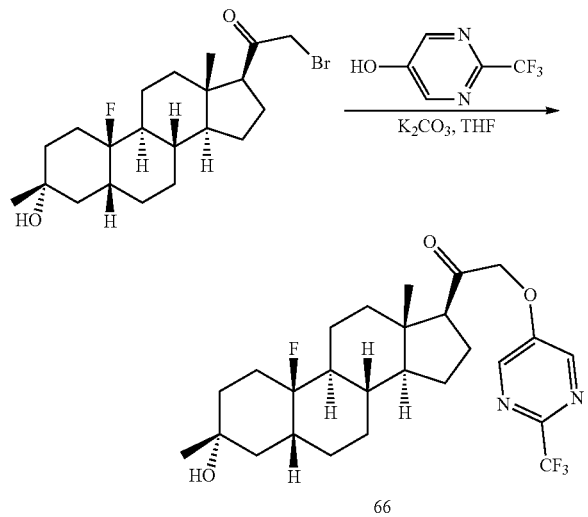

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-((2-(trifluoromethyl)pyrimidin-5-yl)oxy)ethan-1-one (39.2 mg, white solid, yield: 65.5%) was obtained.

MS m/z (ESI): 499.2[M+H]⁺.

¹H NMR (400 MHz, CDCl₃) δ 8.45 (s, 2H), 4.84-4.70 (m, 2H), 2.68 (t, J=8.9 Hz, 1H), 2.23 (m, 1H), 2.09 (d, J=10.8 Hz, 1H), 1.98 (t, J=12.6 Hz, 3H), 1.91-1.83 (m, 1H), 1.79 (t, J=8.4 Hz, 2H), 1.60-1.52 (m, 4H), 1.48 (dd, J=19.5, 12.9 Hz, 5H), 1.38 (s, 3H), 1.35-1.21 (m, 4H), 1.20-1.05 (m, 1H), 0.73 (s, 3H).

Example 67

3-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethyl)thiazolidine-2,4-dione

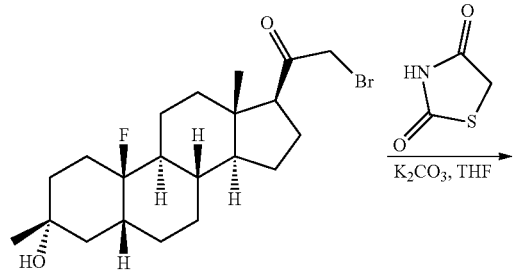

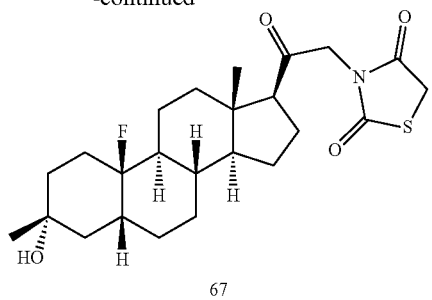

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 3-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethyl)thiazolidine-2,4-dione (18.5 mg, white solid, yield: 28.3%) was obtained.

¹H NMR (400 MHz, CDCl₃) δ 4.43-4.32 (m, 2H), 4.03 (s, 2H), 2.56 (t, J=8.7 Hz, 1H), 2.21-1.54 (m, 18H), 1.37 (s, 3H), 1.32-1.25 (m, 3H), 1.17-1.08 (m, 1H), 0.68 (s, 3H).

Example 68

(1R,3R,5R)-2-(2-((3R,5R,8S,10R,13S,14S,17S)-10-Fluoro-3-hydroxy-3,13-dimethylhexadecahydro-1H-cyclopenta[a]phenanthren-17-yl)-2-oxoethyl)-2-azabicyclo[3.1.0]hexane-3-carbonitrile

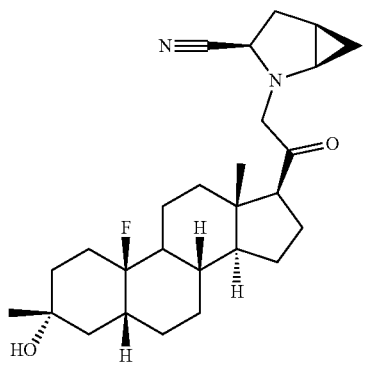

Step 1: Preparation of tert-butyl (1R,3R,5R)-3-cyano-2-azabicyclo[3.1.0]hexane-2-carboxylate

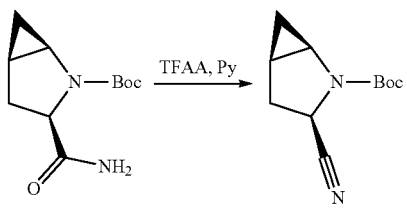 [SMILES: CC(C)(C)OC(=O)N1[C@@H](C(N)=O)C[C@H]2C[C@H]21 ; CC(C)(C)OC(=O)N1[C@@H]2C[C@@H]2C[C@@H]1C#N]

Trifluoroacetic anhydride (5 mL, 35.3 mmol) was slowly added dropwise to a suspension of tert-butyl (1R,3R,5R)-3- carbamoyl-2-azabicyclo[3.1.0]hexane-2-carboxylate (2 g, 8.85 mmol) and pyridine (25 mL) at −20° C. After stirring at −20° C. for 1 hour, the reaction solution was warmed up to room temperature, and stirred for 8 hours. Ice-water was added to quench the reaction, and the reaction solution was extracted with ethyl acetate (30 mL×3). The organic phases were combined, washed with dilute hydrochloric acid (10%) and saturated saline, dried over anhydrous sodium sulfate and filtrated. The filtrate was concentrated under reduced pressure to dryness, and the resulting residue was purified by column chromatography (petroleum ether/ethyl acetate=4:1) to obtain tert-butyl (1R,3R,5R)-3-cyano-2-azabicyclo[3.1.0]hexane-2-carboxylate (1.5 g, white solid, yield: 83%).

$^1$H NMR (400 MHz, CDCl$_3$) δ 4.71 (dd, J=41.1, 9.6 Hz, 1H), 3.58 (d, J=33.8 Hz, 1H), 2.63-2.47 (m, 1H), 2.35 (d, J=12.7 Hz, 1H), 1.70-1.60 (m, 1H), 1.52 (s, 9H), 1.02 (s, 1H), 0.90-0.81 (m, 1H).

Step 2: Preparation of (1R,3R,5R)-2-azabicyclo[3.1.0]hexane-3-carbonitrile

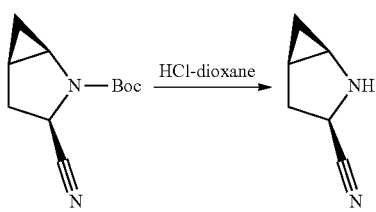 [SMILES: CC(C)(C)OC(=O)N1[C@@H]2C[C@@H]2C[C@@H]1C#N ; N#C[C@H]1C[C@H]2C[C@H]2N1]

Tert-butyl (1R,3R,3R)-3-cyano-2-azabicyclo[3.1.0]hexane-2-carboxylate (0.8 g, 3.85 mmol) was dissolved in dioxane (2 mL). Hydrochloric acid-dioxane (8 mL) was added, and the reaction solution was stirred at room temperature for 2 hours. The reaction solution was concentrated under reduced pressure to dryness, to the resulting residue was added water (50 mL), and the mixture was extracted with dichloromethane/methanol=10:1. The organic phases were combined, washed with saturated saline, dried over anhydrous sodium sulfate and filtrated. The filtrate was concentrated under reduced pressure to dryness to obtain (1R,3R,5R)-2-azabicyclo[3.1.0]hexane-3-carbonitrile (0.5 g, brown oil, crude product).

Step 3: Preparation of (1R,3R,5R)-2-(2-((3R,5R,8S,10R,13S,14S,17S)-10-fluoro-3-hydroxy-3,13-dimethylhexadecahydro-1H-cyclopenta[a]phenanthren-17-yl)-2-oxoethyl)-2-azabicyclo[3.1.0]hexane-3-carbonitrile

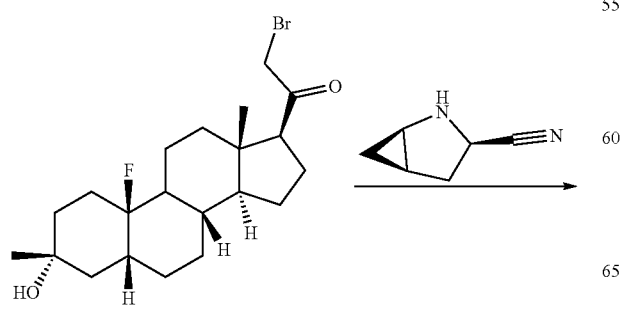

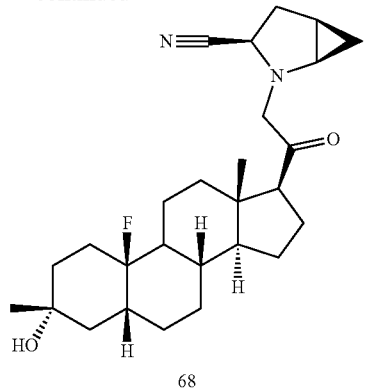

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product (1R,3R,5R)-2-(2-((3R,5R,8S,10R,13S,14S,17S)-10-fluoro-3-hydroxy-3,13-dimethylhexadecahydro-1H-cyclopenta[a]phenanthren-17-yl)-2-oxoethyl)-2-azabicyclo[3.1.0]hexane-3-carbonitrile (12 mg, white solid, yield: 23%) was obtained.

MS m/z (ESI): 443.2 [M+H]$^+$.

$^1$H NMR (400 MHz, CDCl$_3$) δ 4.08 (s, 2H), 3.70 (s, 2H), 2.49 (t, J=8.7 Hz, 1H), 2.24-2.16 (m, 2H), 2.12-1.82 (m, 11H), 1.74-1.70 (m, 2H), 1.60-1.48 (m, 6H), 1.37 (s, 3H), 1.31-1.25 (m, 6H), 1.12-1.07 (m, 1H), 0.65 (s, 3H).

Example 69

1-((3R,5R,8S,9S,10R,13S,14S,17S)-10-Fluoro-3-hydroxy-3,13-dimethylhexadecahydro-1H-cyclopenta[a]phenanthren-17-yl)-2-((1-methyl-1H-pyrazol-4-yl)oxy)ethan-1-one

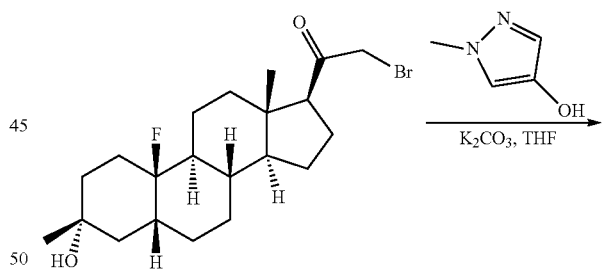

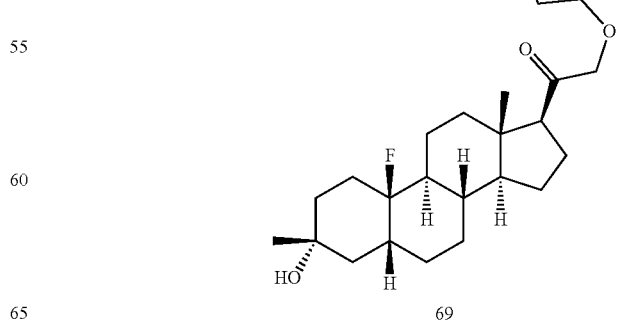

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-((1-methyl-1H-pyrazol-4-yl)oxy)ethan-1-one (20 mg, white solid, yield: 32.0%) was obtained.

MS m/z (ESI): 433.3[M+H]⁺.

¹H NMR (400 MHz, CDCl₃) δ 7.21 (s, 1H), 7.08 (s, 1H), 4.48-4.28 (m, 2H), 3.82 (s, 3H), 2.74 (t, J=8.9 Hz, 1H), 2.22-1.50 (m, 18H), 1.37 (s, 3H), 1.30-1.10 (m, 4H), 0.68 (s, 3H).

Example 70

7-(2-((3R,5R,8S,9S,10R,13S,14S,17S)-10-Fluoro-3-hydroxy-3,13-dimethylhexadecahydro-1H-cyclopenta[a]phenanthren-17-yl)-2-oxoethoxy)quinolone 1-oxide

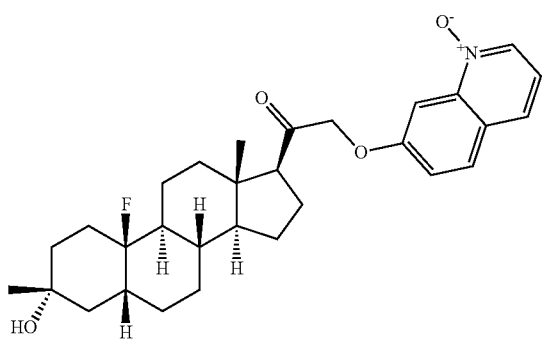

Step 1: Preparation of 1-((3R,5R,8S,9S,10R,13S,14S,17S)-10-fluoro-3-hydroxy-3,13-dimethylhexadecahydro-1H-cyclopenta[a]phenanthren-17-yl)-2-(quinolin-7-yloxy)ethan-1-one

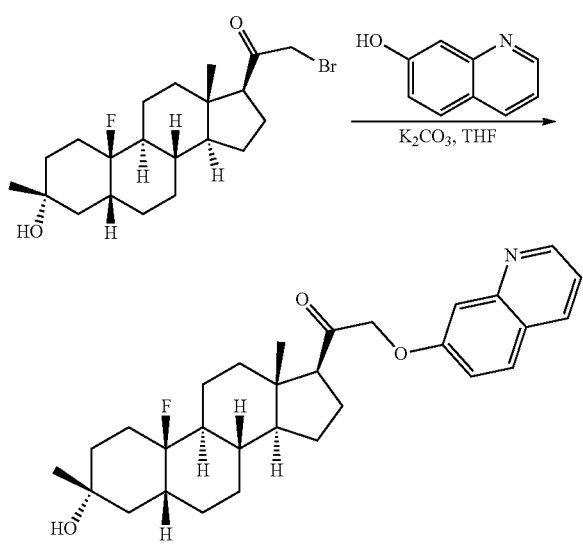

In accordance with Step 2 of Example 2, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3,13-dimethylhexadecahydro-1H-cyclopenta[a]phenanthren-17-yl)-2-(quinolin-7-yloxy)ethan-1-one (60.0 mg, white solid, yield 52.1%) was obtained.

MS m/z (ESI): 480.2[M+H]⁺.

Step 2: Preparation of 7-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)quinolone 1-oxide

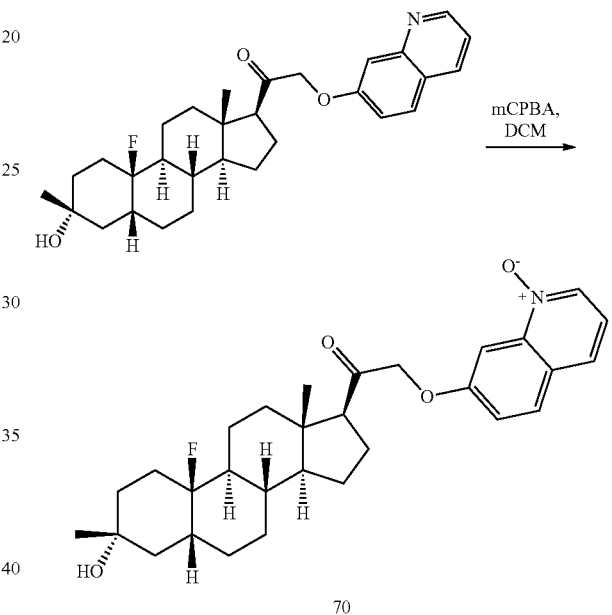

70

1-((3R,5R,8S,9S,10R,13S,14S,17S)-10-Fluoro-3-hydroxy-3,13-dimethylhexadecahydro-1H-cyclopenta[a]phenanthren-17-yl)-2-(quinolin-7-yloxy)ethan-1-one (60 mg, 0.125 mmol) and dichloromethane (10 ml) were added to a 100 ml single-neck flask, followed by the addition of m-chloroperoxybenzoic acid (78 mg, 0.313 mmol). The reaction solution was stirred at room temperature overnight. The reaction solution was washed with saturated sodium bicarbonate solution and concentrated. The crude product obtained after concentration was purified by prep-HPLC to obtain 7-(2-((3R,5R,8S,9S,10R,13S,14S,17S)-10-fluoro-3-hydroxy-3,13-dimethylhexadecahydro-1H-cyclopenta[a]phenanthren-17-yl)-2-oxoethoxy)quinolone 1-oxide (29.2 mg, white solid, yield 47.1%).

MS m/z (ESI): 496.2[M+H]⁺.

¹H NMR (400 MHz, CDCl₃) δ 8.59 (d, J=6.0 Hz, 1H), 7.97 (d, J=2.2 Hz, 1H), 7.83 (d, J=9.0 Hz, 1H), 7.78 (d, J=8.3 Hz, 1H), 7.43 (dd, J=9.0, 2.4 Hz, 1H), 7.26-7.20 (m, 1H), 4.87-4.73 (m, 2H), 2.83-2.75 (m, 1H), 2.33-2.21 (m, 1H), 2.13-2.07 (m, 1H), 2.06-1.95 (m, 4H), 1.94-1.84 (m, 2H), 1.82-1.74 (m, 2H), 1.62-1.42 (m, 8H), 1.38 (s, 3H), 1.35-1.25 (m, 3H), 1.20-1.06 (m, 1H), 0.75 (s, 3H).

Example 71

N-(2-((3S,5R,8S,9S,10R,13S,14S,17S)-10-Fluoro-3-hydroxy-3,13-dimethylhexadecahydro-1H-cyclopenta[a]phenanthren-17-yl)-2-oxoethyl)benzenesulfonamide

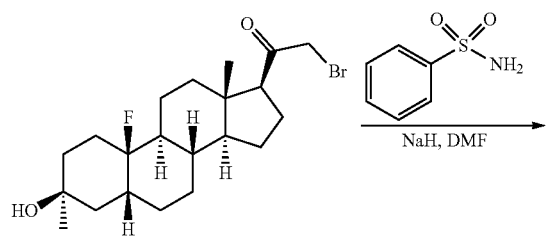

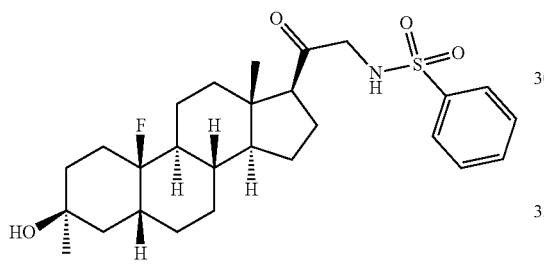

Benzenesulfonamide (28 mg, 0.18 mmol) was dissolved in N,N-dimethylformamide (5 mL). Sodium hydride (7.2 mg, 0.18 mmol) was added at 0° C., and the reaction solution was stirred at 0° C. for 0.5 hour. 2-Bromo-1-((3R,5R,8S,9S,10R,13S,14S,17S)-10-fluoro-3-hydroxy-3,13-dimethyl-hexadecahydro-1H-cyclopenta[a]phenanthren-17-yl)ethan-1-one (50 mg, 0.12 mmol) was added at 0° C., and the reaction solution was stirred at room temperature overnight. 5 mL of water was added, and the reaction solution was extracted with ethyl acetate (30 mL×3). The organic phase was washed with saturated saline (20 mL) once, dried over anhydrous sodium sulfate and concentrated by rotary evaporation to dryness. The resulting residue was purified by prep-HPLC to obtain the product (7.1 mg, white solid, yield: 12%).

$^1$H NMR (400 MHz, CDCl$_3$) δ 7.86 (d, J=7.2 Hz, 2H), 7.58 (t, J=7.4 Hz, 1H), 7.51 (t, J=7.5 Hz, 2H), 5.48 (s, 1H), 3.87-3.68 (m, 2H), 2.36 (t, J=8.9 Hz, 1H), 2.06-2.08 (m, 2H), 1.94-1.97 (m, 2H), 1.90-1.80 (m, 1H), 1.71-1.62 (m, 4H), 1.52-1.39 (m, 6H), 1.37 (s, 3H), 1.34-1.25 (m, 4H), 1.24-1.01 (m, 3H), 0.38 (s, 3H).

Example 72

(3R,5R,8S,9S,10R,13S,14S,17S)-10-Fluoro-N-(4-fluorophenyl)-3-hydroxy-3,13-dimethylhexadecahydro-1H-cyclopenta[a]phenanthrene-17-carboxamide

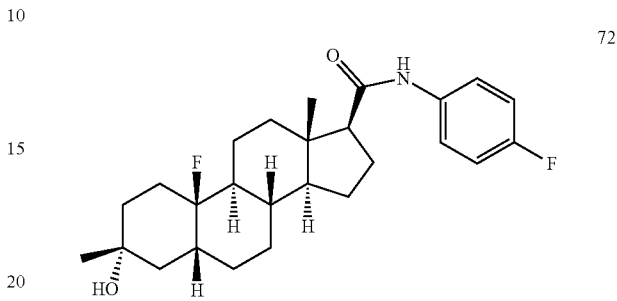

Step 1: Preparation of (3R,5R,8S,9S,10R,13S,14S)-10-fluoro-3,13-dimethyl-17-methylenehexadecahydro-1H-cyclopenta[a]phenanthren-3-ol

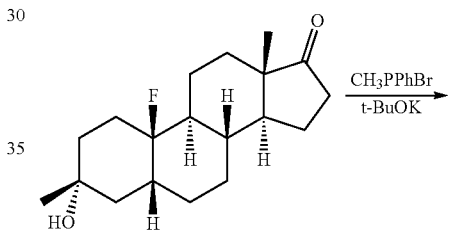

Potassium tert-butoxide (4.36 g, 38.961 mmol) was added to a solution of methyltriphenylphosphonium bromide (13.9 g, 38.961 mmol) and tetrahydrofuran (50 mL), and the reaction solution was stirred at 65° C. for 1 hour. A mixed solution of (3R,5R,8S,9S,10R,13S,14S)-10-fluoro-3-hydroxy-3,13-dimethylhexadecahydro-17H-cyclopenta[a]phenanthren-17-one (2 g, 6.494 mmol) and tetrahydrofuran (30 mL) was added dropwise. After stirring at 65° C. for 1 hour, the reaction solution was cooled to room temperature. Water was added to quench the reaction, and the reaction solution was extracted with ethyl acetate (50 mL×3). The organic phases were combined, washed with saturated saline, dried over anhydrous sodium sulfate and filtrated. The filtrate was concentrated under reduced pressure to dryness, and the resulting residue was purified by column chromatography (petroleum ether/ethyl acetate=10:1) to obtain (3R,5R,8S,9S,10R,13S,14S)-10-fluoro-3,13-dimethyl-17-methylenehexadecahydro-1H-cyclopenta[a]phenanthren-3-ol (1.8 g, white solid, yield: 90%).

Step 2: Preparation of (3R,5R,8S,9S,10R,13S,14S, 17S)-10-fluoro-17-(hydroxymethyl)-3,13-dimethyl-hexadecahydro-1H-cyclopenta[a]phenanthren-3-ol

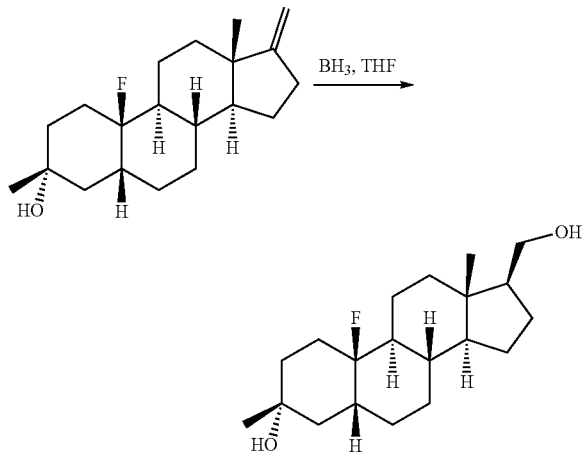

(3R,5R,8S,9S,10R,13S,14S)-10-Fluoro-3,13-dimethyl-17-methylenehexadecahydro-1H-cyclopenta[a] phenanthren-3-ol (0.5 g, 1.634 mmol) was dissolved in tetrahydrofuran (8 mL). Borane-tetrahydrofuran (8.2 mL, 8.169 mmol) was added dropwise, and the reaction solution was stirred at room temperature for 1.5 hours. The reaction solution was cooled to 0° C., and a solution of sodium hydroxide (327 mg, 8.169 mmol) in water (3 mL) was added. Hydrogen peroxide (3 mL, 30%) was slowly added dropwise, and the reaction solution was stirred at room temperature for 1.5 hours. Water (50 mL) was added, and the reaction solution was extracted with ethyl acetate (50 mL×3). The organic phases were combined, washed with saturated saline, dried over anhydrous sodium sulfate and filtrated. The filtrate was concentrated under reduced pressure to dryness to obtain (3R,5R,8S,9S,10R,13S,14S,17S)-10-fluoro-17-(hydroxymethyl)-3,13-dimethylhexadecahydro-1H-cyclopenta[a]phenanthren-3-ol (600 mg, crude product).

Step 3: Preparation of (3R,5R,8S,9S,10R,13S,14S, 17S)-10-fluoro-3-hydroxy-3,13-dimethylhexadecahydro-1H-cyclopenta[a]phenanthrene-17-carboxylic acid

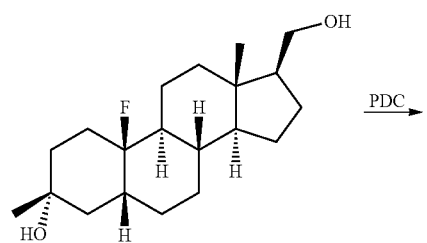

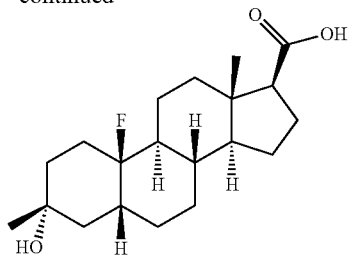

Pyridinium dichromate (4.6 g, 12.34 mmol) was added to a mixture of (3R,5R,8S,9S,10R,13S,14S,17S)-10-fluoro-17-(hydroxymethyl)-3,13-dimethylhexadecahydro-1H-cyclopenta[a]phenanthren-3-ol (400 mg, 1.234 mmol), N,N-dimethylformamide (15 mL) and water (1 mL), and the reaction solution was stirred at room temperature for 16 hours. Saturated sodium sulfite solution (50 mL) was added to quench the reaction, and the reaction solution was extracted with ethyl acetate (40 mL×3). The organic phases were combined, washed with saturated saline, dried over anhydrous sodium sulfate and filtrated. The filtrate was concentrated under reduced pressure to dryness to obtain a light yellow solid, (3R,5R,8S,9S,10R,13S,14S,17S)-10-fluoro-3-hydroxy-3,13-dimethylhexadecahydro-1H-cyclopenta[a] phenanthrene-17-carboxylic acid (400 mg, light yellow solid, crude product).

$^1$H NMR (400 MHz, DMSO) δ 11.92 (s, 1H), 4.38 (s, 1H), 2.90-2.70 (m, 2H), 2.05-1.52 (m, 9H), 1.39-1.19 (m, 15H), 0.61 (s, 3H).

Step 4: Preparation of (3R,5R,8S,9S,10R,13S,14S, 17S)-10-fluoro-N-(4-fluorophenyl)-3-hydroxy-3,13-dimethylhexadecahydro-1H-cyclopenta[a] phenanthrene-17-carboxamide

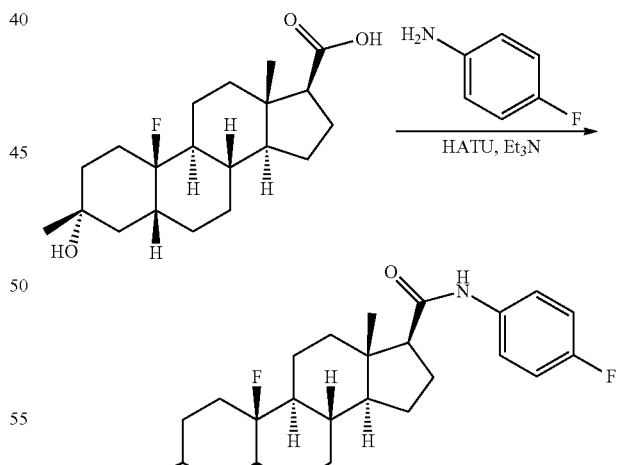

72

A mixture of (3R,5R,8S,9S,10R,13S,14S,17S)-10-fluoro-3-hydroxy-3,13-dimethylhexadecahydro-1H-cyclopenta[a] phenanthrene-17-carboxylic acid (200 mg, 0.592 mmol), O-(7-azabenzotriazol-1-yl)-N,N,N',N'-tetramethylurea hexafluorophosphate (270 mg, 0.71 mmol), triethylamine (119 mg, 1.18 mmol) and dichloromethane (5 mL) was stirred at room temperature for 30 minutes. p-Fluoroaniline (79 mg, 0.71 mmol) was added, and the reaction solution was stirred at room temperature for 3 hours. Water (30 mL) was added, and the reaction solution was extracted with dichloromethane (40 mL×3). The organic phases were combined, washed with saturated saline, dried over anhydrous sodium sulfate and filtrated. The filtrate was concentrated under reduced pressure to dryness, and the resulting residue was purified by preparative chromatography to obtain (3R,5R,8S,9S,10R,13S,14S,17S)-10-fluoro-N-(4-fluorophenyl)-3-hydroxy-3,13-dimethylhexadecahydro-1H-cyclopenta[a]phenanthrene-17-carboxamide (25 mg, white solid, yield: 10%).

MS m/z (ESI): 432.2 [M+H]$^+$.

$^1$H NMR (400 MHz, CDCl$_3$) δ 7.51-7.41 (m, 2H), 7.05-6.95 (m, 2H), 2.43-2.17 (m, 2H), 2.14-1.80 (m, 8H), 1.72-1.69 (m, 3H), 1.51-1.11 (m, 15H), 0.93 (s, 3H).

Example 73

2-((4-Fluoro-2-methoxyphenyl)amino)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one

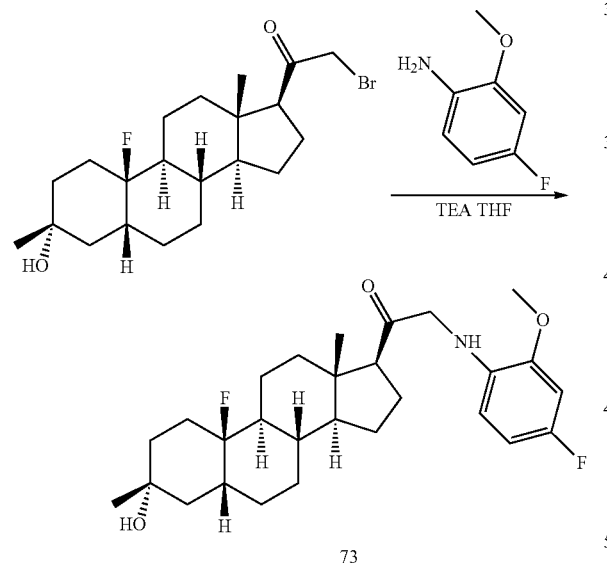

73

In accordance with Example 23, 2-bromo-1-((3R,5R,8S,10R,13S,14S,17S)-10-fluoro-3-hydroxy-3,13-dimethylhexadecahydro-1H-cyclopenta[a]phenanthren-17-yl)ethan-1-one was used as the starting material, accordingly, the product 2-((4-fluoro-2-methoxyphenyl)amino)-1-((3R,5R,8S,9S,10R,13S,14S,17S)-10-fluoro-3-hydroxy-3,13-dimethylhexadecahydro-1H-cyclopenta[a]phenanthren-17-yl)ethan-1-one (29 mg, white solid, yield: 42.2%) was obtained.

MS m/z (ESI): 476.3[M+H]$^+$.

$^1$H NMR (400 MHz, CDCl$_3$) δ 6.61-6.49 (m, 2H), 6.40-6.31 (m, 1H), 3.91 (d, J=6.3 Hz, 2H), 3.87-3.82 (m, 3H), 2.58 (t, J=8.8 Hz, 1H), 2.31-1.42 (m, 18H), 1.38 (s, 3H), 1.35-1.03 (m, 4H), 0.69 (s, 3H).

Example 79A 1-(2-((3R,5R,8S,9S,10R,13S,14S,17S)-10-(Fluoromethyl)-3-hydroxy-3,13-dimethylhexadecahydro-1H-cyclopenta[a]phenanthren-17-yl)-2-oxoethyl)-1H-pyrazole-4-carbonitrile

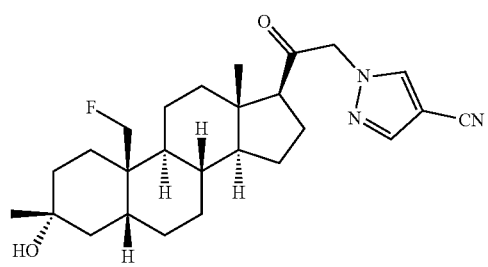

Example 79A was synthesized by the following specific scheme:

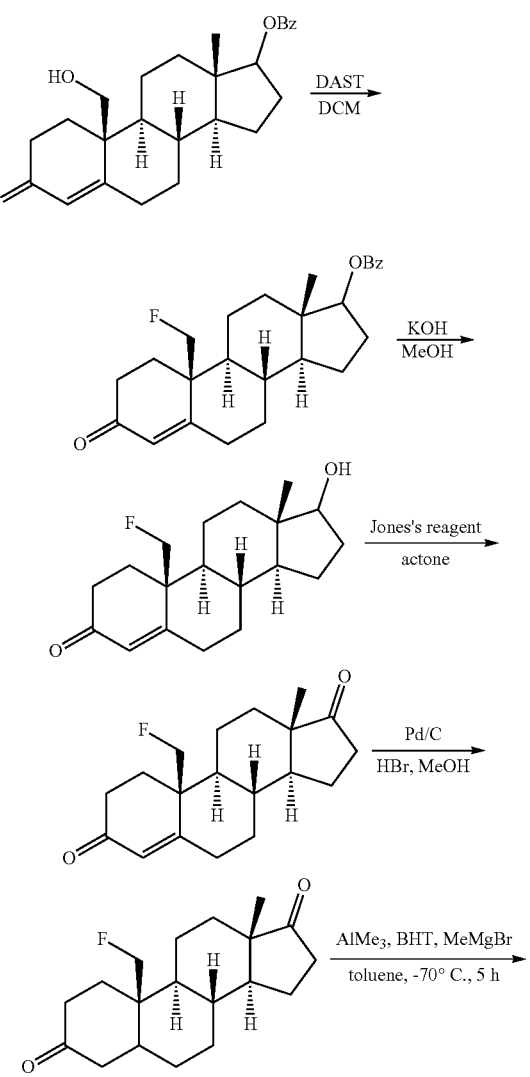

133
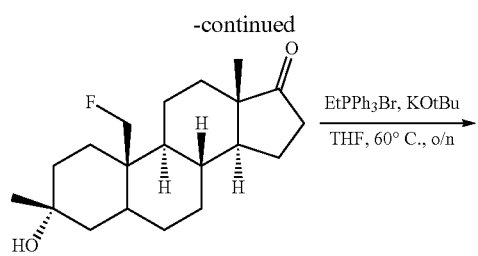
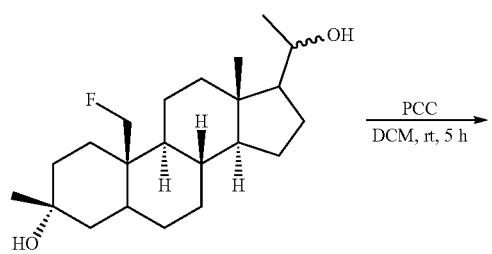
134
Example 82A
1-(2-((3R,5R,8S,9S,10R,13S,14S,17S)-10-(Difluoromethyl)-3-hydroxy-3,13-dimethylhexadecahydro-1H-cyclopenta[a]phenanthren-17-yl)-2-oxoethyl)-1H-pyrazole-4-carbonitrile
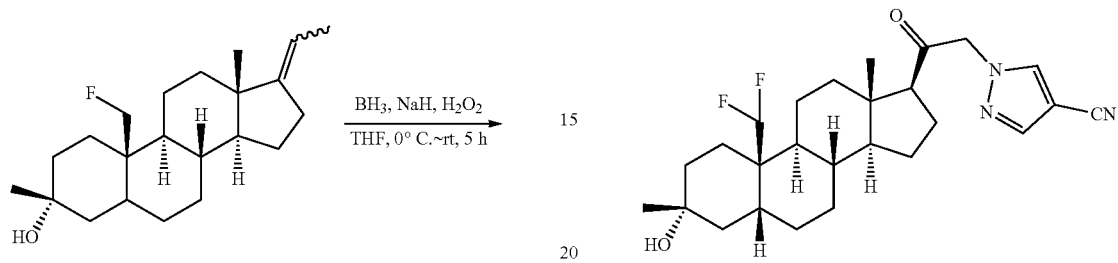
Example 82A was synthesized by the following specific scheme:
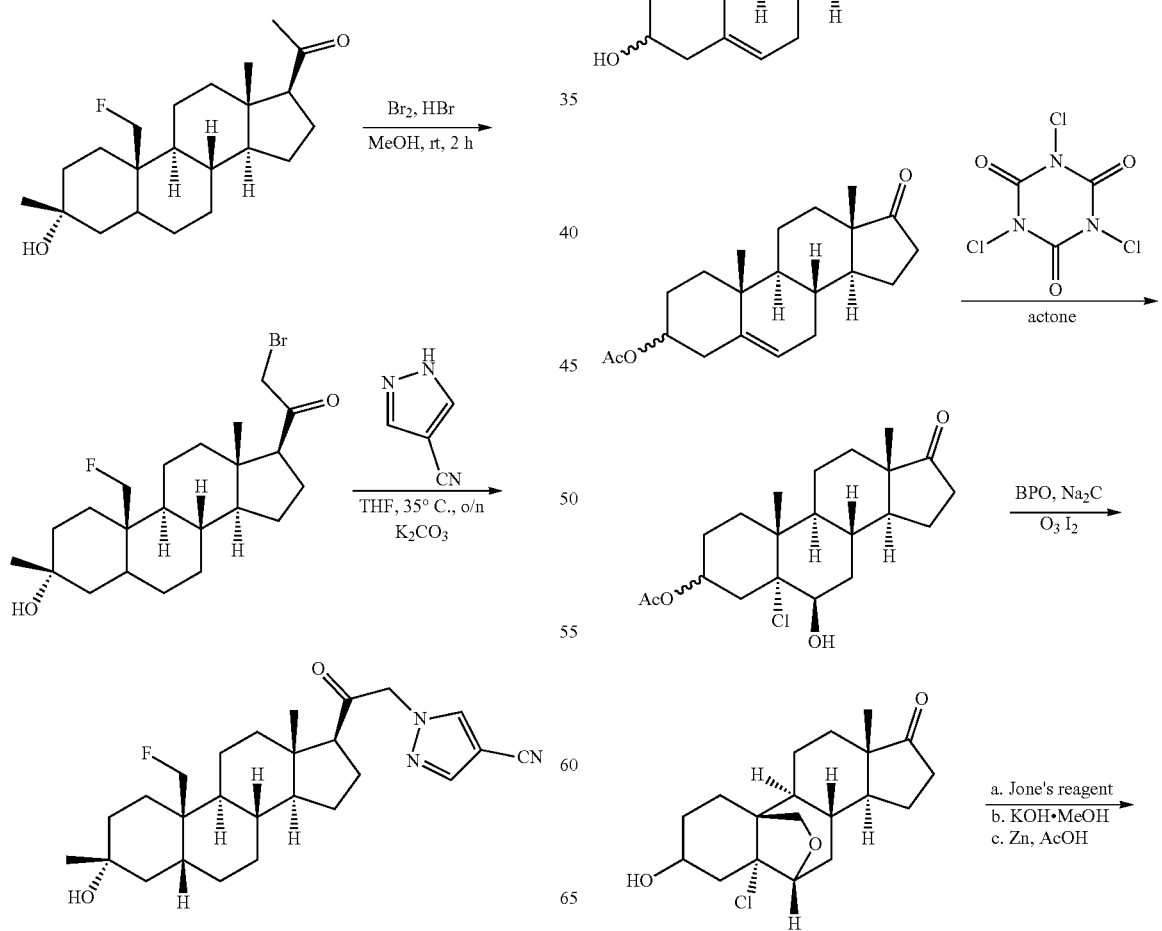

135
-continued
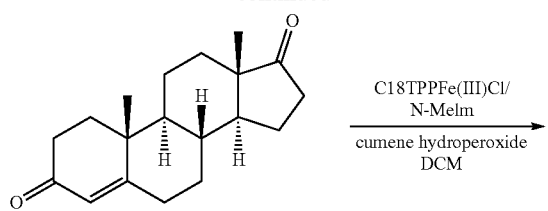
C18TPPFe(III)Cl/ N-MeIm
cumene hydroperoxide
DCM
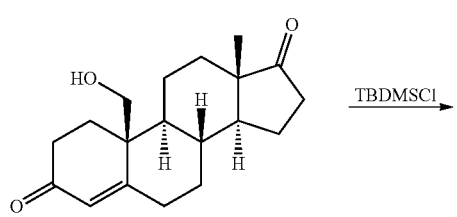
TBDMSCl
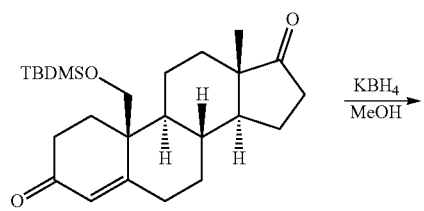
KBH4
MeOH
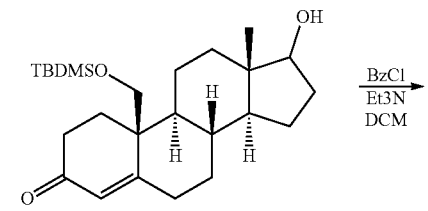
BzCl
Et3N
DCM
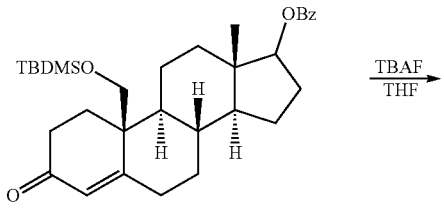
TBAF
THF
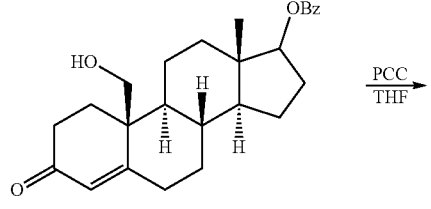
PCC
THF
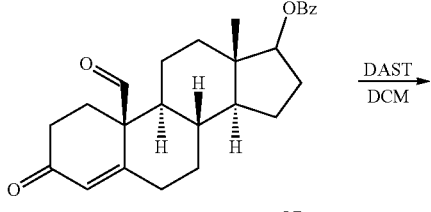
DAST
DCM
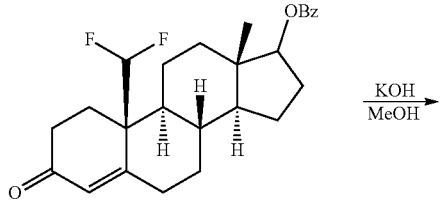
KOH
MeOH
136
-continued
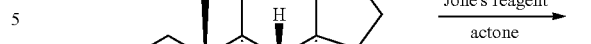
Jone's reagent
acetone
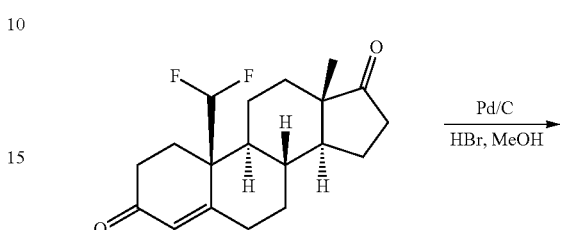
Pd/C
HBr, MeOH
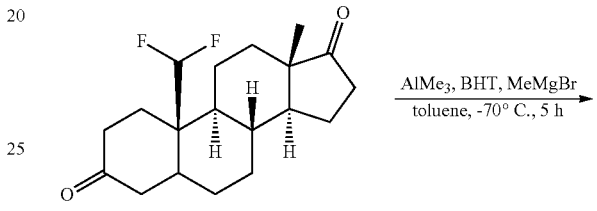
AlMe3, BHT, MeMgBr
toluene, -70° C., 5 h
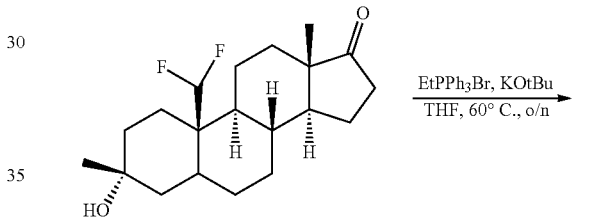
EtPPh3Br, KOtBu
THF, 60° C., o/n
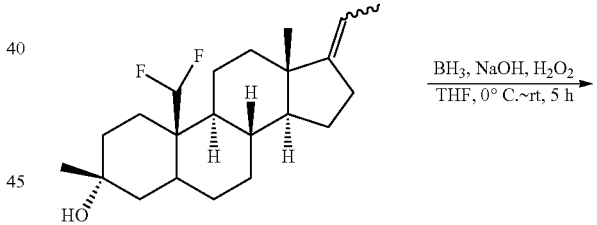
BH3, NaOH, H2O2
THF, 0° C.~rt, 5 h
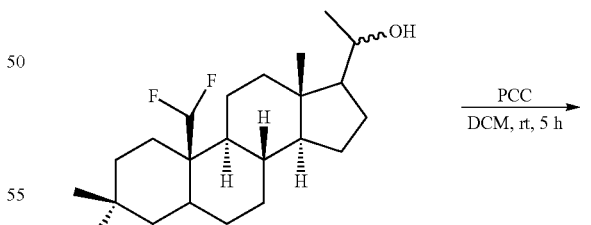
PCC
DCM, rt, 5 h
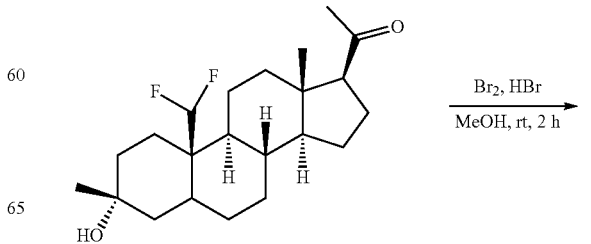
Br2, HBr
MeOH, rt, 2 h

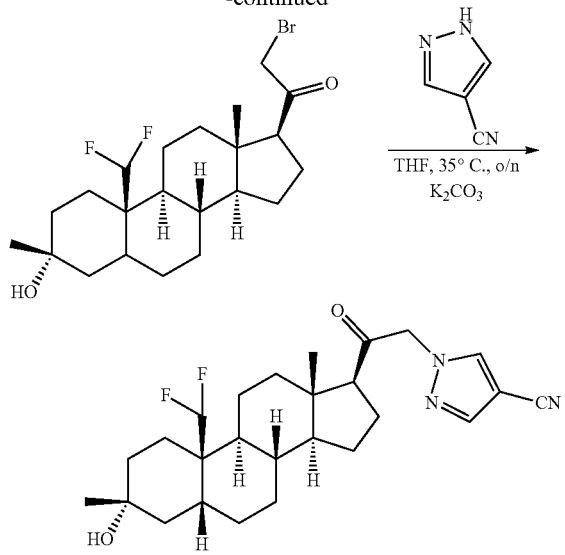
Example 90
1-(2-((2R,4aR,4bS,6aS,8bS,8cR,10aR)-2-Hydroxymethyl-4a-(methoxymethyl)-2,6a-dimethyl-hexadecahydrocyclopropa[4,5]cyclopenta[1,2-a]phenanthren-7-yl)-2-oxoethyl)-1H-pyrazole-4-carbonitrile
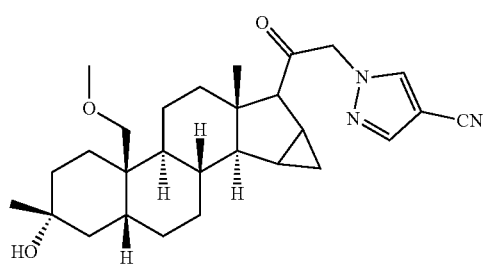
Example 90 was synthesized by the following specific scheme:
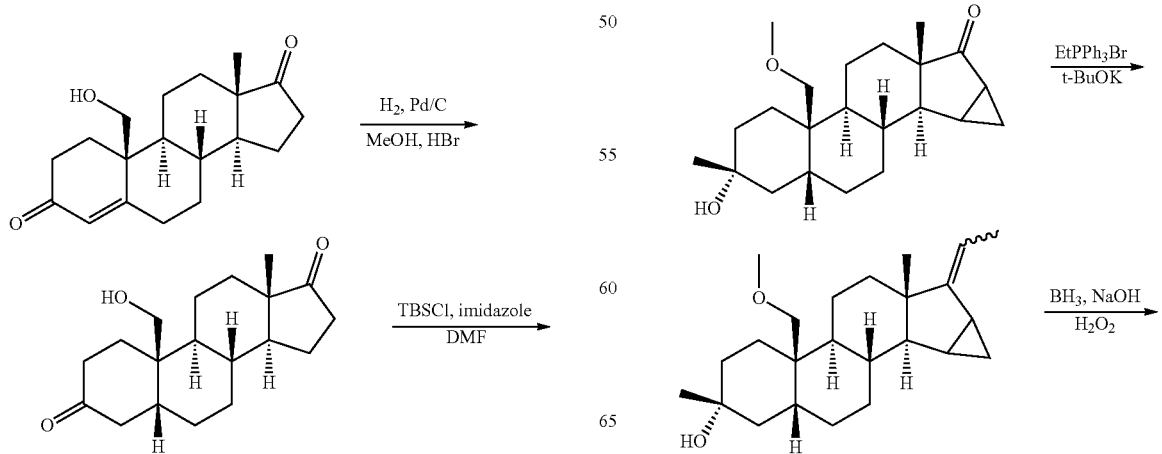
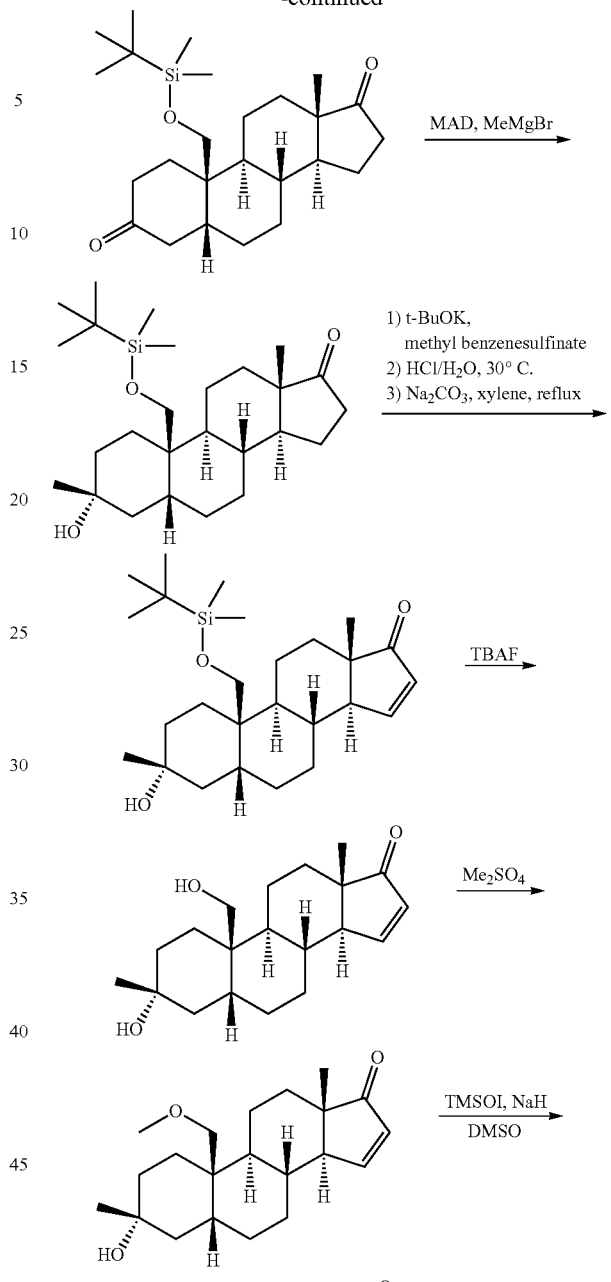

-continued

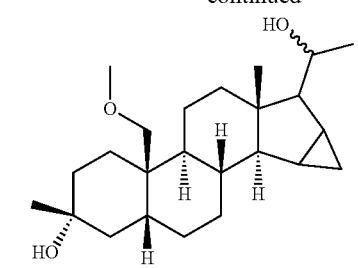

PCC →

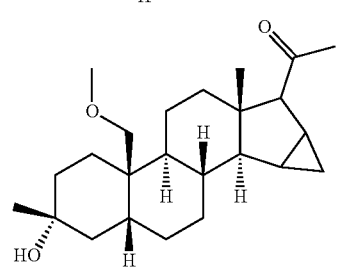

Br₂, HBr / MeOH →

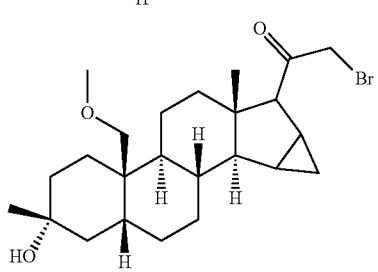

Cs₂CO₃ / MeCN →

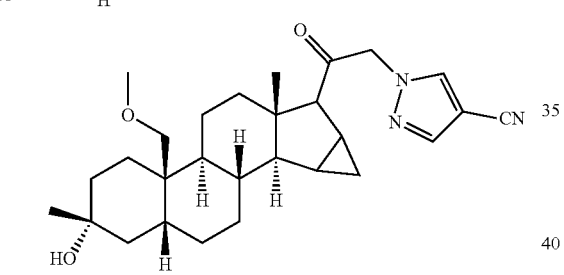

MS m/z (ESI): 465.3 [M]⁺.

Example 91

1-(2-((2R,4aR,4bS,6aS,8bS,8cR,10aR)-2-Hydroxymethyl-4a-(methoxymethyl)-2,6a-dimethyl-hexadecahydrocyclopropa[4,5]cyclopenta[1,2-a]phenanthren-7-yl)-2-oxoethyl)-1H-pyrazole-3-carbonitrile

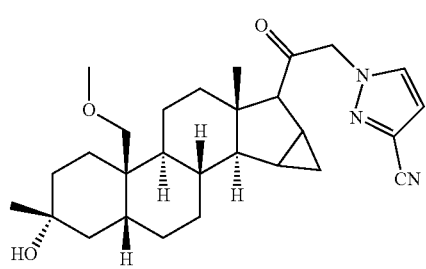

-continued

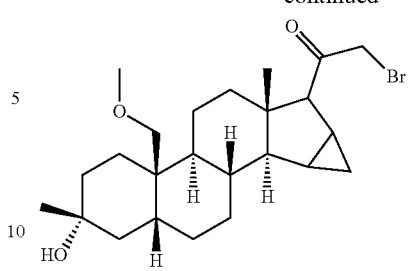

Cs₂CO₃ / MeCN →

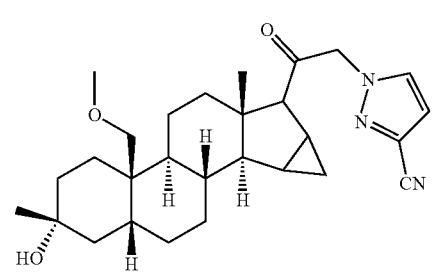

MS m/z (ESI): 465.3 [M]⁺.

Example 92

1-(2-((2R,4aR,4bS,6aS,8bS,8cR,10aR)-2-thiomethyl-4a-(methoxymethyl)-2,6a-dimethylhexadeca-hydrocyclopenta[4,5]cyclopenta[1,2-α]phenanthren-7-yl)-2-oxoethyl)-1H-pyrazole-4-carbonitrile

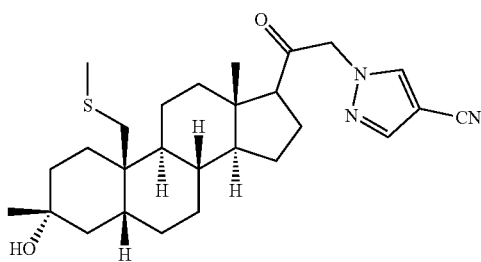

Example 92 was synthesized by the following specific scheme:

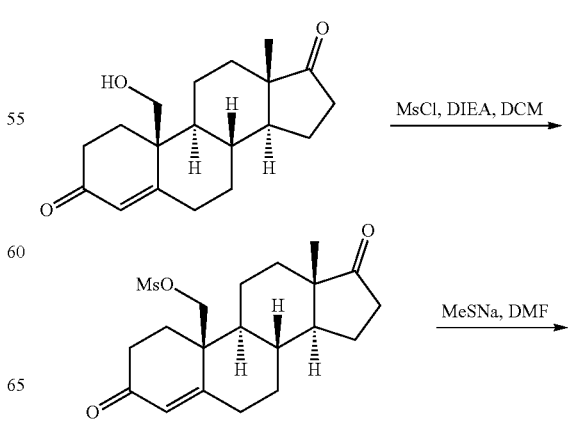

MsCl, DIEA, DCM →

MeSNa, DMF →

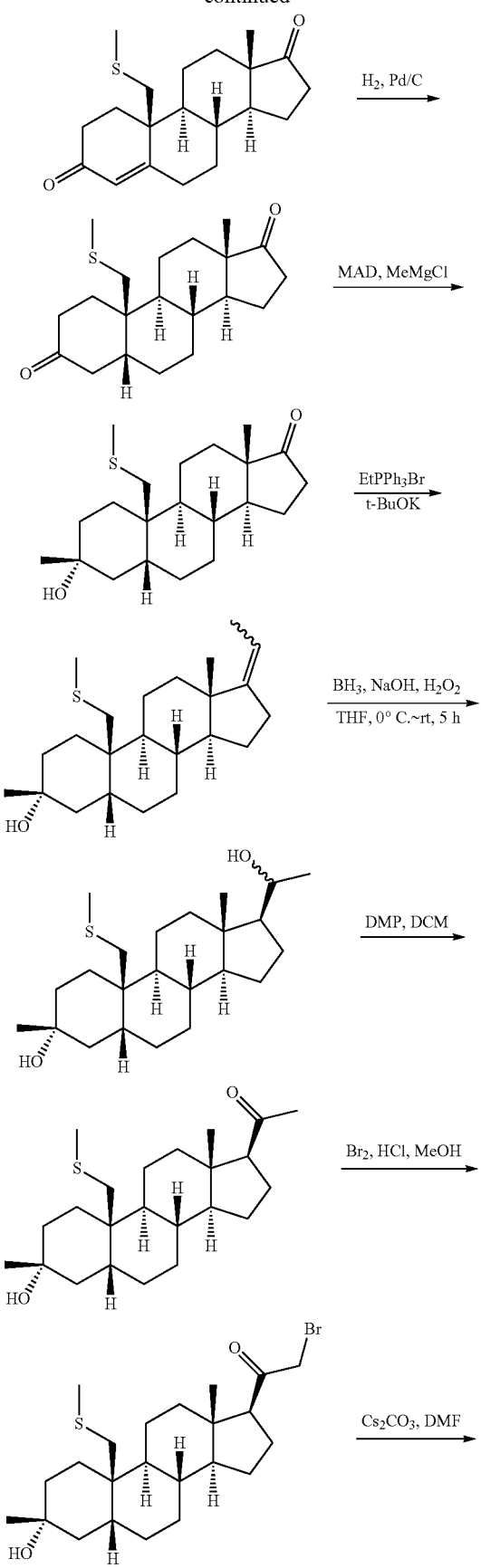
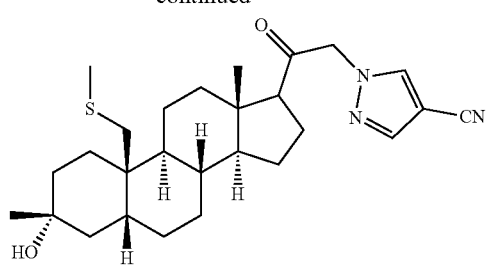
MS m/z (ESI): 469.3 [M]+.
Example 93
2-(5-Chloro-1H-benzo[d][1,2,3]triazol-1-yl)-1-((3R, 5R,8S,9S,10R,13S,14S,17S)-3-((methylthio)methyl) hexahydrodecahydro-1H-cyclopenta[a]phenanthren-17-yl)ethan-1-one
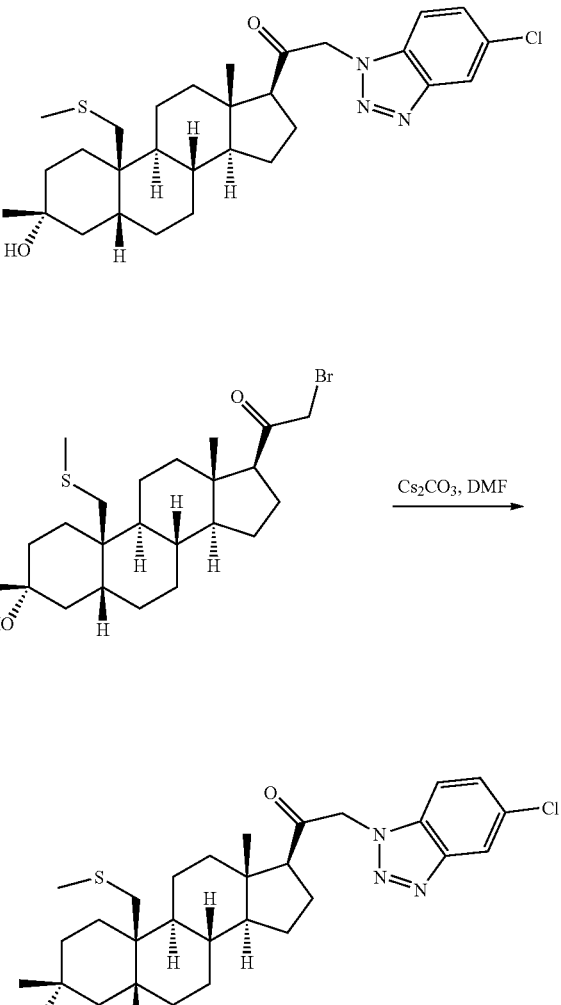
MS m/z (ESI): 529.3 [M]+.

Example 94

2-(4,5-Difluoro-1H-benzo[d][1,2,3]triazol-1-yl)-1-((3R,5R,8S,9S,10R,13S,14S,17S)-3-hydroxy-3,13-dimethyl-10-((methylthio)methyl)hexadecahydro-1H-cyclopenta[a]phenanthren-17-yl)ethan-1-one

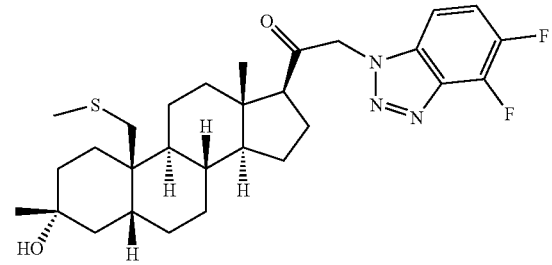

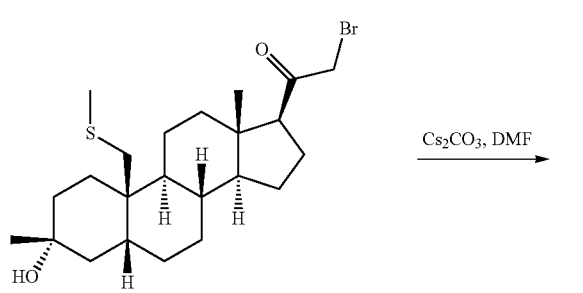

MS m/z (ESI): 531.3 [M]+.

Example 95

2-(3H-[1,2,3]Triazolo[4,5-b]pyridin-3-yl)-1-((3R,5R,8S,9S,10R,13S,14S,17S)-3-hydroxy-3,13-dimethyl-10-((methylthio)methyl)hexadecahydro-1H-cyclopenta[a]phenanthren-17-yl)ethan-1-one

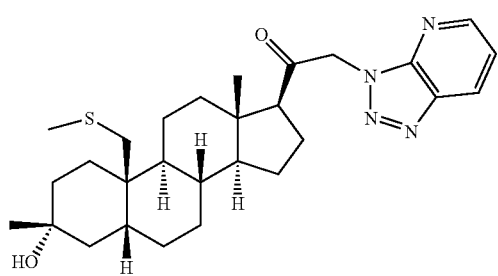

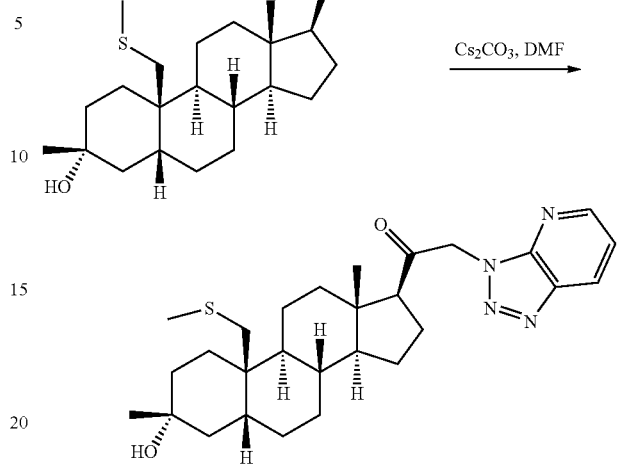

MS m/z (ESI): 496.3 [M]+.

Example 96

1-(2-((3R,5R,8S,9S,10R,13S,14S,17S)-3-Hydroxy-3,13-dimethyl-10-((methylsulfonyl)methyl)hexadecahydro-1H-cyclopenta[a]phenanthren-17-yl)-2-oxoethyl)-1H-pyrazole-4-carbonitrile

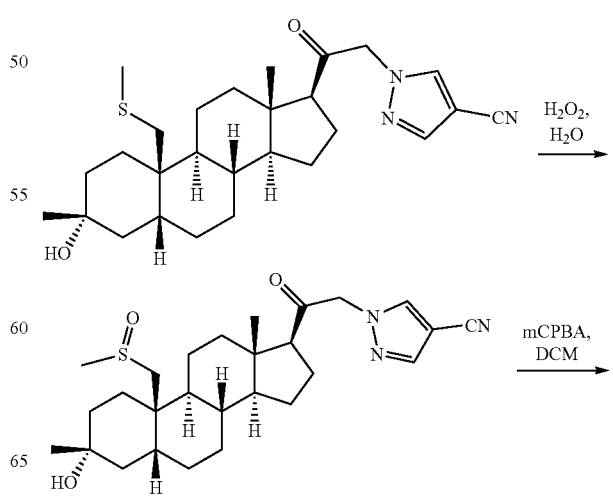

145

-continued

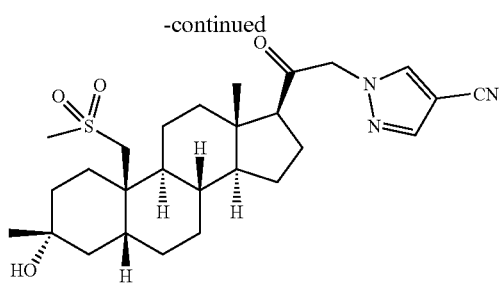

MS m/z (ESI): 501.3 [M]+.

Example 97

1-(2-((3R,5R,8S,9S,10R,13S,14S,17S)-3-Hydroxy-3,
13-dimethyl-10-((S-methylsulfonimidoyl)methyl)
hexadecahydro-1H-cyclopenta[a]phenanthren-17-
yl)-2-oxoethyl)-1H-pyrazole-4-carbonitrile

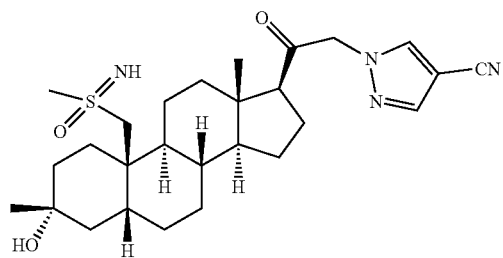

146

MS m/z (ESI): 500.3 [M]+.
MS m/z (ESI): 456.3 [M]+.

Example 114

1-(2-((3R,5R,8S,9S,10R,13S,14S,17S)-10-Fluoro-3-
hydroxy-3-(methoxymethyl)-13-methylhexadeca-
hydro-1H-cyclopenta[a]phenanthren-17-yl)-2-oxo-
ethyl)-1H-pyrazole-4-carbonitrile

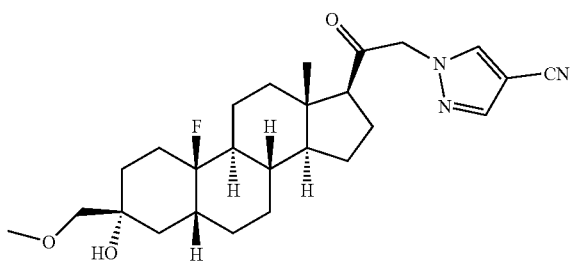

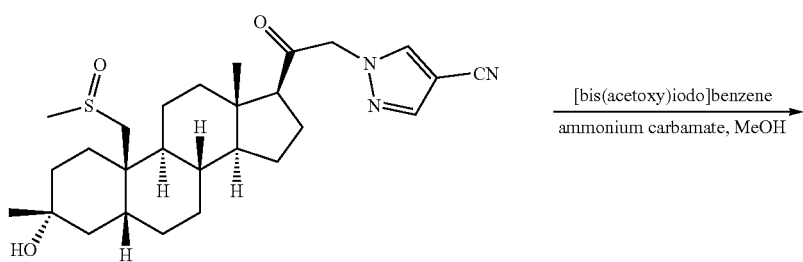

[bis(acetoxy)iodo]benzene
—————————————→
ammonium carbamate, MeOH

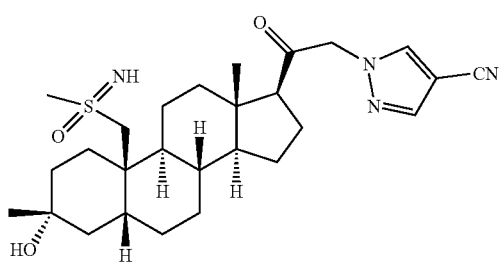

147

Step 1: (5R,8S,10R,13S,14S)-10-Fluoro-13-methyl-tetradecahydrospiro[cyclopenta[a]phenanthrene-3,2'-oxiran]-17(2H)-one

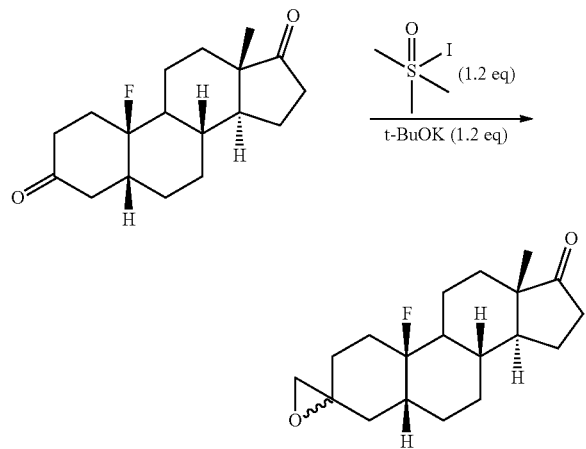

Trimethylsulfoxonium iodide (2.65 g, 12 mmol) and tetrahydrofuran (50 mL) were added successively to a 100 mL three-neck flask, followed by the addition of potassium tert-butoxide (1.35 g, 12 mmol) under stirring. The reaction solution was stirred at room temperature for 0.5 hour. (5R,8S,9S,10R,13S,14S)-10-Fluoro-13-methyltetradeca-hydro-3H-cyclopenta[a]phenanthrene-3,17(2H)-dione (3.0 g, 10 mmol) was added, and the reaction solution was reacted at room temperature for 2 hours. Saturated aqueous ammonium chloride solution was added to quench the reaction, and the reaction solution was extracted with ethyl acetate (30 mL). The organic phase was washed with saline (10 mL×3), dried over anhydrous sodium sulfate, filtrated and concentrated by rotary evaporation to dryness. The crude product was purified by column chromatography (petroleum ether/ethyl acetate: 3/1) to obtain (5R,8S,10R,13S,14S)-10-fluoro-13-methyltetradecahydrospiro[cyclopenta[a]phenanthrene-3,2'-oxiran]-17(2H)-one (2.5 g, light yellow solid, yield: 79.5%).

$^1$H NMR (400 MHz, CDCl$_3$) δ 2.72-2.67 (m, 2H), 2.52-2.43 (m, 1H), 2.31-1.06 (m, 21H), 0.92 (s, 3H).

Step 2: (3R,5R,8S,10R,13S,14S)-10-Fluoro-3-hydroxy-3-(methoxymethyl)-13-methylhexadecahydro-17H-cyclopenta[a]phenanthren-17-one

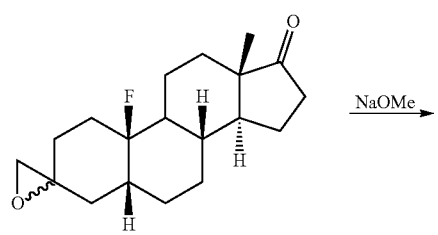

148

-continued

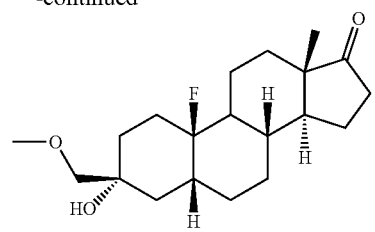

(5R,8S,10R,13S,14S)-10-Fluoro-13-methyltetradecahydrospiro[cyclopenta[a]phenanthrene-3,2'-oxiran]-17(2H)-one (2.5 g, 7.5 mmol) was dissolved in methanol (50 mL) in a 100 mL single-neck flask. After the solution was stirred at room temperature for 2-3 minutes, sodium methoxide (1.25 g, 22.5 mmol) was added. After completion of the addition, the reaction solution was stirred at 60° C. for 5 hours. The reaction solution was cooled to room temperature, saturated aqueous ammonium chloride solution was added to quench the reaction, and the reaction solution was extracted with ethyl acetate (30 mL). The organic phase was washed with saline (10 mL×3), dried over anhydrous sodium sulfate, filtrated and concentrated by rotary evaporation to dryness. The crude product was purified by column chromatography (petroleum ether/ethyl acetate: 3/1) to obtain (3R,5R,8S,10R,13S,14S)-10-fluoro-3-hydroxy-3-(methoxymethyl)-13-methylhexadecahydro-17H-cyclopenta[a]phenanthren-17-one (1.6 g, light yellow solid, yield: 57.9%).

$^1$H NMR (400 MHz, CDCl$_3$) δ 3.39 (s, 3H), 3.21 (s, 2H), 2.51-2.40 (m, 1H), 2.37-1.04 (m, 21H), 0.90 (s, 3H).

Step 3: (3R,5R,8S,10R,13S,14S)-17-Ethylidene-10-fluoro-3-(methoxymethyl)-13-methylhexadecahydro-1H-cyclopenta[a]phenanthren-3-ol

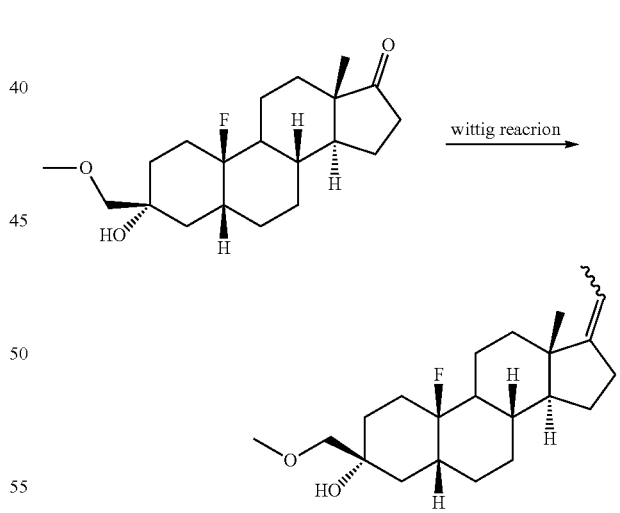

In accordance with Step 4 of Example 1, (3R,5R,8S,10R,13S,14S)-10-fluoro-3-hydroxy-3-(methoxymethyl)-13-methylhexadecahydro-17H-cyclopenta[a]phenanthren-17-one was used as the starting material, accordingly, the product (3R,5R,8S,10R,13S,14S)-17-ethylidene-10-fluoro-3-(methoxymethyl)-13-methylhexadecahydro-1H-cyclopenta[a]phenanthren-3-ol (600 mg, white solid, yield: 36.2%) was obtained.

$^1$H NMR (400 MHz, CDCl$_3$) δ 5.18-4.96 (m, 1H), 3.39 (s, 3H), 3.20 (s, 2H), 2.44-0.99 (m, 25H), 0.90 (s, 3H).

Step 4: (3R,5R,8S,10R,13S,14S,17R)-10-Fluoro-17-(1-hydroxyethyl)-3-(methoxymethyl)-13-methyl-hexadecahydro-1H-cyclopenta[a]phenanthren-3-ol

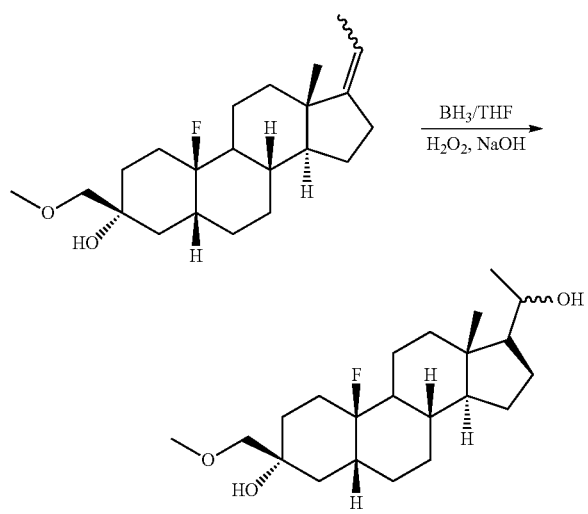

In accordance with Step 5 of Example 1, (3R,5R,8S,10R,13S,14S)-17-ethylidene-10-fluoro-3-(methoxymethyl)-13-methylhexadecahydro-1H-cyclopenta[a]phenanthren-3-ol was used as the starting material, accordingly, the product (3R,5R,8S,10R,13S,14S,17R)-10-fluoro-17-(1-hydroxyethyl)-3-(methoxymethyl)-13-methylhexadecahydro-1H-cyclopenta[a]phenanthren-3-ol (600 mg, white solid, yield: 95.1%) was obtained.

Step 5: 1-((3R,5R,8S,10R,13S,14S,17S)-10-Fluoro-3-hydroxy-3-(methoxymethyl)-13-methylhexadecahydro-1H-cyclopenta[a]phenanthren-17-yl)ethan-1-one

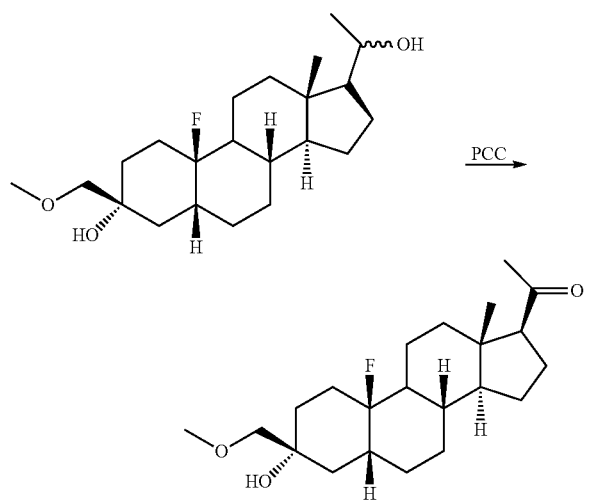

In accordance with Step 6 of Example 1, (3R,5R,8S,10R,13S,14S,17R)-10-fluoro-17-(1-hydroxyethyl)-3-(methoxymethyl)-13-methylhexadecahydro-1H-cyclopenta[a]phenanthren-3-ol was used as the starting material, accordingly, the product 1-((3R,5R,8S,10R,13S,14S,17S)-10-fluoro-3-hydroxy-3-(methoxymethyl)-13-methylhexadecahydro-1H-cyclopenta[a]phenanthren-17-yl)ethan-1-one (500 mg, white solid, yield: 83.7%) was obtained.

$^1$H NMR (400 MHz, CDCl$_3$) δ 3.40 (s, 3H), 3.21 (s, 2H), 2.56-2.47 (m, 1H), 2.39-2.16 (m, 4H), 2.12 (s, 3H), 2.07-0.98 (m, 18H), 0.65 (s, 3H).

Step 6: 2-Bromo-1-((3R,5R,8S,10R,13S,14S,17S)-10-fluoro-3-hydroxy-3-(methoxymethyl)-13-methyl-hexadecahydro-1H-cyclopenta[a]phenanthren-17-yl)ethan-1-one

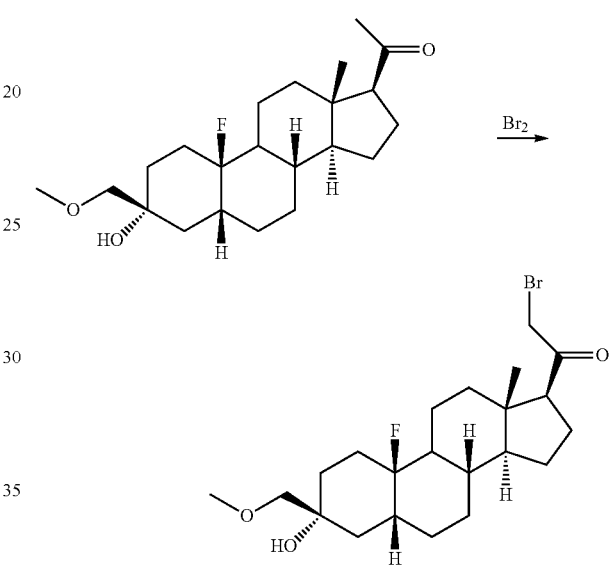

In accordance with Step 1 of Example 2, 1-((3R,5R,8S,10R,13S,14S,17S)-10-fluoro-3-hydroxy-3-(methoxymethyl)-13-methylhexadecahydro-1H-cyclopenta[a]phenanthren-17-yl)ethan-1-one was used as the starting material, accordingly, the product 2-bromo-1-((3R,5R,8S,10R,13S,14S,17S)-10-fluoro-3-hydroxy-3-(methoxymethyl)-13-methylhexadecahydro-1H-cyclopenta[a]phenanthren-17-yl)ethan-1-one (500 mg, white solid, yield: 82.2%) was obtained.

Step 7: 1-(2-((3R,5R,8S,9S,10R,13S,14S,17S)-10-Fluoro-3-hydroxy-3-(methoxymethyl)-13-methyl-hexadecahydro-1H-cyclopenta[a]phenanthren-17-yl)-2-oxoethyl)-1H-pyrazole-4-carbonitrile

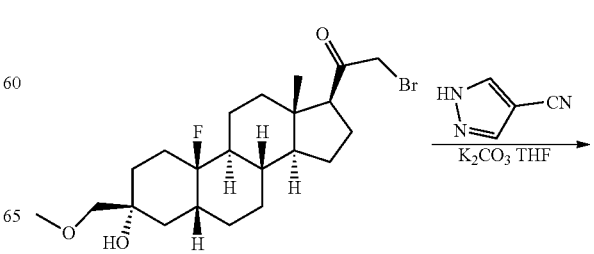

-continued

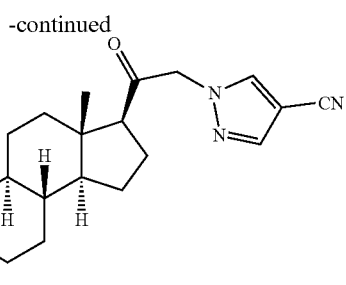

In accordance with Step 2 of Example 2, 2-bromo-1-((3R,5R,8S,9S,10R,13S,14S,17S)-10-fluoro-3-hydroxy-3-(methoxymethyl)-13-methylhexadecahydro-1H-cyclopenta[a]phenanthren-17-yl)ethan-1-one was used as the starting material, accordingly, the product 1-(2-((3R,5R,8S,9S,10R,13S,14S,17S)-10-fluoro-3-hydroxy-3-(methoxymethyl)-13-methylhexadecahydro-1H-cyclopenta[a]phenanthren-17-yl)-2-oxoethyl)-1H-pyrazole-4-carbonitrile (11 mg, white solid, yield: 17.8%) was obtained.

MS m/z (ESI): 458.3[M+H]+.

1H NMR (400 MHz, CDCl3) δ 7.87 (s, 1H), 7.82 (s, 1H), 5.04-4.90 (m, 2H), 3.40 (s, 3H), 3.22 (s, 2H), 2.58 (t, J=8.9 Hz, 1H), 2.22-1.01 (m, 22H), 0.71 (s, 3H).

Example 115

1-((3R,5R,8S,9S,10R,13S,14S,17S)-10-Fluoro-3-hydroxy-3-(methoxymethyl)-13-methylhexadecahydro-1H-cyclopenta[a]phenanthren-17-yl)-2-(4-(trifluoromethyl)-1H-pyrazol-1-yl)ethan-1-one

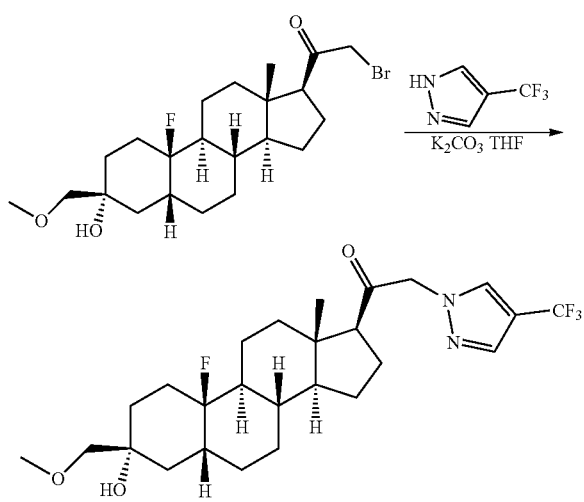

In accordance with Step 2 of Example 2, 2-bromo-1-((3R,5R,8S,9S,10R,13S,14S,17S)-10-fluoro-3-hydroxy-3-(methoxymethyl)-13-methylhexadecahydro-1H-cyclopenta[a]phenanthren-17-yl)ethan-1-one was used as the starting material, accordingly, the product 1-((3R,5R,8S,9S,10R,13S,14S,17S)-10-fluoro-3-hydroxy-3-(methoxymethyl)-13-methylhexadecahydro-1H-cyclopenta[a]phenanthren-17-yl)-2-(4-(trifluoromethyl)-1H-pyrazol-1-yl)ethan-1-one (25 mg, white solid, yield: 37.0%) was obtained. MS m/z (ESI): 501.2[M+H]+.

1H NMR (400 MHz, CDCl3) δ 7.74 (s, 2H), 5.05-4.82 (m, 2H), 3.40 (s, 3H), 3.22 (s, 2H), 2.59 (t, J=8.6 Hz, 1H), 2.45-1.05 (m, 22H), 0.72 (s, 3H).

Example 116

1-(2-((3R,5R,8S,9S,10R,13S,14S,17S)-10-Fluoro-3-hydroxy-3-(methoxymethyl)-13-methylhexadecahydro-1H-cyclopenta[a]phenanthren-17-yl)-2-oxoethyl)-1H-pyrazole-3-carbonitrile

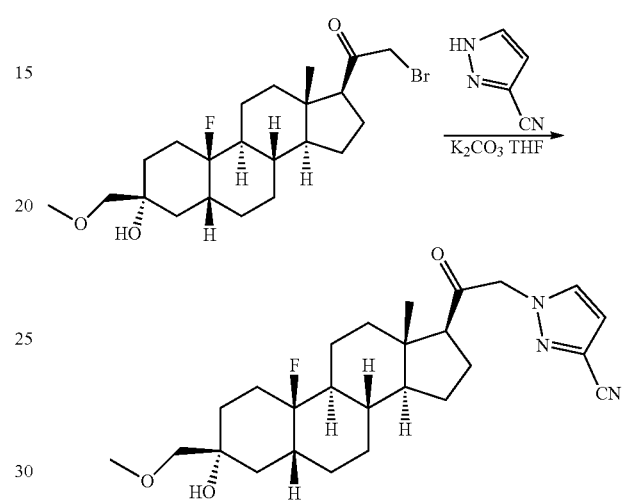

In accordance with Step 2 of Example 2, 2-bromo-1-((3R,5R,8S,9S,10R,13S,14S,17S)-10-fluoro-3-hydroxy-3-(methoxymethyl)-13-methylhexadecahydro-1H-cyclopenta[a]phenanthren-17-yl)ethan-1-one was used as the starting material, accordingly, the product 1-(2-((3R,5R,8S,9S,10R,13S,14S,17S)-10-fluoro-3-hydroxy-3-(methoxymethyl)-13-methylhexadecahydro-1H-cyclopenta[a]phenanthren-17-yl)-2-oxoethyl)-1H-pyrazole-3-carbonitrile (19 mg, white solid, yield: 30.8%) was obtained. MS m/z (ESI): 458.3[M+H]+.

1H NMR (400 MHz, CDCl3) δ 7.50 (d, J=2.4 Hz, 1H), 6.74 (d, J=2.4 Hz, 1H), 5.03-4.88 (m, 2H), 3.39 (s, 3H), 3.22 (s, 2H), 2.59 (t, J=8.8 Hz, 1H), 2.38-1.05 (m, 22H), 0.71 (s, 3H).

Example 117

1-(2-((3R,5S,8S,9S,10S,13S,14 S,17S)-3-Hydroxy-3,13-dimethyltetradecahydro-6H-5,10-methanocyclopenta[a]phenanthren-17-yl)-2-oxoethyl)-1H-pyrazole-4-carbonitrile

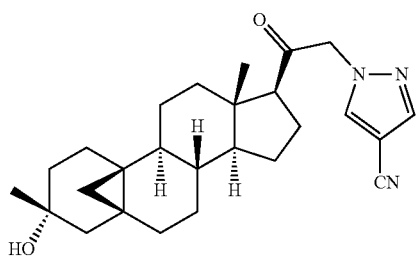

Step 1: ((8R,9S,10S,13S,14S)-13-Methyl-3,17-dioxo-1,2,3,6,7,8,9,11,12,13,14,15,16,17-tetradecahydro-10H-cyclopenta[a]phenanthren-10-yl)methyl 4-methylbenzenesulfonate

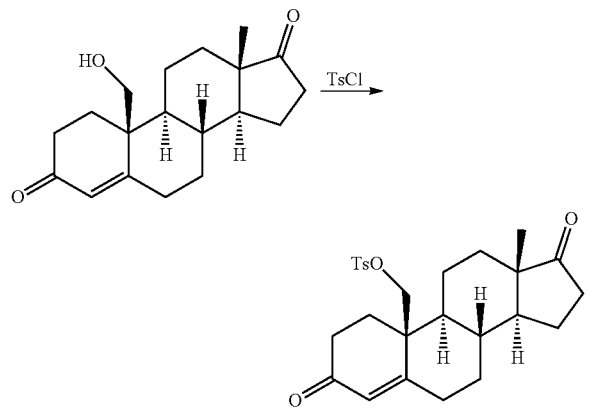

Pyridine (20 mL) and (8R,9S,10S,13S,14S)-10-(hydroxymethyl)-13-methyl-1,6,7,8,9,10,11,12,13,14,15,16-dodecahydro-3H-cyclopenta[a]phenanthrene-3,17(2H)-dione (6.0 g, 20 mmol) were added successively to an 100 mL three-neck flask, followed by the addition of 4-methylbenzenesulfonyl chloride (11.4 g, 60 mmol) under stirring. The reaction solution was stirred at room temperature for 12 hours, then poured into an ice-water bath to precipitate a white solid. The solid was filtrated out, washed with water and dried to obtain the product ((8R,9S,10S,13S,14S)-13-methyl-3,17-dioxo-1,2,3,6,7,8,9,11,12,13,14,15,16,17-tetradecahydro-10H-cyclopenta[a]phenanthren-10-yl)methyl 4-methylbenzenesulfonate (8.0 g, white solid, yield: 88%).

MS m/z (ESI): 457.2[M+H]$^+$.

$^1$H NMR (400 MHz, CDCl$_3$) δ 7.75 (d, J=8.0 Hz, 2H), 7.36 (d, J=8.0 Hz, 2H), 5.87 (s, 1H), 4.39-4.23 (m, 2H), 2.52-2.47 (m, 1H), 2.46 (s, 3H), 2.38-2.25 (m, 5H), 2.12-1.70 (m, 7H), 1.65-1.40 (m, 2H), 1.30-1.05 (m, 4H), 0.89 (s, 3H).

Step 2: (5S,8R,9S,10S,13S,14S)-13-Methyldodecahydro-17H-5,10-methanocyclopenta[a]phenanthrene-3,17(4H)-dione

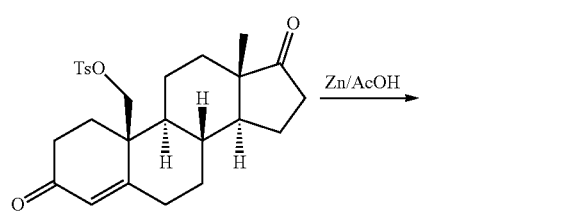

((8R,9S,10S,13S,14S)-13-Methyl-3,17-dioxo-1,2,3,6,7,8,9,11,12,13,14,15,16,17-tetradecahydro-10H-cyclopenta[a]phenanthren-10-yl)methyl 4-methylbenzenesulfonate (7.1 g, 15.5 mmol), acetic acid (300 mL) and water (300 mL) were added to a 100 mL single-neck flask. After the reaction solution was stirred at room temperature for 2-3 minutes, zinc powder (35 g, 538 mmol) was added. After completion of the addition, the reaction solution was reacted at 120° C. for 1.5 hours. The reaction solution was filtrated, and the filtrate was concentrated by rotary evaporation to dryness. The crude product was purified by column chromatography (petroleum ether/ethyl acetate: 35/1) to obtain (5S,8R,9S,10S,13S,14S)-13-methyldodecahydro-17H-5,10-methanocyclopenta[a]phenanthrene-3,17(4H)-dione (2.5 g, white solid, yield: 56%).

$^1$H NMR (400 MHz, CDCl$_3$) δ 2.56-2.53 (m, 2H), 2.49-2.27 (m, 2H), 2.14-1.70 (m, 9H), 1.55-0.90 (m, 8H), 0.89 (s, 3H), 0.55 (d, J=6.0 Hz, 1H), 0.45 (d, J=6.0 Hz, 1H).

Step 3: (3R,5S,8R,9S,10S,13S,14S)-3-Hydroxy-3,13-dimethyltetradecahydro-17H-5,10-methanocyclopenta[a]phenanthren-17-one

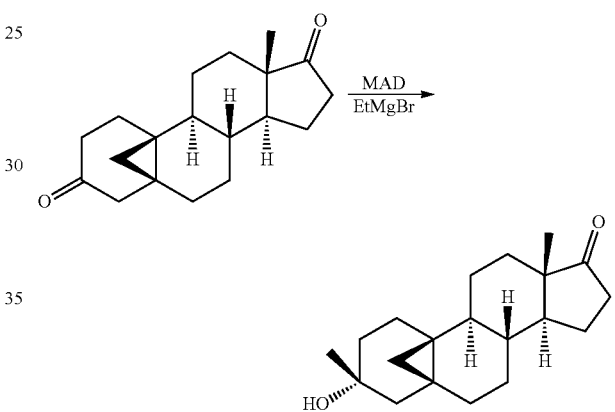

In accordance with Step 3 of Example 1, (5S,8R,9S,10S,13S,14S)-13-methyldodecahydro-17H-5,10-methanocyclopenta[a]phenanthrene-3,17(4H)-dione was used as the starting material, accordingly, the product (3R,5S,8R,9S,10S,13S,14S)-3-hydroxy-3,13-dimethyltetradecahydro-17H-5,10-methanocyclopenta[a]phenanthren-17-one (white solid, yield: 52%) was obtained.

$^1$H NMR (400 MHz, CDCl$_3$) δ 2.47-2.39 (m, 1H), 2.10-1.25 (m, 16H), 1.19 (s, 3H), 1.15-0.85 (m, 4H), 0.86 (s, 3H), 0.42 (s, 2H).

Step 4: (3R,5S,8S,9S,10S,13S,14S)-17-Ethylidene-3,13-dimethyltetradecahydro-6H-5,10-methanocyclopenta[a]phenanthren-3-ol

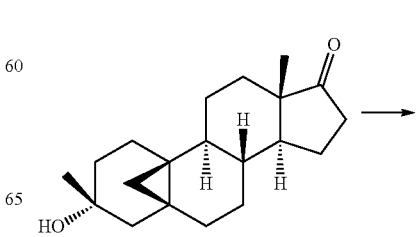

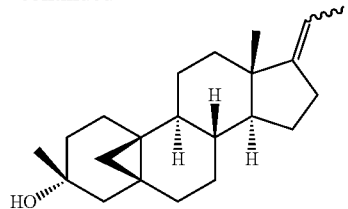

In accordance with Step 4 of Example 1, (3R,5S,8R,9S,10S,13S,14S)-3-hydroxy-3,13-dimethyltetradecahydro-17H-5,10-methanocyclopenta[a]phenanthren-17-one was used as the starting material, accordingly, the product (3R,5S,8S,9S,10S,13S,14S)-17-ethylidene-3,13-dimethyltetradecahydro-6H-5,10-methanocyclopenta[a]phenanthren-3-ol (white solid, yield: 61.5%) was obtained.

$^1$H NMR (400 MHz, CDCl$_3$) δ 5.15-5.08 (m, 1H), 2.40-1.20 (m, 18H), 1.19 (s, 3H), 1.16-0.87 (m, 6H), 086 (s, 3H), 0.43 (d, J=4.4 Hz, 1H), 0.35 (d, J=4.4 Hz, 1H).

Step 5: (3R,5S,8S,9S,10S,13S,14S)-17-(1-Hydroxyethyl)-3,13-dimethyltetradecahydro-6H-5,10-methanocyclopenta[a]phenanthren-3-ol

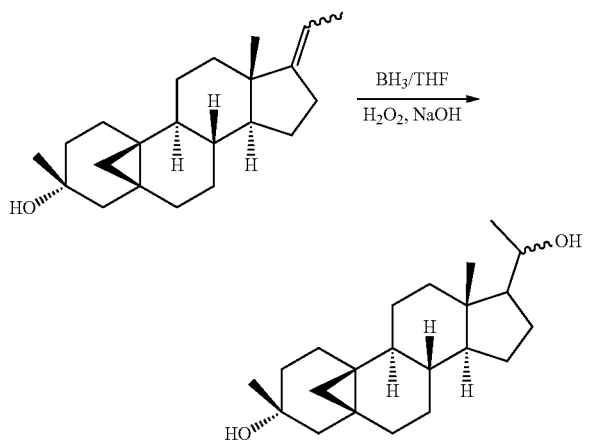

In accordance with Step 5 of Example 1, (3R,5S,8S,9S,10S,13S,14S)-17-ethylidene-3,13-dimethyltetradecahydro-6H-5,10-methanocyclopenta[a]phenanthren-3-ol was used as the starting material, accordingly, the product (3R,5 S,8 S,9S,10S,13S,14S)-17-(1-hydroxyethyl)-3,13-dimethyltetradecahydro-6H-5,10-methanocyclopenta[a]phenanthren-3-ol (white solid, yield: 100%) was obtained.

Step 6: 1-((3R,5S,8S,9S,10S,13S,14S,17S)-3-Hydroxy-3,13-dimethyltetradecahydro-6H-5,10-methanocyclopenta[a]phenanthren-17-yl)ethan-1-one

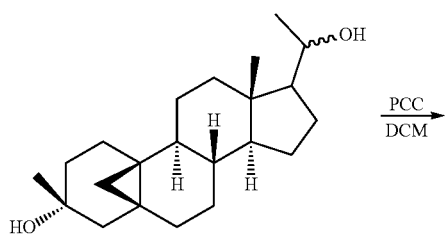

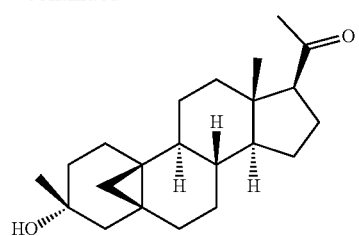

In accordance with Step 6 of Example 1, (3R,5S,8S,9S,10S,13S,14S)-17-(1-hydroxyethyl)-3,13-dimethyltetradecahydro-6H-5,10-methanocyclopenta[a]phenanthren-3-ol was used as the starting material, accordingly, the product 1-((3R,5S,8S,9S,10S,13S,14S,17S)-3-hydroxy-3,13-dimethyltetradecahydro-6H-5,10-methanocyclopenta[a]phenanthren-17-yl)ethan-1-one (white solid, yield: 71%) was obtained.

$^1$H NMR (400 MHz, CDCl$_3$) δ 2.54 (t, J=8.0 Hz, 1H), 2.12 (s, 3H), 2.10-1.25 (m, 17H), 1.19 (s, 3H), 1.15-0.72 (m, 4H), 0.60 (s, 3H), 0.41 (d, J=4.4 Hz, 1H), 0.36 (d, J=4.4 Hz, 1H).

Step 7: 2-Bromo-1-((3R,5S,8S,9S,10S,13S,14S,17S)-3-hydroxy-3,13-dimethyltetradecahydro-6H-5,10-methanocyclopenta[a]phenanthren-17-yl)ethan-1-one

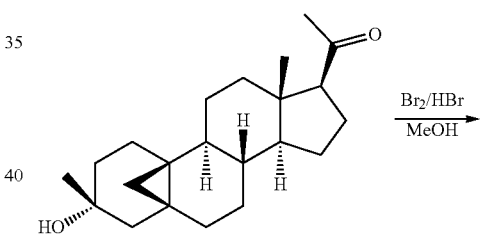

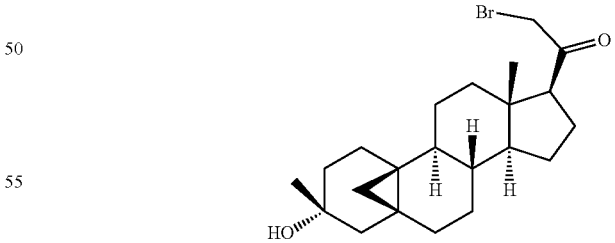

In accordance with Step 1 of Example 2, 1-((3R,5S,8S,9S,10S,13S,14S,17S)-3-hydroxy-3,13-dimethyltetradecahydro-6H-5,10-methanocyclopenta[a]phenanthren-17-yl)ethan-1-one was used as the starting material, accordingly, the product 2-bromo-1-((3R,5S,8S,9S,10S,13S,14S,17S)-3-hydroxy-3,13-dimethyltetradecahydro-6H-5,10-methanocyclopenta[a]phenanthren-17-yl)ethan-1-one (white solid, yield: 100%) was obtained.

Step 8: 1-(2-((3R,5S,8S,9S,10S,13S,14S,17S)-3-Hydroxy-3,13-dimethyltetradecahydro-6H-5,10-methanocyclopenta[a]phenanthren-17-yl)-2-oxoethyl)-1H-pyrazole-4-carbonitrile

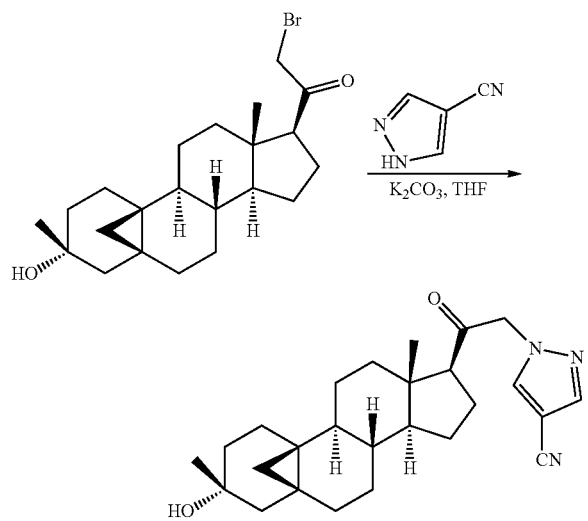

In accordance with Step 2 of Example 2, 2-bromo-1-((3R,5S,8S,9S,10S,13S,14S,17S)-3-hydroxy-3,13-dimethyltetradecahydro-6H-5,10-methanocyclopenta[a]phenanthren-17-yl)ethan-1-one was used as the starting material, accordingly, the product 1-(2-((3R,5S,8S,9S,10S,13S,14S,17S)-3-hydroxy-3,13-dimethyltetradecahydro-6H-5,10-methanocyclopenta[a]phenanthren-17-yl)-2-oxoethyl)-1H-pyrazole-4-carbonitrile (18 mg, white solid, yield: 21.9%) was obtained.

MS m/z (ESI): 404.2 [M-17]+.

$^1$H NMR (400 MHz, CDCl$_3$) δ 7.86 (s, 1H), 7.81 (s, 1H), 5.05-4.85 (m, 2H), 2.61 (t, J=8.8 Hz, 1H), 2.25-2.15 (m, 1H), 2.10-1.95 (m, 2H), 1.90-1.25 (m, 15H), 1.19 (s, 3H), 1.15-1.05 (m, 1H), 0.90-0.80 (m, 2H), 0.66 (s, 3H), 0.43-0.38 (m, 2H).

Example 118

1-(2-((3R,5S,8S,9S,10S,13S,14 S,17S)-3-Hydroxy-3,13-dimethyltetradecahydro-6H-5,10-methanocyclopenta[a]phenanthren-17-yl)-2-oxoethyl)-1H-pyrazole-3-carbonitrile

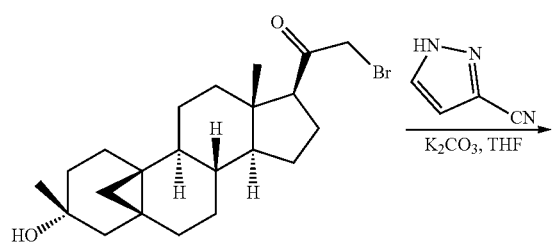

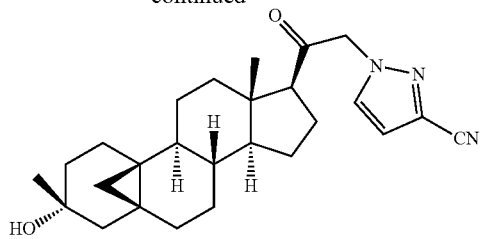

In accordance with Step 2 of Example 2, 2-bromo-1-((3R,5S,8S,9S,10S,13S,14S,17S)-3-hydroxy-3,13-dimethyltetradecahydro-6H-5,10-methanocyclopenta[a]phenanthren-17-yl)ethan-1-one was used as the starting material, accordingly, the product 1-(2-((3R,5S,8S,9S,10S,13S,14S,17S)-3-hydroxy-3,13-dimethyltetradecahydro-6H-5,10-methanocyclopenta[a]phenanthren-17-yl)-2-oxoethyl)-1H-pyrazole-3-carbonitrile (10.5 mg, white solid, yield: 15.4%) was obtained.

MS m/z (ESI): 404.2 [M-H$_2$O+H]+.

$^1$H NMR (400 MHz, CDCl$_3$) δ 7.48 (d, J=2.4 Hz, 1H), 6.73 (d, J=2.4 Hz, 1H) 5.10-4.85 (m, 2H), 2.61 (t, J=8.9 Hz, 1H), 2.24-1.98 (m, 3H), 1.90-1.25 (m, 15H), 1.16 (s, 3H), 1.15-1.05 (m, 1H), 0.90-0.80 (m, 2H), 0.67 (s, 3H), 0.43-0.37 (m, 2H).

Example 119

1-((3R,5 S,8 S,9S,10S,13S,14S,17S)-3-Hydroxy-3,13-dimethyltetradecahydro-6H-5,10-methanocyclopenta[a]phenanthren-17-yl)-2-(4-(trifluoromethyl)-1H-pyrazol-1-yl)ethan-1-one

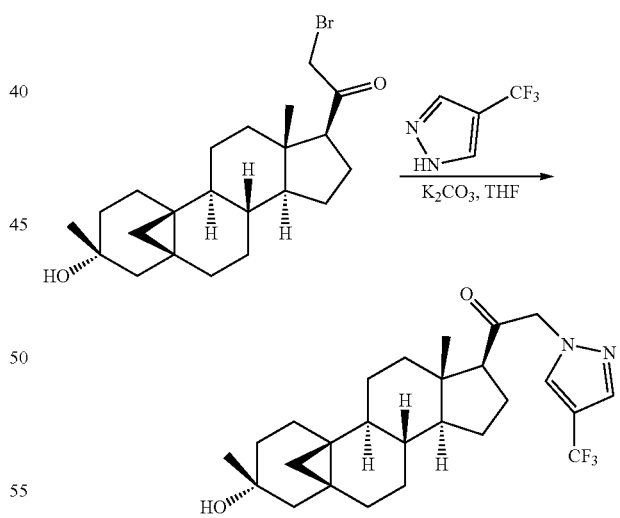

In accordance with Step 2 of Example 2, 2-bromo-1-((3R,5S,8S,9S,10S,13S,14S,17S)-3-hydroxy-3,13-dimethyltetradecahydro-6H-5,10-methanocyclopenta[a]phenanthren-17-yl)ethan-1-one was used as the starting material, accordingly, the product 1-((3R,5S,8S,9S,10S,13S,14S,17S)-3-hydroxy-3,13-dimethyltetradecahydro-6H-5,10-methanocyclopenta[a]phenanthren-17-yl)-2-(4-(trifluoromethyl)-1H-pyrazol-1-yl)ethan-1-one (10.5 mg, white solid, yield: 15.4%) was obtained.

MS m/z (ESI): 465.2 [M+H]+.

$^1$H NMR (400 MHz, CDCl$_3$) δ 7.72 (s, 2H), 5.10-4.85 (m, 2H), 2.61 (t, J=8.9 Hz, 1H), 2.26-1.98 (m, 3H), 1.90-1.25 (m, 15H), 1.19 (s, 3H), 1.15-1.05 (m, 1H), 0.90-0.80 (m, 2H), 0.67 (s, 3H), 0.43-0.37 (m, 2H).

Example 120 and Example 121

1-((3R,5 S,8 S,9S,10S,13S,14S,17S)-3-Hydroxy-3, 13-dimethyltetradecahydro-6H-5,10-methanocyclopenta[a]phenanthren-17-yl)-2-(1H-1,2,3-triazol-1-yl) ethan-1-one (120)

1-((3R,5 S,8 S,9S,10S,13S,14S,17S)-3-Hydroxy-3, 13-dimethyltetradecahydro-6H-5,10-methanocyclopenta[a]phenanthren-17-yl)-2-(1H-1,2,3-triazol-1-yl) ethan-1-one (121)

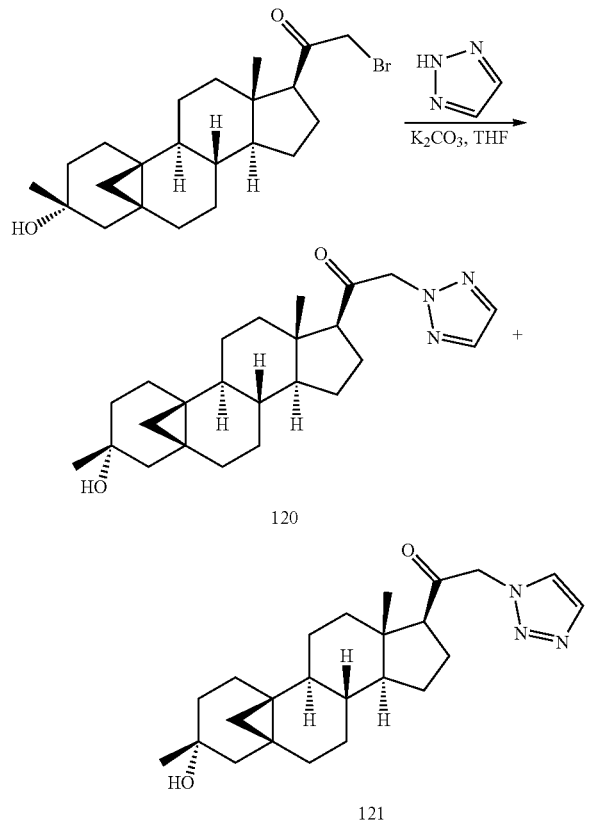

120

121

In accordance with Step 2 of Example 2, 2-bromo-1-((3R, 5S,8S,9S,10S,13S,14S,17S)-3-hydroxy-3,13-dimethyltetradecahydro-6H-5,10-methanocyclopenta[a]phenanthren-17-yl)ethan-1-one was used as the starting material, accordingly, the products 1-((3R,5S,8S,9S,10S,13S,14S, 17S)-3-hydroxy-3,13-dimethyltetradecahydro-6H-5,10-methanocyclopenta[a]phenanthren-17-yl)-2-(1H-1,2,3-triazol-1-yl)ethan-1-one (120) (7.2 mg, white solid, yield: 12.2%) and 1 ((3R,5S,8S,9S,10S,13S,14S,17S)-3-hydroxy-3,13-dimethyltetradecahydro-6H-5,10-methanocyclopenta[a]phenanthren-17-yl)-2-(1H-1,2,3-triazol-1-yl)ethan-1-one (121) (10 mg, white solid, yield: 17.1%) were obtained.

Example 120

MS m/z (ESI): 398.2[M+H]$^+$.
$^1$H NMR (400 MHz, CDCl$_3$) δ 7.68 (s, 2H), 5.26-5.20 (m, 2H), 2.59 (t, J=8.0 Hz, 1H), 2.24-1.95 (m, 3H), 1.90-1.25 (m, 15H), 1.19 (s, 3H), 1.15-1.05 (m, 1H), 0.90-0.80 (m, 2H), 0.70 (s, 3H), 0.43-0.37 (m, 2H).

Example 121

MS m/z (ESI): 398.2[M+H]$^+$.
$^1$H NMR (400 MHz, CDCl$_3$) δ 7.76 (s, 1H), 7.65 (s, 1H), 5.35-5.10 (m, 2H), 2.66 (t, J=8.0 Hz, 1H), 2.25-1.97 (m, 3H), 1.90-1.25 (m, 15H), 1.20 (s, 3H), 1.13-1.05 (m, 1H), 0.90-0.80 (m, 2H), 0.67 (s, 3H), 0.43-0.36 (m, 2H).

Biological Assay and Evaluation

The present invention is further described below in combination with the following test examples, which are not intended to limit the scope of the present invention.

I. GABA$_A$ Receptor Binding Ability Test of the Compounds of the Present Invention 1.1 Experimental objective: The objective of this test example is to measure the ability of the compounds to allosterically inhibit the binding of the ion channel blocker (tert-butylbicyclophosphorothionate (TBPS)) to the GABA-A receptor.

Experimental Instruments:

| Instruments/Consumables | Supplier | Model |
|---|---|---|
| Vortex mixer | IKA | MS3 basic |
| Electric thermostat incubator | Shanghai Yiheng Instrument Co., Ltd. | DHP-9032 |
| TopCount | PerkinElmer | NTX |
| Universal Harvester | Perkin Elmer | UNIFILTER-96 |
| High-speed floor-standing centrifuge | Thermo | LYNX 4000 |
| Glass tissue homogenizer | Nanjing Luanyu Glass Instrument Co., Ltd. | 50 ml |
| Sprague-Dawley Rat | Pharmaron | |
| Protease inhibitor | roche | 11836170001 |
| 1.1 ml deep 96-well plate round bottom | Axygen | P-DW-11-C |
| ULTIMA GOLD | Perkin Elmer | 77-16061 |
| UNIFILTER-96 GF/B filter plate | Perkin Elmer | 6005177 |
| Polyethylenimine (PEI), branched | Sigma | 408727 |

1.2 Experimental Procedures
1.2.1 Extraction of Cerebral Cortex Cell Membrane:
1. The cerebral cortex of male Sprague-Dawley rat was isolated.
2. A pre-chilled 0.32 M sucrose solution (one tablet of protease inhibitor was added per 100 ml) was added to the cerebral cortex (the volume of sucrose solution was 10 times the volume of the cerebral cortex). The mixture was crushed with a 50 ml glass tissue homogenizer in batches and mixed well.
3. The mixture was centrifuged at 1500 g, 4° C. for 10 minutes, and the supernatant was collected.
4. The mixture was centrifuged at 20000 g, 4° C. for 30 minutes, and the supernatant was discarded.
5. The precipitate was resuspended with the pre-chilled phosphate buffer saline (PBS) (one tablet of protease inhibitor was added per 100 ml). An average of 4 ml of PBS was added per rat, and the mixture was mixed well with a glass tissue homogenizer.
6. The mixture was centrifuged at 10000 g, 4° C. for 10 minutes, and the supernatant was discarded.

7. Steps 5 and 6 were repeated three times.

8. Finally, the precipitate was resuspended with 4 volumes of PBS. The resulting solution was dispensed, frozen in liquid nitrogen, and stored at −80° C.

9. The protein concentration was measured by the bicinchoninic acid (BCA) method.

1.2.2 $^{35}$S-TBPS Binding Assay 1. 230 μL of PBS was added to each well of a well plate with 1.1 ml volume.

2. 60 μL of the cerebral cortex cell membrane (5 μg/μL) solution was added to each well, and the mixture was mixed well.

3. The test compound (3 μL per well) was added, and the plate was incubated at 25° C. for 5 minutes. The DMSO concentration was 1%. The initial compound concentration was 1 NM, and a 3-fold dilution in gradient was carried out to obtain a total of 8 gradients and 2 replicates. 1% DMSO was used as a negative control, and 10 μM P026-2 was used as a positive control.

4. GABA was added at a final concentration of 5 NM, and incubated at 25° C. for 5 minutes. 1 mM GABA solution was formulated, and 1.5 μL of the solution was added to each well.

5. $^{35}$S-TBPS was added at a final concentration of 2 nM. The concentration of isotope mother solution was 9.7 μM. After dilution with PBS for 100 times, 6 μL of the diluted isotope solution was added to each well.

6. The plate was incubated at 4° C. for 20 hours.

7. The FilterMate GF/C plate was pre-treated with 0.5% PEI, and incubated at 4° C. for 1 hour.

8. The FilterMate GF/C plate was washed with Universal Harvester twice, 50 ml PBS each time.

9. The reaction solution was transferred to the GF/C plate, and each well was washed 4 times with 900 μL PBS.

10. The washed GF/C plate was placed at 55° C. and dried for 10 minutes.

11. 40 μL of scintillation solution was added to each well, and the CPM value was read with TopCount.

1.2.3 Experimental Data Processing Method:

In the experiment, the CPM (counts per minute) value was read with TopCount. According to the readings of the High control (DMSO) and the Low control (10 μM of the positive compound) experimental groups, the % inhibition was calculated based on the following formula:

% Inhibition=100×(CPM$_{High\ control}$−CPM$_{Sample}$)/(CPM$_{High\ control}$−CPM$_{Low\ control}$)

The IC$_{50}$ of the compound was calculated according to the following 4-parameter nonlinear logic formula:

Y=Bottom+(Top−Bottom)/(1+10^((Log IC50−X)*Hill Slope)), wherein:

X represents the log of compound concentration,

Y represents the % Inhibition.

The effect of the compound of the present invention on the TBPS binding activity was determined by the above test, and the measured IC50 values are shown in Table 1.

TABLE 1

IC$_{50}$ of the compounds of the present invention on inhibiting the TBPS binding activity

| Compound No. | $^{35}$S-TBPS bindng test (nM) | Compound No. | $^{35}$S-TBPS bindng test (nM) |
|---|---|---|---|
| 1 | 42.4 | 35 | 15.1 |
| 2 | 11.8 | 36 | 13.7 |
| 3 | 10.9 | 37 | 17.0 |
| 5 | 8.3 | 38 | 34.0 |
| 7 | 12.4 | 40 | 12.0 |
| 10 | 5.3 | 41 | 13.6 |
| 11 | 41.3 | 45 | 34.4 |
| 12 | 13.5 | 46 | 5.6 |
| 14 | 10.4 | 47 | 7.3 |
| 15 | 8.7 | 48 | 7.3 |
| 16 | 40.0 | 49 | 48.0 |
| 18 | 10.0 | 50 | 12.5 |
| 19 | 15.2 | 51 | 14.3 |
| 21 | 36.1 | 52 | 23.0 |
| 23 | 30.9 | 55 | 42.5 |
| 24 | 10.2 | 58 | 37.8 |
| 25 | 6.7 | 59 | 9.4 |
| 26 | 10.5 | 62 | 7.1 |
| 27 | 7.5 | 63 | 25.8 |
| 30 | 7.2 | 64 | 24.8 |
| 31 | 11.1 | 66 | 27.0 |
| 33 | 13.8 | 70 | 7.6 |
| 34 | 9.3 | 71 | 49.0 |

Conclusion: The compounds of the present invention have a significant inhibitory effect on the TBPS binding activity.

II. Pharmacokinetic Assay in Balb/c Mice

1. Test Objective:

Balb/c mice were used as test animals. The pharmacokinetic behavior in mice (plasma and brain tissue) of the compounds of Example 2, Example 5, Example 7, Example 12, Example 18, Example 23, Example 26, Example 38, Example 41, Example 50, Example 51 and Example 66 orally administrated at a dose of 5 mg/kg was studied.

2. Test Protocol:

2.1 Test Compounds:

Compounds of Example 2, Example 5, Example 7, Example 12, Example 18, Example 23, Example 26, Example 38, Example 41, Example 50, Example 51 and Example 66 of the present invention, prepared by the applicant.

2.2 Test Animals:

Male Balb/c mice were purchased from Shanghai Jiesijie Laboratory Animal Co., LTD, with Certificate No.: SCXK (Shanghai) 2013-0006 NO. 311620400001794.

2.3 Administration:

Each group had 24 male Balb/c mice. After an overnight fast, Balb/c mice were administrated p.o. with the test compound at an administration dose of 5 mg/kg and an administration volume of 10 mL/kg.

2.4 Sample Collection:

0.2 ml of blood was taken from the heart before administration and at 0, 0.5, 1, 2, 4, 6, 8 and 24 hours after administration. The samples were stored in EDTA-K$_2$ tubes, and centrifuged for 6 minutes at 4° C., 6000 rpm to separate the plasma. The plasma samples were stored at −80° C. The mice were sacrificed with CO$_2$, and the whole brain tissue was taken out, weighed, placed in a 2 mL centrifuge tube and stored at −80° C.

2.5 Sample Process:

1) 160 μL of acetonitrile was added to 40 μL of the plasma sample for precipitation, and then the mixture was centrifuged for 5-20 minutes at 3500×g.

2) 90 μL of acetonitrile containing the internal standard (100 ng/mL) was added to 30 μL of the plasma and brain homogenate samples for precipitation, and then the mixture was centrifuged for 8 minutes at 13000 rpm.

3) 70 μL of the treated supernatant was taken and added to 70 μL of water, and mixed by vortex for 10 minutes. 20 μL of the mixture was taken to analyze the concentration of the test compound by LC/MS/MS. LC/MS/MS analysis instrument: AB Sciex API 4000 Qtrap.

2.6 Liquid Chromatography Analysis

Liquid chromatography condition: Shimadzu LC-20AD pump.

Chromatographic column: Agilent ZORBAX XDB-C18 (50×2.1 mm, 3.5 μm); Mobile phase: Eluent A was 0.1% formic acid in water, and Eluent B was acetonitrile.

Flow rate: 0.4 mL/min

Elution time: 0-4.0 minutes the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | | Stop |

3. Test Results and Analysis

The main parameters of pharmacokinetics were calculated by WinNonlin 6.1. The results of pharmacokinetic test in mice are shown in Table 2 below:

TABLE 2

Results of pharmacokinetic test in mice

| | Pharmacokinetic test (5 mg/kg) | | | | | |
|---|---|---|---|---|---|---|
| Example No. | Peak time $t_{max}$(ng/mL) | Plasma concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
| Example 2 plasma | 1.0 | 846.3 | 2655.8 | 2707.2 | 1.49 | 2.49 |
| Example 2 brain tissue | 1.0 | 655.0 | 1765.2 | 1794.9 | 1.49 | 2.26 |
| Example 5 plasma | 0.5 | 242.0 | 515.2 | 524.1 | 1.16 | 1.94 |
| Example 5 brain tissue | 0.5 | 233.7 | 470.9 | 485.5 | 0.94 | 1.74 |
| Example 7 plasma | 1.0 | 888.3 | 3779.8 | 3782.8 | 1.73 | 3.67 |
| Example 7 brain tissue | 1.0 | 1263.3 | 5106.0 | 5514.3 | 1.89 | 3.37 |
| Example 12 plasma | 0.5 | 5160.0 | 4288.5 | 4294.4 | 1.17 | 0.86 |
| Example 12 brain tissue | 0.5 | 583.0 | 422.6 | 424.5 | 0.20 | 0.73 |
| Example 18 plasma | 1.0 | 236 | 1518.1 | 1544.3 | 4.2 | 5.5 |
| Example 18 brain tissue | 1.0 | 281.7 | 2141.1 | 2186.8 | 4.7 | 6.1 |
| Example 23 plasma | 0.5 | 408.0 | 544.7 | 555.7 | 1.08 | 1.78 |
| Example 23 brain tissue | 0.5 | 558.0 | 1067.1 | 1126.7 | 1.36 | 2.42 |
| Example 26 plasma | 0.5 | 232.3 | 767 | 771.5 | 2.57 | 4.08 |
| Example 26 brain tissue | 0.5 | 172.3 | 722.9 | 828.4 | 2.06 | 3.84 |
| Example 38 plasma | 0.5 | 1113.7 | 1945.1 | 1974.3 | 1.08 | 1.7 |
| Example 38 brain tissue | 0.5 | 746.7 | 1216.1 | 1230.2 | 1.14 | 1.6 |
| Example 41 plasma | 0.5 | 1226.7 | 1144.4 | 1147.4 | 0.72 | 0.94 |
| Example 41 brain tissue | 0.5 | 625.3 | 553.5 | 559.5 | 0.35 | 0.91 |
| Example 50 plasma | 1.0 | 324.0 | 1080.7 | 1097.3 | 1.11 | 2.36 |
| Example 50 brain tissue | 1.0 | 656.0 | 2215.1 | 2265.7 | 1.10 | 2.48 |
| Example 51 plasma | 0.5 | 711.2 | 1955.1 | 2079.5 | 1.93 | 2.65 |
| Example 51 brain tissue | 1.0 | 512.3 | 1625.9 | 1796.0 | 2.19 | 3.28 |
| Example 66 plasma | 0.5 | 917.7 | 6040.9 | 6124.7 | 4.39 | 5.54 |
| Example 66 brain tissue | 1.0 | 2006.0 | 14940.0 | 15020.9 | 3.60 | 5.01 |

It can be seen from the results of the pharmacokinetic test in mice in the table that the compounds of the examples of the present invention showed good metabolic properties, and both the exposure AUC and the maximum blood drug concentration $C_{max}$ performed well.

III. In Vivo Pharmacodynamic Test in the Forced Swimming Model in Mice 3.1 Experimental Objective The antidepressant effect of the compound was evaluated by the forced swimming model in mice.

3.2 Main Instruments and Reagents of the Experiment 3.2.1 Instruments

Forced swimming device (JLBehv-FSC-4, Shanghai Jiliang Software Technology Co., Ltd.).

3.2.2 Reagents

Sodium carboxymethyl cellulose (CMC-Na, SLBV9664, Sigma)

Tween 80 (BCBV8843, Sigma)

3.2.3 Test Compounds

Compounds of Example 2, Example 5, Example 7, Example 18, Example 23, Example 26 and Example 50 of the present invention, prepared by the applicant.

3.3 Experimental Procedures 3.3.1 Adaptation:

Male ICR mice (25-35 g) were adapted in the test environment for 3 days before the forced swimming test.

3.3.2 Grouping and Administration:

According to the test design, the mice were randomly grouped on the day before the test according to body weight, with 12 mice in each group. Before the test, the compounds of each example were administrated intragastrically according to the Tmax thereof in the brain in mice pharmacokinetic test as follows:

1) Model group (0.5% CMC-Na+1% Tween 80 solution, p.o., 10 mL/kg);

2) Compounds of Example 2, Example 5, Example 7, Example 18, Example 23, Example 26 and Example 50 (10 mg/kg, p.o., 10 mL/kg).

When being administrated, the compounds of each example were suspended in 0.5% CMC-Na-1% Tween 80 solution to the desired concentration.

3.3.2 Forced Swimming Test:

0.5-1 hour after administration, ICR mice were placed in a forced swimming device (transparent glass drum (water depth 18 cm, water temperature 25-26° C.), one mouse per tank) and forced to swim for 6 minutes. The forced swimming device recorded the floating time of the ICR mice during the entire 6 minutes, and the data of the latter four minutes were used for data analysis. The mice were taken out immediately after the swimming test, wiped dry and put back in their original cages.

Note: The criterion for determining the immobility time is that the mouse stops struggling in water and floats, and there are only slight limb movements to keep the head floating on the water.

3.4 Data Analysis

Floating time percentage=100*floating time/240 s.

3.5 Test Data:

| Example No. | Dose (mpk) | Mean (immobility, s) | Mean (immobility, %) |
|---|---|---|---|
| Vehicle | / | 163.70 | 68.22 |
| Example 2 | 10 | 87.34 | 36.39 |
| Example 5 | 10 | 65.07 | 27.11 |
| Example 7 | 10 | 141.58 | 58.99 |
| Example 18 | 10 | 146.86 | 61.19 |
| Example 23 | 10 | 68.51 | 28.55 |
| Example 26 | 10 | 128.30 | 53.46 |
| Example 50 | 10 | 101.07 | 42.11 |

3.6 Test Results

It can be seen from the above results that the compounds of the examples of the present application can significantly shorten the cumulative immobility time of the forced-swimming mice, and have a significant antidepressant effect.

The immobility time during the latter four minutes of the compound of Example 2 was significantly different compared with that of the model group; and the immobility time during the latter four minutes of the compounds of Example 5, Example 23 and Example 50 was very significantly different compared with that of the model group.

IV. In Vivo Pharmacodynamic Test in the PTZ-Induced Epilepsy Model in Mice 4.1 Test Objective The PTZ-induced epilepsy model in CD-1 mice was established, and the antiepileptic effect of the compounds of Example 5 and Example 23 was evaluated using this model.

4.2 Test Method 4.2.1 Test Animals 30 male CD-1 mice were purchased from Beijing Vital River Laboratory Animal Technology Co. Ltd. The test animals were adapted at the animal room in the third building of Shanghai ChemPartner Co., Ltd for 7 days before the test. The average body weight of the animals on the test day was 32.2±0.2 grams. Feeding environment: 5 animals/cage, room temperature 23±2° C., 12/12 hours of light and dark cycle, free access to food and water.

The mice were randomly grouped for the test on the test day.

4.2.2 Test Compounds

Compounds of Example 5 and Example 23 (prepared by the applicant). The test compounds were stored in a refrigerator at 4° C.

TABLE 3

Test reagent information

| Name | Article number | Batch number | Property | Supplier | Total weight | Purity | Store condition |
|---|---|---|---|---|---|---|---|
| pentylenetetrazol (PTZ) | P6500 | SLBD3876V | White crystal | Sigma | 25 g | 100% | −20° C. refrigeration |
| Sodium carboxymethyl cellulose | 9004-32-4 | LAB0R36 | White solid | Beijing J&K Scientific Co., Ltd. | 100 G | 800 cps | Room temperature/dry/in the dark |
| Tween-80 | 9005-65-6 | P1279207 | Transparent liquid | GENERAL-REAGENT ® | 500 mL | 100% | Room temperature/dry |

TABLE 3-continued

Test reagent information

| Name | Article number | Batch number | Property | Supplier | Total weight | Purity | Store condition |
|---|---|---|---|---|---|---|---|
| Hydroxypropyl β-cyclodextrin | 19184C | OP1901A | White powder | Seebio Biotech | 500 g | ≥98% | 2-8° C. refrigeration |
| 0.9% sodium chloride injection | H37022749 | H18010314 | Transparent liquid | Shandong Hualu Pharmaceutical Co., Ltd. | 500 mL | 100% | Room temperature/dry |

4.2.1 Test Equipments
1 ml sterile disposable syringe with needle (purchased from Zhejiang Kangdelai Medical Devices Co., Ltd.)
Pipette: Eppendorf Research Plus (100-1000 μL)
Vortex mixer: Kylin-Bell Vortex 5
Ultrasonic instrument: JL-360 ultrasonic cleaner
Balance: METTLER TOLEDO XS204 precision balance
Balance: METTLER TOLEDO XS6002S electronic balance
Plexiglass box: 25 cm length*15 cm width*15 cm height with one opaque side wall, custom made by Suzhou Fengshi Laboratory Animal Equipment Co., Ltd
3-channel timer: Oregon/Model NO. WB-388

4.2.2 Test Animal Grouping
1) Vehicle/PTZ: 0.5% CMC-Na+1% Tween-80 (10 ml/kg, p.o.), administrated 0.5 hr before the PTZ administration; PTZ (120 ml/kg, s.c.), administrated before the test;
2) 3 mg/kg of the compounds of Examples/PTZ: the compounds of Example 5 and Example 23 (3 mg/kg, 10 ml/kg, p.o.), administrated 0.5 hr before the PTZ administration; PTZ (120 ml/kg, s.c.), administrated before the test.

4.3 Experimental Procedures
4.3.1 Solvent Formulation
1) 0.5% CMC-NA+1% Tween-80 (administration volume: 10 mL/kg):

1 g of sodium carboxymethyl cellulose was precisely weighed and added to a 250 mL solvent bottle, then 150 mL of double-distilled water was added. The mixture was stirred at room temperature for 4 hours with a magnetic stirrer to obtain a uniform and clear solution. 2 mL of Tween-80 was slowly added, and the mixture was stirred at room temperature for 3 hours to obtain a uniform and clear solution. The solution was slowly transferred to a 200 mL volumetric flask, and double distilled water was added to the constant volume of 200 mL. The solution was transferred to a 250 mL solvent bottle, and stirred for 1 hour with a magnetic stirrer to obtain a uniform and clear solution.

2) 30% hydroxypropyl-β-cyclodextrin:

30.6122 g of hydroxypropyl-β-cyclodextrin (purity: 98%) was precisely weighed and added to a 100 mL solvent bottle, then 60 mL of double-distilled water was added. The mixture was mixed by vortex for 3 minutes, and treated by ultrasound at room temperature for 15 minutes to obtain a uniform and clear solution. Double distilled water was added to the constant volume of 100 mL, mixed by vortex for 1 minute, and treated by ultrasound at room temperature for 5 minutes to obtain a uniform and clear solution.

4.3.2 Test Compound Formulation
1) 12 mg/mL PTZ (dose: 120 mg/kg; administration volume: 10 mL/kg):

248 mg of PTZ was precisely weighed and added to a 40 mL brown flask, then 20.667 mL of physiological saline was added. The mixture was mixed by vortex for 2 minutes, and treated by ultrasound at room temperature for 2 minutes to obtain a uniform and clear solution (concentration: 12 mg/mL).

2) 0.3 mg/mL of the compounds of Example 5 or Example 23 (dose: 3 mg/kg; administration volume: 10 mL/kg):

A certain amount of 0.5% CMC-NA+1% Tween-80 was taken and added to a flask containing a certain amount of the compounds of Example 5 or Example 23. The mixture was mixed by vortex for 3 minutes, and treated by ultrasound at room temperature for 15 minutes to obtain a uniform suspension (concentration: 0.3 mg/mL).

4.3.3 Test Method
1) The test animals were transferred to the operating room to adapt to the environment 1 hour before the test;
2) The animals were randomly grouped, marked and weighed;
3) The compounds of Example 5 and Example 23 were administrated respectively 1 hour before the PTZ administration, or 0.5% CMC-NA+1% Tween-80, the compounds of Example 5 and Example 23 were administrated respectively 0.5 hour before the PTZ administration;
4) PTZ (120 mg/kg) was administrated subcutaneously before the test observation, and this time point was recorded as the observation start point;
5) After the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died, 6) if the animal did not have seizures during the 30-minute observation period, the incubation period was recorded as 1800 sec and the number of seizures was recorded as 0.

Clonic seizure: generalized clonic seizure in animals lasts for more than 3 seconds, and is accompanied by a fall;
Tonic seizure: the limbs straightens 90° to the body;
6) The possible side effects induced by the drug after the administration were observed and recorded, which can be divided into four levels:
None: normal
Mild sedation
Moderate sedation
Severe sedation
7) The test was carried out from 12:00 am to 16:30 pm.

4.4 Adaptation to the Environment
The test animals were transferred to the operating room to adapt to the environment 1 hour before the test.

4.5 Grouping and Administration
The mice were randomly grouped, marked and weighed; 10 mice per group. The test compound was administrated orally at an administration volume of 10 mL/kg 30-60 minutes before the PTZ administration.

4.6 PTZ Modeling and Testing

PTZ (120 mg/kg) was administered subcutaneously before the test observation, and this time point was recorded as the observation start point; after the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died. If the animal did not have seizures during the 30-minute observation period, the incubation period was recorded as 1800 sec and the number of seizures was recorded as 0.

4.7 Data Analysis

All measurement data were expressed as Mean±SEM, and analysed with Prism 6.0 statistical software.

4.8 Test Data:

| Example No. | Dose (mpk) | Incubation period of the clonic seizure (sec) Mean ± SEM | Number of clonic seizures Mean | Incubation period of the generalized tonic seizure (sec) Mean | Number of generalized tonic seizures Mean | Time when the animal died (sec) Mean | Mortality rate (%) |
|---|---|---|---|---|---|---|---|
| Vehicle | / | 331.4 ± 61.2 | 2.1 ± 0.2 | 821.6 ± 107.7 | 1.0 ± 0.0 | 839.8 ± 108.0 | 100% |
| 5 | 3 | 644.5 ± 122.0 | 1.8 ± 0.3 | 1576.7 ± 108.8 | 0.4 ± 0.2 | 1623.0 ± 105.5 | 40% |
| 23 | 3 | 366.5 ± 21.1 | 1.8 ± 0.2 | 1519.9 ± 117.9 | 0.4 ± 0.2 | 1527.7 ± 114.6 | 40% |

4.9 Test Results

The compounds of the examples significantly prolonged the incubation period of clonic seizure and generalized tonic seizure and reduced the number of clonic seizures and generalized tonic seizures, compared with the control group. The compounds of the examples can protect 60% of animals from death, significantly prolong the incubation period of death, and have a good antiepileptic effect.

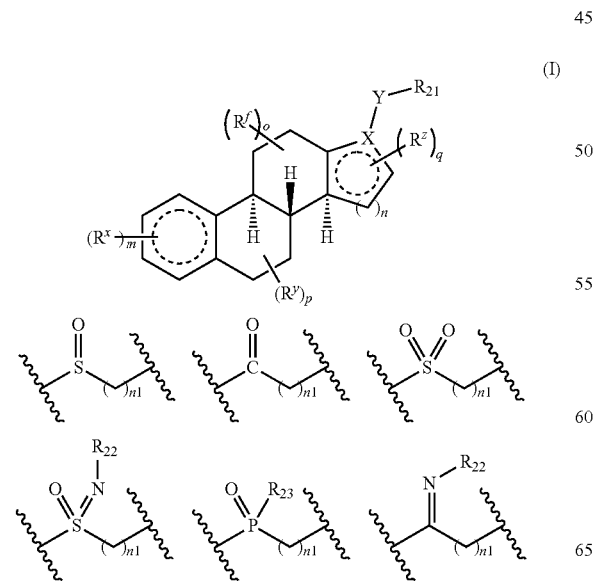
(I)

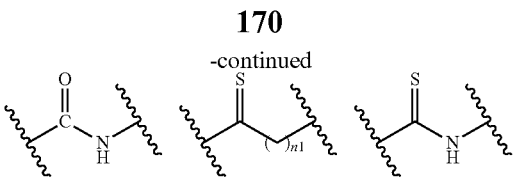

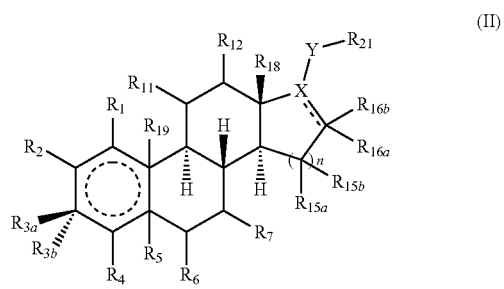
(II)

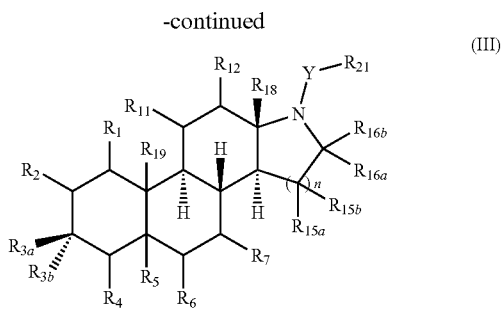
(III)

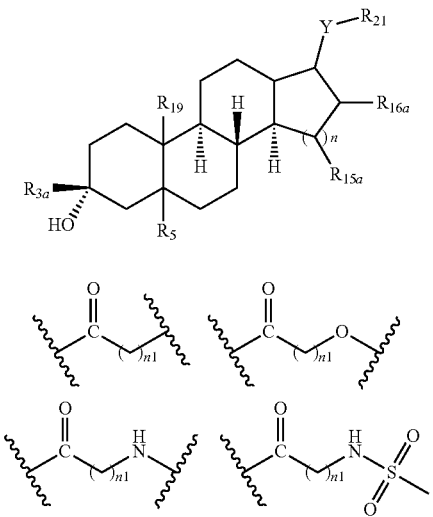

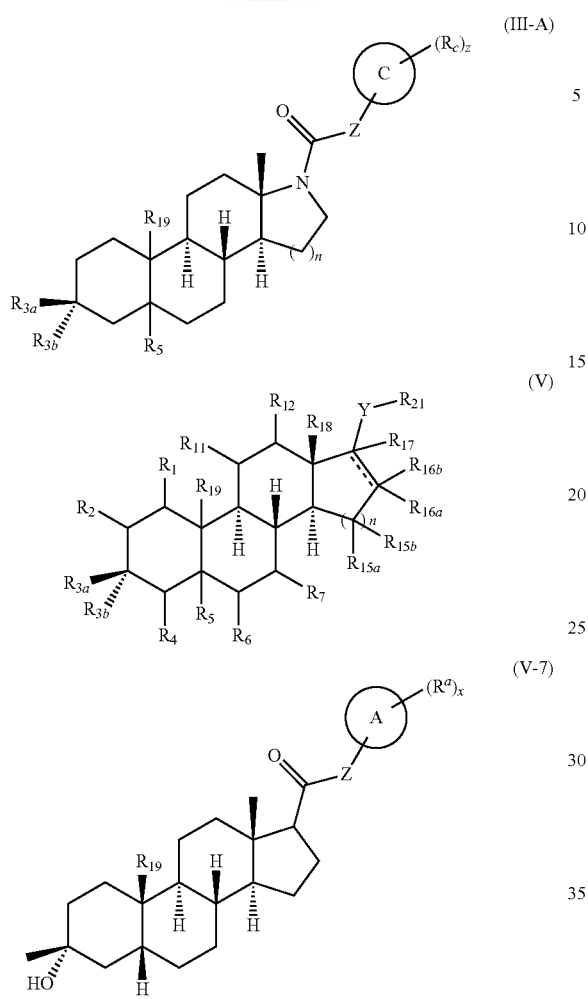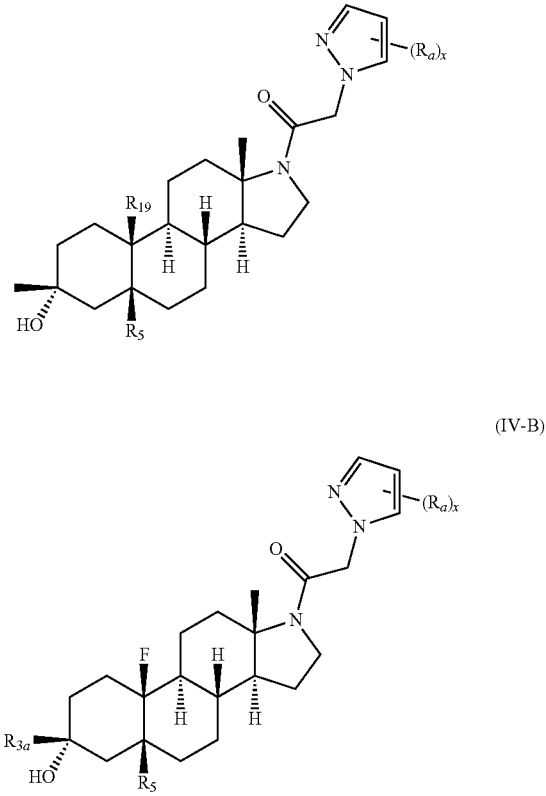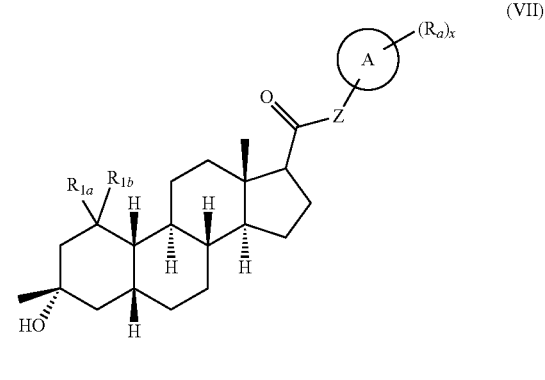

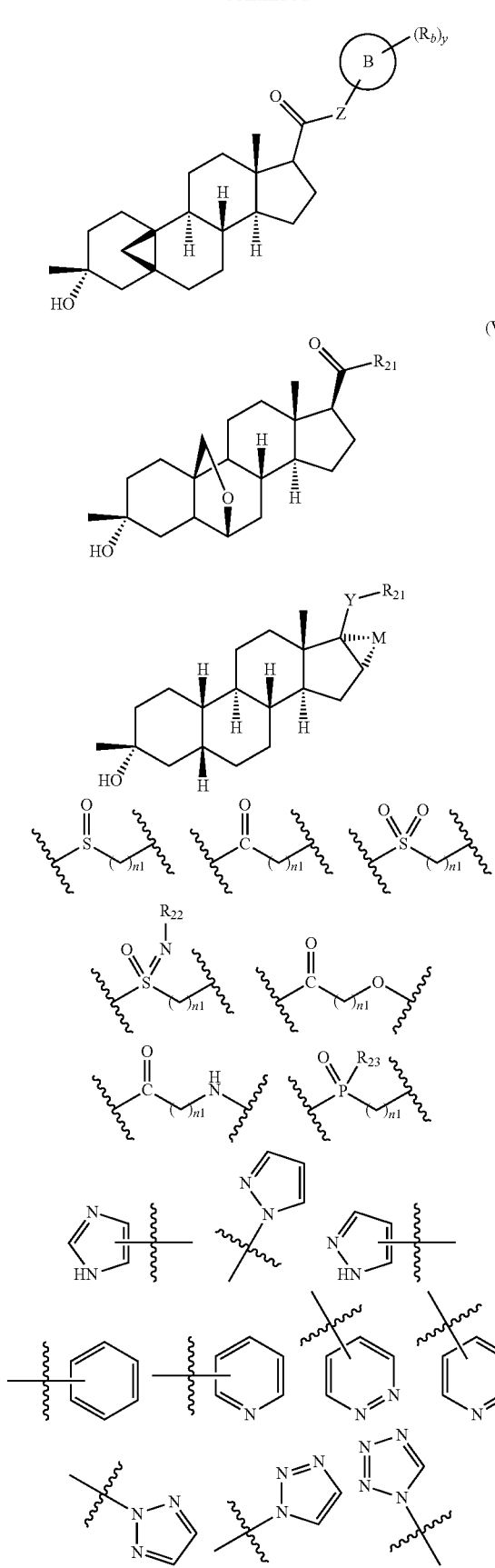
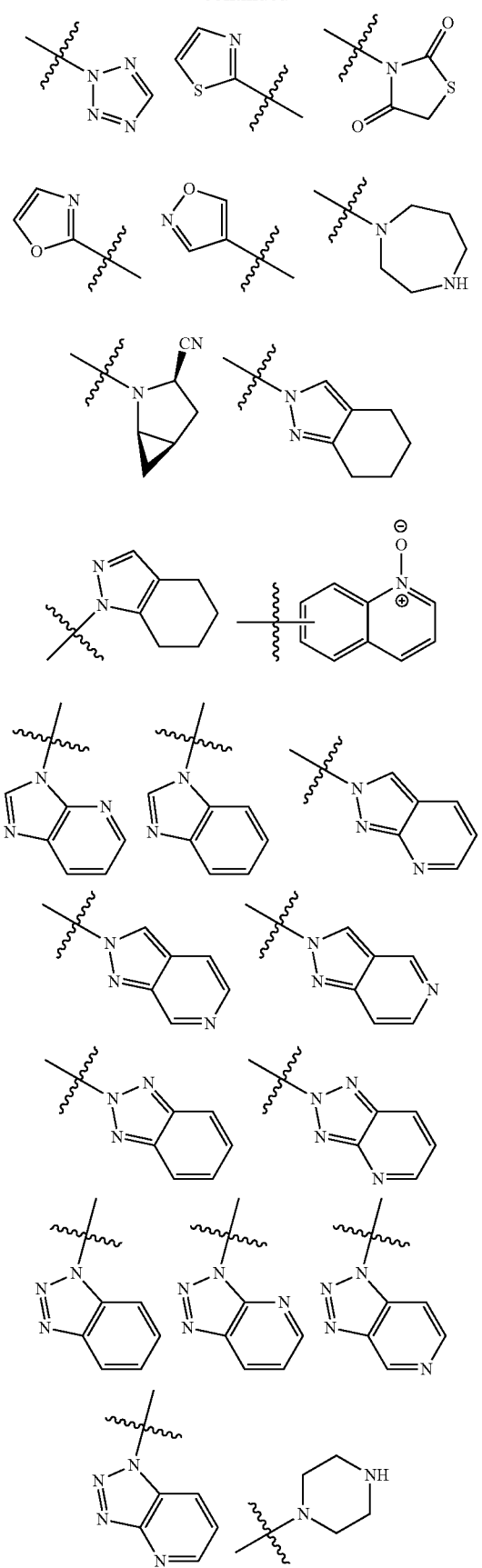

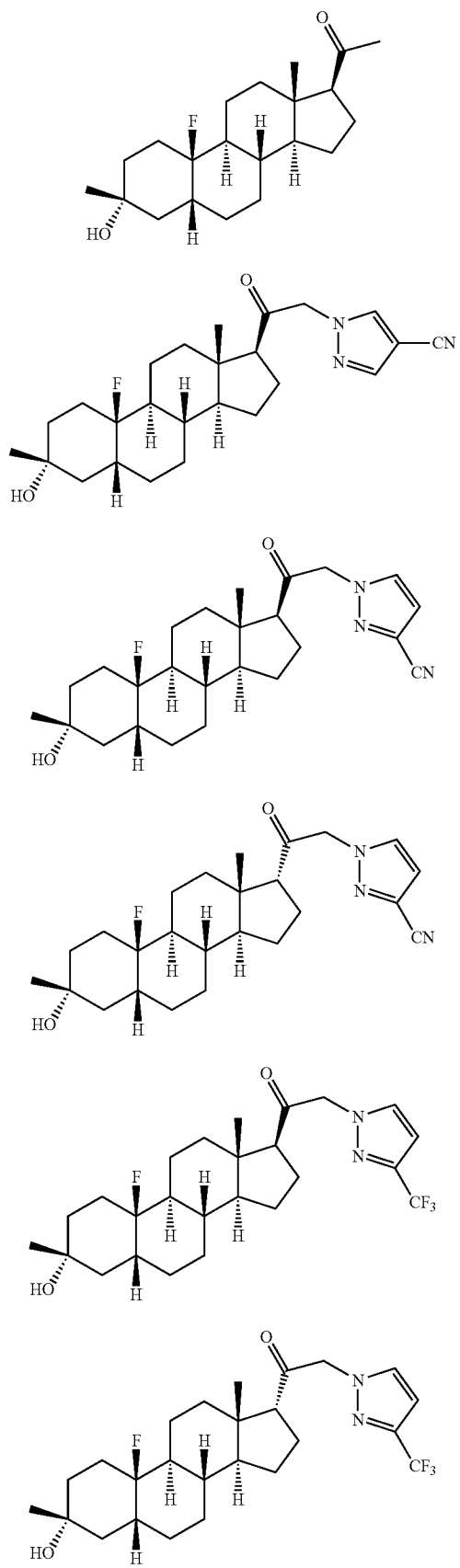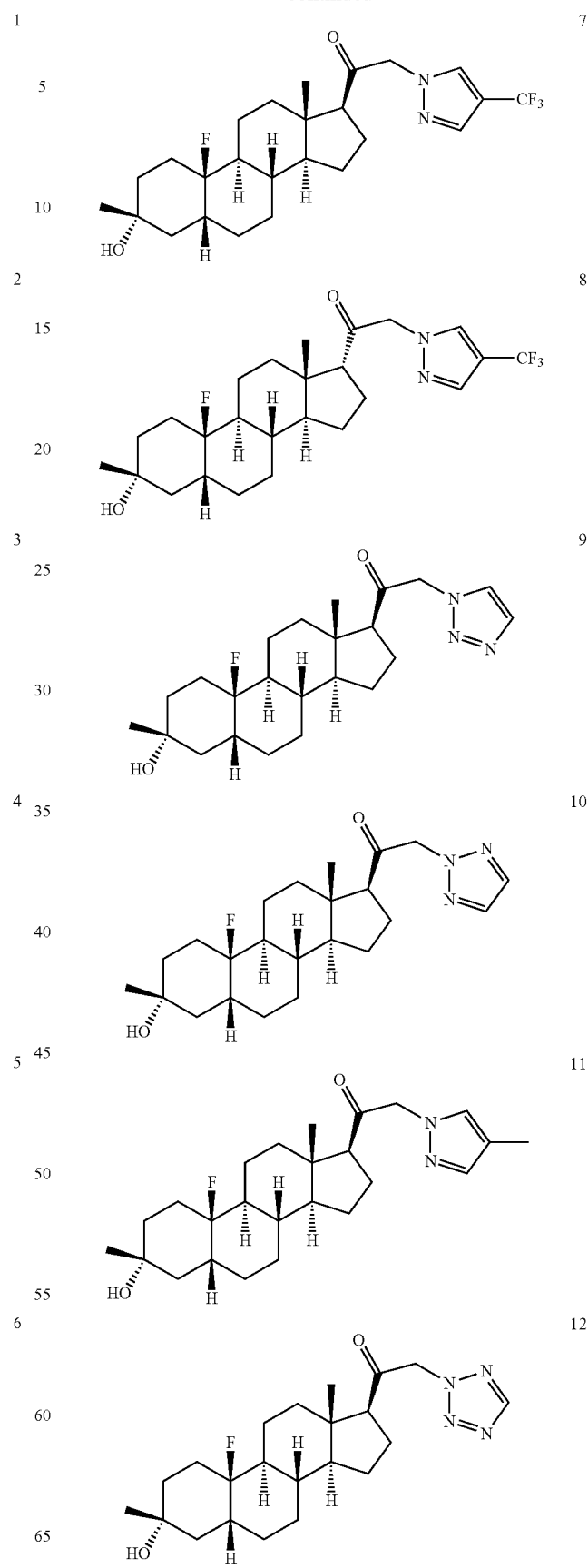

13
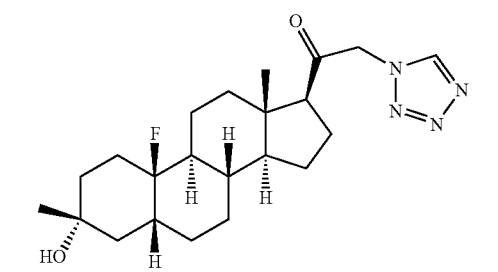
14
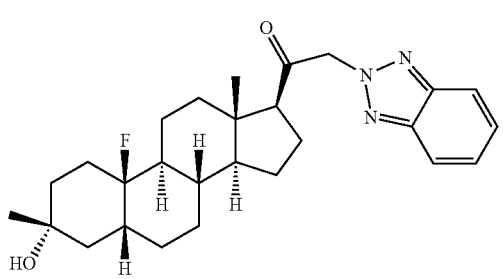
15
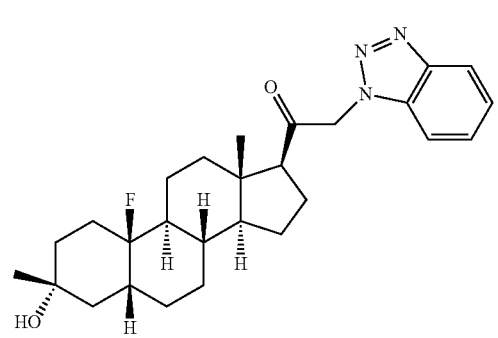
16
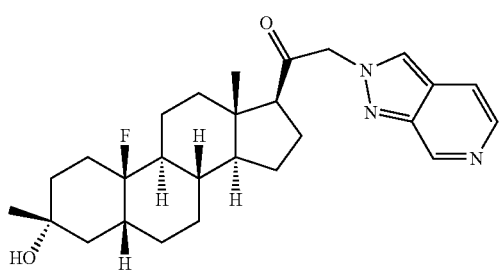
17
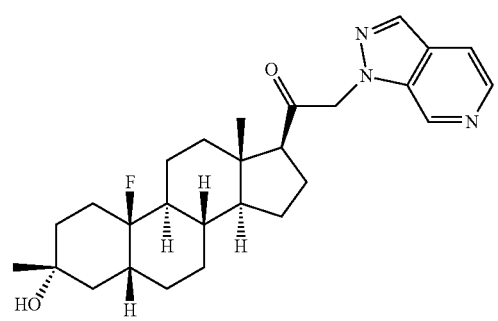
18
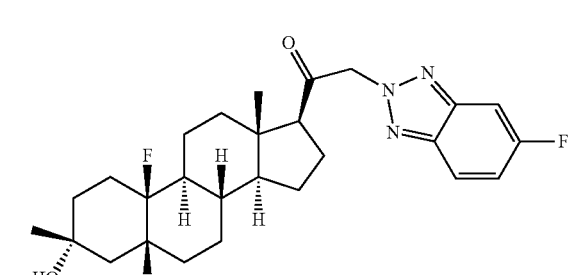
19
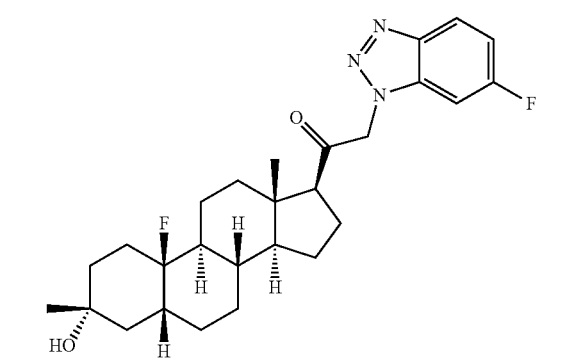
20
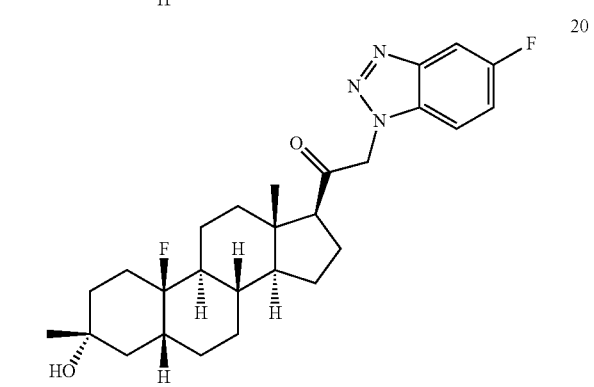
21
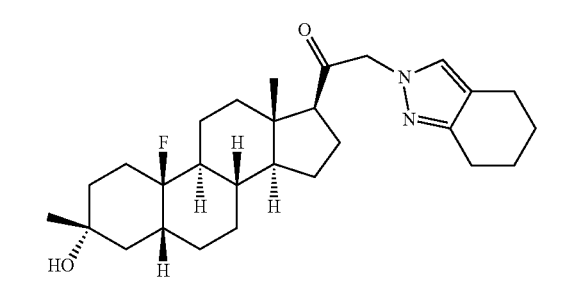
22
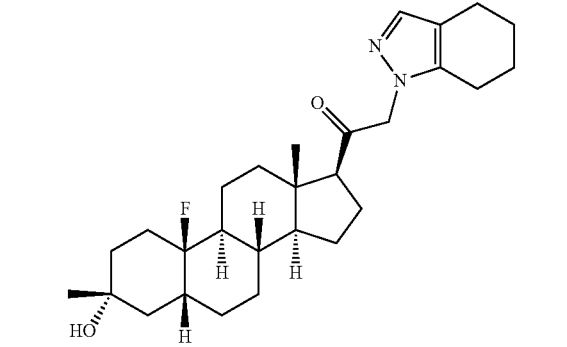

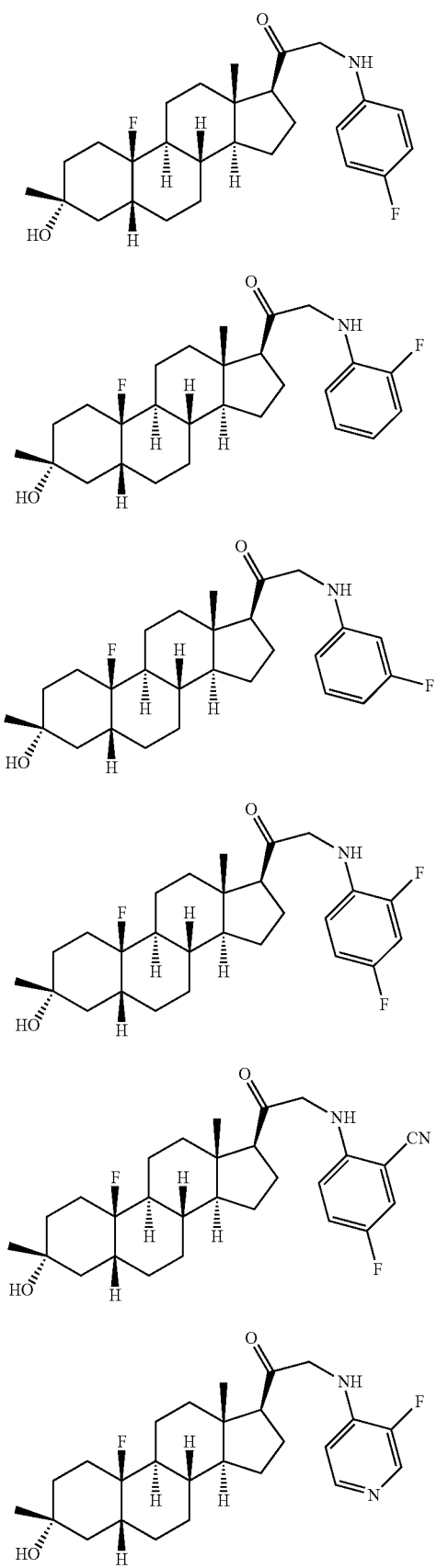
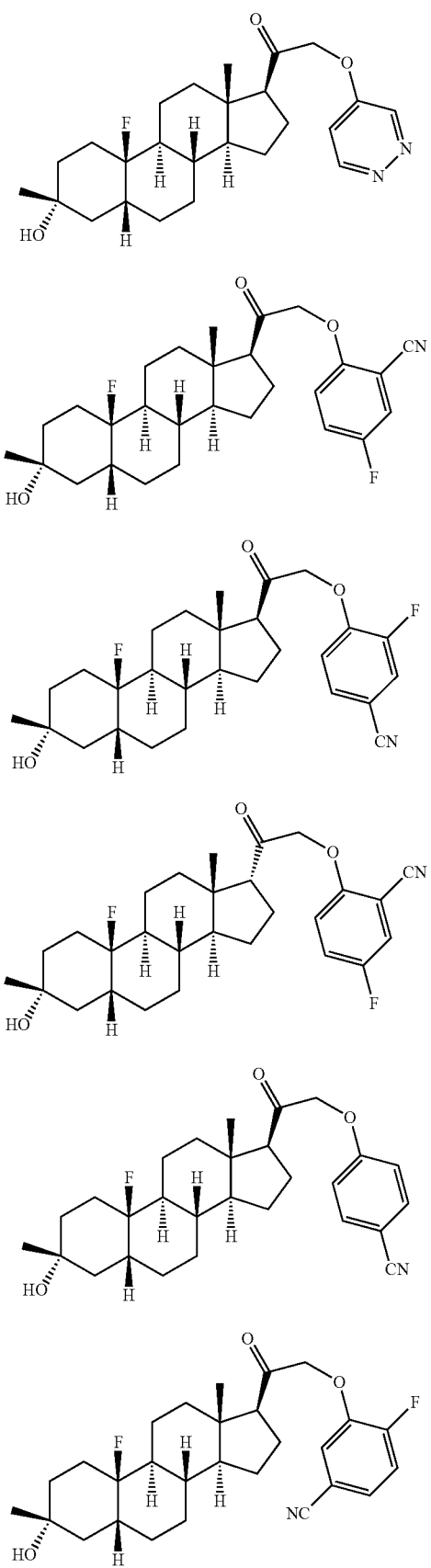

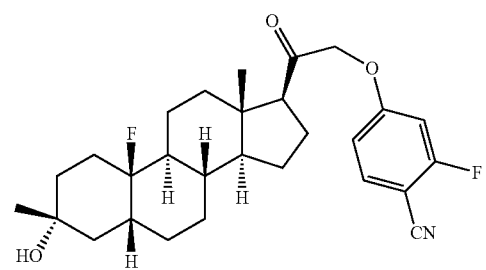
35
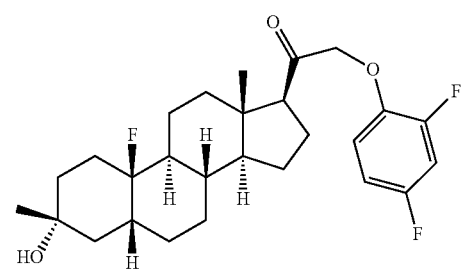
36
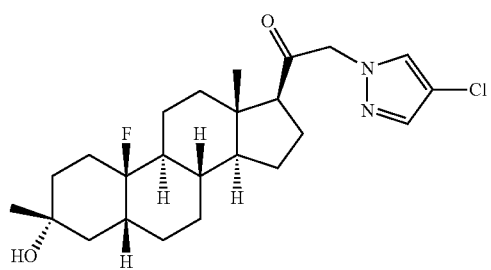
37
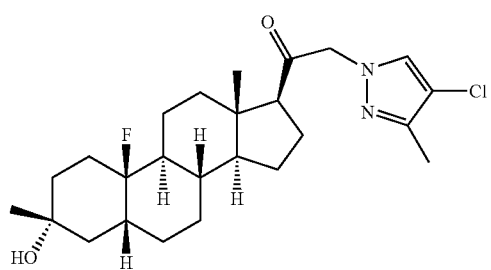
38
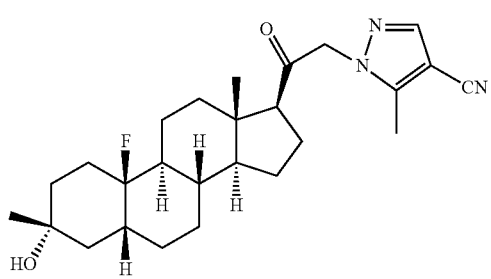
39
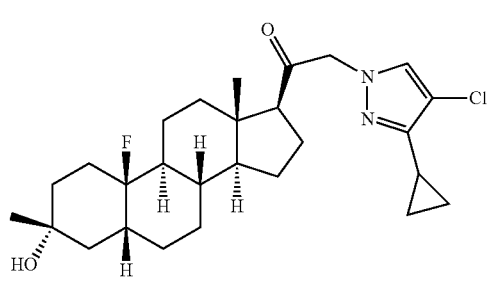
40
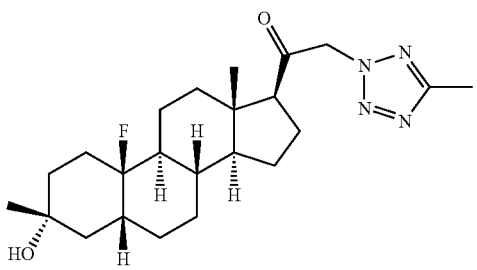
41
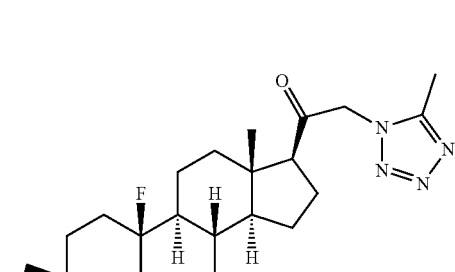
42
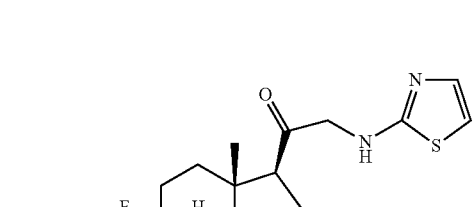
43
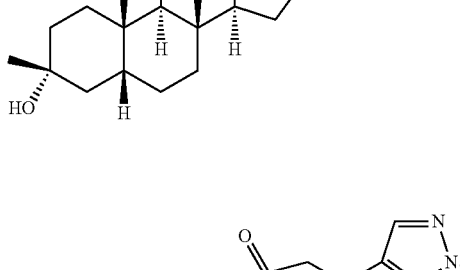
44
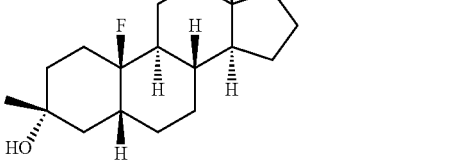
45

46
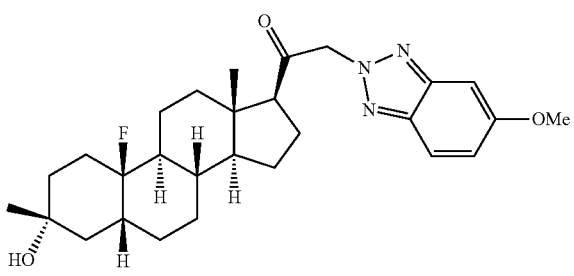
47
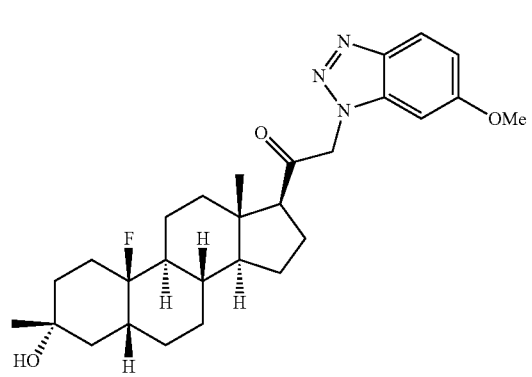
48
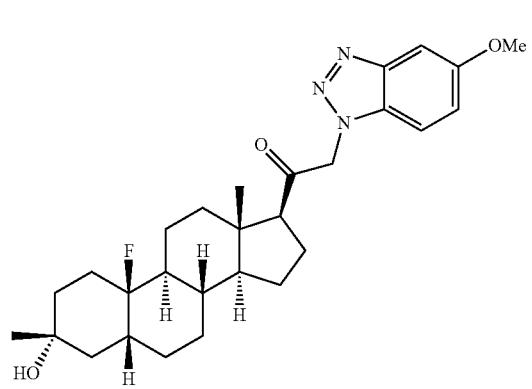
49
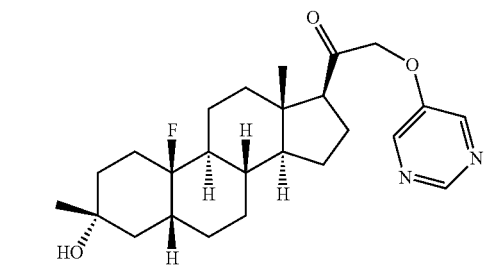
50
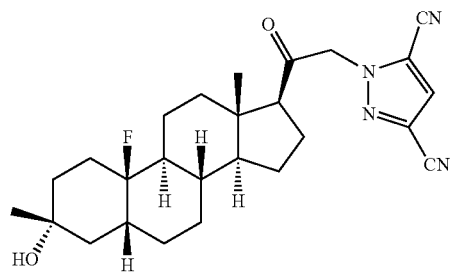
51
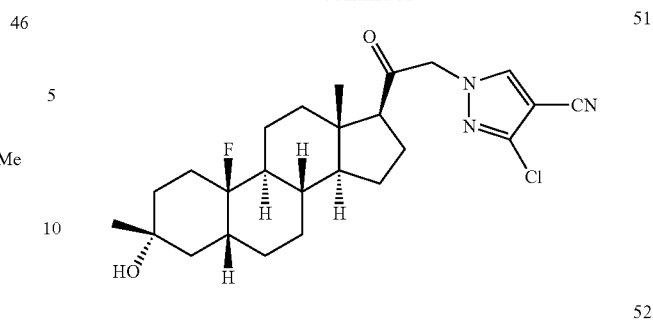
52
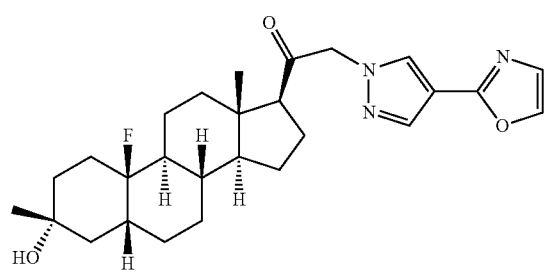
53
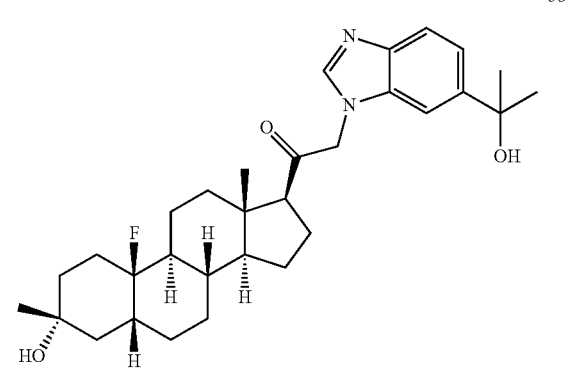
54
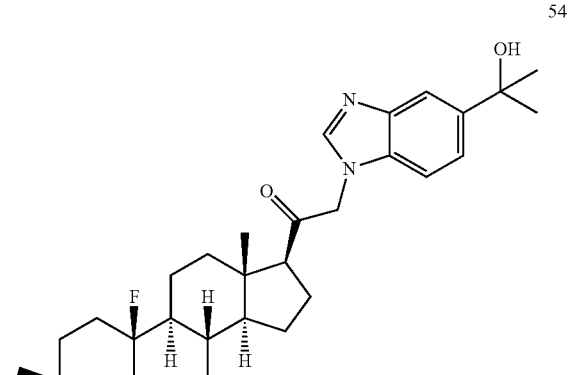
55
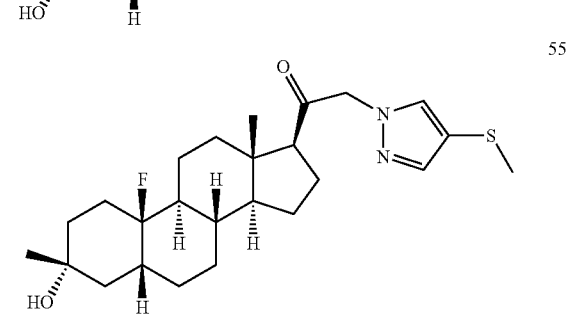

185
-continued
56
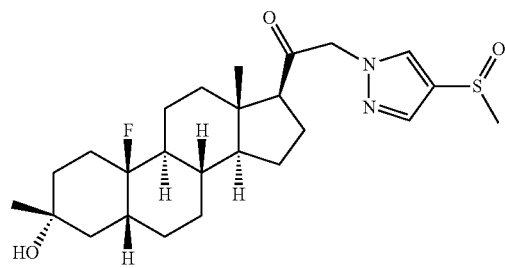
57
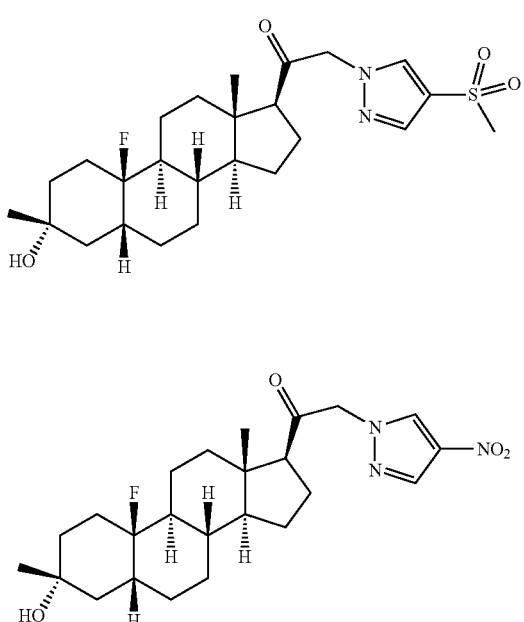
58
59
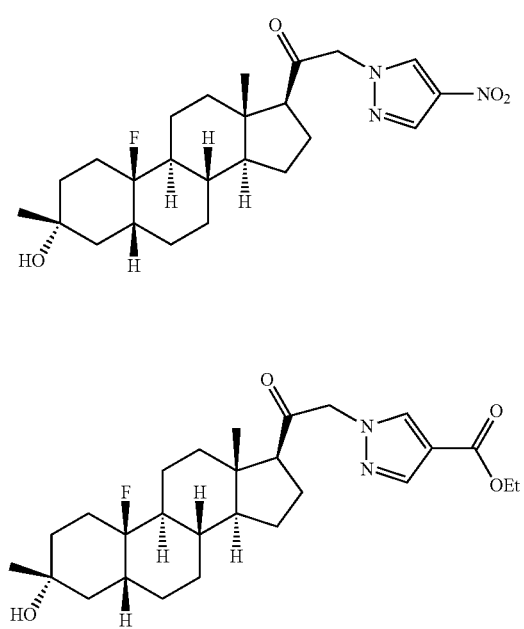
60
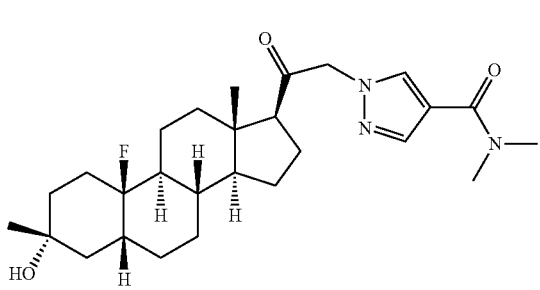
186
-continued
61
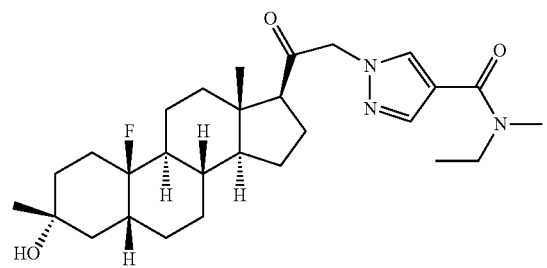
62
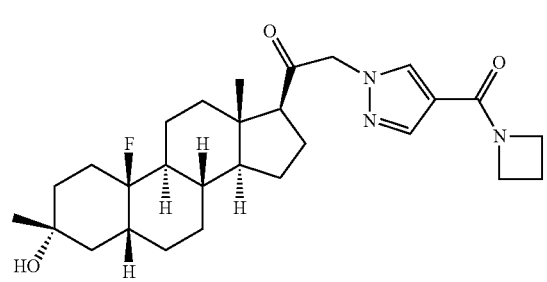
63
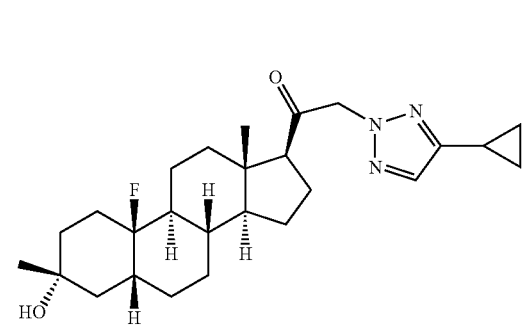
64
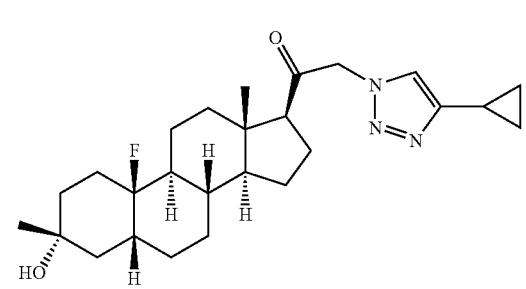
65
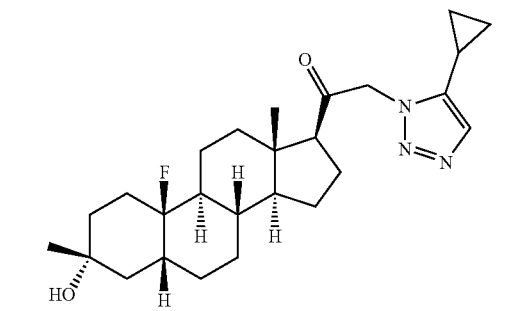

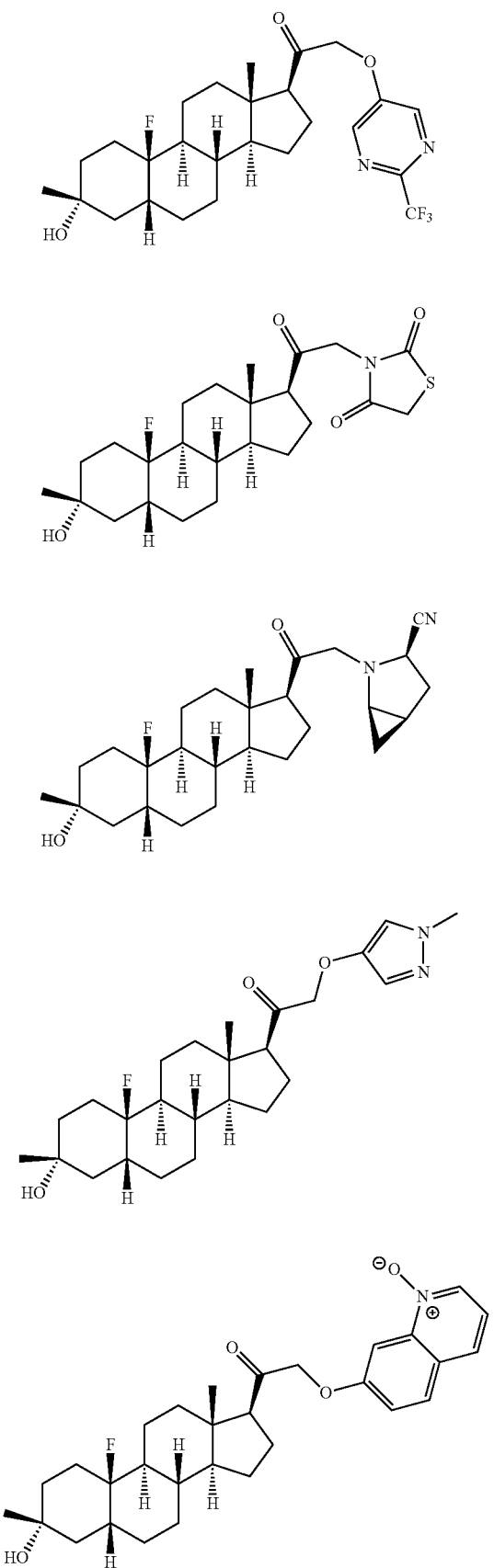
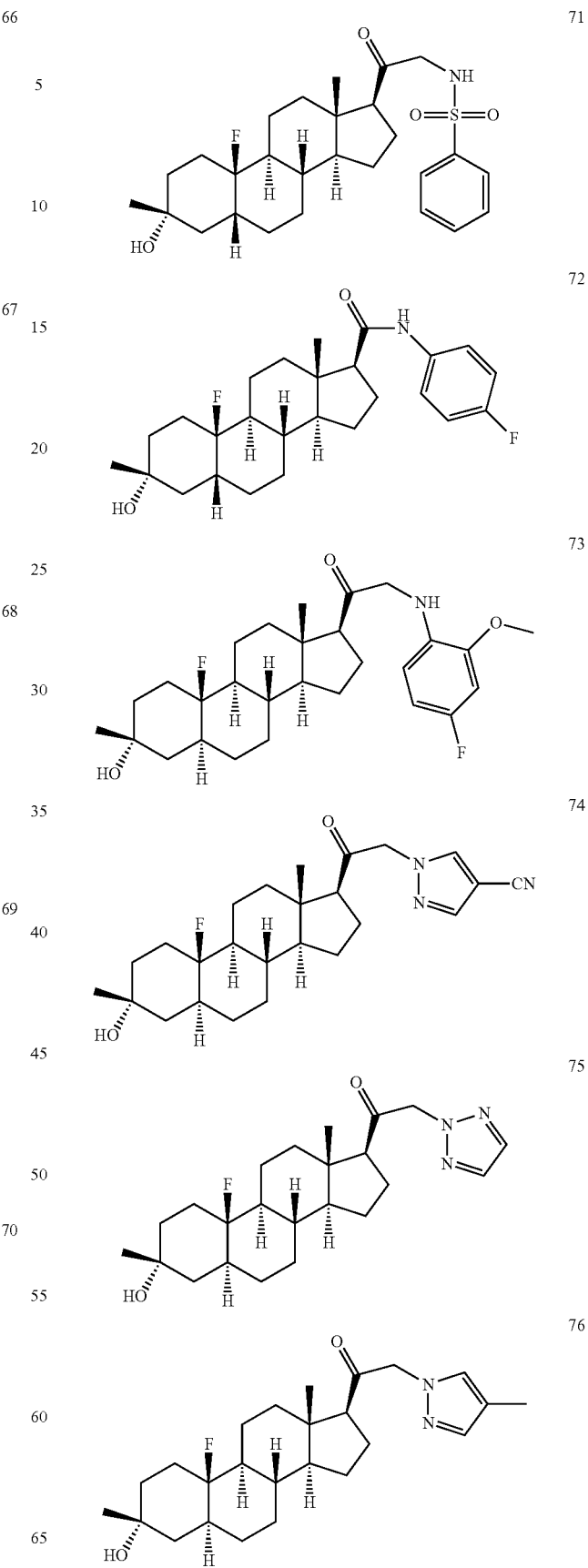

77
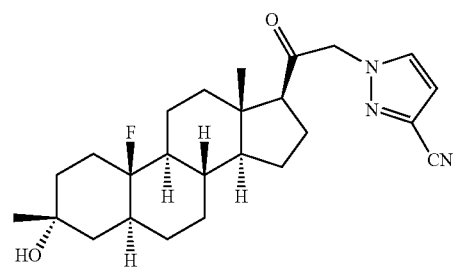
78
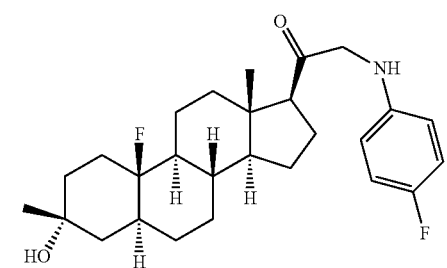
79A
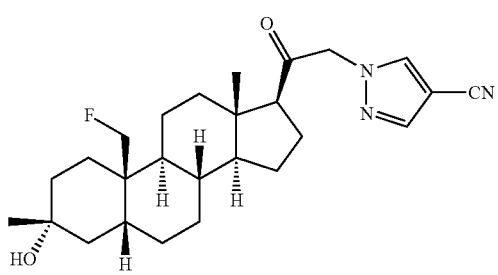
79B
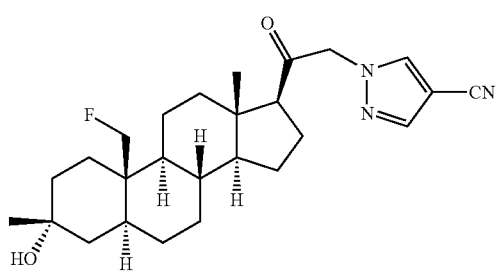
80A
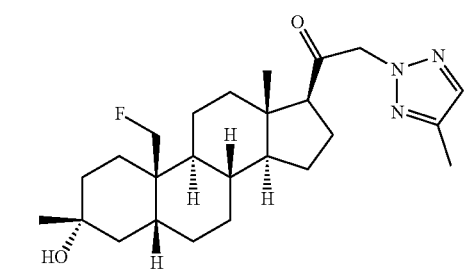
80B
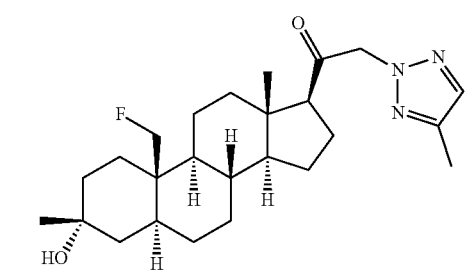
81A
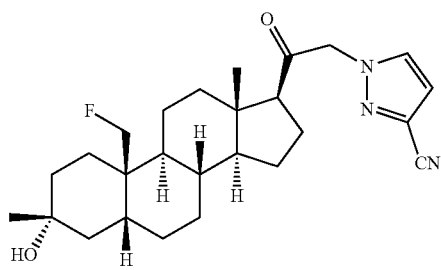
81B
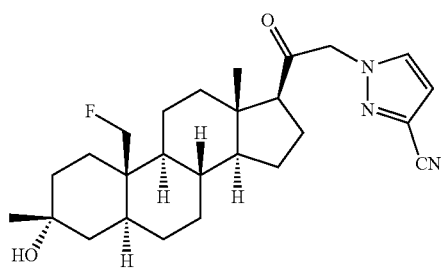
82A
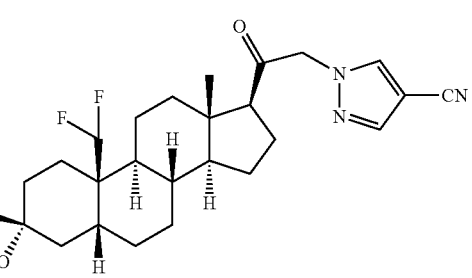
82B
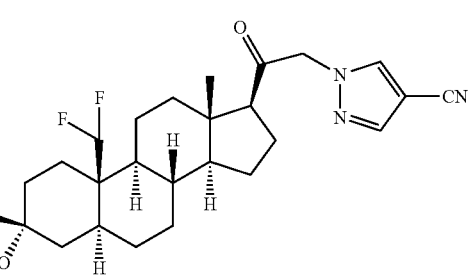
83A
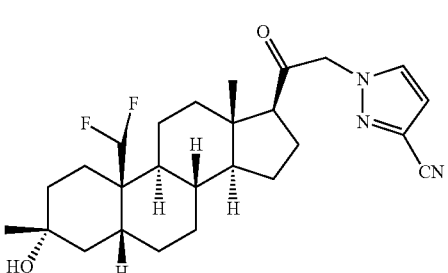
83B
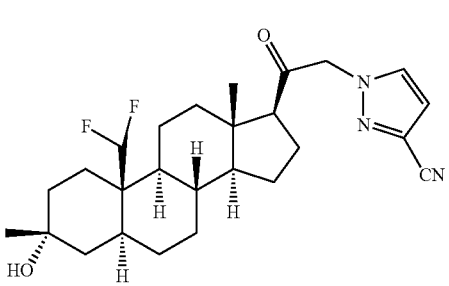

-continued
84A
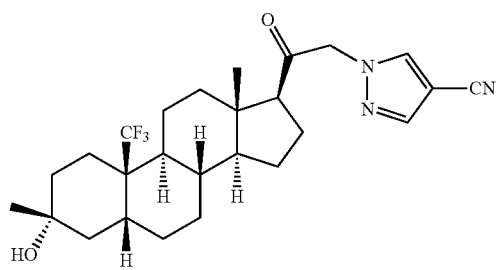
84B
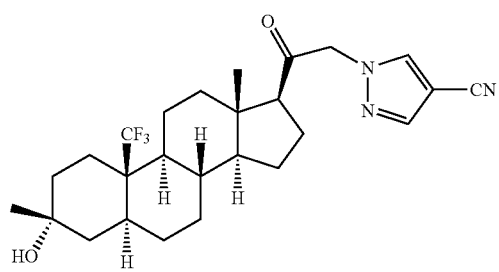
85A
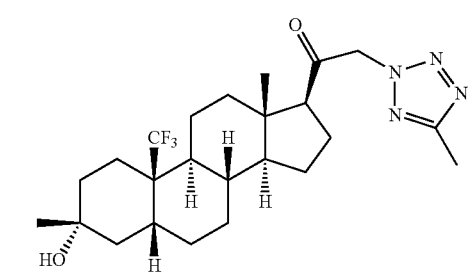
85B
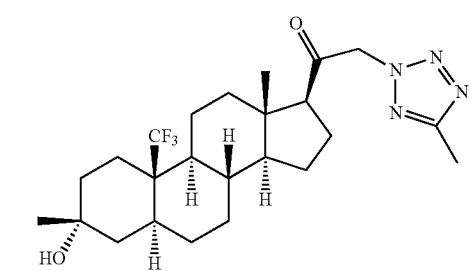
86A
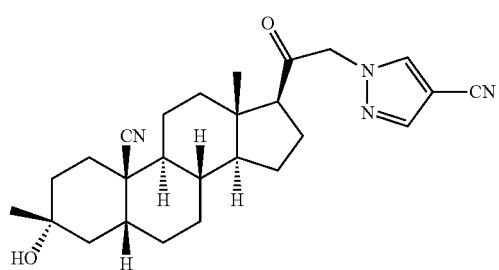
86B
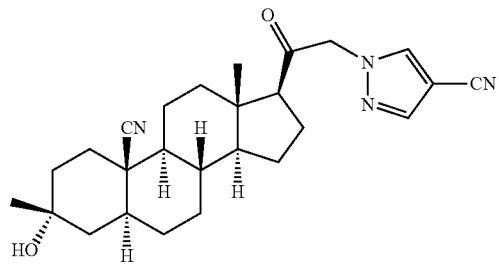
-continued
87A
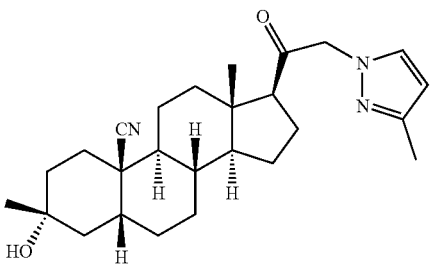
87B
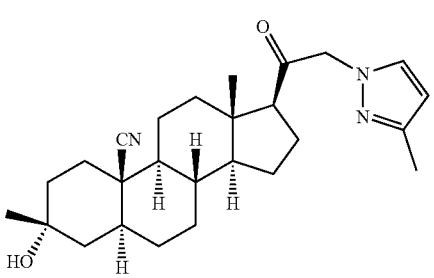
88
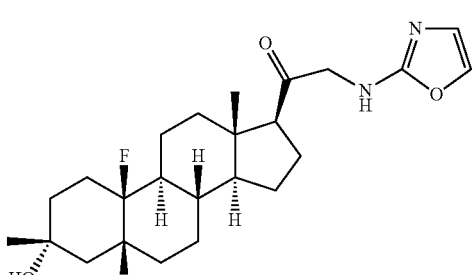
89
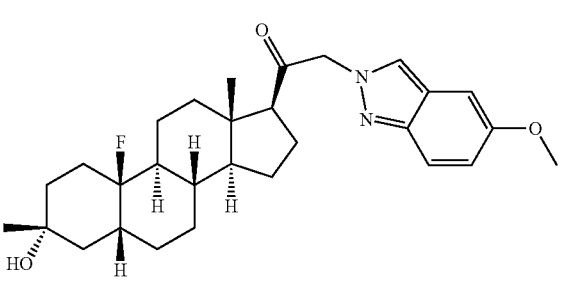
90
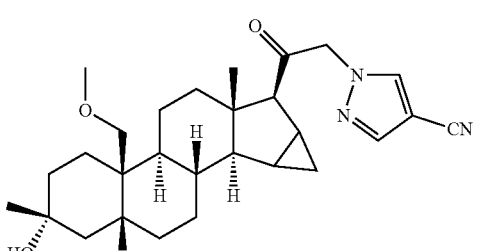
91
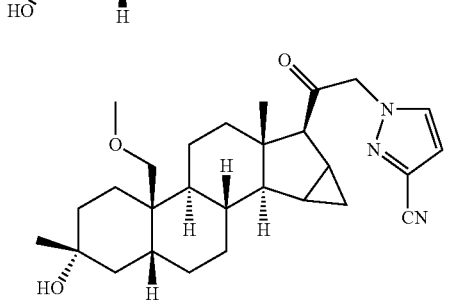

92
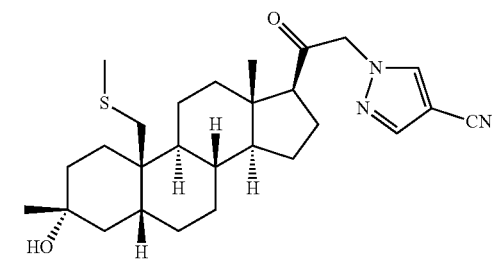
93
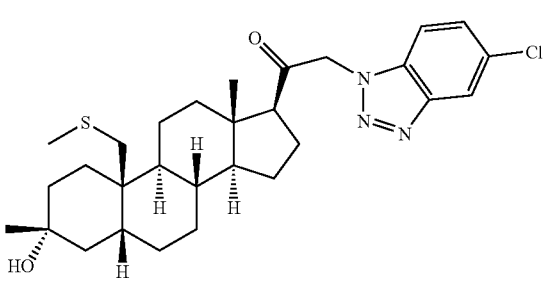
94
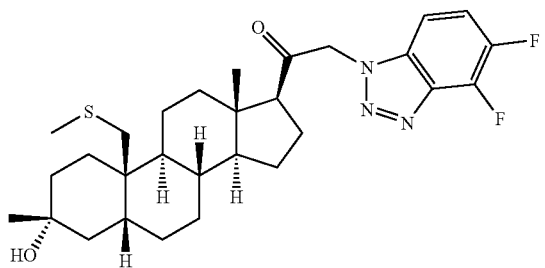
95
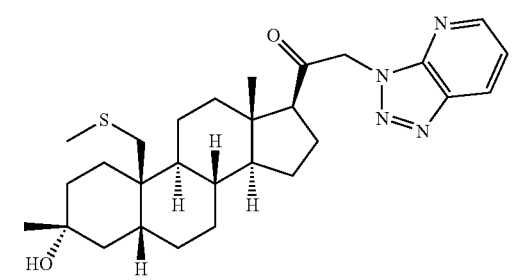
96
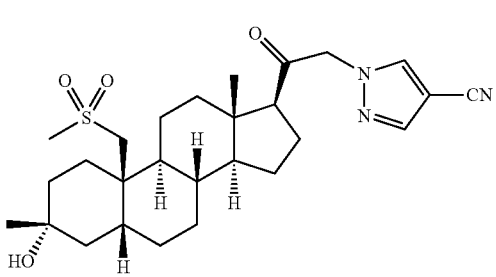
97
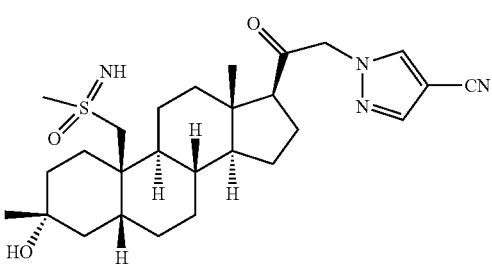
98
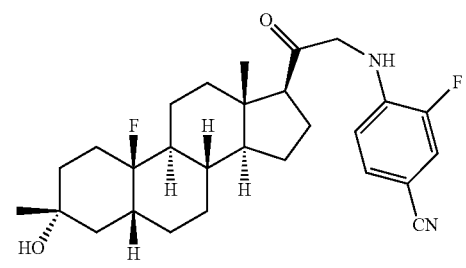
99
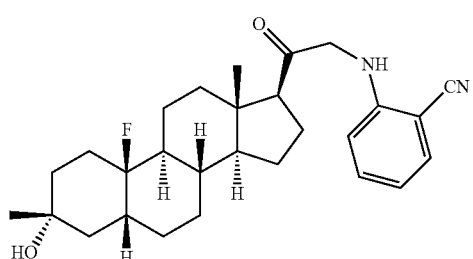
100
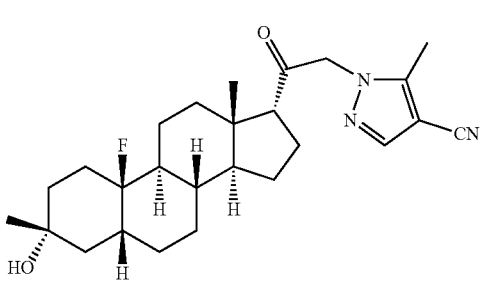
101
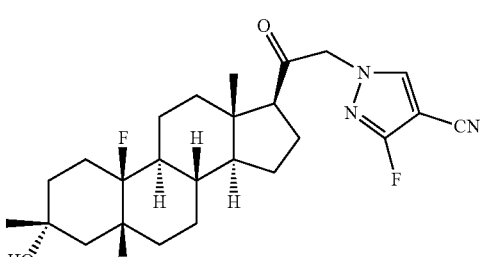
102
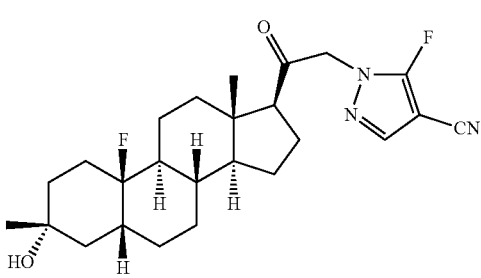

103
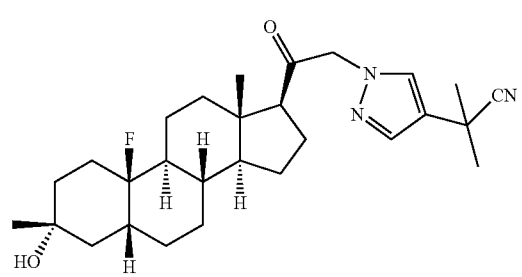
104
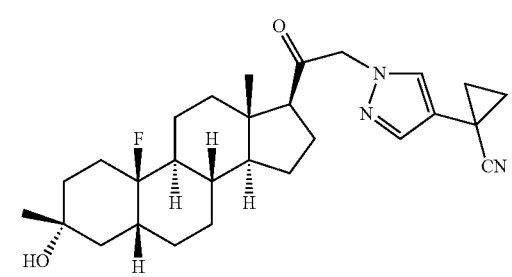
105
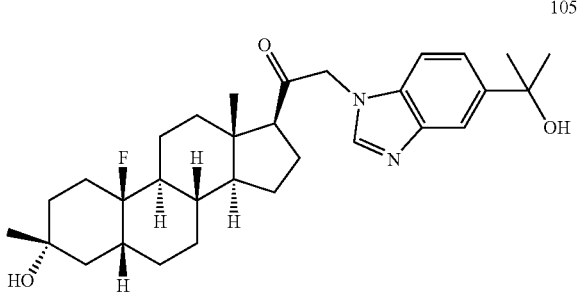
106
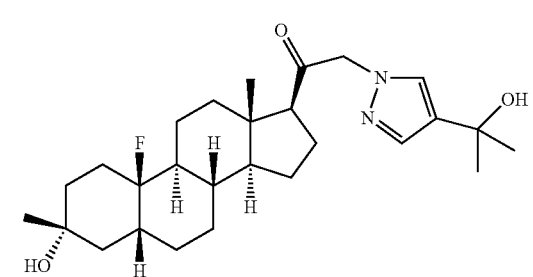
107
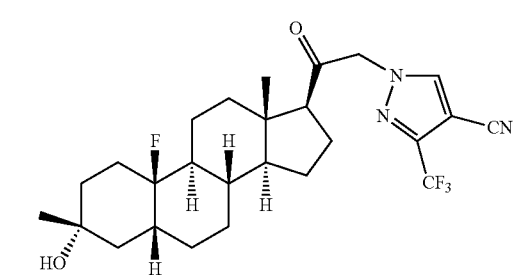
108
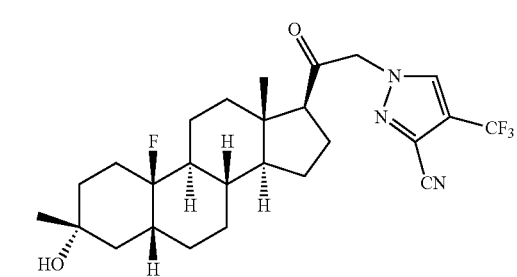
109
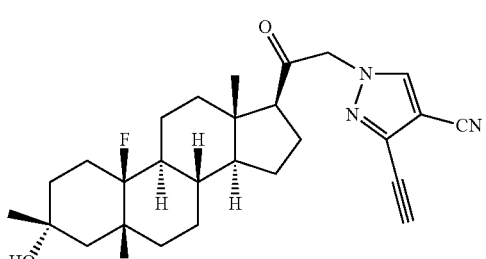
110
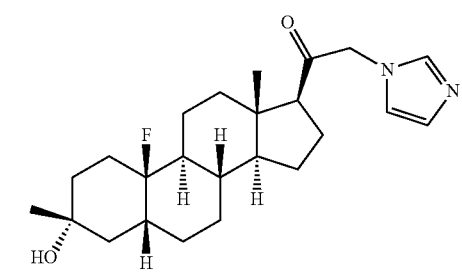
111
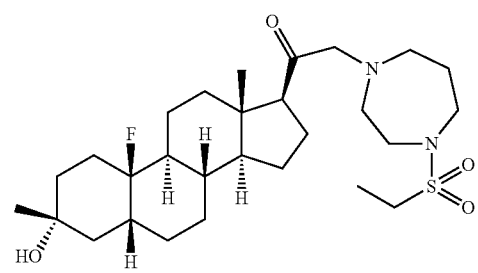
112
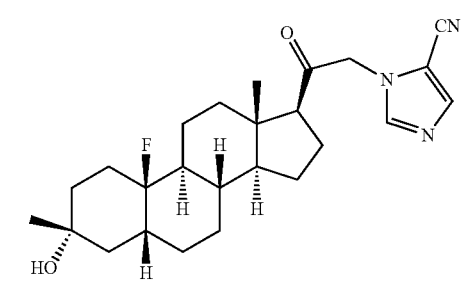
113
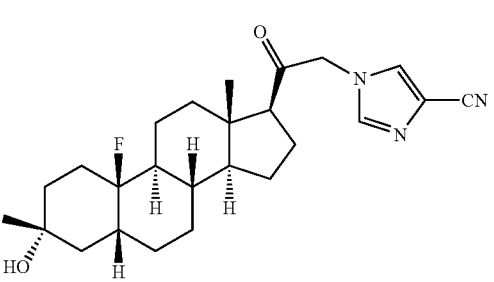
114
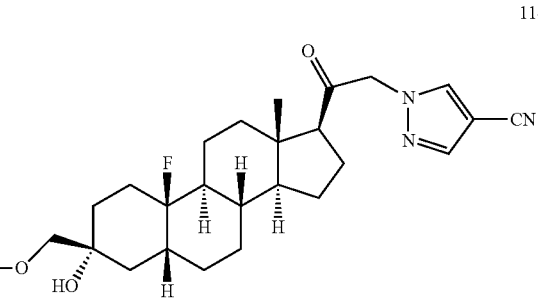

-continued
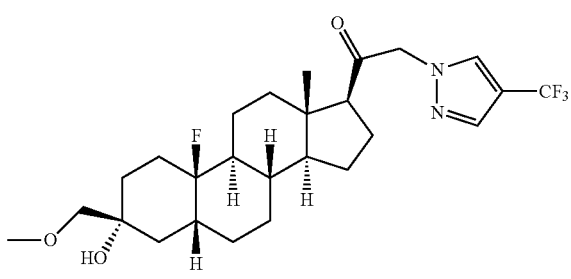
115
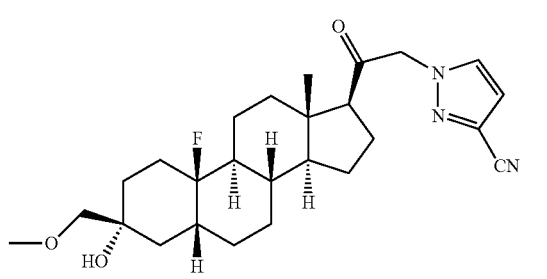
116
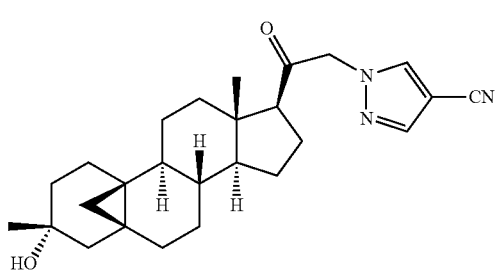
117
118
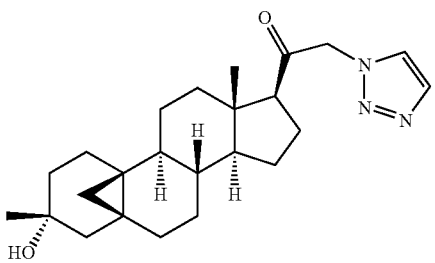
119
120
-continued
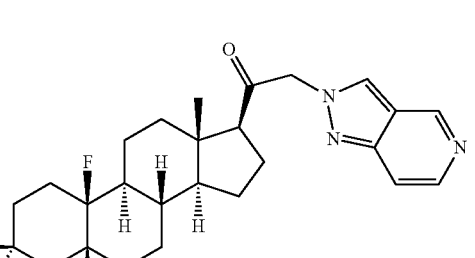
121
122
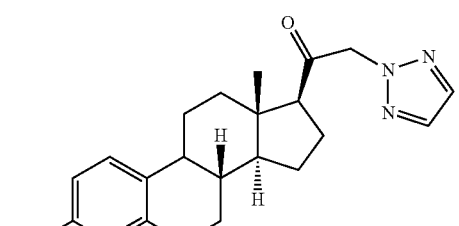
123
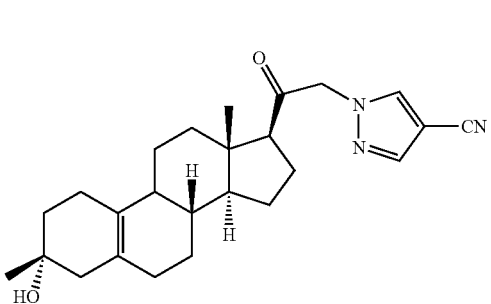
124
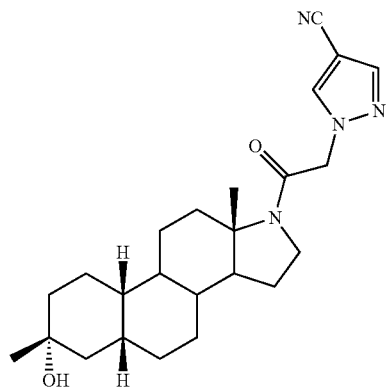
125

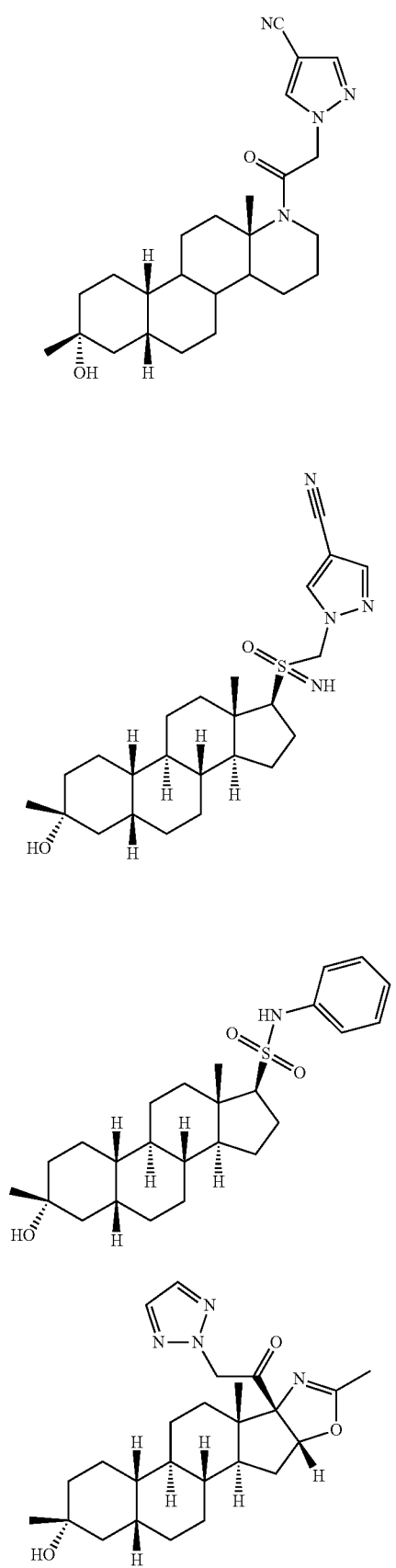
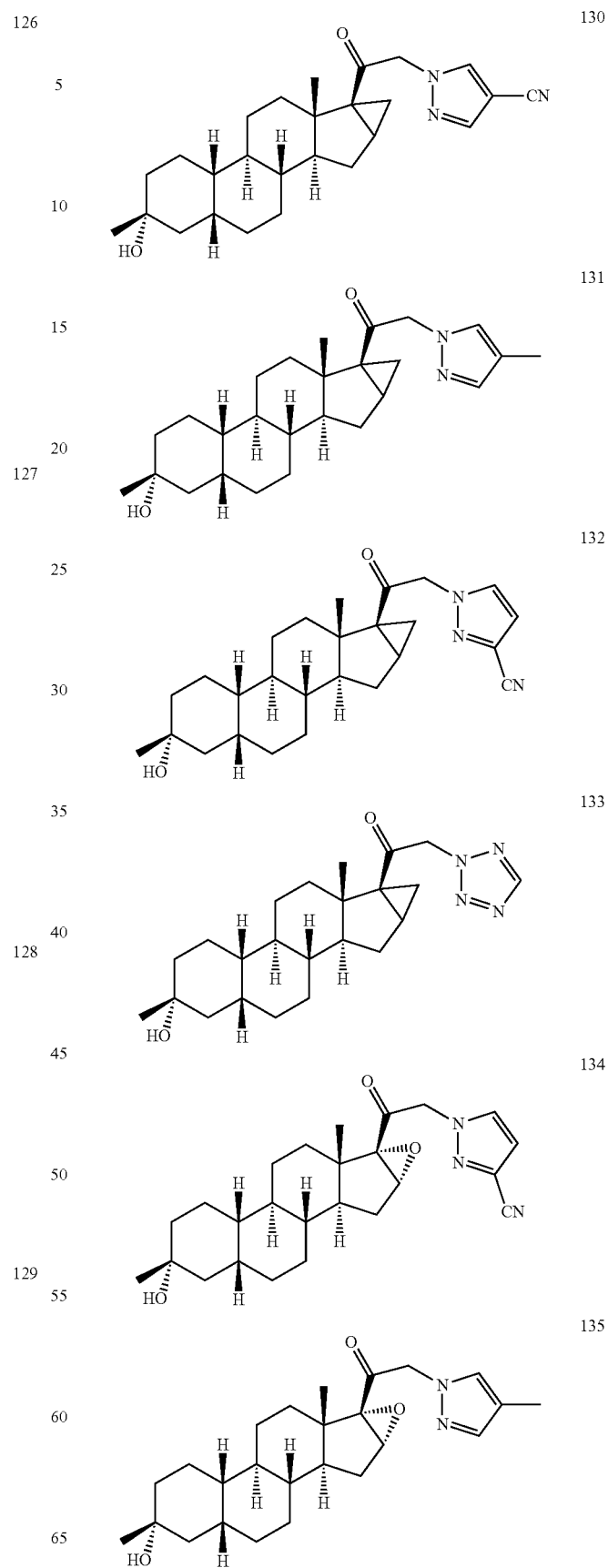

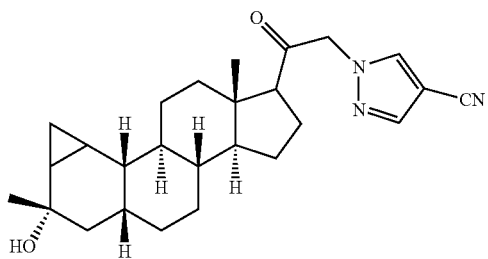
136
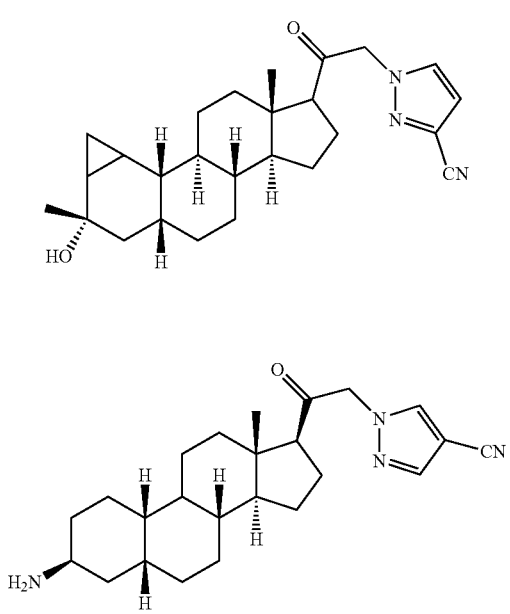
137
138
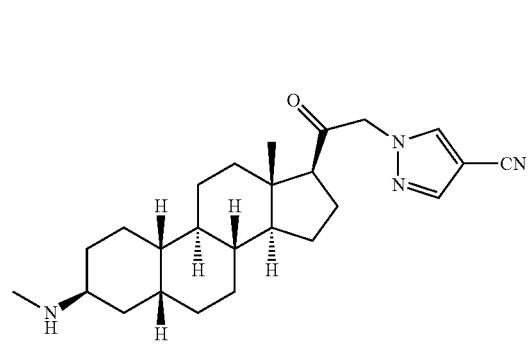
139
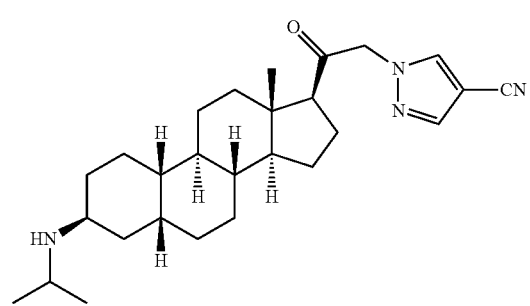
140
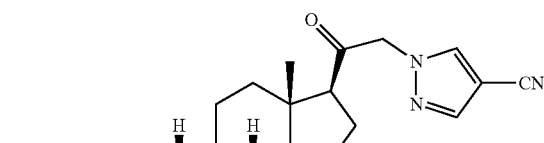
141
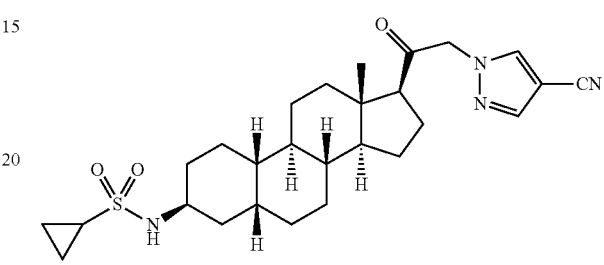
142
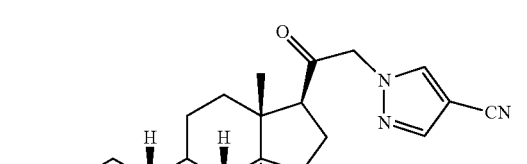
143
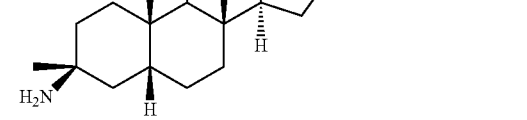
144
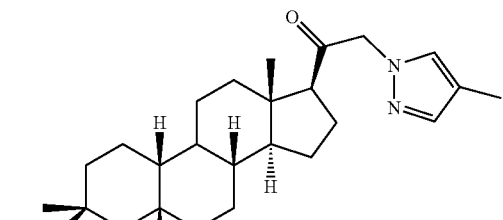
145
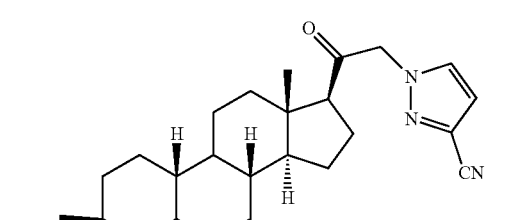
146
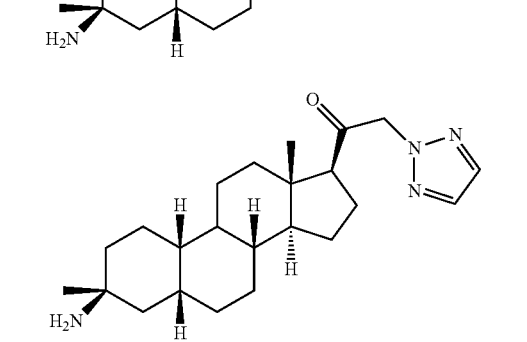

147
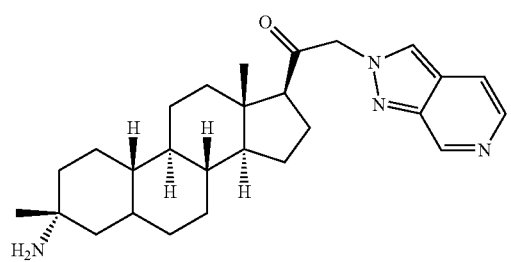
148
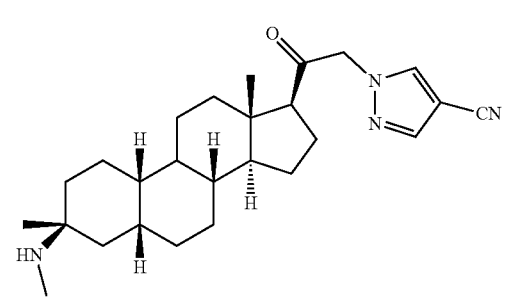
149
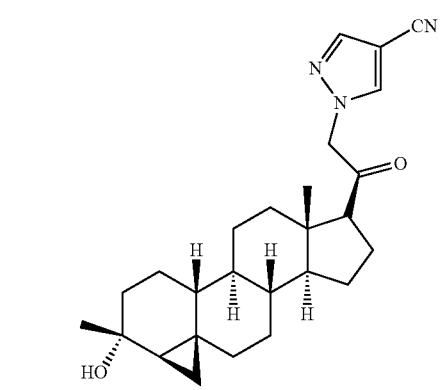
150
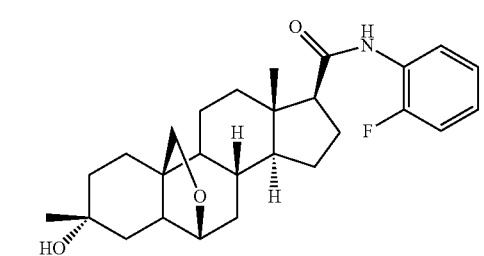
151
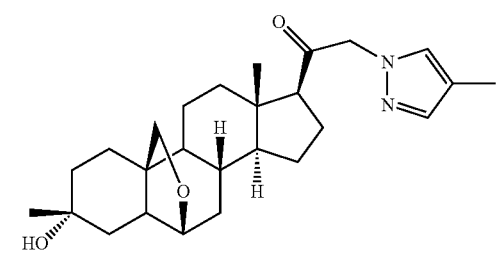
152
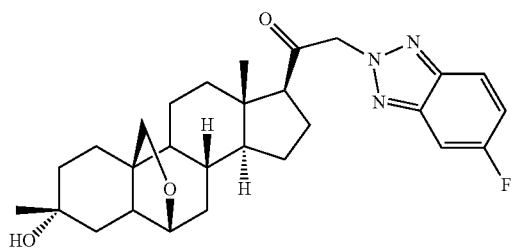
153
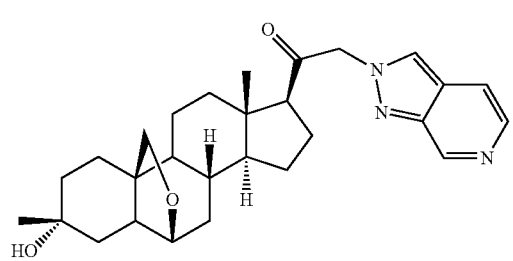
154
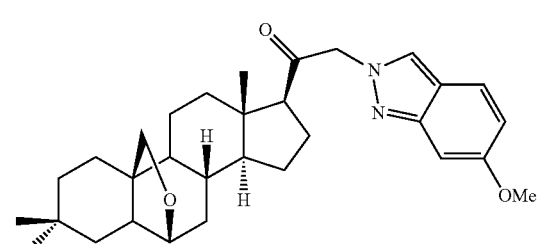
155
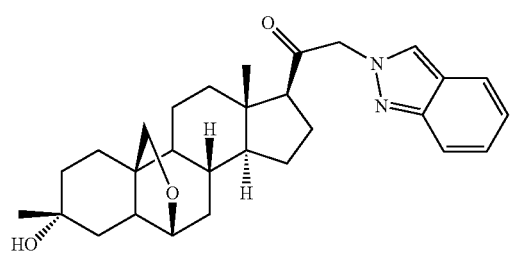
156
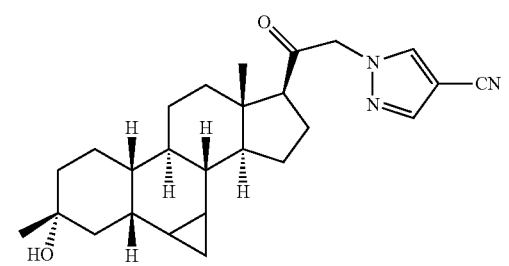
157
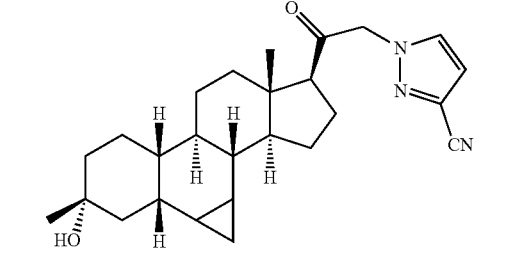

158
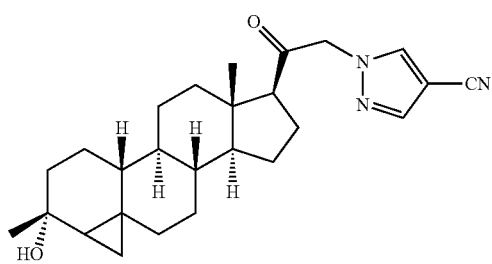
159
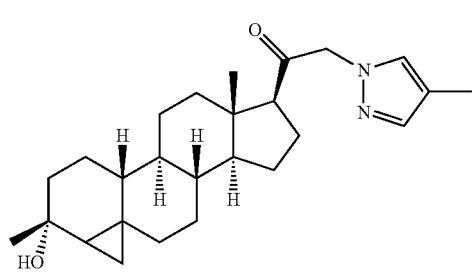
160
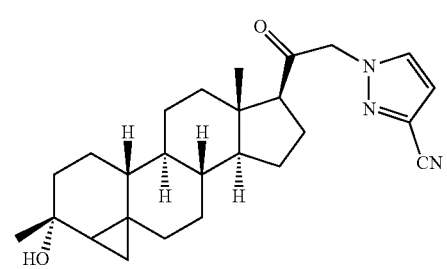
161
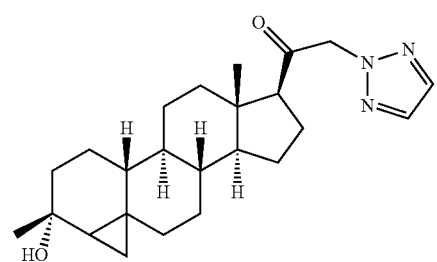
162
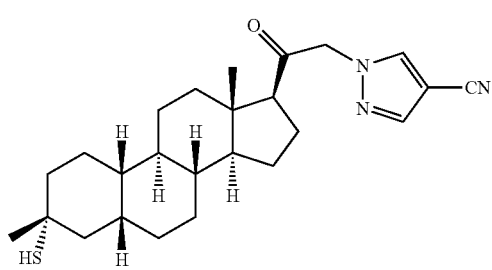
163
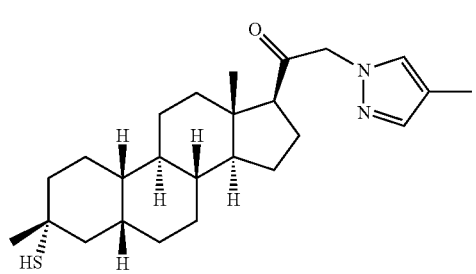
164
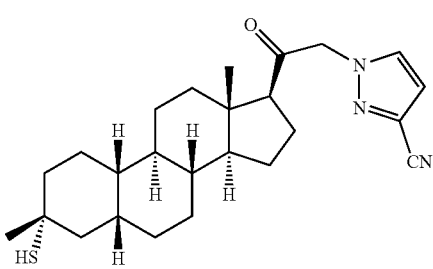
165
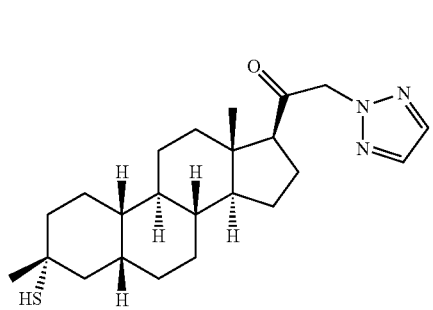
166
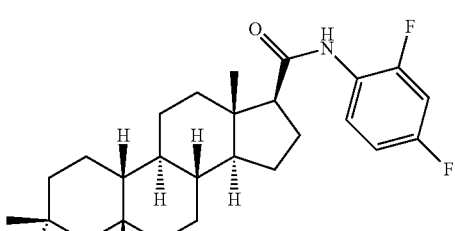
167
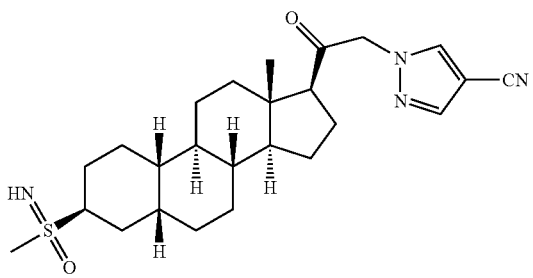
168
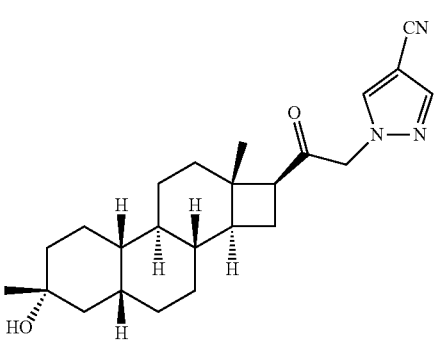

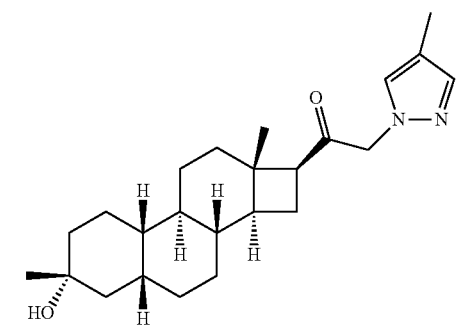
169
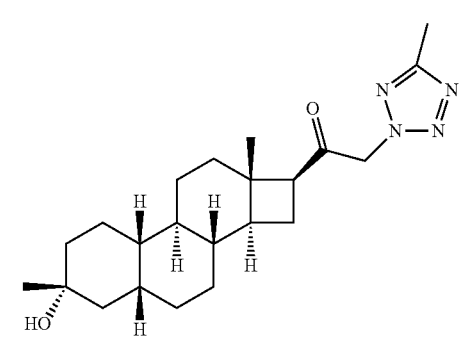
170
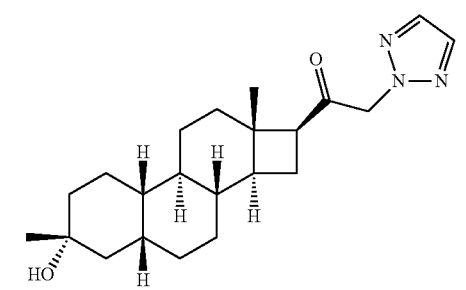
171
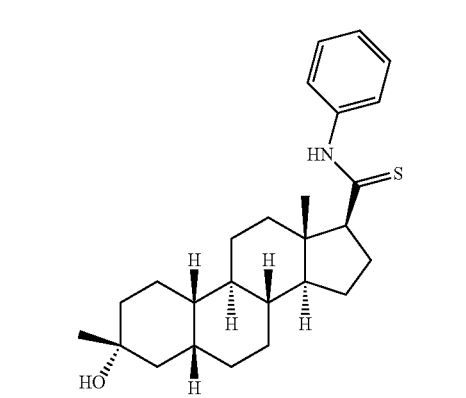
172
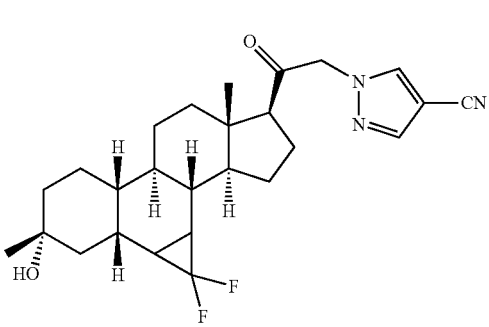
173
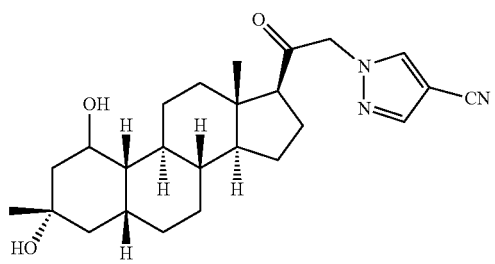
174
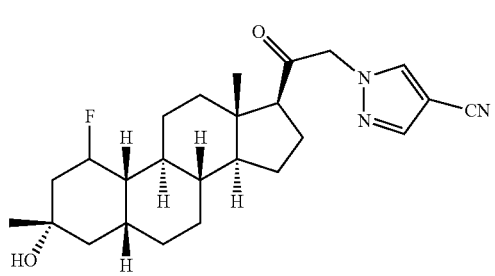
175
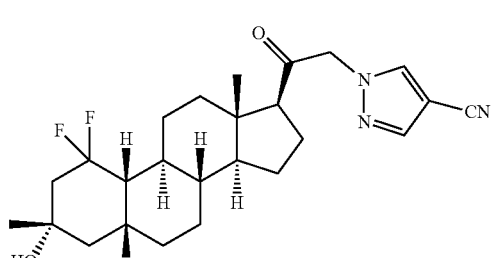
176
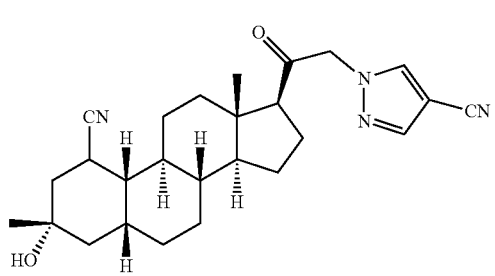
177
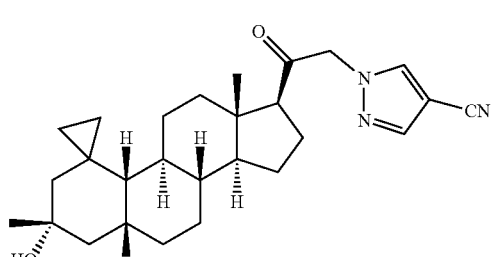
178
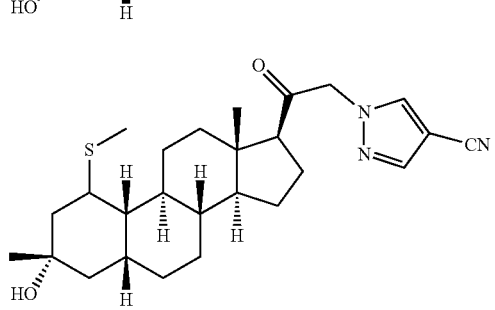
179

180
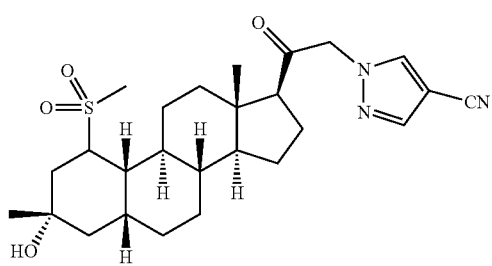
181
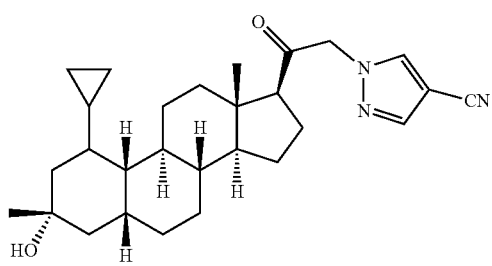
182
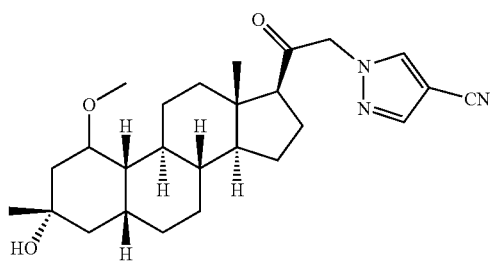
183
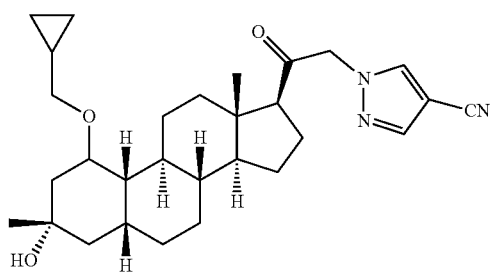
184
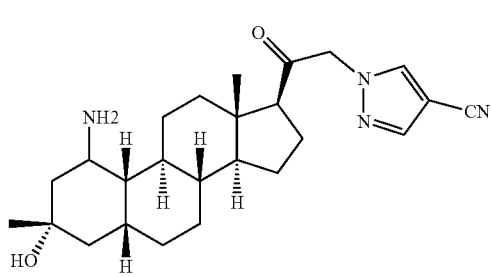
185
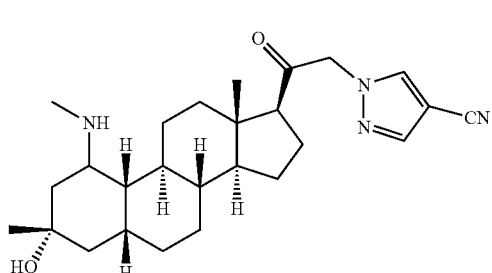
186
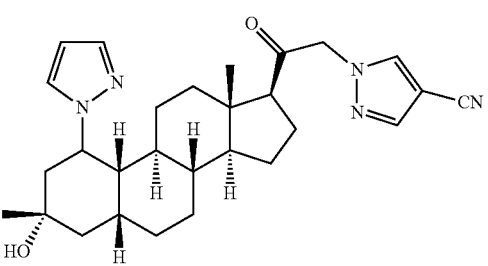
187
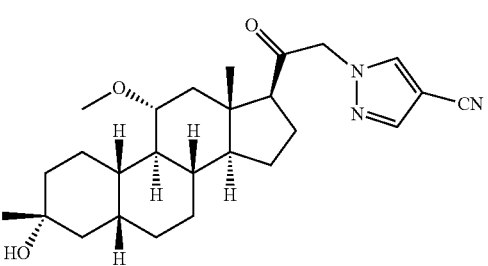
188
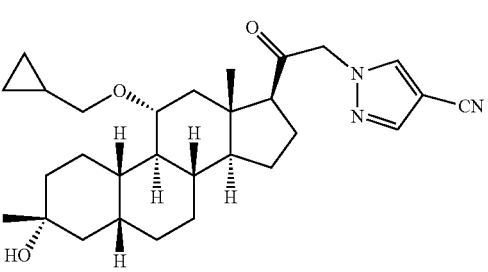
189
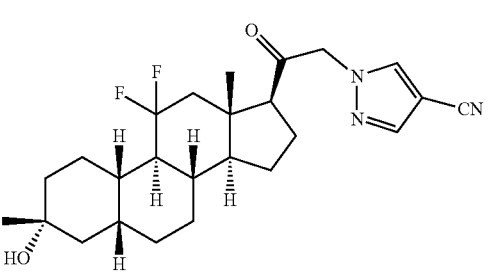
190
191
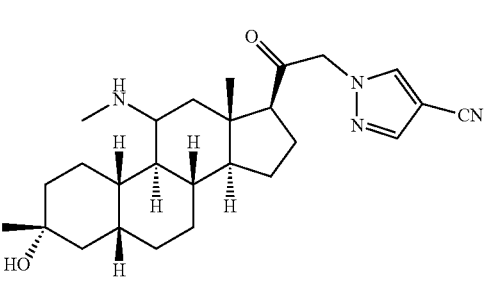

-continued
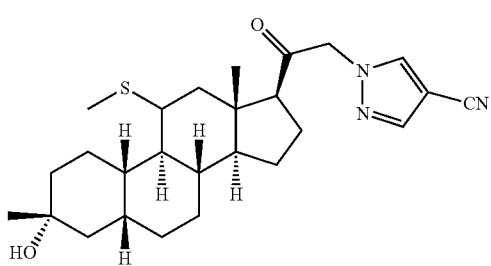
192
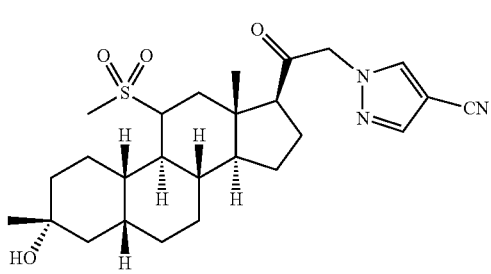
193
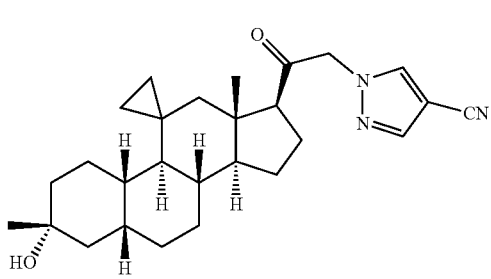
194
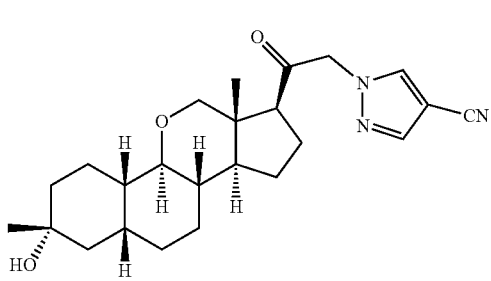
195
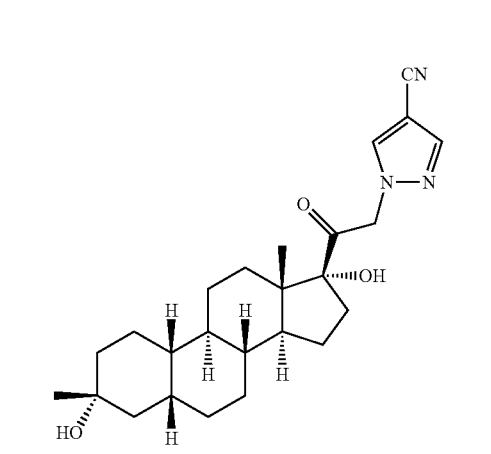
196
-continued
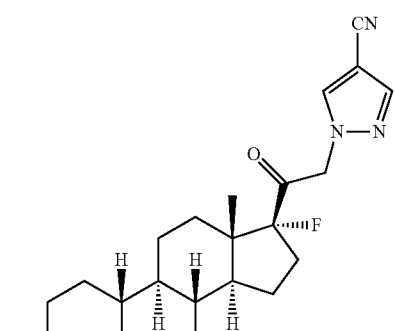
197
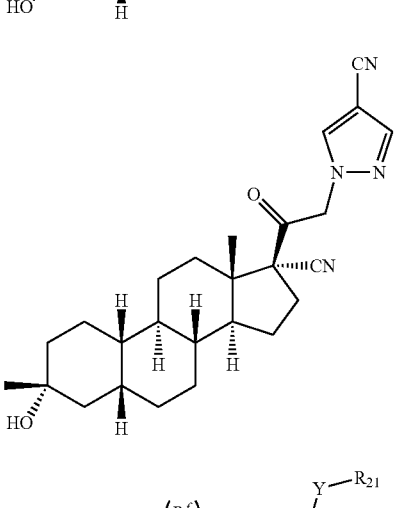
198
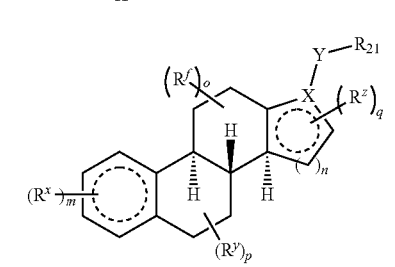
(I)

What is claimed is:
1. A compound of:

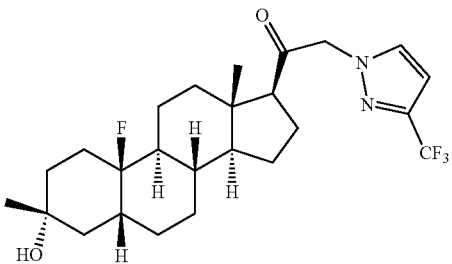

, or a stereoisomer thereof, or a pharmaceutically acceptable salt thereof.

2. A pharmaceutical composition, comprising the compound, the stereoisomer thereof, or the pharmaceutically acceptable salt thereof according to claim 1, and one or more pharmaceutically acceptable carriers, diluents or excipients.

3. A method of agonizing $GABA_A$ receptor in a subject in need thereof, comprising administering a therapeutically effective amount of the pharmaceutical composition according to claim 2 to the subject.

4. The method according to claim 3, wherein the subject has a CNS-related disease and the CNS-related disease is selected from the group consisting of sleep disorder, mood disorder, schizophrenia spectrum disorder, spasmodic disorder, memory disorder and/or cognitive disorder, dyskinesia, personality disorder, autism spectrum disorder, pain, traumatic brain injury, vascular disease, substance abuse disorder and/or withdrawal syndrome, and tinnitus.

* * * * *